US012799152B2

(12) United States Patent
Hardick et al.

(10) Patent No.: US 12,799,152 B2
(45) Date of Patent: Nov. 17, 2026

(54) INHIBITORS OF METTL3

(71) Applicant: Storm Therapeutics Limited, Cambridge (GB)

(72) Inventors: David James Hardick, Cambridge (GB); Wesley Peter Blackaby, Cambridge (GB); Elizabeth Jane Thomas, Cambridge (GB); Frederick Arthur Brookfield, Abingdon (GB); Jon Shepherd, Abingdon (GB); Christian Bubert, Abingdon (GB); Mark Peter Ridgill, Abingdon (GB)

(73) Assignee: Storm Therapeutics Limited, Cambridge (GB)

( * ) Notice: Subject to any disclaimer, the term of this patent is extended or adjusted under 35 U.S.C. 154(b) by 681 days.

(21) Appl. No.: 18/247,191

(22) PCT Filed: Oct. 7, 2021

(86) PCT No.: PCT/GB2021/052591

§ 371 (c)(1),
(2) Date: Mar. 29, 2023

(87) PCT Pub. No.: WO2022/074391

PCT Pub. Date: Apr. 14, 2022

(65) Prior Publication Data

US 2024/0101589 A1 Mar. 28, 2024

(30) Foreign Application Priority Data

Oct. 8, 2020 (GB) ..................................... 2015998
Jun. 2, 2021 (GB) ..................................... 2107909

(51) Int. Cl.
*C07H 19/14* (2006.01)
*A61P 35/00* (2006.01)
*C07D 487/04* (2006.01)

(52) U.S. Cl.
CPC .............. *C07H 19/14* (2013.01); *A61P 35/00* (2018.01); *C07D 487/04* (2013.01)

(58) Field of Classification Search
CPC ....... C07H 19/14; A61P 35/00; C07D 487/04; C07D 471/04
See application file for complete search history.

(56) References Cited

U.S. PATENT DOCUMENTS 5,668,180 A 9/1997 Lesieur et al.
5,928,323 A 7/1999 Gosling et al.
8,202,524 B2 6/2012 Sah
9,464,065 B2 10/2016 Schultz et al.
9,708,348 B2 7/2017 Castro et al.
11,725,010 B2 8/2023 Blackaby et al.
12,195,458 B2 1/2025 Blackaby et al.
12,358,915 B2 * 7/2025 Blackaby ............ C07D 471/04
2010/0317673 A1 12/2010 Peyronel
2019/0048014 A1 * 2/2019 Lin ........................ A61P 35/02
2023/0002378 A1 1/2023 Blackaby et al.
2023/0116403 A1 4/2023 Blackaby et al.
2023/0391770 A1 12/2023 Hardick et al.
2025/0122195 A1 4/2025 Blackaby et al.

FOREIGN PATENT DOCUMENTS

EP 2058309 A1 5/2009
EP 3262057 A1 1/2018
WO WO-98/42698 A1 10/1998
WO WO-00/17190 A2 3/2000
WO WO-02/50091 A1 6/2002
WO WO-02/066469 A2 8/2002
WO WO-2004022572 A1 * 3/2004 .............. A61P 43/00
WO WO-2005/048922 A2 6/2005
WO WO-2005/097261 A1 10/2005
WO WO-2006/100208 A1 9/2006
WO WO-2006/138549 A1 12/2006
WO WO-2007/039218 A1 4/2007
WO WO-2007/048070 A2 4/2007
WO WO-2007/081597 A2 7/2007
WO WO-2007/095124 A2 8/2007
WO WO-2007/147217 A1 12/2007
WO WO-2008/016666 A2 2/2008
WO WO-2008/074068 A1 6/2008
WO WO-2008/077188 A1 7/2008

(Continued)

OTHER PUBLICATIONS

Lerner, C.; et al. "Bisubstrate Inhibitors for the Enzyme Catechol O-Methyltransferase (COMT): Dramatic Effects of Ribose Modifications on Binding Affinity and Binding Mode", Helvetica Chimica Acta 2003, vol. 86, pp. 1045-1062. (Year: 2003).*
Walker, T. E..; et al. "The Synthesis of 5'-C-Alkyl Analogs of Adenosine" Carbohydrate Research 1973, vol. 27, pp. 225-234. (Year: 1973).*
Wu, F, Cheng, W.; et al. "Association of N6-methyladenosine with viruses and related diseases", Virology Journal 2019, vol. 16, 133. (Year: 2019).*
International Search Report for Application No. PCT/GB2021/052591 dated Jan. 5, 2022.
Yankova et al., "Small molecule inhibition of METTL3 as a strategy against myeloid leukaemia" Nature: 26 pages (2021).
"Harnessing the Power of RNA Modification: 1st in Class Inhibitors of RNA Modifying Enzymes (RME) to Treat Cancer and Other Diseases" Storm Therapeutics. (2022).

(Continued)

*Primary Examiner* — Andrea Olson
*Assistant Examiner* — Benjamin M Brandsen
(74) *Attorney, Agent, or Firm* — Foley Hoag LLP; David P. Halstead; Alexander J. Chatterley

(57) ABSTRACT

The present invention relates to compounds of formula (I) that function as inhibitors of METTL3 (N6-adenosine-methvltransferase 70 kDa subunit) enzyme activity: W-X-Y-Z (I) wherein X, Y and Z are each as defined herein. The present invention also relates to processes for the preparation of these compounds, to pharmaceutical compositions comprisind them, and to their use in the treatment of proliferative disorders, such as cancer, and autoimmune diseases, as well as other diseases or conditions in which METTL3 activity is implicated.

24 Claims, No Drawings

(56) References Cited

FOREIGN PATENT DOCUMENTS

| | | | | |
|---|---|---|---|---|
| WO | WO-2008/100448 A2 | | 8/2008 | |
| WO | WO-2009/025478 A1 | | 2/2009 | |
| WO | WO-2009/100294 A2 | | 8/2009 | |
| WO | WO-2009/127678 A1 | | 10/2009 | |
| WO | WO-2010/000030 A1 | | 1/2010 | |
| WO | WO-2010/000031 A1 | | 1/2010 | |
| WO | WO-2010/000032 A1 | | 1/2010 | |
| WO | WO-2010/006496 A1 | | 1/2010 | |
| WO | WO-2010/065760 A1 | | 6/2010 | |
| WO | WO-2010/065898 A2 | | 6/2010 | |
| WO | WO-2010/114898 A1 | | 10/2010 | |
| WO | WO-2010/138600 A2 | | 12/2010 | |
| WO | WO-2011/050245 A1 | | 4/2011 | |
| WO | WO-2012/006680 A1 | | 1/2012 | |
| WO | WO-2012/131031 A1 | | 10/2012 | |
| WO | WO-2013/119916 A2 | | 8/2013 | |
| WO | WO-2014/148557 A1 | | 9/2014 | |
| WO | WO-2015/105657 A1 | | 7/2015 | |
| WO | WO-2015/192760 A1 | | 12/2015 | |
| WO | WO-2015/192761 A1 | | 12/2015 | |
| WO | WO-2016/027249 A1 | | 2/2016 | |
| WO | WO-2016/054491 A1 | | 4/2016 | |
| WO | WO-2016/135582 A1 | | 9/2016 | |
| WO | WO-2016/196386 A1 | | 12/2016 | |
| WO | WO-2017/032840 A1 | | 3/2017 | |
| WO | WO-2017/214269 A1 | | 12/2017 | |
| WO | WO-2018/065365 A1 | | 4/2018 | |
| WO | WO-2018/098446 A1 | | 5/2018 | |
| WO | WO-2018152548 A1 | * | 8/2018 | ........... C07D 487/04 |
| WO | WO-2018/160824 A1 | | 9/2018 | |
| WO | WO-2018/183145 A1 | | 10/2018 | |
| WO | WO-2019/032859 A1 | | 2/2019 | |
| WO | WO-2019/112719 A1 | | 6/2019 | |
| WO | WO-2019/197024 A1 | | 10/2019 | |
| WO | WO-2020/033285 A1 | | 2/2020 | |
| WO | WO-2020/037079 A1 | | 2/2020 | |
| WO | WO-2020/112872 A1 | | 6/2020 | |
| WO | WO-2020/201773 A1 | | 10/2020 | |
| WO | WO-2021/079196 A2 | | 4/2021 | |
| WO | WO-2021/081211 A1 | | 4/2021 | |
| WO | WO-2021/111124 A1 | | 6/2021 | |
| WO | WO-2022/074379 A1 | | 4/2022 | |
| WO | WO-2022/074391 A1 | | 4/2022 | |

OTHER PUBLICATIONS

"Oral Administration of STC-15 in Subjects With Advanced Malignancies" ClinicalTrials.gov identifier: NCT05584111, https://clinicaltrials.gov/ct2/show/NCT05584111, last visited Feb. 8, 2023.

Alvarez et al., "Allosteric Indole Amide Inhibitors of p97: Identification of a Novel Probe of the Ubiquitin Pathway," ACS Medicinal Chemistry Letters, 7(2): 182-187 (2016).

Bedi et al., "Small-Molecule Inhibitors of METTL3, the Major Human Epitranscriptomic Writer," Chemmedchem Communications 15(9):pp. 744-748 (May 6, 2020).

Belikov, "Pharmaceutical Chemistry", textbook, 2007, Moscow, "MEDpress-inform", pp. 27-29.

Burgess et al., "Targeting the m6A RNA modification pathway blocks SARS-CoV-2 and HCoV-OC43 replication" Genes and Development, 35:1005-1019 (2021).

CAS Registry, Columbus, Ohio, US, XP002798995, compound with RN=1311663-16-7 (Jul. 7, 2011).

Cheng et al., "The m6A methyltransferase METTL3 promotes bladder cancer progression via AFF4/NF-kB/MYC signaling network" Oncogene, 38(19): 3667-3680 (2019).

Choe et al., "mRNA circularization by METTL3-elF3h enhances translation and promotes oncogenesis" Nature, 561 (7724): (2018).

Cui et al., "m6A RNA Methylation Regulates the Self-Renewal and Tumorigenesis of Glioblastoma Stem Cells" Cell Rep, 18(11): 2622-2634 (2017).

Du et al., ""MiR-33a suppresses proliferation of NSCLC cells via targeting METTL3 mRNA"" Biochem Biophys Res Commun, 482(4): 582-589 (2017).

Dyson et al., "Chemistry of Synthetic Medicinal Substances, M." World: 12-19 (1964).

Fang et al., "Transcriptome-Wide Analysis of RNA N6-Methyladenosine Modification in Adriamycin-Resistant Acute Myeloid Leukemia Cells" Frontiers in Genetics, 13(833694): 13 pages (2022).

Han et al., "Anti-tumor immunity controlled through mRNA m6A and YTHDF1 in dendritic cells" Nature, 566(7743): 270-274 (2019).

Han et al., "METTL3 promote tumor proliferation of bladder cancer by accelerating pri-miR221/222 maturation in m6A-dependent manner" Mol Cancer, 18(1):110, 15 pages (2019).

Heidenreich et al., "Structure-Based Approach toward Identification of Inhibitory Fragments for Eleven-Nineteen-Leukemia Protein (ENL)," Journal of Medicinal Chemistry, 61: 10929-10934 (2018).

International Search Report and Written Opinion for International Application No. PCT/GB20/53081 dated Feb. 16, 2021.

International Search Report and Written Opinion for International Application No. PCT/GB21/52573 dated Dec. 14, 2021.

Kümmerer, "Pharmaceuticals in the environment." Annual Review of Environment and Resources 35(1) (2010): 57-75.

Li et al., "METTL3 facilitates tumor progression via an m6A-IGF2BP2-dependent mechanism in colorectal carcinoma" Mol Cancer, 18(1):(2019).

Li et al., "METTL3 inhibition reduces N6-methyladenosine levels and prevents allogeneic CD4+ T-cell responses" Immunology and Cell Biology, 100:718-730 (2022).

Lin et al., "RNA m6A methylation regulates the epithelial mesenchymal transition of cancer cells and translation of Snail" Nat Commun May 6, 2019;10(1):2065. doi: 10.1038/s41467-019-09865-9. PMID: 31061416; PMCID: PMC6502834.

Lin et al., "METTL3 promotes translation in human cancer cells" Mol Cell, 62(3): 335-345 (2016).

Liu et al., "m6A mRNA methylation regulates AKT activity to promote the proliferation and tumorigenicity of endometrial cancer" Nat Cell Biol, 20(9): 1074-1083 (2018).

Miao et al., "The m6A methyltransferase METTL3 promotes osteosarcoma progression by regulating the m6A level of LEF1" Biochem Biophys Res Commun, 516(3): 719-725 (2019).

Moroz-Omori et al., "Abstract" for "METTL3 inhibitors for epitranscriptomic modulation of cellular processes," Biorxiv (Sep. 25, 2020).

Moustakim et al., "Discovery of an MLLT1/3 Yeats Domain Chemical Probe," Angewandte Chemie International Edition, 57: 16302-16307 (2018).

Obacz et al., "STC-15, an oral small molecule inhibitor of the RNA methyltransferase METTL3, inhibits tumour growth through activation of anti-cancer immune responses and synergizes with immune checkpoint blockade," Storm Therapeutics, 37th Society for Immunotherapy of Cancer Annual Meeting (SITC 2022), Nov. 2022.

Ofir-Rosenfeld et al., "STC-15, an oral small molecule inhibitor of the RNA methyltransferase METTL3, inhibits tumour growth through activation of anti-cancer immune responses associated with increased interferon signalling, and synergizes with T cell checkpoint blockade," Storm Therapeutics, 34th EORTC-NCI-AACR Symposium on Molecular Targets and Cancer Therapeutics, Oct. 2022.

Ofir-Rosenfeld et al., "STC-15, an oral small molecule inhibitor of the RNA methyltransferase METTL3, inhibits tumour growth through activation of anti-cancer immune responses associated with increased interferon signalling, and synergises with T cell checkpoint blockade," Abstracts, 34th EORTC-NCI AACR Symposium, Poster 345, Poster Session (Oct. 28, 2022), Eur. J. Cancer, vol. 174, suppl. 1, S123, Oct. 2022.

Search Report for GB Application No. GB1917603.1 dated May 19, 2020.

Search Report for GB Application No. GB2015832.5 dated Mar. 3, 2021, 5 pages.

Shivakumar et al. "Synthesis and Antioxidant Activity of New Pyrazoles of 6-Methylbenzimidazoles", World Journal of Pharmaceutical Research, vol. 7, No. 16, pp. 1017-1028, Oct. 23, 2018.

Visvanathan et al., "Essential role of METTL3-mediated m6A modification in glioma stem-like cells maintenance and radioresistance" Oncogene, 37(4):522-533 (2018).

(56) References Cited

OTHER PUBLICATIONS

Visvanathan et al., "N6-Methyladenosine Landscape of Glioma Stem-Like Cells: METTL3 Is Essential for the Expression of Actively Transcribed Genes and Sustenance of the Oncogenic Signaling" Genes (Basel).Feb. 13, 2019;10(2):141. doi: 10.3390/genes10020141. PMID: 30781903; PMCID: PMC6410051.
Wang et al "N6-methyladenosine METTL3 promotes the breast cancer progression via targeting Bcl-2" Gene, Jan. 5, 2020;722:144076. doi: 10.1016/j.gene.2019.144076.
Weng et al., ""METTL14 Inhibits Hematopoietic Stem/Progenitor Differentiation and Promotes Leukemogenesis via mRNA m6A Modification"" Cell Stem Cell, 22(2): 191-205 (2018).
Wu et al., "The Role of RNA Methyltransferase METTL3 in Normal and Malignant Hematopoiesis" Frontiers in Oncology, 12(873903): 10 pages (2022).
Xu et al., "METTL3 promotes intrahepatic cholangiocarcinoma progression by regulating IFIT2 expression in an m6A-YTHDF2-dependent manner" Oncogene, 41:1622-1633 (2022).
Yue et al., "METTL3-mediated N6-methyladenosine modification is critical for epithelial-mesenchymal transition and metastasis of gastric cancer" Mol Cancer, 18(1): (2019).
Zhang et al., "METTL3 regulates m6A methylation of PTCH1 and GLI2 in Sonic hedgehog signaling to promote tumor progression in SHH-medulloblastoma" Cell Reports, 41(111530): 26 pages (2022).
Zhou et al., "METTL3 mediated m6A modification plays an oncogenic role in cutaneous squamous cell carcinoma by regulating DNp63" Biochem Biophys Res Commun, 515(2):310-317 (2019).
Tommasi et al., "Arginine analogues incorporating carboxylate bioisosteric functions are micromolar inhibitors of human recombinant DDAH-1." Organic Biomolecular Chemistry, 13.46, 11315-11330, (2015).

* cited by examiner

INHIBITORS OF METTL3

RELATED APPLICATIONS

This application is a U.S. National Stage filing under 35 U.S.C. § 371 of PCT Application No. PCT/GB2021/052591, filed Oct. 7, 2021, which claims priority from United Kingdom Application No. 2107909.0, filed Jun. 2, 2021; and United Kingdom Application No. 2015998.4 filed Oct. 8, 2020. The contents of International Patent Application No. PCT/GB2021/052591 are incorporated herein by reference in their entirety.

FIELD OF THE INVENTION

The present invention relates to certain compounds that function as inhibitors of METTL3 (N6-adenosine-methyltransferase 70 kDa subunit) activity. The present invention also relates to processes for the preparation of these compounds, to pharmaceutical compositions comprising them, and to their use in the treatment of proliferative disorders, such as cancer, autoimmune, neurological, infectious and inflammatory diseases, as well as other diseases or conditions in which METTL3 activity is implicated.

BACKGROUND OF THE INVENTION

N6-methyladenosine (m6A) is the most common and abundant covalent modification of messenger RNA, modulated by 'writers', 'erasers' and 'readers' of this mark (Meyer & Jaffrey 2014, Niu Y et al, 2013, Yue et al 2015). Approximately 0.1 to 0.5% of all mRNA adenosines are m6A modified (Li Y et al 2015). In vitro data have shown that m6A influences fundamental aspects of mRNA biology, mainly mRNA expression, splicing, stability, localisation and translation (Meyer et al, 2015; Sledz & Jinek 2016). M6A modifications are tissue specific and there is significant variability in their occurrence profiles in non-diseased tissues (eg brain, heart, kidney) and diseased tissues and cells (lung, renal, breast, and leukeamic cancer cells) (Meyer et al 2012).

The m6A modifications and its erasers and writers such as FTO, ALKBH5, methyltransferese like 3 (METTL3) and METTL14 are associated with major diseases such as solid organ cancers, leukaemia, type 2 diabetes, neuropsychiatric behavioural and depressive disorders (Chandola et al 2015; Koranda et al 2018).

The RNA methyltransferase, METTL3, is the major, but not the sole enzyme, that catalyses m6A modification of RNA. It exists as a hetero-trimeric complex with METTL14 (Liu et al 2014, Wang et al 2016) and Wilm's Tumour Associated Protein (WTAP) (Ping et al 2014). Catalytic activity resides in METTL3, which transfers a methyl group from the co-factor S-adenosyl methionine to the substrate RNA and METTL14 facilitates substrate RNA binding. WTAP localises the complex in specific nuclear regions and also localises RNA substrates to the complex (Wang X et al 2016).

METTL3 has been reported to play a role in many aspects of the development of cancer (Fry et al 2018). Genetic knockdown of METTL3 in lung cancer cell lines (A549, H1299 and H1792) and HeLa cells leads to decreased growth, survival and invasion of human lung cancer cells (Lin S et al 2016). METTL3 is significantly up-regulated in human bladder cancer (Cheng et al 2019). Knockdown of METTL3 drastically reduced bladder cancer cell proliferation, invasion, and survival in vitro and tumorigenicity in vivo. AF4/FMR2 family member 4 (AFF4), two key regulators of NF-κB pathway (IKBKB and RELA) and MYC were further identified as direct targets of METTL3-mediated m6A modification. In renal carcinoma cell lines (CAK-1, CAK-2 and ACHN), genetic knockdown reduced cell proliferation via the phosphatidinylinositol 3-kinase (PI3K)/AKT/mammalian target of rapamycin (mTOR) signalling pathway (Li X et al 2017).

Recently Barbieri et al (2017), defined a set of RNA-modifying enzymes that are necessary for AML leukaemia and identified a key leukaemic pathway for the METTL3 RNA methyltransferase. In this pathway, METTL3 is stably recruited by the CCAAT-box binding transcription factor CEBPZ to promoters of a specific set of active genes, resulting in m6A methylation of the respective mRNAs and increased translation. One important target is SP1, an oncogene in several cancers, which regulates c-MYC expression. Consistent with these findings, it has been reported that METTL3 can methylate its targets co-transcriptionally.

The pathway described by Barbieri et al., is critical for AML leukaemia, as three of its components are required for AML cell growth: (i) the m6A RNA methyltransferase METTL3; (ii) the transcription factor CEBPZ, which targets this enzyme to promoters; and (iii) SP1, whose translation is dependent upon the m6A modification by METTL3. Together, the observations of Barbieri et al define METTL3 enzymatic activity as a new candidate target for the treatment of AML.

In separate, independent studies it has been reported that METTL3 plays an essential role in controlling myeloid differentiation of mammalian normal hematopoietic and leukemic cells (Vu et al 2017). Forced expression of wild type METTL3, but not a mutant METTL3 (with defect in catalytic activity), significantly promotes cell proliferation and inhibits cell differentiation of human cord blood-derived CD34+ haematopoietic stem/progenitor cells (HSPCs). Genetic knockdown of METTL3 has the opposite effects. METTL3 is highly expressed in AML compared to normal HSPCs or other types of cancers. Knockdown of METTL3 in human AML cell lines significantly induces cell differentiation and apoptosis and inhibits leukemia progression in mice xeno-transplanted with MOLM-13 AML cells. The biological function of METTL3 is likely attributed to the promotion of translation of its mRNA targets such as MYC, BCL-2, and PTEN in an m6A-dependent manner.

Recently, METTL3 mediated m6A modification has been demonstrated to play an important role in T cell homeostasis and signal dependent induction of mRNA degradation in CD4 positive T cell lineages (Li et al 2017). Deletion of METTL3 in mouse T cells disrupts T cell homeostasis and differentiation. In a lymphopenic mouse adoptive transfer model, naive Mett/3-deficient T cells failed to undergo homeostatic expansion and remained in the naive state for up to 12 weeks, thereby preventing colitis. Consistent with these observations, the mRNAs of SOCS family genes encoding the STAT signalling inhibitory proteins SOCS1, SOCS3 and CISH were marked by m6A, exhibited slower mRNA decay and showed increased mRNAs and levels of protein expression in Mettl3-deficient naive T cells. This increased SOCS family activity consequently inhibited IL-7-mediated STAT5 activation and T cell homeostatic proliferation and differentiation. Thus METTL3 mediated m6A methylation has important roles for inducible degradation of Socs mRNAs in response to IL-7 signalling in order to reprogram naive T cells for proliferation and differentiation, pointing to a role in auto-immunity.

Recent studies have revealed that depletion of METTL3 leads to alterations in the propagation of diverse viruses (Winkler et al). Following viral infection or stimulation of cells with an inactivated virus, deletion of the m6A 'writer' METTL3 led to an increase in the induction of interferon-stimulated genes. Consequently, propagation of different viruses was suppressed in an interferon-signaling-dependent manner. Significantly, the mRNA of IFNB, was m6A modified and was stabilized following repression of METTL3. m6A serves as a negative regulator of interferon response by dictating the fast turnover of interferon mRNAs and consequently facilitating viral propagation.

METTL3-dependent m6A on HBV and HCV viral genome regulates recognition of the viral genome by RIG-1 RNA sensor. Depletion of METTL3 enhances viral dsRNA recognition and induces an anti-viral immune response (Kim et al.).

Therefore METTL3 inhibitors may provide a novel therapeutic approach to a range of infectious and inflammatory diseases. In particular, they provide a potential treatments for viral diseases (e.g. DNA and RNA viruses).

Furthermore, METTL3-dependent m6A on endogenous mRNAs regulates recognition of by MAVS-dependent RNA sensors. Depletion of METTL3 enhances endogenous dsRNA recognition and induces an auto-immune response (Gao et al.). This implies that an anti-tumour immune response might be enhanced by METTL3 inhibition.

Thus, METTL3 inhibitors may also provide a novel therapeutic approach to enhance an anti-tumour immune response.

REFERENCES

Barbieri I, Tzelepis K, Pandolfini L, Shi J, Millsn-Zambrano G, Robson S C, Aspris D, Migliori V, Bannister A J, Han N, De Braekeleer E, Ponstingl H, Hendrick A, Vakoc C R, Vassiliou G S, Kouzarides T. *Nature.* 2017 Dec. 7; 552 (7683):126-131.

Chandola U, Das R, Panda B. *Brief Funct Genomics.* 2015 May; 14(3):169-79.

Cheng M, Gao Q, Wu M, Liang Y, Zhu F, Zhang Y, Zhang X, Li Y, Sheng L, Zhang H, Xiong Q, Yuan Q, *Oncogene* (2019; e-publication ahead of print).

Fry N J, Law B A, Ilkayeva O R, Carraway K R, Holley C L, Mansfield K D. *Oncotarget.* 2018 Jul. 27; 9(58):31231-31243.

Koranda J L, Dore L, Shi H, Patel M J, Vaasjo L O, Rao M N, Chen K, Lu Z, Yi Y, Chi W, He C, Zhuang X. *Neuron.* 2018 Jul. 25; 99(2): 283-292.

Li H B, Tong J, Zhu S, Batista P J, Duffy E E, Zhao J, Bailis W, Cao G, Kroehling L, Chen Y, Wang G, Broughton J P, Chen Y G, Kluger Y, Simon M D, Chang H Y, Yin Z, Flavell R A. *Nature.* 2017 Aug. 17; 548 (7667):338-342

Li X, Tang J, Huang W, Wang F, Li P, Qin C, Qin Z, Zou Q, Wei J, Hua L, Yang H, Wang Z. *Oncotarget.* 2017 Oct. 10; 8(56):96103-96116.

Li Y, Wang Y, Zhang Z, Zamudio A V, Zhao J C. *RNA.* 2015 August; 21(8):1511-8.

Lin S, Choe J, Du P, Triboulet R, Gregory R I. *Mol Cell.* 2016 May 5; 62(3):335-345.

Liu J, Yue Y, Han D, Wang X, Fu Y, Zhang L, Jia G, Yu M, Lu Z, Deng X, Dai Q, Chen W, He C. *Nat Chem Biol.* 2014 February; 10(2):93-5.

Meyer K D, Patil D P, Zhou J, Zinoviev A, Skabkin M A, Elemento O, Pestova T A, Qian S B, Jaffrey S R. *Cell.* 2015 Nov. 5; 163(4): 999-1010.

Meyer K D, Jaffrey S R. *Nat Rev Mol Cell Biol.* 2014 May; 15(5):313-26.

Meyer K D, Saletore Y, Zumbo P, Elemento O, Mason C E, Jaffrey S R. *Cell.* 2012 Jun. 22; 149(7):1635-46.

Niu Y, Zhao X, Wu Y S, Li M M, Wang X J, Yang Y G. *Genomics Proteomics Bioinformatics.* 2013 February; 11(1):8-17.

Ping X L, Sun B F, Wang L, Xiao W, Yang X, Wang W J, Adhikari S, Shi Y, Lv Y, Chen Y S, Zhao X, Li A, Yang Y, Dahal U, Lou X M, Liu X, Huang J, Yuan W P, Zhu X F, Cheng T, Zhao Y L, Wang X, Rendtlew Danielsen J M, Liu F, Yang Y G. *Cell Res.* 2014 February; 24(2):177-89.

Śledź P, Jinek M. *Elife.* 2016 Sep. 14; 5.

Vu L P, Pickering B F, Cheng Y, Zaccara S, Nguyen D, Minuesa G, Chou T, Chow A, Saletore Y, MacKay M, Schulman J, Famulare C, Patel M, Klimek V M, Garrett-Bakelman F E, Melnick A, Carroll M, Mason C E, Jaffrey S R, Kharas M G. *Nat Med.* 2017 November; 23(11): 1369-1376.

Wang X, Feng J, Xue Y, Guan Z, Zhang D, Liu Z, Gong Z, Wang Q, Huang J, Tang C, Zou T, Yin P. *Nature.* 2016 Jun. 23; 534(7608):575-8

Wang P, Doxtader K A, Nam Y. *Mol Cell.* 2016 Jul. 21; 63(2):306-317.

Winkler R, Gillis E, Lasman L, Safra M, Geula S, Soyris C, Nachshon A, Tai-Schmiedel J, Friedman N, Le-Trilling Vu T K, Trilling M, Mandelboim M, Hanna, J H, Schwartz S, Stern-Ginossar N. *Nature Immunology* (2018, e-publication ahead of print).

Yue Y, Liu J, He C. *Genes Dev.* 2015 Jul. 1; 29(13):1343-55.

Geon-Woo Kim, Hasan Imam, Mohsin Khan, Aleem Siddiqui, *J Biol Chem*, (27 Jul. 2020; online publication ahead of print).

Yimeng Gao, Radovan Vasic, Yuanbin Song, Rhea Teng, Chengyang Liu, Rana Gbyli, Giulia Biancon, Raman Nelakanti, Kirsten Lobben, Eriko Kudo, Wei Liu, Anastasia Ardasheva, Xiaoying Fu, Xiaman Wang, Poorval Joshi, Veronica Lee, Burak Dura, Gabriella Viero, Akiko Iwasaki, Rong Fan, Andrew Xiao, Richard A Flavell, Hua-Bing Li, Toma Tebaldi, Stephanie Halene; *Immunity* (16 Jun. 2020; Volume 52; 6; p 887-1132).

Rosa M Rubio, Daniel P Depledge, Christopher Bianco, Letitia Thompson, Ian Mohr; *Genes Dev.* 2018 Dec. 1; 32(23-24):1472-1484.

An object of this invention is to provide inhibitors of METTL3 activity.

SUMMARY OF THE INVENTION

In one aspect, the present invention provides a compound as defined herein, or a pharmaceutically acceptable salt thereof.

In another aspect, the present invention provides a pharmaceutical composition as defined herein which comprises a compound as defined herein, or a pharmaceutically acceptable salt thereof, and one or more pharmaceutically acceptable excipients.

In another aspect, the present invention provides a compound as defined herein, or a pharmaceutically acceptable salt thereof, or a pharmaceutical composition as defined herein, for use in therapy.

In another aspect, the present invention provides a compound as defined herein, or a pharmaceutically acceptable salt thereof, or a pharmaceutical composition as defined herein, for use in the treatment of a proliferative condition.

In another aspect, the present invention provides a compound as defined herein, or a pharmaceutically acceptable salt thereof, or a pharmaceutical composition as defined herein, for use in the treatment of cancer. In a particular embodiment, the cancer is a human cancer.

In another aspect, the present invention provides a compound as defined herein, or a pharmaceutically acceptable salt thereof, or a pharmaceutical composition as defined herein, for use in the inhibition of METTL3 activity.

In another aspect, the present invention provides a compound as defined herein, or a pharmaceutically acceptable salt thereof, or a pharmaceutical composition as defined herein, for use in promoting an immune response (e.g. anti-viral or anti-tumour immune response).

In another aspect, the present invention provides a compound as defined herein, or a pharmaceutically acceptable salt thereof, or a pharmaceutical composition as defined herein, for use in increasing an innate immune response in a subject.

In another aspect, the present invention provides a compound as defined herein, or a pharmaceutically acceptable salt thereof, or a pharmaceutical composition as defined herein, for use in increasing or enhancing an anti-tumour immune response during immune-oncology therapy.

In another aspect, the present invention provides a compound as defined herein, or a pharmaceutically acceptable salt thereof, or a pharmaceutical composition as defined herein, for use in the treatment of an autoimmune disease.

In another aspect, the present invention provides a compound as defined herein, or a pharmaceutically acceptable salt thereof, or a pharmaceutical composition as defined herein, for use in the treatment of a neurological disease.

In another aspect, the present invention provides a compound as defined herein, or a pharmaceutically acceptable salt thereof, or a pharmaceutical composition as defined herein, for use in the treatment of an infectious disease.

In another aspect, the present invention provides a compound as defined herein, or a pharmaceutically acceptable salt thereof, or a pharmaceutical composition as defined herein, for use in the treatment of a viral infection. Suitably, the viral infection is a RNA viral infection. Suitably, the viral infection is human papillomavirus (HPV) or hepatitis.

In another aspect, the present invention provides a compound as defined herein, or a pharmaceutically acceptable salt thereof, or a pharmaceutical composition as defined herein, for use in the treatment of an inflammatory disease.

In another aspect, the present invention provides the use of a compound as defined herein, or a pharmaceutically acceptable salt thereof, in the manufacture of a medicament for use in the treatment of a proliferative condition.

In another aspect, the present invention provides the use of a compound as defined herein, or a pharmaceutically acceptable salt thereof, in the manufacture of a medicament for use in the treatment of cancer. In a particular embodiment, the medicament is for use in the treatment of human cancers.

In another aspect, the present invention provides the use of a compound as defined herein, or a pharmaceutically acceptable salt thereof, in the manufacture of a medicament for the inhibition of METTL3 activity.

In another aspect, the present invention provides the use of a compound as defined herein, or a pharmaceutically acceptable salt thereof, in the manufacture of a medicament for promoting an immune response (e.g. anti-viral or anti-tumour immune response).

In another aspect, the present invention provides the use of a compound as defined herein, or a pharmaceutically acceptable salt thereof, in the manufacture of a medicament for for use in increasing an innate immune response in a subject.

In another aspect, the present invention provides the use of a compound as defined herein, or a pharmaceutically acceptable salt thereof, in the manufacture of a medicament for use in increasing or enhancing an anti-tumour immune response during immune-oncology therapy.

In another aspect, the present invention provides the use of a compound as defined herein, or a pharmaceutically acceptable salt thereof, in the manufacture of a medicament for use in the treatment of an autoimmune disease.

In another aspect, the present invention provides the use of a compound as defined herein, or a pharmaceutically acceptable salt thereof, in the manufacture of a medicament for use in the treatment of a neurological disease.

In another aspect, the present invention provides the use of a compound as defined herein, or a pharmaceutically acceptable salt thereof, in the manufacture of a medicament for use in the treatment of an infectious disease.

In another aspect, the present invention provides the use of a compound as defined herein, or a pharmaceutically acceptable salt thereof, in the manufacture of a medicament for use in the treatment of a viral infection. Suitably, the viral infection is a RNA viral infection. Suitably, the viral infection is human papillomavirus (HPV) or hepatitis.

In another aspect, the present invention provides the use of a compound as defined herein, or a pharmaceutically acceptable salt thereof, in the manufacture of a medicament for use in the treatment of an inflammatory disease.

In another aspect, the present invention provides a method of inhibiting METTL3 activity in vitro or in vivo, said method comprising contacting a cell with an effective amount of a compound as defined herein, or a pharmaceutically acceptable salt thereof, or a pharmaceutical composition as defined herein.

In another aspect, the present invention provides a method of inhibiting cell proliferation in vitro or in vivo, said method comprising contacting a cell with an effective amount of a compound as defined herein, or a pharmaceutically acceptable salt, or a pharmaceutical composition as defined herein.

In another aspect, the present invention provides a method of inhibiting metastasis in vitro or in vivo, said method comprising contacting a cell with an effective amount of a compound as defined herein, or a pharmaceutically acceptable salt, or a pharmaceutical composition as defined herein.

In another aspect, the present invention provides a method of promoting an immune response (e.g. anti-viral or anti-tumour immune response) in a subject in need thereof, said method comprising administering to the subject a therapeutically effective amount of a compound as defined herein, or a pharmaceutically acceptable salt, or a pharmaceutical composition as defined herein.

In another aspect, the present invention provides a method of increasing an innate immune response in a subject in need thereof, said method comprising administering to the subject a therapeutically effective amount of a compound as defined herein, or a pharmaceutically acceptable salt, or a pharmaceutical composition as defined herein.

In another aspect, the present invention provides a method of increasing or enhancing an anti-tumour immune response during immune-oncology therapy, said method comprising administering to a subject in need thereof a therapeutically effective amount of a compound as defined herein, or a pharmaceutically acceptable salt, or a pharmaceutical composition as defined herein.

In another aspect, the present invention provides a method of treating a proliferative disorder, said method comprising administering to a subject in need thereof a therapeutically effective amount of a compound as defined herein, or a pharmaceutically acceptable salt, or a pharmaceutical composition as defined herein.

In another aspect, the present invention provides a method of treating cancer, said method comprising administering to a subject in need thereof a therapeutically effective amount of a compound as defined herein, or a pharmaceutically acceptable salt, or a pharmaceutical composition as defined herein.

In another aspect, the present invention provides a method of treating an autoimmune disease, said method comprising administering to a subject in need thereof a therapeutically effective amount of a compound as defined herein, or a pharmaceutically acceptable salt, or a pharmaceutical composition as defined herein.

In another aspect, the present invention provides a method of treating a neurological disease, said method comprising administering to a subject in need thereof a therapeutically effective amount of a compound as defined herein, or a pharmaceutically acceptable salt, or a pharmaceutical composition as defined herein.

In another aspect, the present invention provides a method of treating an infectious disease, said method comprising administering to a subject in need thereof a therapeutically effective amount of a compound as defined herein, or a pharmaceutically acceptable salt, or a pharmaceutical composition as defined herein.

In another aspect, the present invention provides a method of treating a viral infection, said method comprising administering to a subject in need thereof a therapeutically effective amount of a compound as defined herein, or a pharmaceutically acceptable salt, or a pharmaceutical composition as defined herein. Suitably, the viral infection is a RNA viral infection. Suitably, the viral infection is human papillomavirus (HPV) or hepatitis.

In another aspect, the present invention provides a method of treating an inflammatory disease, said method comprising administering to a subject in need thereof a therapeutically effective amount of a compound as defined herein, or a pharmaceutically acceptable salt, or a pharmaceutical composition as defined herein.

In one aspect, the present invention provides a combination comprising a compound as defined herein, or a pharmaceutically acceptable salt thereof, with one or more additional therapeutic agents.

The present invention further provides a method of synthesising a compound, or a pharmaceutically acceptable salt, as defined herein.

In another aspect, the present invention provides a compound as defined herein, or a pharmaceutically acceptable salt, obtainable by, or obtained by, or directly obtained by a method of synthesis as defined herein.

In another aspect, the present invention provides novel intermediates as defined herein which are suitable for use in any one of the synthetic methods as set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "$C_{1-6}$alkyl" includes $C_{1-4}$alkyl, $C_{1-3}$alkyl, propyl, isopropyl and t-butyl. A similar convention applies to other radicals, for example "phenyl($C_{1-6}$alkyl)" includes phenyl($C_{1-4}$alkyl), benzyl, 1-phenylethyl and 2-phenylethyl.

The term "(m-nC)" or "Cm-n", or "(m-nC) group" or "Cm-n" used alone or as a prefix, refers to any group having m to n carbon atoms.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

An "alkylene" group is an alkyl group that is positioned between and serves to connect two other chemical groups. Thus, "$C_{1-3}$alkylene" means a linear saturated divalent hydrocarbon radical of one to three carbon atoms or a branched saturated divalent hydrocarbon radical of three atoms, for example, methylene, ethylene, propylene, and the like.

The term "$C_{m-n}$cycloalkyl" means a hydrocarbon ring containing from m to n carbon atoms, for example "$C_{3-6}$cycloalkyl" means a hydrocarbon ring containing from 3 to 6 carbon atoms, for example, cyclopropyl, cyclobutyl, cyclopentyl, cyclohexyl. The term "$C_{m-n}$cycloalkyl" also encompasses non-aromatic saturated or partially saturated monocyclic, fused, bridged, or spiro bicyclic carbocyclic ring system(s). The term "$C_{m-n}$cycloalkyl" includes both monovalent species and divalent species. Monocyclic "$C_{m-n}$cycloalkyl" rings contain from about 3 to 12 (suitably from 3 to 8, most suitably from 5 to 6) ring carbon atoms. Bicyclic "$C_{m-n}$cycloalkyl" contain from 7 to 17 ring carbon atoms, suitably 7 to 12 ring carbon atoms. Bicyclic "$C_{m-n}$cycloalkyl" rings may be fused, spiro (e.g. spiro[3,3] heptane), or bridged ring systems (e.g. bicyclo[2.2.1]hept-2-ene and bicyclo[1.1.1]pentanyl).

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7, most suitably from 5 to 6) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (═O) or thioxo (═S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example Advanced Organic Chemistry, by Jerry March, $4^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane, quinuclidine, 6-azabicyclo[3.1.1]heptane, 8-azabicyclo[3.2.1]octane, bicyclo[3.2.1]octane, 7-oxabicyclo[2.2.1]hept-2-ene and 3-oxa-8-azabicyclo[3.2.1]octane.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:

- a benzene ring fused to a 5- or 6-membered ring containing 1, 2 or 3 ring heteroatoms;
- a pyridine ring fused to a 5- or 6-membered ring containing 1, 2 or 3 ring heteroatoms;
- a pyrimidine ring fused to a 5- or 6-membered ring containing 1 or 2 ring heteroatoms;
- a pyrrole ring fused to a 5- or 6-membered ring containing 1, 2 or 3 ring heteroatoms;
- a pyrazole ring fused to a 5- or 6-membered ring containing 1 or 2 ring heteroatoms;
- a pyrazine ring fused to a 5- or 6-membered ring containing 1 or 2 ring heteroatoms;
- an imidazole ring fused to a 5- or 6-membered ring containing 1 or 2 ring heteroatoms;
- an oxazole ring fused to a 5- or 6-membered ring containing 1 or 2 ring heteroatoms;
- an isoxazole ring fused to a 5- or 6-membered ring containing 1 or 2 ring heteroatoms;
- a thiazole ring fused to a 5- or 6-membered ring containing 1 or 2 ring heteroatoms;
- an isothiazole ring fused to a 5- or 6-membered ring containing 1 or 2 ring heteroatoms;
- a thiophene ring fused to a 5- or 6-membered ring containing 1, 2 or 3 ring heteroatoms;
- a furan ring fused to a 5- or 6-membered ring containing 1, 2 or 3 ring heteroatoms;
- a cyclohexyl ring fused to a 5- or 6-membered heteroaromatic ring containing 1, 2 or 3 ring heteroatoms; and
- a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention relates to compounds of the formula (I), or a pharmaceutically acceptable salt thereof, $$W—X—Y—Z \qquad (I)$$

wherein:

W is selected from:

(i) $C_{3-6}$cycloalkyl, a carbon-linked 3- to 6-membered heterocycle, aryl or heteroaryl, each of which being optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or $—S(O)_{0-2}R_{1ca}R_{1da}$, wherein $R_{1ca}$ and $R_{1da}$ are H or $C_{1-2}$alkyl;

(ii) $C_{1-4}$alkyl or $C_{1-4}$alkoxy, each of which being optionally subsetted by halo, cyano, hydroxy, $C_{3-6}$cycloalkyl, $C_{1-4}$alkoxy, $C_{1-4}$haloalkoxy, aryl or heteroaryl; or (iii) a group of the formula:

$$—(CR_{w1}R_{w2})_p—NR_{w3}R_{w4};$$

wherein p is an integer selected from 0, 1, 2, 3, 4 or 5;

each occurance of $R_{w1}$ and $R_{w2}$ is independently selected from:

(i) hydrogen (including deuterium), (ii) $C_{1-6}$alkyl which is optionally substituted by one more substituents selected from cyano, oxo, hydroxy, $C_{1-4}$alkoxy, halo, $C_{1-4}$haloalkoxy, $C_{3-6}$cycloalkyl, $—O—C_{3-6}$cycloalkyl, $NR_{1ca}R_{1da}$ or $—S(O)_{0-2}R_{1ca}R_{1da}$, wherein $R_{1ca}$ and $R_{1da}$ are H or $C_{1-2}$alkyl; and wherein $C_{3-6}$cycloalkyl and $—O—C_{3-6}$cycloalkyl are optionally further substituted with halo, cyano or hydroxy;

(iii) $C_{3-4}$cycloalkyl or 3 to 5 membered heterocyclyl, each of which is optionally substituted by $C_{1-4}$alkyl, $C_{1-4}$haloalkyl, cyano, hydroxy, $C_{1-2}$alkoxy, halo, $C_{1-2}$haloalkoxy, $NR_{1ca}R_{1da}$ or $—S(O)_{0-2}R_{1ca}R_{1da}$, wherein $R_{1ca}$ and $R_{1da}$ are H or $C_{1-2}$alkyl; or;

(iv) either:

$R_{w1}$ and $R_{w2}$ taken together form an oxo group; or $R_{w1}$ and $R_{w2}$ are linked together such that, together with the carbon atom to which they are attached, they form a 3- to 6-membered cycloalkyl or heterocyclic ring, or a spirocyclic ring system, each of which is optionally substituted by one or more substituents selected from $C_{1-2}$alkyl, $C_{1-2}$-haloalkyl, cyano, hydroxy, $C_{1-2}$alkoxy, halo, $C_{1-2}$haloalkoxy, $NR_{1ca}R_{1da}$ or $—S(O)_{0-2}R_{1ca}R_{1da}$, wherein $R_{1ca}$ and $R_{1da}$ are H or $C_{1-2}$alkyl;

$R_{w3}$ and $R_{w4}$ are each independently selected from:

(i) hydrogen (including deuterium);

(ii) $C_{1-6}$alkyl which is optionally substituted by one more substituents selected from cyano, oxo, hydroxy, $C_{1-2}$alkoxy, halo, $C_{1-2}$haloalkoxy, $NR_{1ea}R_{1fa}$ or $—S(O)_{0-2}R_{1ea}R_{1fa}$, wherein $R_{1ea}$ and $R_{1fa}$ are H or $C_{1-2}$alkyl; or (iii) a group with the formula:

$-(CR_{w5}R_{w6})_q$-$T_1$ wherein:

q is 0, 1, 2, 3, 4, 5 or 6;

$R_{w5}$ and $R_{w6}$ are independently selected from:

a) hydrogen (including deuterium);

b) $C_{1-6}$alkyl which is optionally substituted by one more substituents selected from cyano, oxo, hydroxy, $C_{1-4}$alkoxy, halo, $C_{1-4}$haloalkoxy, —O—$C_{3-6}$cycloalkyl, $NR_{1ga}R_{1ha}$ or —$S(O)_{0-2}R_{1ga}R_{1ha}$, wherein $R_{1ga}$ and $R_{1ha}$ are H or $C_{1-2}$alkyl; and wherein —O—$C_{3-6}$cycloalkyl is optionally substituted with halo, cyano or hydroxy;

c) an aryl-$C_{1-6}$alkyl, heteroaryl$C_{1-6}$alkyl, $C_{3-6}$cycloalkyl or $C_{3-6}$-cycloalkyl$C_{1-6}$alkyl group, each of which is optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$alkyl; or d) or $R_{w5}$ and $R_{w6}$ are optionally linked together such that, together with the carbon atom to which they are attached, they form a 3-to 6-membered cycloalkyl or heterocyclic ring which is optionally substituted by one or more substituents selected from $C_{1-2}$alkyl, cyano, $C_{1-2}$haloalkyl, hydroxy, $C_{1-2}$alkoxy, halo, $C_{1-2}$-haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$alkyl;

and $T_1$ is selected from hydrogen, cyano, hydroxy, $NR_{1t}R_{2t}$ or —$S(O)_{0-2}R_{1t}R_{2t}$ (wherein $R_{1t}$ and $R_{2t}$ are H or $C_{1-4}$alkyl), $C_{3-8}$cycloalkyl, $C_{2-3}$alkenyl, $C_{2-3}$alkynyl, aryl, heterocyclyl, heteroaryl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{3t}R_{4t}$ or —$S(O)_{0-2}R_{3t}R_{4t}$, wherein $R_{3t}$ and $R_{4t}$ are H or $C_{1-2}$alkyl;

or $R_{w3}$ and $R_{w4}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl, and/or the mono- or bicyclic heterocyclic ring formed by $R_{w3}$ and $R_{w4}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl;

X is selected from:

a) a group selected from;

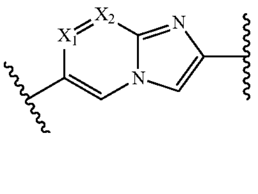
,
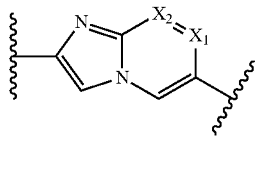
,

-continued

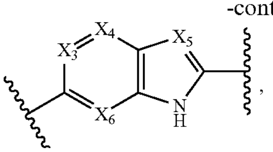
,
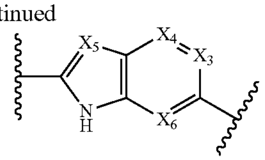
,

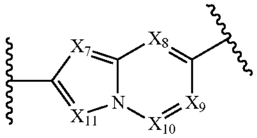
;
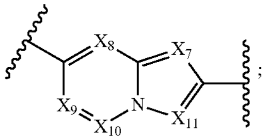
;

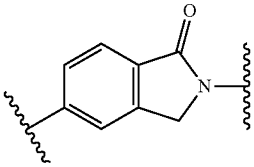
and
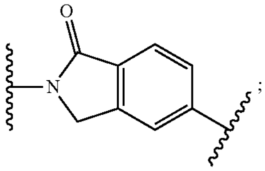
;

wherein $X_1$ is N or $CR_{X1}$, wherein $R_{X1}$ is H or halo;

$X_2$ is N or $CR_{X2}$, wherein $R_{X2}$ is H or halo;

$X_3$ is N or $CR_{X3}$, wherein $R_{X3}$ is H or halo;

$X_4$ is N or $CR_{X4}$, wherein $R_{X4}$ is H or halo;

$X_5$ is N or $CR_{X5}$, wherein $R_{X5}$ is H or halo;

$X_6$ is N or $CR_{X6}$, wherein $R_{X6}$ is H or halo;

$X_7$ is N or $CR_{X7}$, wherein $R_{X7}$ is H or halo;

$X_8$ is N or $CR_{X8}$, wherein $R_{X8}$ is H or halo;

$X_9$ is N or $CR_{X9}$, wherein $R_{X9}$ is H or halo;

$X_{10}$ is N or $CR_{X10}$, wherein $R_{X10}$ is H or halo;

$X_{11}$ is N or $CR_{X11}$, wherein $R_{X11}$ is H or halo;

b) $C_{2-6}$alkenylene, optionally substituted by one or more hydroxy;

c) a group of the formula;

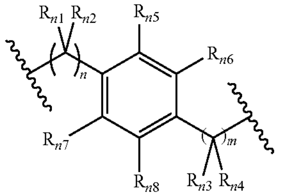

wherein n and m are each independently an integer selected from 0, 1, 2, 3 or 4; and each occurrence of $R_{n1}$, $R_{n2}$, $R_{n3}$ and $R_{n4}$ is independently selected from hydrogen or halo; $R_{n5}$, $R_{n6}$, $R_{n7}$ and $R_{n6}$ are each independently selected from hydrogen, halo, hydroxy, cyano, $C_{1-3}$alkyl, $C_{1-3}$haloalkyl, $C_{1-3}$alkoxy, $C_{1-3}$haloalkoxy and $NR_{n9}R_{n10}$, wherein each of $R_{n5}$ and $R_{n10}$ are independently selected from hydrogen or $C_{1-2}$alkyl;

wherein each of $C_{1-3}$alkyl and $C_{1-3}$alkoxy are optionally further substituted by halo, cyano or hydroxy;

Y is a group of the formula:

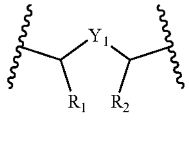

wherein:

$Y_1$ is selected from O, $CR_{y1}R_{y2}$ or $C{=}CR_{y1'}R_{y2'}$, wherein each of $R_{y1}$, $R_{y2}$, $R_{y1'}$ and $R_{y2'}$ are independently selected from hydrogen, $C_{1-4}$alkyl, halo and cyano;

$R_1$ and $R_2$, together with the carbon atoms to which they are attached, are linked together to form a saturated or unsaturated 4 to 7 membered carbocyclic or heterocyclic ring system, wherein the carbocylic or heterocyclic ring is optionally substituted with one or more substituents selected from $C_{1-4}$alkyl, cyano, halo, hydroxy, $C_{1-4}$alkoxy, $C_{1-4}$haloalkoxy or amino; and Z is is a group of the formula:

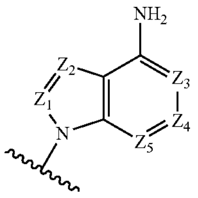

wherein $Z_1$ is $CR_{Z1}$ or N, $Z_3$ is $CR_{Z3}$ or N, $Z_4$ is $CR_{Z4}$ or N, $Z_5$ is $CR_{Z5}$ or N, wherein each of $R_{Z1}$, $R_{Z3}$, $R_{Z4}$ and $R_{Z5}$ are independently selected from hydrogen, halo or cyano;

$Z_2$ is selected from $CR_{Z2}$ or N, wherein $R_{Z2}$ is selected from hydrogen, halo, cyano, $C_{1-4}$alkyl, $C_{1-4}$haloalkyl, $C_{1-4}$alkoxy, $C_{1-4}$haloalkoxy, $C_{3-6}$cycloalkyl, aryl, heterocyclyl or heteroaryl, wherein each of any $C_{1-4}$alkyl, $C_{1-4}$haloalkyl, $C_{1-4}$alkoxy, $C_{1-4}$haloalkoxy, $C_{3-6}$cycloalkyl, heteroaryl, aryl, heterocyclyl is optionally substituted with one or more substituents selected from, $C_{1-4}$alkyl, $C_{1-4}$haloalkyl, halo, trifluoromethyl, trifluoromethoxy, amino, cyano, hydroxy, or amino;

with the proviso that no more than three of $Z_1$, $Z_2$, $Z_3$, $Z_4$ and $Z_5$ are nitrogen.

Particular compounds of the invention include, for example, compounds of formula (I), or pharmaceutically acceptable salts thereof, wherein, unless otherwise stated, each of W, X, Y, Z, $X_1$, $X_2$, $X_3$, $X_4$, $X_5$, $X_6$, $X_7$, $X_8$, $X_9$, $X_{10}$, $X_{11}$, $Y_1$, $Z_1$, $Z_2$, $Z_3$, $Z_4$, $Z_5$, $R_1$, $R_2$, $R_{y3}$, $R_{y4}$, $R_{y5}$, $R_{Z1}$, $R_{Z2}$, $R_{Z3}$, $R_{Z4}$ and $R_{Z5}$ and any associated substituent group has any of the meanings defined hereinbefore or in any one of paragraphs (1) to (86) hereinafter:—

(1) W is either:

(i) $C_{3-6}$cycloalkyl, a carbon-linked 3- to 6-membered heterocycle, aryl or heteroaryl, each of which being optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or $—S(O)_{0-2}R_{1ca}R_{1da}$, wherein $R_{1ca}$ and $R_{1da}$ are H or $C_{1-2}$alkyl; or (ii) a group of the formula:

$$—(CR_{w1}R_{w2})_p—NR_{w3}R_{w4};$$

wherein p is an integer selected from 0, 1, 2, 3 or 4;

each occurance of $R_{w1}$ and $R_{w2}$ is independently selected from:

(i) hydrogen (including deuterium), (ii) $C_{1-6}$alkyl which is optionally substituted by one more substituents selected from cyano, oxo, hydroxy, $C_{1-4}$alkoxy, halo, $C_{1-4}$haloalkoxy, $C_{3-6}$cycloalkyl, $—O—C_{3-6}$cycloalkyl, $NR_{1ca}R_{1da}$ or $—S(O)_{0-2}R_{1ca}R_{1da}$, wherein $R_{1ca}$ and $R_{1da}$ are H or $C_{1-2}$alkyl; and wherein $C_{3-6}$cycloalkyl and $—O—C_{3-6}$cycloalkyl are optionally further substituted with halo, cyano or hydroxy;

(ii) or $R_{w1}$ and $R_{w2}$ taken together form an oxo group; or $R_{w1}$ and $R_{w2}$ are linked together such that, together with the carbon atom to which they are attached, they form a 3- to 6-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or $—S(O)_{0-2}R_{1ca}R_{1da}$, wherein $R_{1ca}$ and $R_{1da}$ are H or $C_{1-2}$alkyl;

$R_{w3}$ and $R_{w4}$ are each independently selected from:

(i) hydrogen (including deuterium); or (ii) $C_{1-3}$alkyl which is optionally substituted by one more substituents selected from cyano, hydroxy, $C_{1-2}$alkoxy, halo, $C_{1-2}$haloalkoxy and $NH_2$;

(iii) a group with the formula:

$$—(CR_{w5}R_{w6})_q\text{-}T_1$$

wherein:

q is an integer selected from 0, 1, 2, 3, 4, each occurance of $R_{w5}$ and $R_{w6}$ is independently selected from:

a) hydrogen (including deuterium); or b) $C_{1-3}$alkyl, which is optionally substituted by one more substituents selected from cyano, hydroxy, $C_{1-2}$alkoxy, halo, $C_{1-2}$haloalkoxy, $—O—C_3$cycloalkyl, wherein $—O—C_3$cycloalkyl is optionally substituted with halo, cyano or hydroxy;

and $T_1$ is selected from hydrogen, cyano, hydroxy, $NR_{1t}R_{2t}$ or $—S(O)_{0-2}R_{1t}R_{2t}$ (wherein $R_{1t}$ and $R_{2t}$ are H or $C_{1-4}$alkyl), $C_{3-8}$cycloalkyl, $C_{2-3}$alkenyl, $C_{2-3}$alkynyl, aryl, heterocyclyl, heteroaryl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$-haloalkoxy, $NR_{3t}R_{4t}$ or $—S(O)_{0-2}R_{3t}R_{4t}$, wherein $R_{3t}$ and $R_{4t}$ are H or $C_{1-2}$alkyl;

or $R_{w3}$ and $R_{w4}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, cyano, hydroxy, $C_{1-4}$alkoxy, halo, $C_{1-4}$haloalkoxy, $NR_{1i}R_{1j}$ or $—S(O)_{0-2}R_{1i}R_{1j}$, wherein $R_{1i}$ and $R_{1j}$ are H or $C_{1-4}$alkyl, and/or the mono- or bicyclic hetereocyclic ring formed by $R_{w3}$ and $R_{q4}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, cyano, hydroxy, $C_{1-4}$alkoxy, halo, $C_{1-4}$haloalkoxy, $NR_{1i}R_{1j}$ or $—S(O)_{0-2}R_{1i}R_{1j}$, wherein $R_{1i}$ and $R_{1j}$ are H or $C_{1-4}$alkyl;

(2) W is a group of the formula:

$$—(CR_{w1}R_{w2})_p—NR_{w3}R_{w4};$$

wherein:

p is an integer selected from 0, 1, 2 or 3 each occurance of $R_{w1}$ and $R_{w2}$ is independently selected from:

(i) hydrogen (including deuterium), (ii) $C_{1-3}$alkyl which is optionally substituted by one more substituents selected from cyano, hydroxy, $C_{1-3}$alkoxy, halo, $C_{1-3}$haloalkoxy, —O—$C_{3-4}$ cycloalkyl, or $NH_2$; wherein —O—$C_{3-6}$cycloalkyl is optionally substituted with halo, cyano or hydroxy, (iii) or $R_{w1}$ and $R_{w2}$ taken together form an oxo group; or $R_{w1}$ and $R_{w2}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

$R_{w3}$ and $R_{w4}$ are each independently selected from:

(i) hydrogen (including deuterium);

(ii) $C_{1-6}$alkyl which is optionally substituted by one more substituents selected from cyano, oxo, hydroxy, $C_{1-2}$alkoxy, halo, $C_{1-2}$haloalkoxy, $NR_{1ea}R_{1fa}$ or —$S(O)_{0-2}R_{1ea}R_{1fa}$, wherein $R_{1ea}$ and $R_{1fa}$ are H or $C_{1-2}$alkyl;

(iii) a group with the formula:

$$—(CR_{w5}R_{w6})_q\text{-}T_1$$

wherein:

q is 0, 1, 2, 3, 4, 5 or 6;

$R_{w5}$ and $R_{we}$ is independently selected from:

a) hydrogen (including deuterium);

b) $C_{1-6}$alkyl which is optionally substituted by one more substituents selected from cyano, oxo, hydroxy, $C_{1-4}$alkoxy, halo, $C_{1-4}$haloalkoxy, —O—$C_{3-6}$cycloalkyl, $NR_{1ga}R_{1ha}$ or —$S(O)_{0-2}R_{1ga}R_{1ha}$, wherein $R_{1ga}$ and $R_{1ha}$ are H or $C_{1-2}$alkyl; and wherein —O—$C_{5-6}$cycloalkyl is optionally substituted with halo, cyano or hydroxy;

c) an aryl-$C_{1-6}$-alkyl, heteroaryl$C_{1-6}$alkyl, $C_{3-6}$cycloalkyl or $C_{3-6}$cycloalkyl$C_{1-6}$alkyl group, each of which is optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$alkyl; or d) or $R_{w5}$ and $R_{w6}$ are optionally linked together such that, together with the carbon atom to which they are attached, they form a 3- to 6-membered cycloalkyl or heterocyclic ring which is optionally substituted by one or more substituents selected from $C_{1-2}$alkyl, cyano, $C_{1-2}$-haloalkyl, hydroxy, $C_{1-2}$alkoxy, halo, $C_{1-2}$haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$alkyl;

and $T_1$ is selected from hydrogen, cyano, hydroxy, $NR_{1t}R_{2t}$ or —$S(O)_{0-2}R_{1t}R_{2t}$ (wherein $R_{1t}$ and $R_{2t}$ are H or $C_{1-4}$alkyl), $C_{3-8}$cycloalkyl, $C_{2-3}$alkenyl, $C_{2-3}$alkynyl, aryl, heterocyclyl, heteroaryl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{3t}R_{4t}$ or —$S(O)_{0-2}R_{3t}R_{4t}$, wherein $R_{3t}$ and $R_{4t}$ are H or $C_{1-2}$alkyl;

or $R_{w3}$ and $R_{w4}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-2}$alkyl, and/or the mono- or bicyclic hetereocyclic ring formed by $R_{w3}$ and $R_{w4}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl;

(3) W is selected from:

(i) $C_{3-6}$cycloalkyl or carbon-linked 3- to 6-membered heterocycle, each of which being optionally substituted by one or more substituents selected from $C_{1-2}$alkyl, $C_{1-2}$-haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl (ii) $C_{1-4}$alkyl optionally subsetted by halo, cyano, hydroxy, $C_{3-6}$cycloalkyl, a 3 to 6 membered heterocyclyl, $C_{1-4}$alkoxy, $C_{1-4}$haloalkoxy, aryl or heteroaryl; or (iii) a group of the formula:

$$—(CR_{w1}R_{w2})_p—NR_{w3}R_{w4};$$

wherein:

p is an integer selected from 0, 1, 2 or 3;

$R_{w1}$ and $R_{w2}$ are independently selected from:

(i) hydrogen (including deuterium), (ii) $C_{1-3}$alkyl which is optionally substituted by one more substituents selected from cyano, oxo, hydroxy, $C_{1-4}$alkoxy, halo, $C_{1-4}$haloalkoxy, —O—$C_{3-6}$cycloalkyl, $NR_{1ca}R_{1da}$ or —$S(O)_{0-2}R_{1ca}R_{1da}$, wherein $R_{1ca}$ and $R_{1da}$ are H or $C_{1-2}$alkyl; and wherein $C_{3-6}$cycloalkyl and —O—$C_{3-6}$cycloalkyl are optionally substituted with halo, cyano or hydroxy;

(iii) $C_{3-4}$cycloalkyl or 3 to 5 membered heterocyclyl, each of which is optionally substituted by $C_{1-4}$alkyl, $C_{1-4}$haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl; or (iv) either:

$R_{w1}$ and $R_{w2}$ taken together form an oxo group; or $R_{w1}$ and $R_{w2}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl;

$R_{w3}$ and $R_{w4}$ are each independently selected from:
(i) hydrogen (including deuterium);
(ii) $C_{1-6}$alkyl which is optionally substituted by one more substituents selected from cyano, oxo, hydroxy, $C_{1-2}$alkoxy, halo, $C_{1-2}$haloalkoxy, $NR_{1ea}R_{1ta}$ or —$S(O)_{0-2}R_{1ea}R_{1fa}$, wherein $R_{1ea}$ and $R_{1fa}$ are H or $C_{1-2}$alkyl;
(iii) a group with the formula:

$$—(CR_{w5}R_{w6})_q\text{-}T_1$$

wherein:
q is 0, 1, 2 or 3;
$R_{w5}$ and $R_{w6}$ are independently selected from:
a) hydrogen (including deuterium); or
b) $C_{1-3}$alkyl which is optionally substituted by one more substituents selected from cyano, oxo, hydroxy, $C_{1-3}$alkoxy, halo, $C_{1-4}$haloalkoxy, —O—$C_{3-4}$cycloalkyl, wherein —O—$C_{3-4}$cycloalkyl is optionally substituted with halo, cyano or hydroxy, $NR_{1ca}R_{1da}$ or —$S(O)_{0-2}R_{1ca}R_{1da}$, wherein $R_{1ca}$ and $R_{1da}$ are H or $C_{1-2}$alkyl$NR_{1ga}R_{1ha}$ or —$S(O)_{0-2}R_{1ga}R_{1ha}$, wherein $R_{1ga}$ and $R_{1ha}$ are H or $C_{1-2}$alkyl;
c) or $R_{w5}$ and $R_{w6}$ are optionally linked together such that, together with the carbon atom to which they are attached, they form a 3- to 6-membered cycloalkyl or heterocyclic ring which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$ alkyl;
and $T_1$ is selected from hydrogen, halo, $C_{1-4}$alkyl, $C_{1-4}$haloalkyl, cyano, hydroxy, $NR_{1t}R_{2t}$ or —$S(O)_{0-2}R_{1t}R_{2t}$ (wherein $R_{1j}$ and $R_{2t}$ are H or $C_{1-4}$alkyl), $C_{3-8}$cycloalkyl, $C_{2-3}$alkenyl, $C_{2-3}$alkynyl, aryl, heterocyclyl, a mono- or bicyclic heteroaryl, a spirocyclic carbocyclic or heterocyclic ring system, a bridged $C_{4-6}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $C_{3-6}$cycloalkyl, $NR_{3t}R_{4t}$ or —$S(O)_{0-2}R_{3t}R_{4t}$, wherein $R_{3t}$ and $R_{4t}$ are H or $C_{1-2}$alkyl; or or $R_{w5}$ and $R_{w4}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl, and/or the mono- or bicyclic hetereocyclic ring formed by $R_{w3}$ and $R_{w4}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl;

wherein any alkyl, alkoxy or $C_{3-6}$cycloalkyl is further optionally substituted by one more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl;

(4) W is:
(i) $C_{3-6}$cycloalkyl or carbon-linked 3- to 6-membered heterocycle, each of which being optionally substituted by one or more substituents selected from $C_{1-2}$alkyl, $C_{1-2}$-haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl; or
(ii) a group of the formula:

$$—(CR_{w1}R_{w2})_p—NR_{w3}R_{w4};$$

wherein:
p is an integer selected from 1 or 2;
$R_{w1}$ and $R_{w2}$ are independently selected from:
(i) hydrogen (including deuterium); or
(ii) $C_{1-3}$alkyl which is optionally substituted by one more substituents selected from cyano, oxo, hydroxy, $C_{1-3}$alkoxy, halo, $C_{1-3}$haloalkoxy, —O—$C_{3-4}$-cycloalkyl, or $NH_2$; wherein —O—$C_{3-6}$cycloalkyl is optionally substituted with halo, cyano or hydroxy,
(iii) $C_{3-4}$cycloalkyl which is optionally substituted by $C_{1-4}$alkyl, $C_{1-4}$haloalkyl, cyano, hydroxy, $C_{1-2}$alkoxy, halo, $C_{1-2}$haloalkoxy or $NR_{1ca}R_{1da}$; and;
(iv) or $R_{w1}$ and $R_{w2}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl;
$R_{w3}$ and $R_{w4}$ are each independently selected from:
(i) hydrogen (including deuterium);
(ii) $C_{1-6}$alkyl which is optionally substituted by one more substituents selected from cyano, oxo, hydroxy, $C_{1-2}$alkoxy, halo, $C_{1-2}$haloalkoxy, $NH_2$;
(iii) a group with the formula:

$$—(CR_{w5}R_{w6})_q\text{-}T_1$$

wherein:
q is 0, 1, 2 or 3;
$R_{w5}$ and $R_{w6}$ are independently selected from:
a) hydrogen (including deuterium); or
b) $C_{1-6}$alkyl which is optionally substituted by one more substituents selected from cyano, oxo, hydroxy, $C_{1-4}$alkoxy, halo, $C_{1-4}$-haloalkoxy, —O—$C_{3-6}$cycloalkyl, $NR_{1ca}R_{1da}$ or —$S(O)_{0-2}R_{1ca}R_{1da}$, wherein $R_{1ca}$ and $R_{1da}$ are H or $C_{1-2}$alkyl$NR_{1ga}R_{1ha}$ or —$S(O)_{0-2}R_{1ga}R_{1ha}$, wherein $R_{1ga}$ and $R_{1ha}$ are H or $C_{1-2}$alkyl; and wherein —O—$C_{3-6}$cycloalkyl is optionally substituted with halo, cyano or hydroxy,
c) or $R_{w5}$ and $R_{w6}$ are optionally linked together such that, together with the carbon atom to which they are attached, they form a 3-to 6-membered cycloalkyl or heterocyclic ring which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$alkyl;

and $T_1$ is selected from hydrogen, halo, $C_{1-4}$alkyl, $C_{1-4}$haloalkyl, cyano, hydroxy, $NR_{1t}R_{2t}$ or —$S(O)_{0-2}R_{1t}R_{2t}$ (wherein $R_{1t}$ and $R_{2t}$ are H or $C_{1-4}$alkyl), $C_{3-8}$cycloalkyl, $C_{2-3}$alkenyl, $C_{2-3}$alkynyl, aryl, heterocyclyl, a mono- or bicyclic heteroaryl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $C_{3-6}$cycloalkyl, $NR_{3t}R_{4t}$ or —$S(O)_{0-2}R_{3t}R_{4t}$, wherein $R_{3t}$ and $R_{4t}$ are H or $C_{1-2}$alkyl;

or $R_{w3}$ and $R_{w4}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl, and/or the mono- or bicyclic hetereocyclic ring formed by $R_{w3}$ and $R_{w4}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl;

wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl.

(5) W is:

(i) $C_{3-6}$cycloalkyl or carbon-linked 3- to 6-membered heterocycle, each of which being optionally substituted by one or more substituents selected from $C_{1-2}$alkyl, $C_{1-2}$-haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl; or (ii) a group of the formula:

$$—(CR_{w1}R_{w2})_p—NR_{w3}R_{w4};$$

wherein:

p is an integer selected from 1 or 2;

$R_{w1}$ and $R_{w2}$ are independently selected from:

(i) hydrogen (including deuterium), (ii) $C_{1-3}$alkyl which is optionally substituted by one more substituents selected from cyano, oxo, hydroxy, $C_{1-3}$alkoxy, halo, $C_{1-3}$haloalkoxy, —O—$C_{3-4}$cycloalkyl, or $NH_2$; wherein —O—$C_{3-6}$cycloalkyl is optionally substituted with halo, cyano or hydroxy, (iii) or $R_{w1}$ and $R_{w2}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl;

$R_{w3}$ is selected from:

(i) hydrogen (including deuterium); and (ii) $C_{1-3}$alkyl which is optionally substituted by one more substituents selected from cyano, oxo, hydroxy, $C_{1-2}$alkoxy, halo, $C_{1-2}$haloalkoxy and $NH_2$;

$R_{w4}$ is selected from:

(i) $C_{1-6}$alkyl which is optionally substituted by one more substituents selected from cyano, oxo, hydroxy, $C_{1-2}$alkoxy, halo, $C_{1-2}$haloalkoxy and $NH_2$;

(ii) a group with the formula:

$$—(CR_{w5}R_{w6})_q\text{-}T_1$$

wherein:

q is 1, 2 or 3;

$R_{w5}$ and $R_{w6}$ are independently selected from:

a) hydrogen (including deuterium); or b) $C_{1-6}$alkyl which is optionally substituted by one more substituents selected from cyano, oxo, hydroxy, $C_{1-4}$alkoxy, halo, $C_{1-4}$haloalkoxy, —O—$C_{3-6}$cycloalkyl, $NR_{1ca}R_{1da}$ or —$S(O)_{0-2}R_{1ca}R_{1da}$, wherein $R_{1ca}$ and $R_{1da}$ are H or $C_{1-2}$alkyl$NR_{1ga}R_{1ha}$ or —$S(O)_{0-2}R_{1ga}R_{1ha}$, wherein $R_{1ga}$ and $R_{1ha}$ are H or $C_{1-2}$alkyl; and wherein —O—$C_{3-6}$cycloalkyl is optionally substituted with halo, cyano or hydroxy;

c) or $R_{w5}$ and $R_{w6}$ are optionally linked together such that, together with the carbon atom to which they are attached, they form a 3- to 4-membered cycloalkyl or heterocyclic ring which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ga}R_{1ha}$ or —$S(O)_{0-2}R_{1ga}R_{1ha}$, wherein $R_{1ga}$ and $R_{1ha}$ are H or $C_{1-2}$alkyl;

and $T_1$ is selected from hydrogen, halo, $C_{1-4}$alkyl, $C_{1-4}$haloalkyl, cyano, hydroxy, $NR_{1t}R_{2t}$ or —$S(O)_{0-2}R_{1t}R_{2t}$ (wherein $R_{1t}$ and $R_{2t}$ are H or $C_{1-4}$alkyl), $C_{3-8}$cycloalkyl, $C_{2-3}$alkenyl, $C_{2-3}$alkynyl, aryl, heterocyclyl, a mono- or bicyclic heteroaryl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$ alkyl, $C_{1-2}$haloalkyl, cyano, hydroxy, $C_{1-2}$alkoxy, halo, $C_{1-2}$haloalkoxy, $C_{3-6}$cycloalkyl, $NR_{3t}R_{4t}$ or —$S(O)_{0-2}R_{3t}R_{4t}$, wherein $R_{3t}$ and $R_{4t}$ are H or $C_{1-2}$alkyl;

or $R_{w3}$ and $R_{w4}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl, and/or the mono- or bicyclic hetereocyclic ring formed by $R_{w3}$ and $R_{w4}$ is optionally spiro-fused to a $C_{3-6}$cycloalkyl or a heterocyclic ring; which in turn is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl;

wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl.

(6) W is either:

(i) a carbon-linked 3- to 6-membered heterocycle, each of which being optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl; or (ii) a group of the formula:

$$—(CR_{w1}R_{w2})_p—NR_{w3}R_{w4}$$

wherein:

p is an integer selected from 1 or 2;

$R_{w1}$ and $R_{w2}$ are independently selected from:

(i) hydrogen (including deuterium), (ii) $C_{1-3}$alkyl which is optionally substituted by one more substituents selected from cyano, oxo, hydroxy, $C_{1-3}$alkoxy, halo, $C_{1-3}$haloalkoxy, —O—$C_{3-4}$cycloalkyl, or $NH_2$; wherein —O—$C_{3-6}$cycloalkyl is optionally substituted with halo, cyano or hydroxy, (iii) or $R_{w1}$ and $R_{w2}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$-haloalkoxy;

$R_{w3}$ is selected from:

(i) hydrogen (including deuterium);

(ii) $C_{1-3}$alkyl which is optionally substituted by one more substituents selected from cyano, oxo, hydroxy, $C_{1-2}$alkoxy, halo, $C_{1-2}$haloalkoxy and $NH_2$;

$R_{w4}$ is a group with the formula:

$$—(CR_{w5}R_{w6})_q\text{-}T_1$$

wherein:

q is 1, 2 or 3;

$R_{w5}$ and $R_{w6}$ are independently selected from:

a) hydrogen (including deuterium); or b) $C_{1-3}$alkyl which is optionally substituted by one more substituents selected from cyano, oxo, hydroxy, $C_{1-4}$alkoxy, halo, $C_{1-4}$haloalkoxy, —O—$C_{3-6}$cycloalkyl, wherein —O—$C_{3-6}$cycloalkyl is optionally substituted with halo, cyano or hydroxy;

c) or $R_{w5}$ and $R_{w6}$ are optionally linked together such that, together with the carbon atom to which they are attached, they form a 3- to 4-membered cycloalkyl or heterocyclic ring which is optionally substituted by one or more substituents selected from $C_{1-2}$alkyl, $C_{1-2}$haloalkyl, cyano, hydroxy, $C_{1-2}$ alkoxy, halo or $C_{1-2}$haloalkoxy;

and $T_1$ is selected from halo, $C_{1-4}$alkyl, $C_{1-4}$haloalkyl, cyano, hydroxy, $NR_{1t}R_{2t}$ or —$S(O)_{0-2}R_{1t}R_{2t}$ (wherein $R_{1j}$ and $R_{2t}$ are H or $C_{1-4}$alkyl), $C_{3-6}$cycloalkyl, $C_{2-3}$alkenyl, $C_{2-3}$alkynyl, aryl, heterocyclyl, a mono- or bicyclic heteroaryl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $C_{3-6}$cycloalkyl, $NR_{3t}R_{4t}$ or —$S(O)_{0-2}R_{3t}R_{4t}$, wherein $R_{3t}$ and $R_{4t}$ are H or $C_{1-2}$ alkyl;

or $R_{w3}$ and $R_{w4}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_1$ and $R_{1i}$ are H or $C_{1-4}$alkyl, and/or the mono- or bicyclic hetereocyclic ring formed by $R_{W3}$ and $R_{w4}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl;

wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl.

(7) W is either:

(i) a carbon-linked 3- to 6-membered heterocycle, each of which being optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl; or (ii) a group of the formula:

$$—(CR_{w1}R_{w2})_p—NR_{w3}R_{w4};$$

wherein p is an integer selected from 1 or 2;

$R_{w1}$ and $R_{w2}$ are independently selected from:

(i) hydrogen (including deuterium), (ii) $C_{1-3}$alkyl which is optionally substituted by one more substituents selected from cyano, oxo, hydroxy, $C_{1-3}$alkoxy, halo, $C_{1-3}$haloalkoxy, —O—$C_{3-4}$cycloalkyl, or $NH_2$; wherein —O—$C_{5-6}$cycloalkyl is optionally substituted with halo, cyano or hydroxy, (iii) or $R_{w1}$ and $R_{w2}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

$R_{w3}$ is selected from:

(i) hydrogen (including deuterium);

(ii) $C_{1-3}$alkyl which is optionally substituted by one more substituents selected from cyano, oxo, hydroxy, $C_{1-2}$alkoxy, halo, $C_{1-2}$haloalkoxy and $NH_2$;

$R_{w4}$ is a group with the formula:

$—(CR_{w5}R_{w6})_q\text{-}T_1$ wherein:

q is 1 or 2;

$R_{w5}$ and $R_{w6}$ are independently selected from:

a) hydrogen (including deuterium); or b) $C_{1-3}$alkyl, which is optionally substituted by one more substituents selected from cyano, oxo, hydroxy, $C_{1-2}$alkoxy, halo, $C_{1-2}$haloalkoxy, —O—$C_3$cycloalkyl, wherein —O—$C_3$cycloalkyl is optionally substituted with halo, cyano or hydroxy;

and $T_1$ is selected from $C_{1-4}$alkyl, $C_{3-8}$cycloalkyl, aryl, heterocyclyl, heteroaryl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy or $C_{3-6}$cycloalkyl;

or $R_{w3}$ and $R_{w4}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo, $C_{1-2}$haloalkoxy, $NR_{1i}R_{1j}$ or —$S(O)_{0-2}R_{1i}R_{1j}$, wherein $R_{1i}$ and $R_{1j}$ are H or $C_{1-2}$alkyl, and/or the mono- or bicyclic hetereocyclic ring formed by $R_{w3}$ and $R_{w4}$ is optionally spiro-fused to a $C_{3-6}$cycloalkyl or a heterocyclic ring, which in turn is optionally substituted by one or more substituents selected from $C_{1-2}$alkyl, $C_{3-6}$cycloalkyl, cyano, hydroxy, $C_{1-2}$alkoxy, halo, $C_{1-2}$haloalkoxy, $NR_{1i}R_{1j}$ or —$S(O)_{0-2}R_{1i}R_{1j}$, wherein $R_{1i}$ and $R_{1j}$ are H or $C_{1-2}$alkyl;

wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl.

(8) W is a group of the formula:

$—(CR_{w1}R_{w2})_p—NR_{w3}R_{w4}$;

wherein p is an integer selected from 1 or 2;

$R_{w1}$ and $R_{w2}$ are independently selected from:

(i) hydrogen (including deuterium) or (ii) $C_{1-3}$alkyl which is optionally substituted by one more substituents selected from cyano, oxo, hydroxy, $C_{1-2}$alkoxy, halo, $C_{1-2}$haloalkoxy, —O—$C_3$cycloalkyl;

$R_{w3}$ is selected from hydrogen (including deuterium) or $C_{1-2}$alkyl; and $R_{w4}$ is a group with the formula:

$—(CR_{w5}R_{w6})_q\text{-}T_1$ wherein:

q is 1 or 2;

$R_{w5}$ and $R_{w6}$ are independently selected from:

a) hydrogen (including deuterium); or b) $C_{1-2}$alkyl, which is optionally substituted by one more substituents selected from cyano, oxo, hydroxy, $C_{1-2}$alkoxy, halo or $C_{1-2}$haloalkoxy;

and $T_1$ is selected from $C_{1-4}$alkyl, $C_{3-8}$cycloalkyl, aryl, heterocyclyl, a mono- or bicyclic heteroaryl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy or $C_{3-6}$cycloalkyl;

or $R_{w3}$ and $R_{w4}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy, and/or the mono- or bicyclic hetereocyclic ring formed by $R_{w3}$ and $R_{w4}$ is optionally spiro-fused to a $C_{3-6}$cycloalkyl or a heterocyclic ring, which in turn is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy; wherein any alkyl, alkoxy or $C_{3-6}$ cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl.

(9) W is either:

(i) a carbon-linked 3- to 6-membered heterocycle, each of which being optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl; or (ii) a group of the formula:

$—(CR_{w1}R_{w2})_p—NR_{w3}R_{w4}$;

wherein p is an integer selected from 1 or 2;

$R_{w1}$ and $R_{w2}$ are independently selected from hydrogen (including deuterium) or $C_{1-2}$ alkyl;

$R_{w3}$ is selected from hydrogen (including deuterium) or $C_{1-2}$alkyl; and $R_{w4}$ is a group with the formula:

$—(CR_{w5}R_{w6})_q\text{-}T_1$ wherein:

q is 1 or 2;

$R_{w5}$ and $R_{w6}$ are independently selected from hydrogen (including deuterium) or $C_{1-2}$alkyl;

and $T_1$ is selected from $C_{1-4}$alkyl, $C_{3-4}$cycloalkyl, aryl, heteroaryl, heterocyclyl, a mono- or bicyclic heteroaryl, a spirocyclic carbocyclic or heterocyclic ring system, a bridged $C_{4-6}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy or $C_{3-6}$cycloalkyl;

or $R_{w3}$ and $R_{w4}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy, and/or the mono- or bicyclic hetereocyclic ring formed by $R_{w3}$ and $R_{w4}$ is optionally spiro-fused to a $C_{3-6}$cycloalkyl or a heterocyclic ring, which in turn is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy; wherein any alkyl, alkoxy or $C_{3-6}$cycloalkyl is further optionally substituted by one or more substituents selected from cyano, hydroxy, halo, $NR_{1k}R_{1l}$ or $—S(O)_{0-2}R_{1k}R_{1l}$, wherein $R_{1k}$ and $R_{1l}$ are H or $C_{1-4}$alkyl.

(10) W is either:

(i) a carbon-linked 3- to 6-membered heterocycle, each of which being optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or $—S(O)_{0-2}R_{1ca}R_{1da}$, wherein $R_{1ca}$ and $R_{1da}$ are H or $C_{1-2}$alkyl; or (ii) a group of the formula:

$—(CR_{w1}R_{w2})_p—NR_{w3}R_{w4}$;

wherein p is 1 or 2;

$R_{w1}$ and $R_{w2}$ are independently selected from hydrogen (including deuterium) or $C_{1-2}$alkyl;

$R_{w3}$ is selected from hydrogen (including deuterium) or $C_{1-2}$alkyl; and $R_{w4}$ is a group with the formula:

$—(CR_{w5}R_{w6})_q-T_1$ wherein:

q is 1 or 2;

$R_{w5}$ and $R_{w6}$ are independently selected from hydrogen (including deuterium) or $C_{1-2}$alkyl;

and $T_1$ is selected from $C_{3-4}$cycloalkyl, aryl, heteroaryl, eterocyclyl, a mono- or bicyclic heteroaryl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy or $C_{3-6}$cycloalkyl;

or $R_{w3}$ and $R_{w4}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy, and/or the mono- or bicyclic hetereocyclic ring formed by $R_{w3}$ and $R_{w4}$ is optionally spiro-fused to a $C_{3-6}$cycloalkyl or a heterocyclic ring; which in turn is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy, wherein any alkyl, alkoxy or $C_{3-6}$cycloalkyl is further optionally substituted by one or more substituents selected from cyano, hydroxy, halo, $NR_{1k}R_{1l}$ or $—S(O)_{0-2}R_{1k}R_{1l}$, wherein $R_{1k}$ and $R_{1l}$ are H or $C_{1-4}$alkyl.

(11) W is a group of the formula:

$—(CR_{w1}R_{w2})_p—NR_{w3}R_{w4}$;

wherein p is 1;

$R_{w1}$ and $R_{w2}$ are independently selected from hydrogen (including deuterium) or $C_{1-2}$alkyl;

$R_{w3}$ is selected from hydrogen (including deuterium) or $C_{1-2}$alkyl; and $R_{w4}$ is a group with the formula:

$—(CR_{w5}R_{w6})_q-T_1$ wherein:

q is 1;

$R_{w5}$ and $R_{w6}$ are independently selected from hydrogen (including deuterium) or $C_{1-2}$alkyl;

and $T_1$ is selected from $C_{3-4}$cycloalkyl, aryl, heterocyclyl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy or $C_{1-6}$cycloalkyl, wherein any alkyl or alkoxy is optionally further substituted by one or more substituents selected from cyano, hydroxy or halo.

(12) W is a group of the formula:

$—(CR_{w1}R_{w2})_p—NR_{w3}R_{w4}$;

wherein p is 1;

$R_{w1}$ and $R_{w2}$ are independently selected from hydrogen (including deuterium) or $C_{1-2}$alkyl; and $R_{w3}$ and $R_{w4}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy, and/or the mono- or bicyclic hetereocyclic ring formed by $R_{w5}$ and $R_{w4}$ is optionally spiro-fused to a $C_{3-6}$cycloalkyl or a heterocyclic ring, which in turn is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy.

(13) W is a group of the formula:

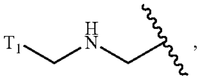

wherein $T_1$ is as defined herein.

(14) W is a group of the formula:

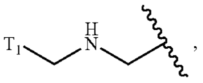

wherein $T_1$ is selected from $C_{3-4}$cycloalkyl, aryl, heterocyclyl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

(15) W is selected from:
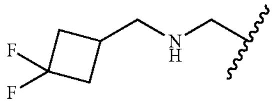 ;
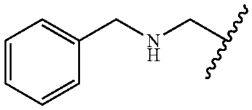 ;
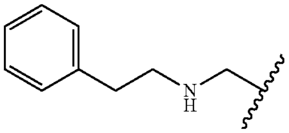 ;
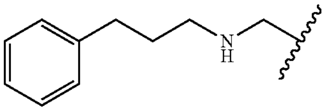 ;
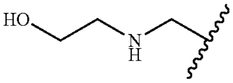 ; 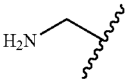 ;
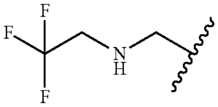 ; 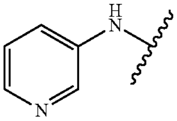 ;
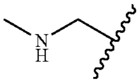 ; 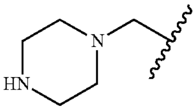 ;
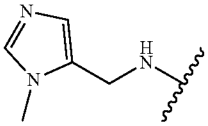 ; 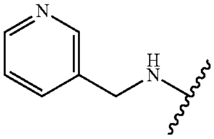 ;
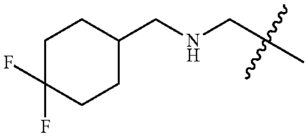 ;
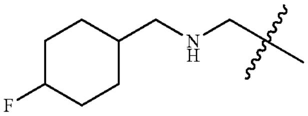 ;
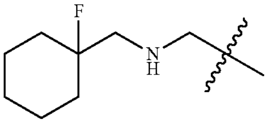 ;
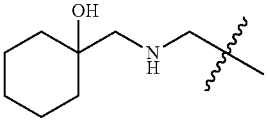 ;
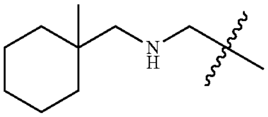 ;
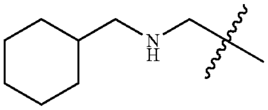 ;
-continued
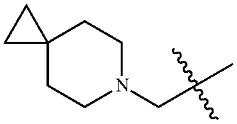 ; 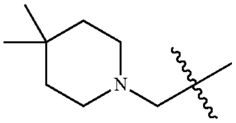 ;
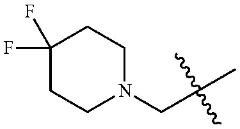 ; 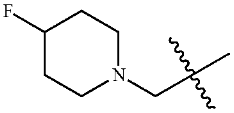 ;
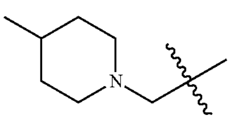 ; 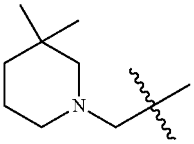 ;
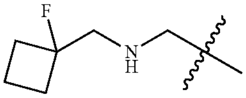 ; 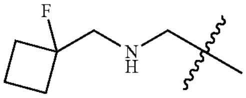 ;
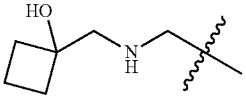 ; 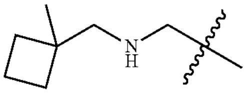 ;
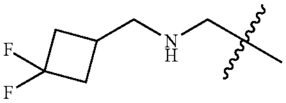 ;
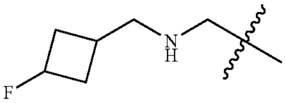 ;
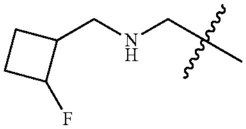 ; 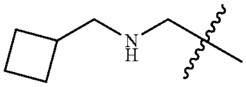 ;
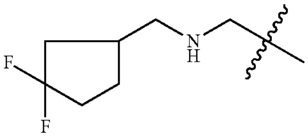 ;
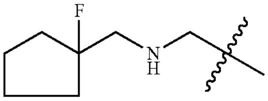 ;
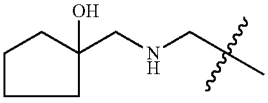 ;
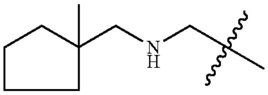 ;
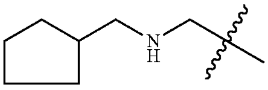 ;
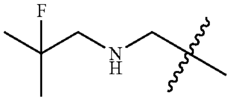 ; 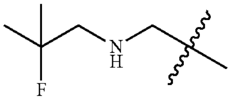 ;
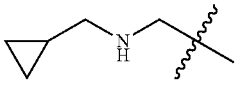 ;

-continued
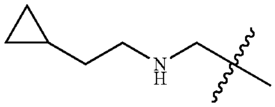
;
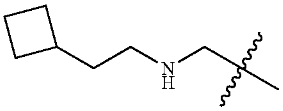
;
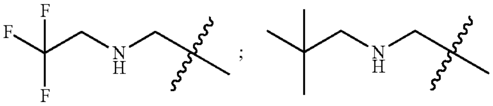
;
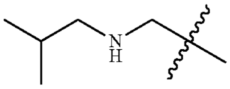
;
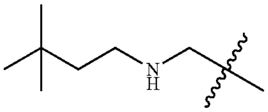
;
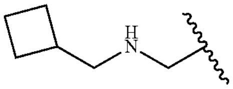
,
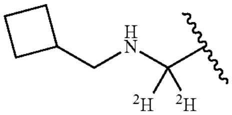
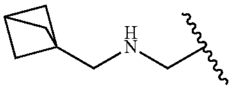
,
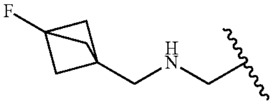
,
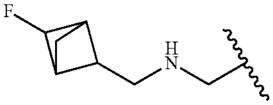
,
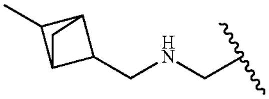
,
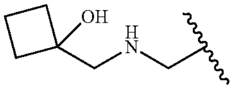
,
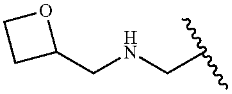
,
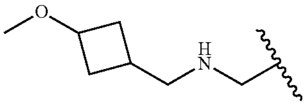
,
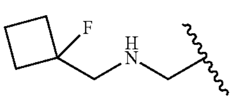
,
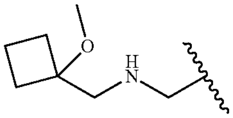
,
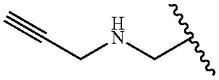
,
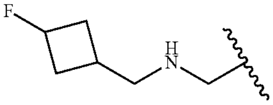
,
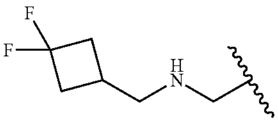
-continued
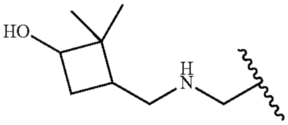
,
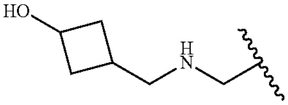
,
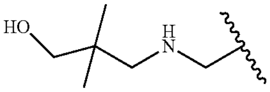
,
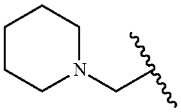
,
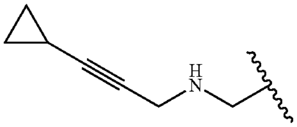
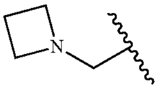
,
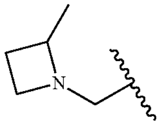
,
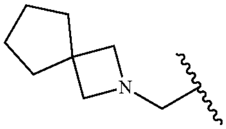
,
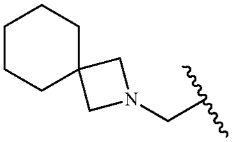
,
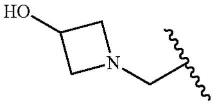
,
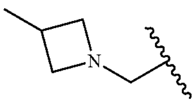
,
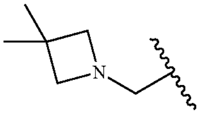
,
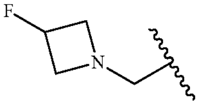
,
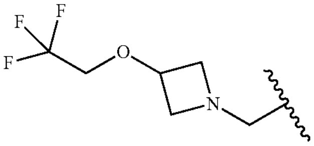
,
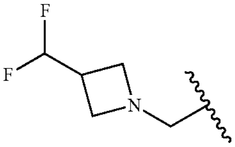
,
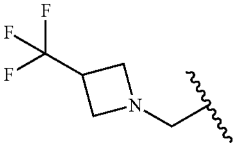
,
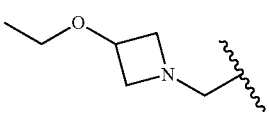
,
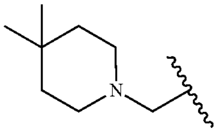
,
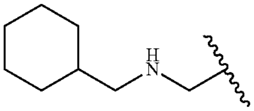
,
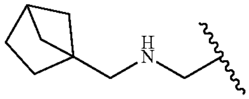
,
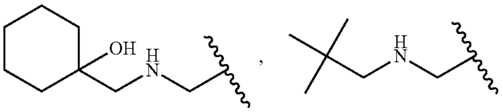
, -continued
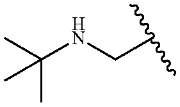,
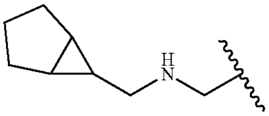,
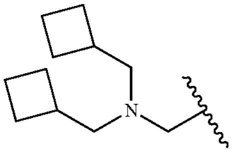;
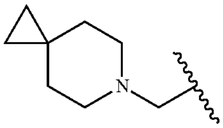,
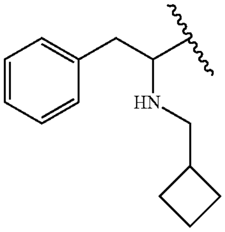,
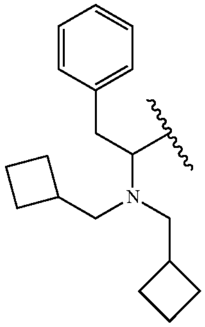,
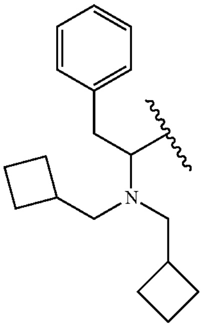,
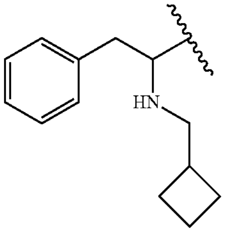,
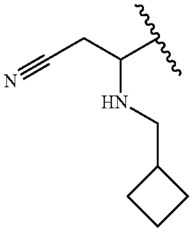,
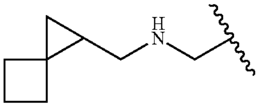,
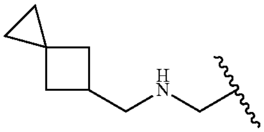,
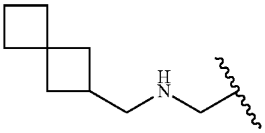,
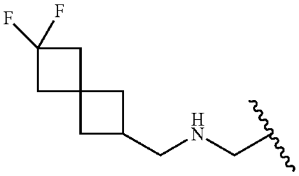,
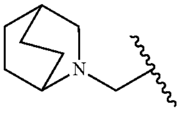,
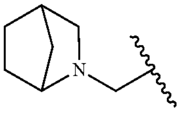,
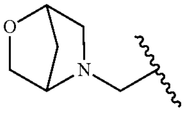,
-continued
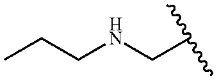,
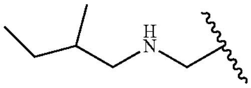,
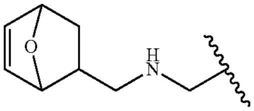,
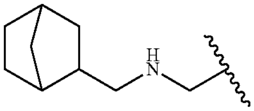,
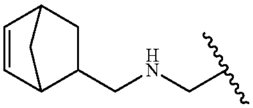,
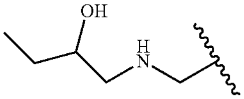,
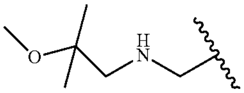,
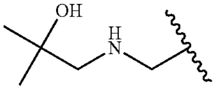,
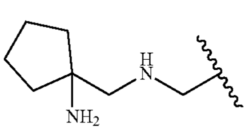,
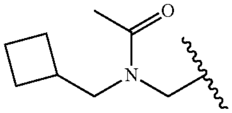,
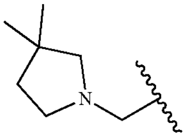,
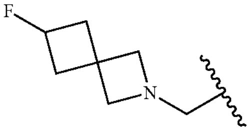,
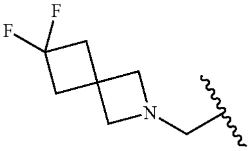,
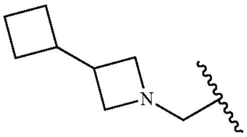,
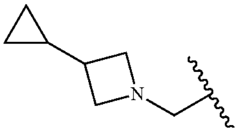,
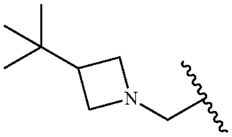,
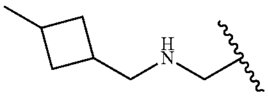,
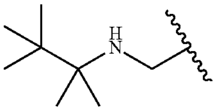,
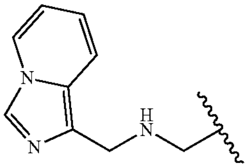,
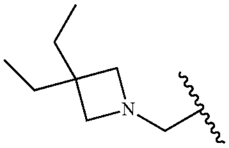,
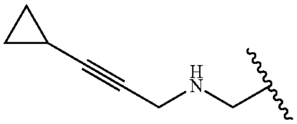,
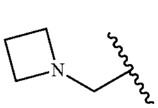,
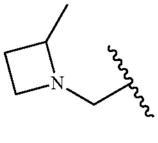,
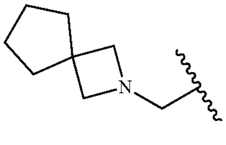, -continued
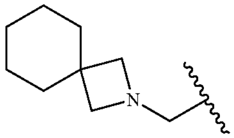 , 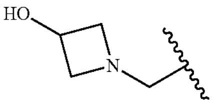 ,
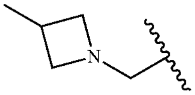 , 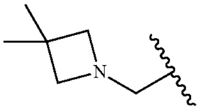 ,
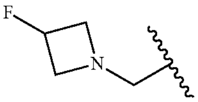 , 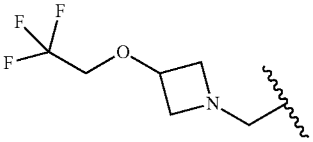 ,
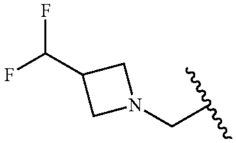 , 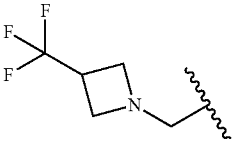 ,
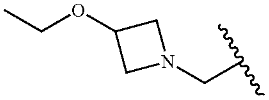 , 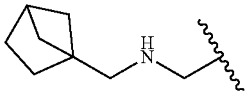 ,
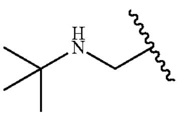 , 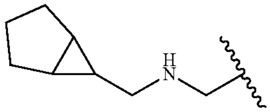 ,
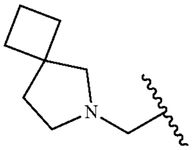 , 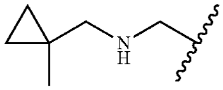 ,
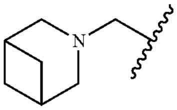 ; 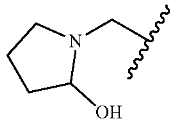 ;
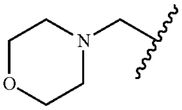 ; 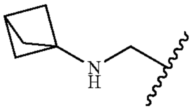 ;
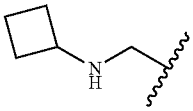 ; 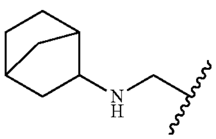 ;
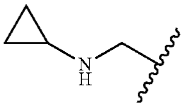 ; 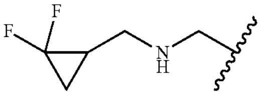 ;
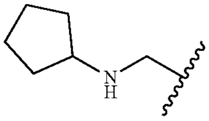 ; 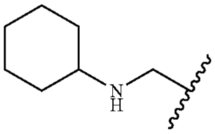 ;
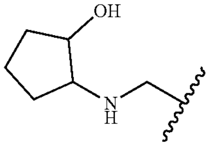 ; 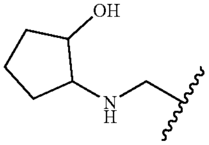 ;
-continued
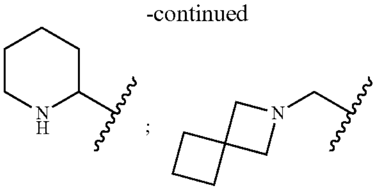 ;
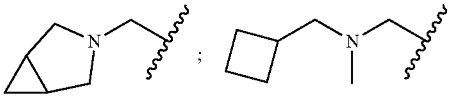 ;
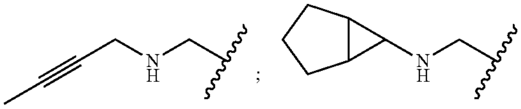 ;
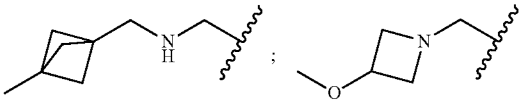 ;
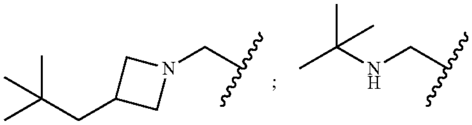 ;
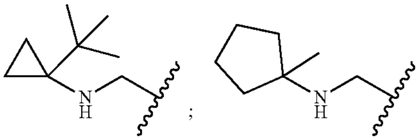 ;
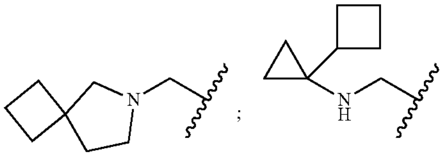 ;
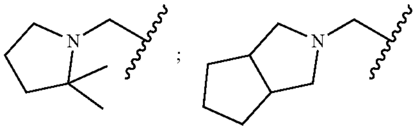 ;
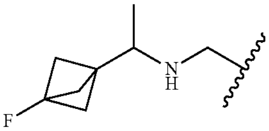 ;
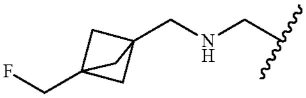 ;
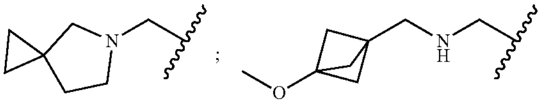 ;
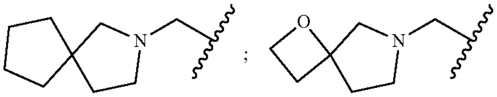 ;
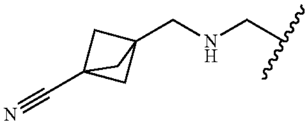 ;
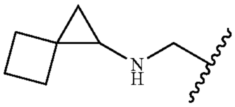 ;

-continued
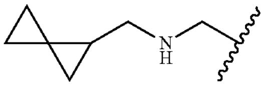 ; 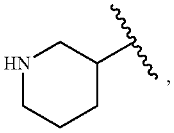 ,
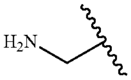 , 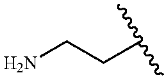 , 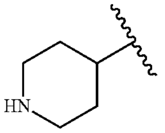 ,
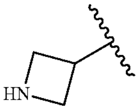 , 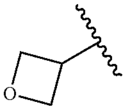 , 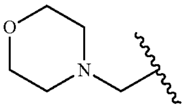 ,
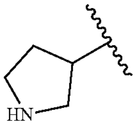 , 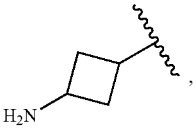 ,
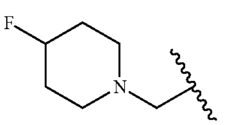 , 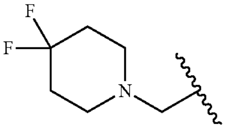 ,
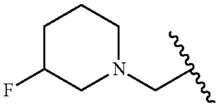 and 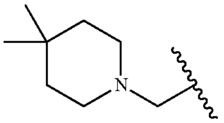 .
(16) W is selected from:
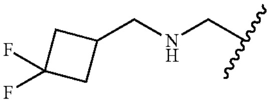 ;
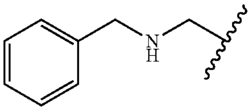 ;
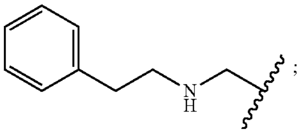 ;
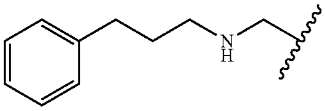 ;
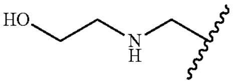 ; 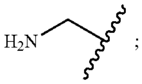 ;
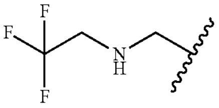 ; 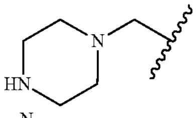 ;
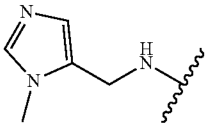 ; 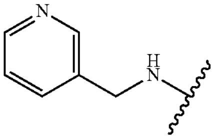 ;
-continued
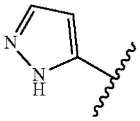 ; 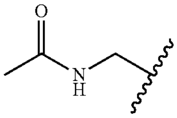 ;
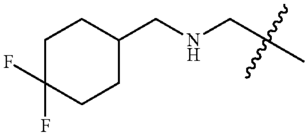 ;
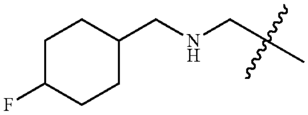 ;
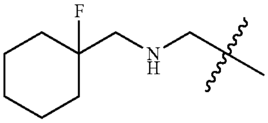 ;
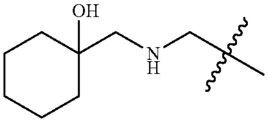 ;
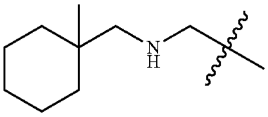 ;
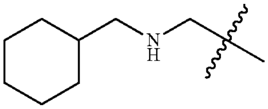 ;
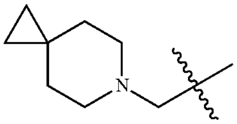 ; 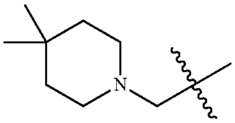 ;
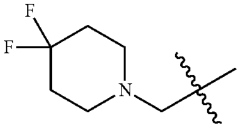 ; 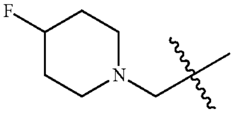 ;
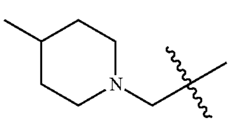 ; 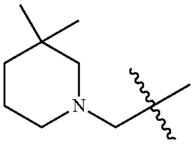 ;
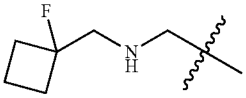 ; 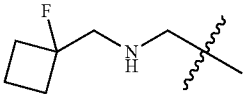 ;

-continued
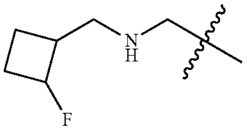 ; 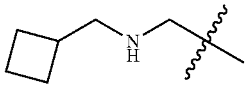 ;
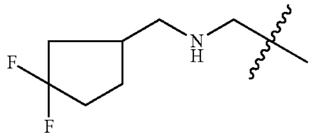 ;
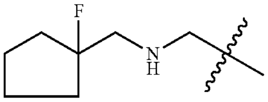 ;
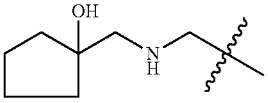 ;
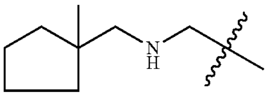 ;
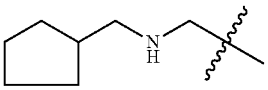 ;
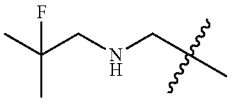 ; 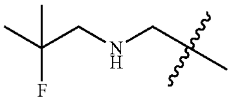 ;
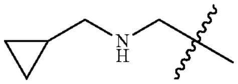 ;
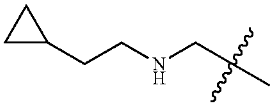 ;
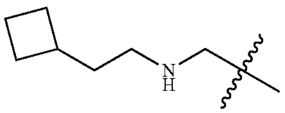 ;
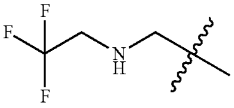 ; 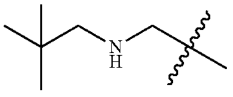 ;
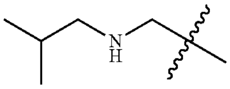 ;
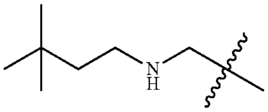 ;
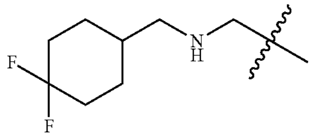 ;
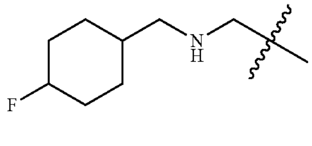 ;
-continued
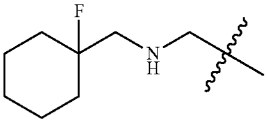 ;
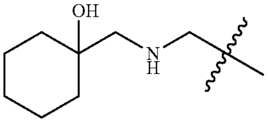 ;
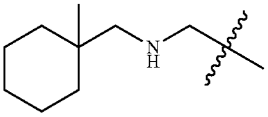 ;
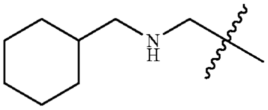 ;
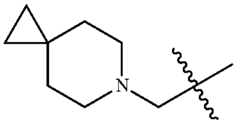 ; 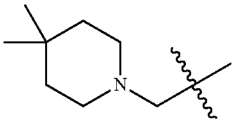 ;
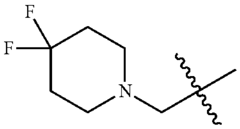 ; 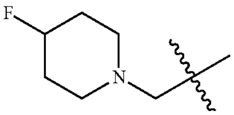 ;
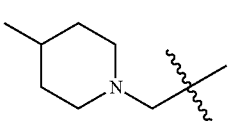 ; 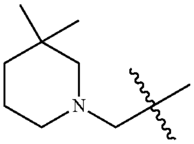 ;
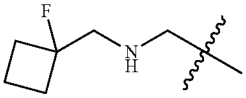 ; 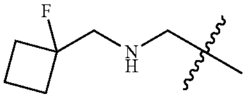 ;
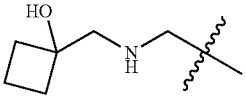 ; 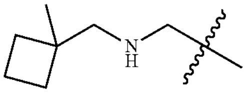 ;
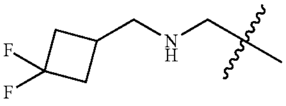 ;
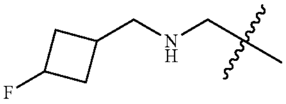 ;
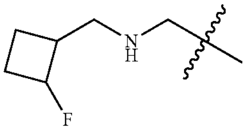 ; 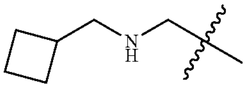 ;
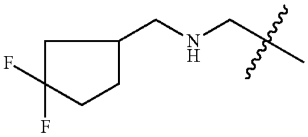 ;
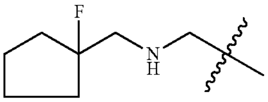 ;

-continued
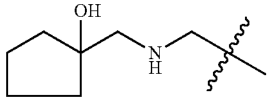 ;
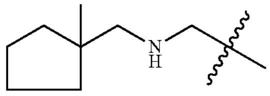 ;
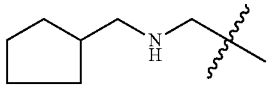 ;
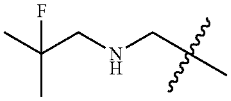 ; 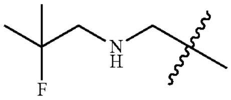 ;
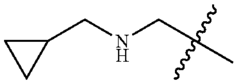 ;
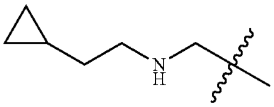 ;
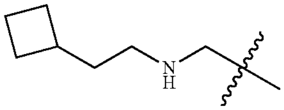 ;
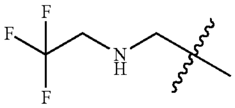 ; 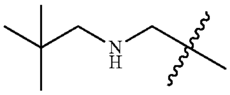 ;
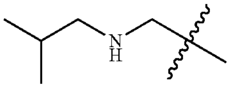 ;
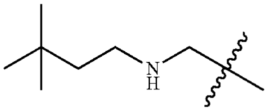 ;
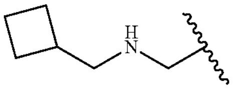 , 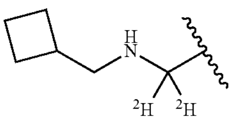
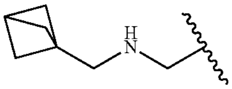 ,
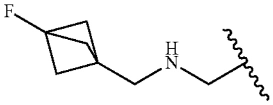 ,
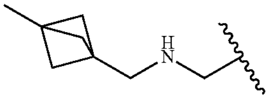
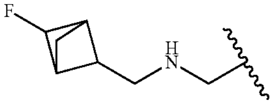 ,
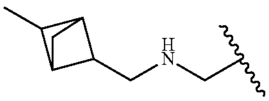 ,
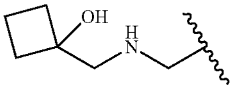 , 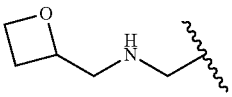 ,
-continued
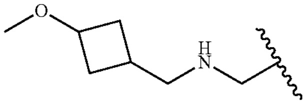 ,
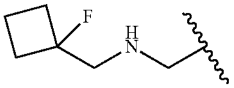 , 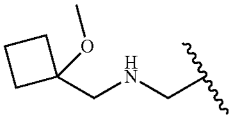 ,
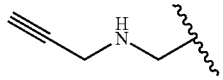 ,
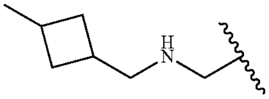 ,
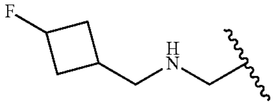 ,
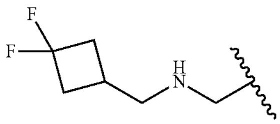
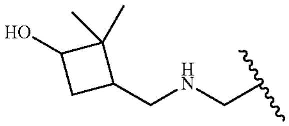 ,
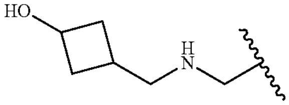 ,
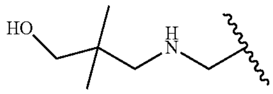 , 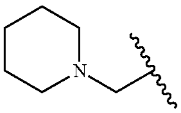 ,
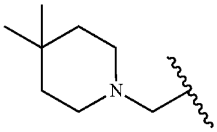 , 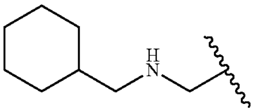 ,
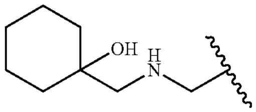 , 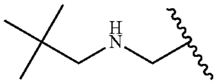 ,
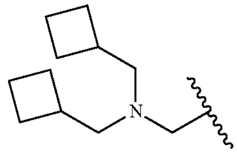 , 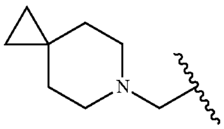 ,
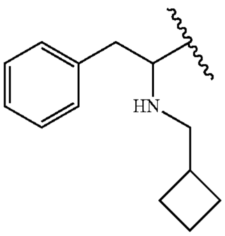 , 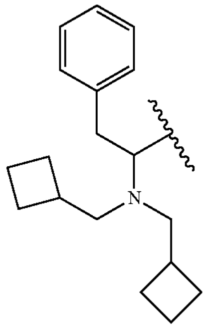 , -continued
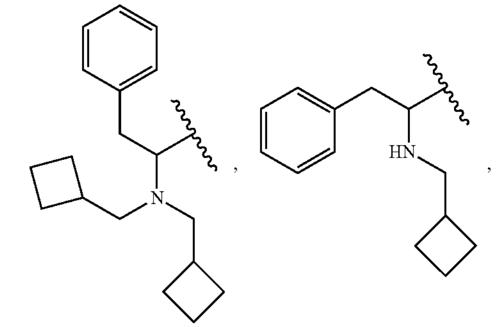
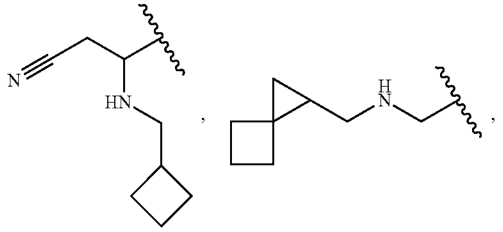
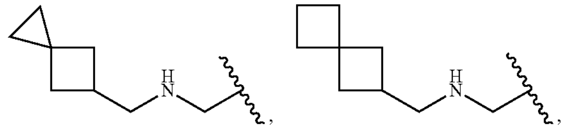
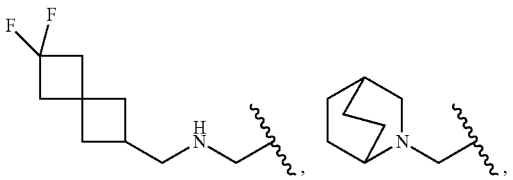
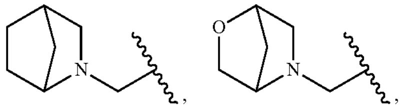
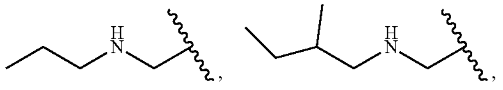
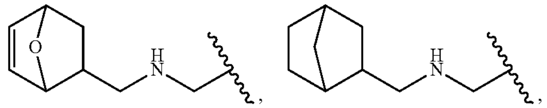
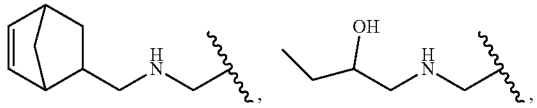
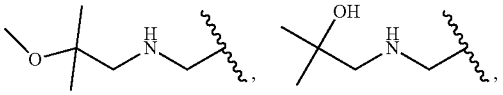
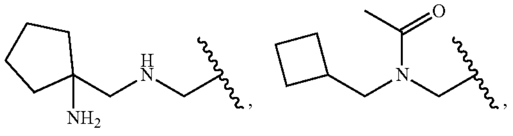
-continued
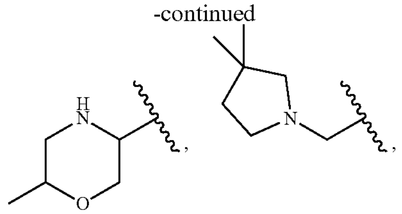
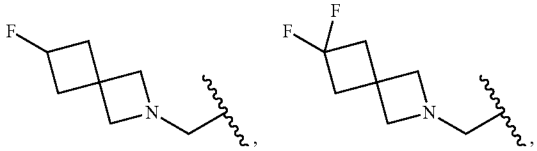
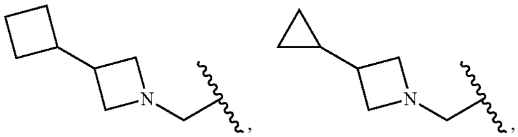
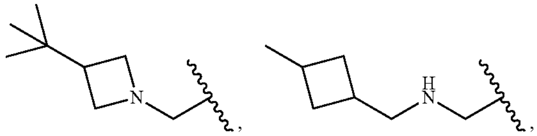
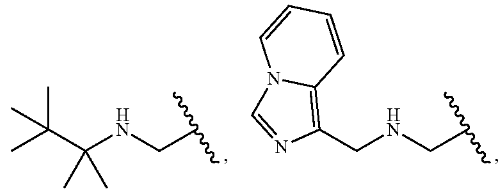
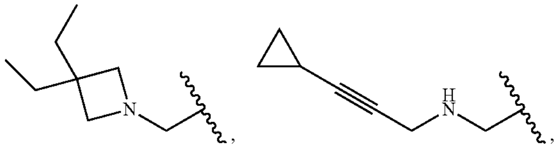
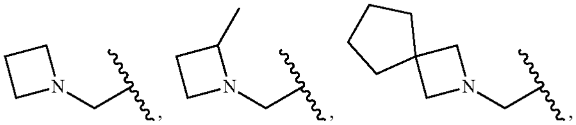
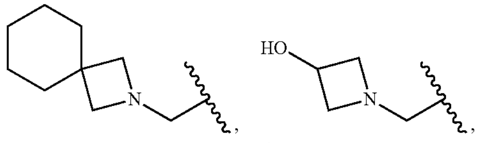
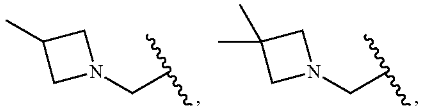
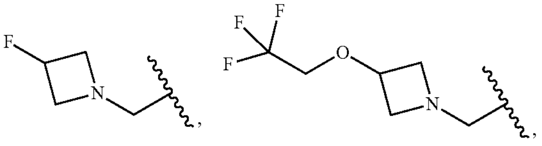
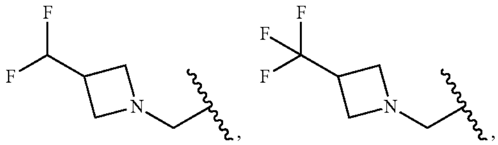
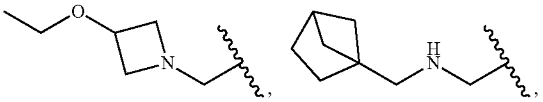

-continued
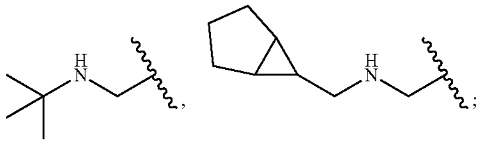
, ;
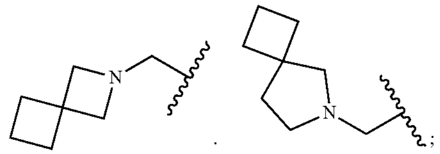
. ;
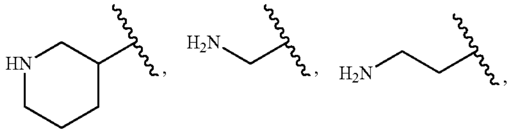
, , ,
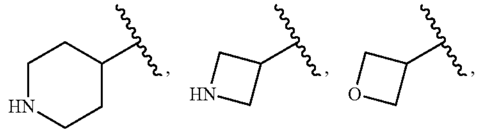
, , ,
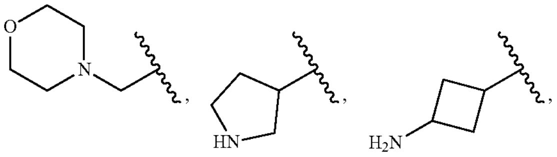
, , ,
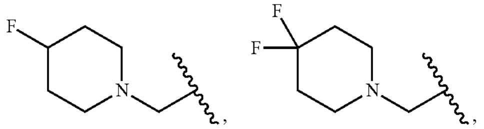
, ,
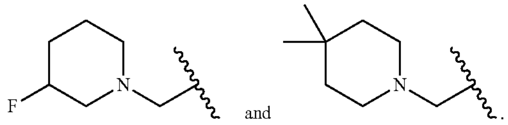
and .
(17)W is selected from:
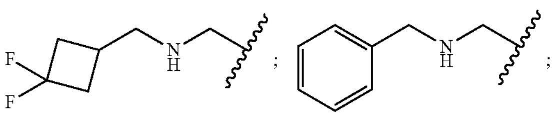
; ;
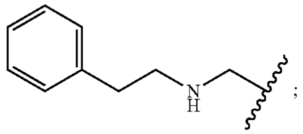
;
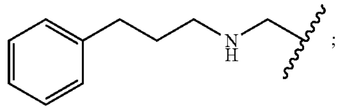
;
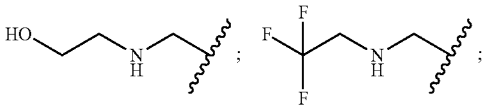
; ;
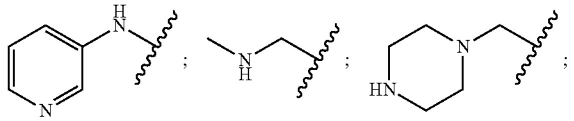
; ; ;
-continued
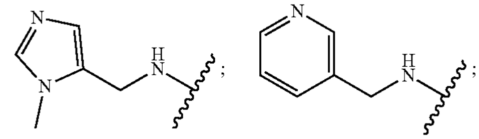
; ;
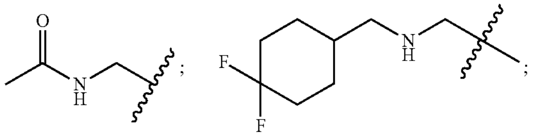
; ;
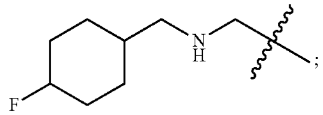
;
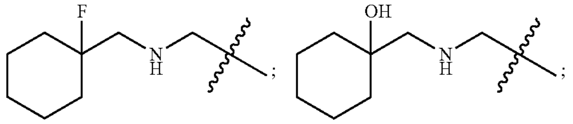
; ;
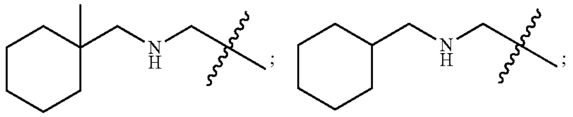
; ;
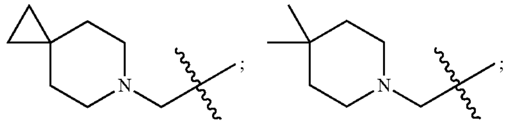
; ;
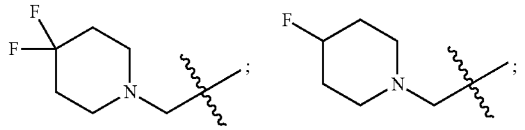
; ;
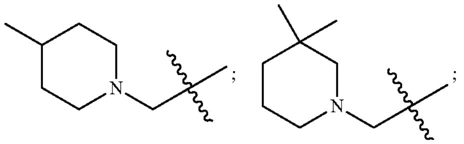
; ;
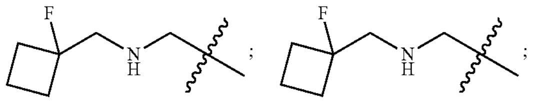
; ;
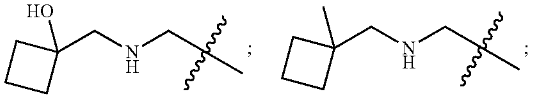
; ;
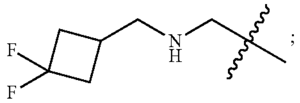
;
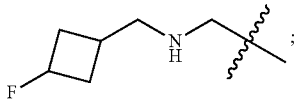
;
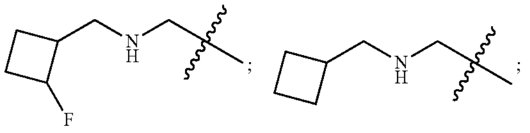
; ;
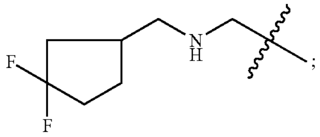
;

-continued
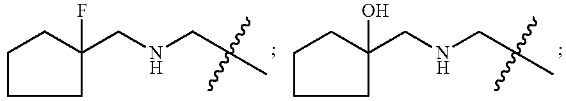
; ;
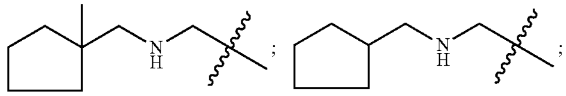
; ;
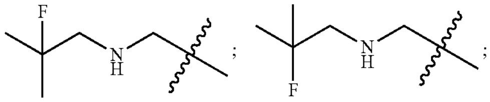
; ;
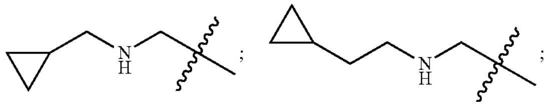
; ;
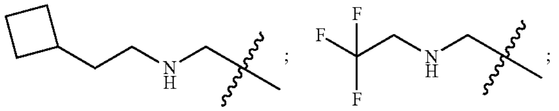
; ;
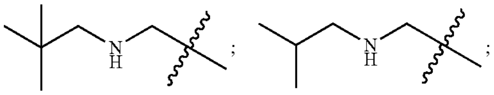
; ;
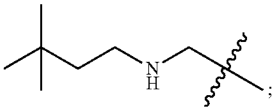
;
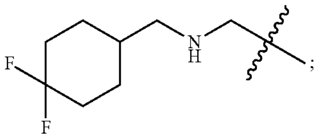
;
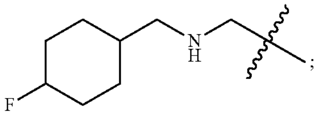
;
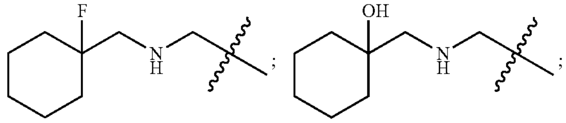
; ;
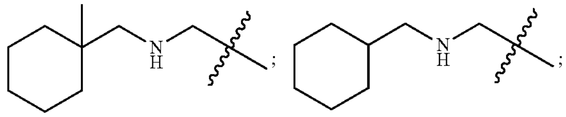
; ;
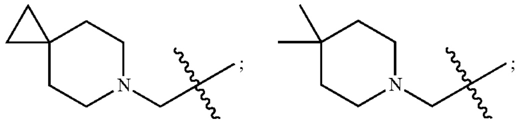
; ;
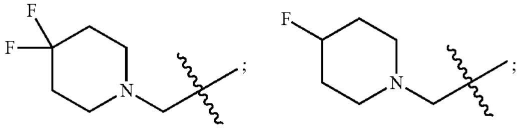
; ;
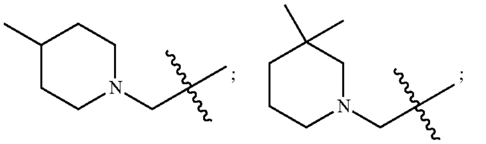
; ;
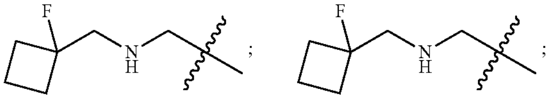
; ;
-continued
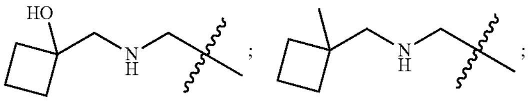
; ;
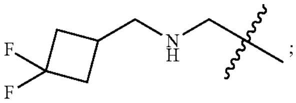
;
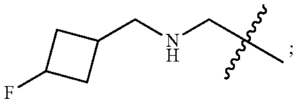
;
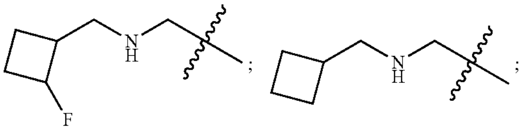
; ;
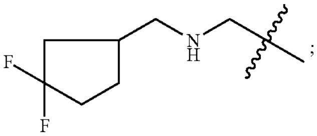
;
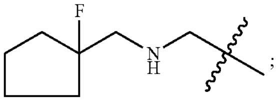
;
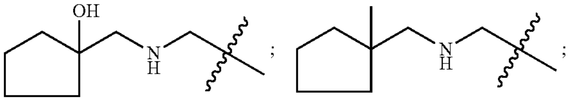
; ;
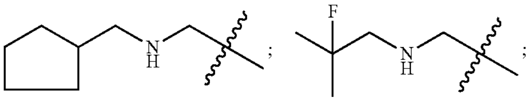
; ;
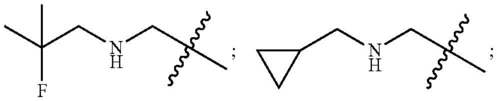
; ;
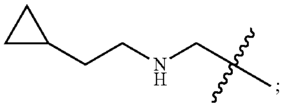
;
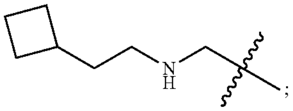
;
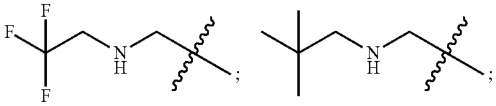
; ;
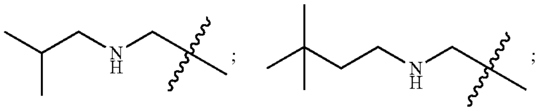
; ;
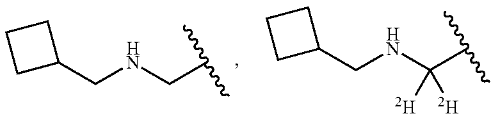
, ,
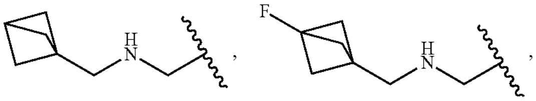
, , -continued
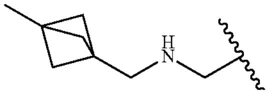, 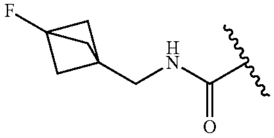,
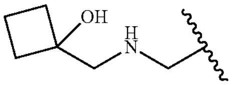, 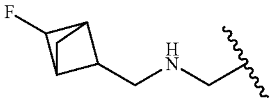,
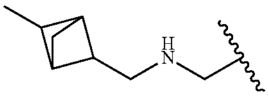, 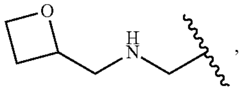,
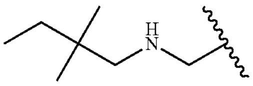, 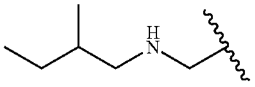,
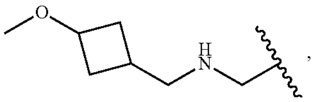, 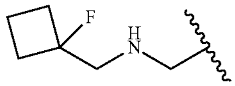,
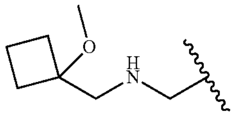, 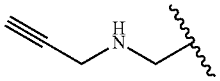,
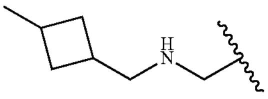, 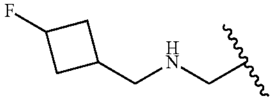,
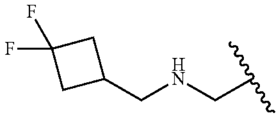,
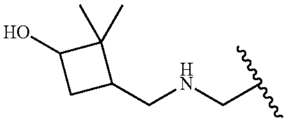,
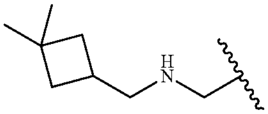,
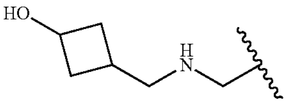,
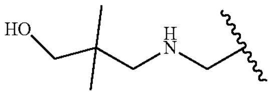, 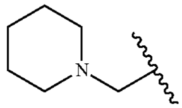,
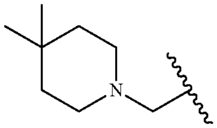, 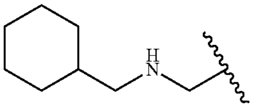,
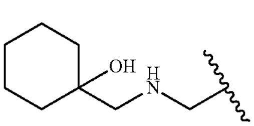, 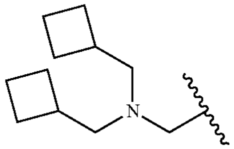,
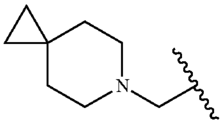, 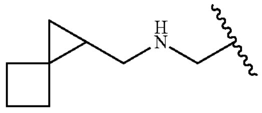,
-continued
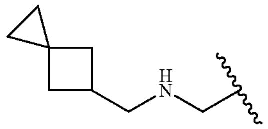,
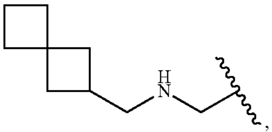,
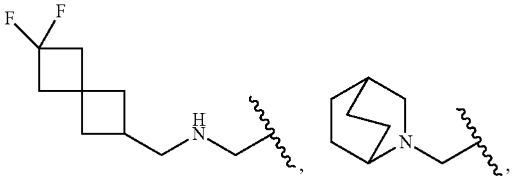,
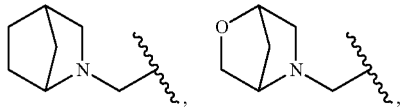,
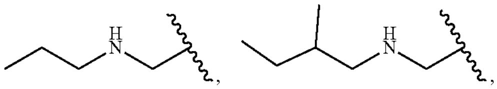,
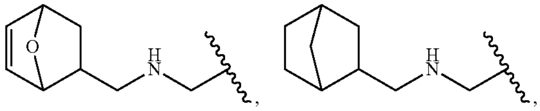,
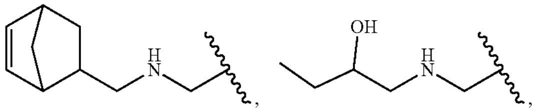,
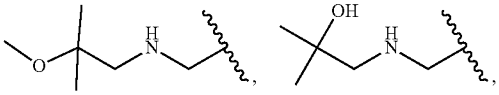,
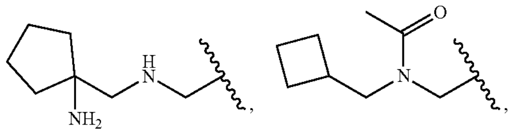,
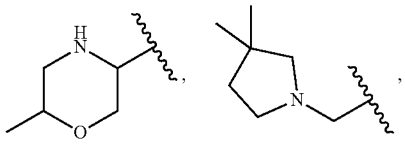,
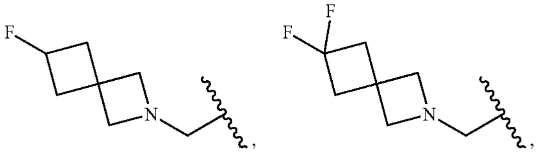,
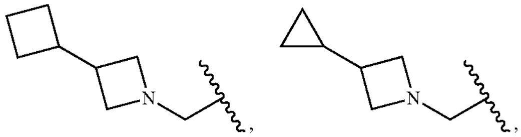

-continued
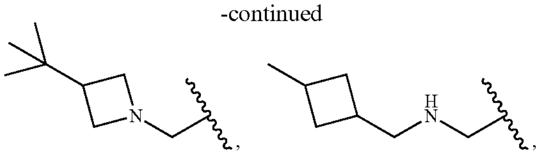
,
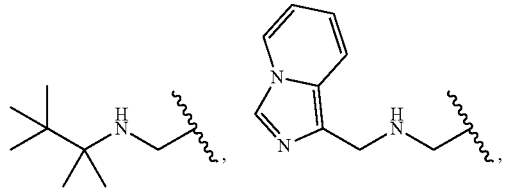
,
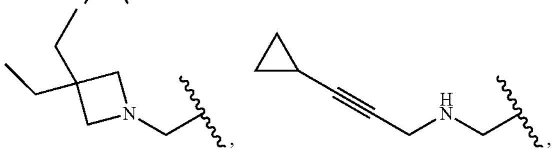
,
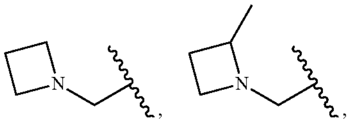
,
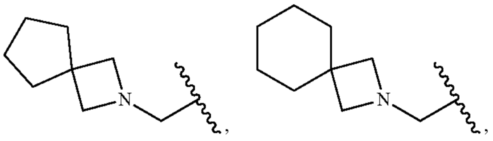
,
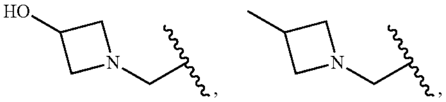
,
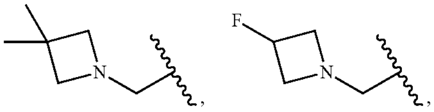
,
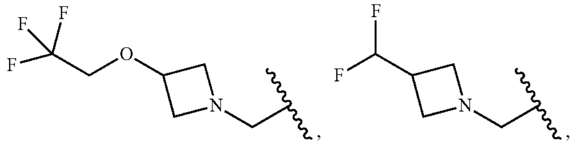
,
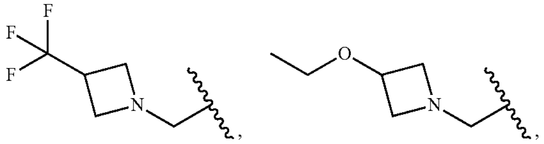
,
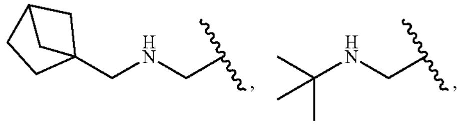
,
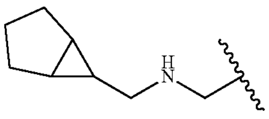
;
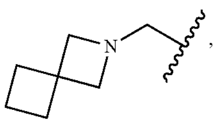
, and
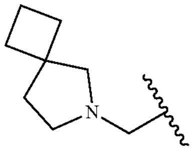
.
(18) W is selected from:
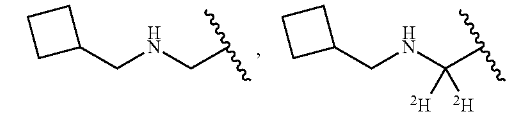
,
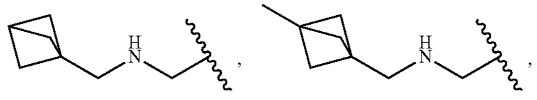
,
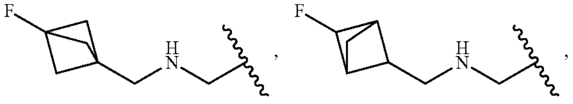
,
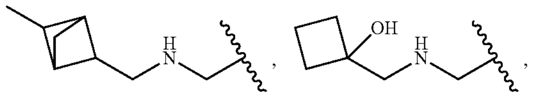
,
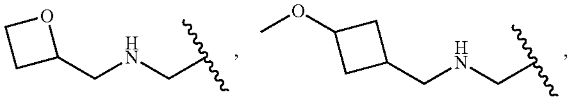
,
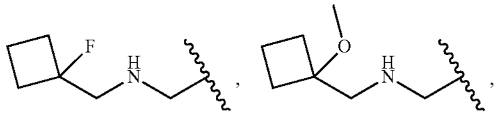
,
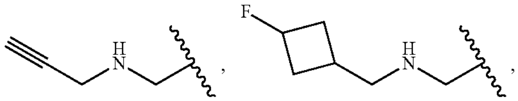
,
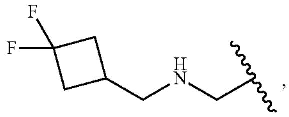
,
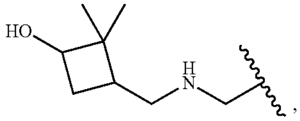
,
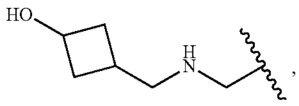
,
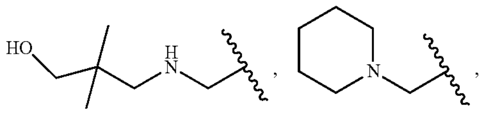
,
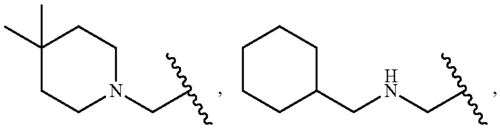
,
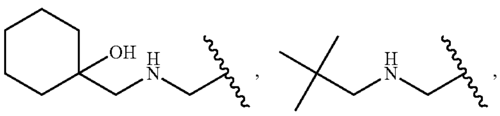
,
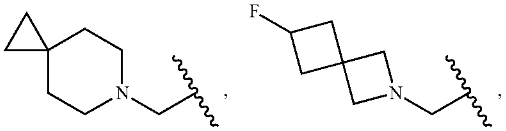
, -continued
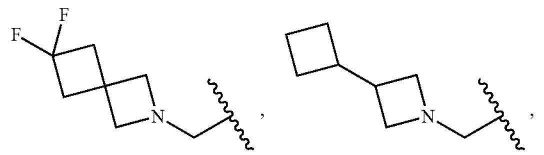
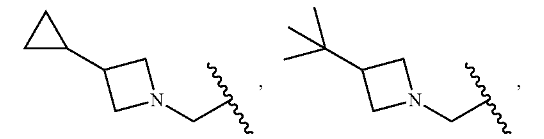
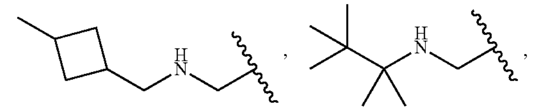
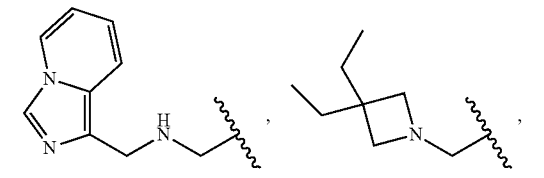
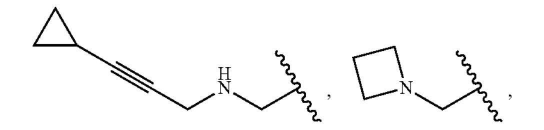
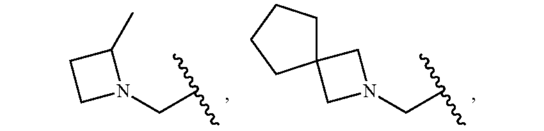
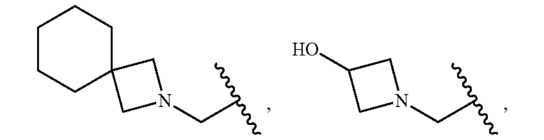
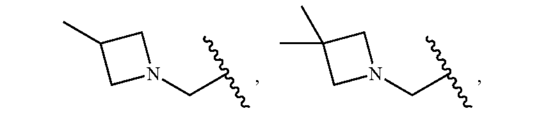
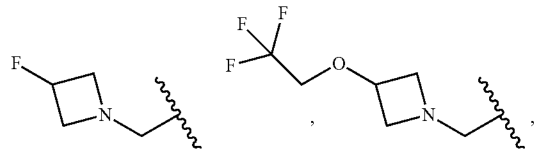
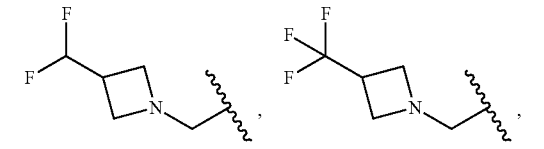
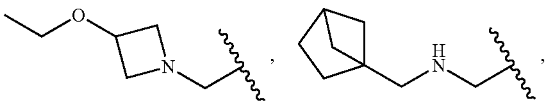
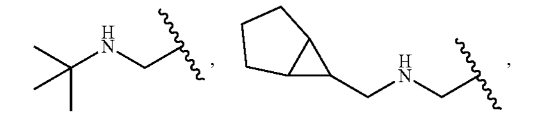
-continued
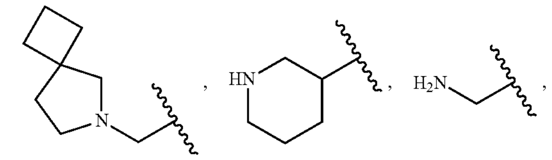
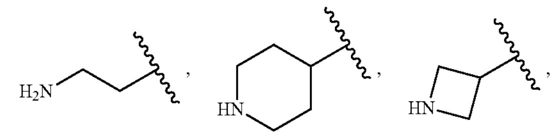
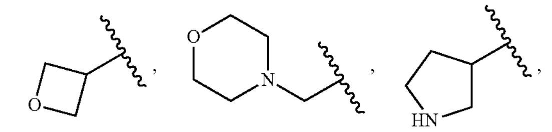
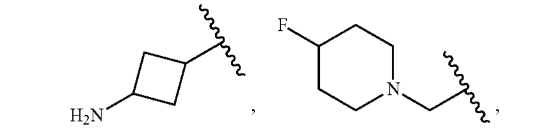
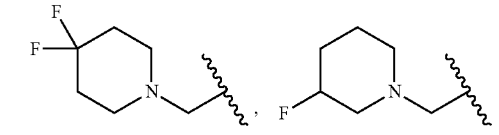
and
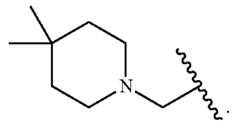
(19) W is selected from:
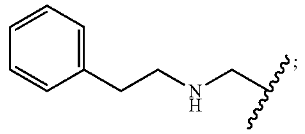
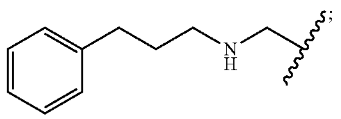
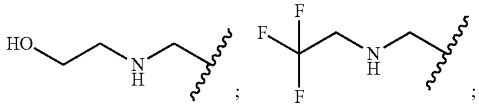
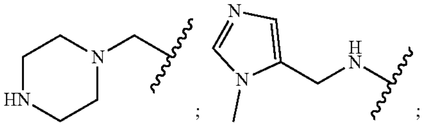
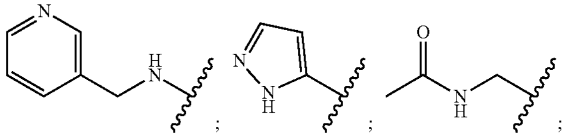
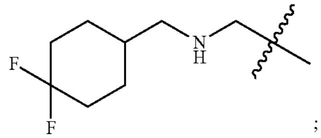

-continued
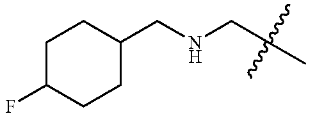
;
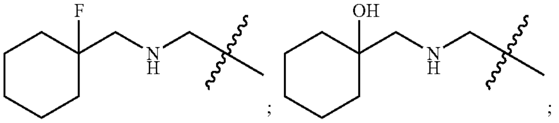
; ;
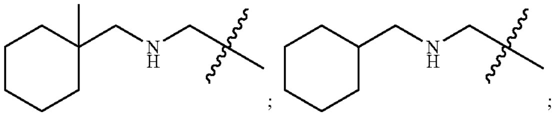
; ;
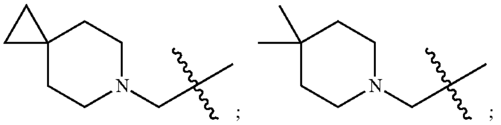
; ;
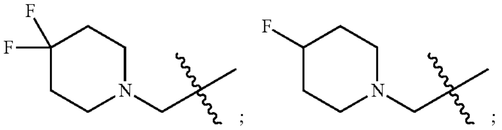
; ;
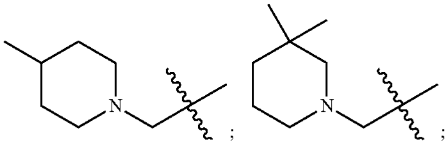
; ;
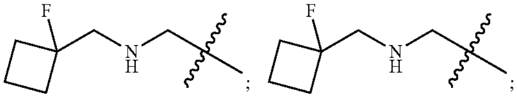
; ;
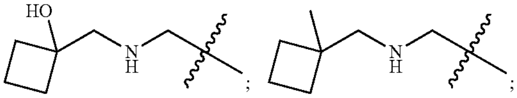
; ;
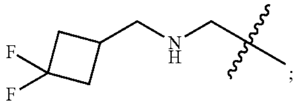
;
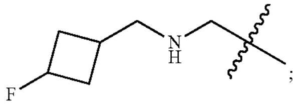
;
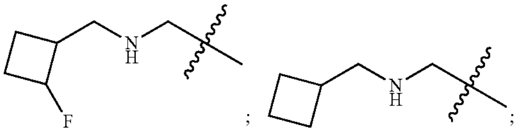
; ;
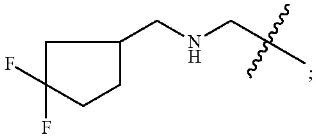
;
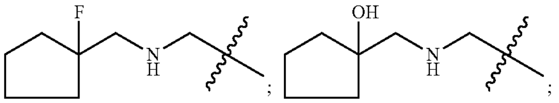
; ;
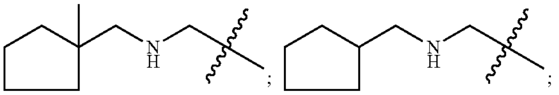
; ;
-continued
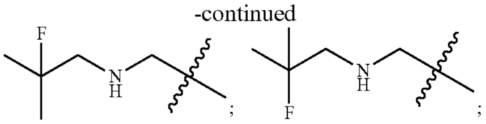
; ;
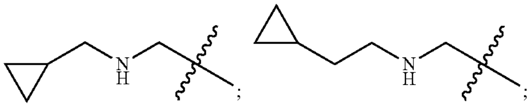
; ;
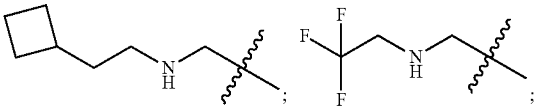
; ;
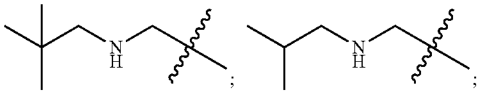
; ;
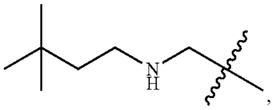
,
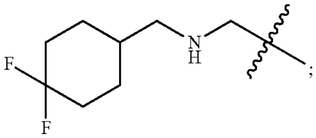
;
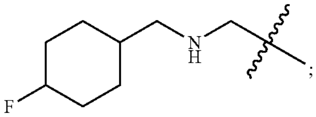
;
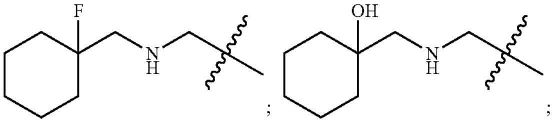
; ;
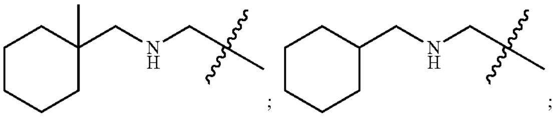
; ;
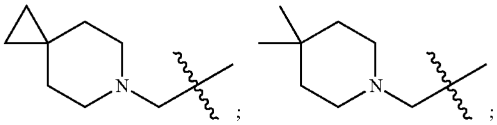
; ;
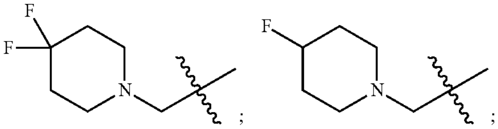
; ;
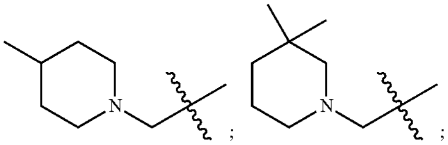
; ;
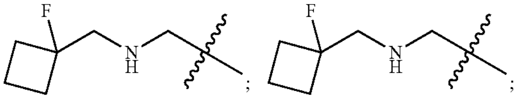
; ;
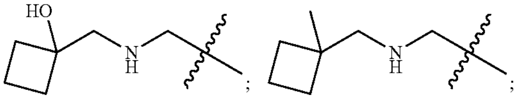
; ;
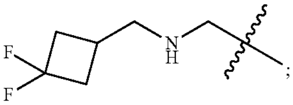
;

-continued
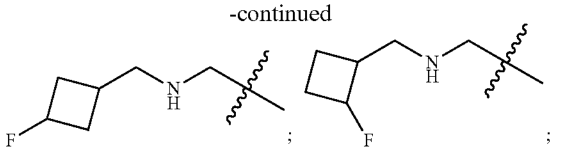
;
;
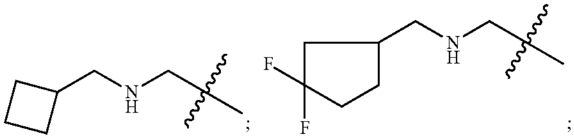
;
;
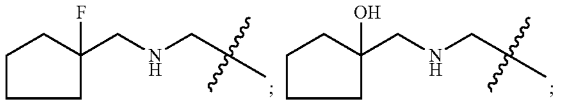
;
;
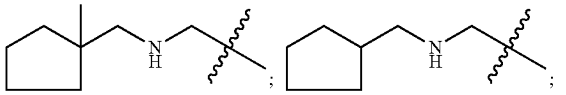
;
;
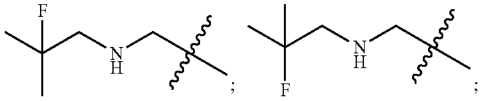
;
;
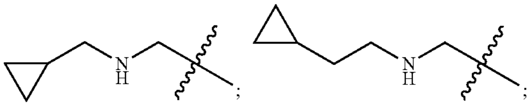
;
;
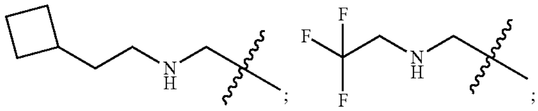
;
;
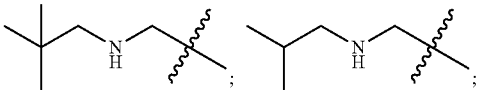
;
;
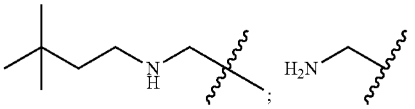
;
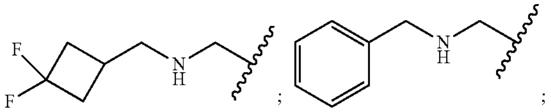
;
;
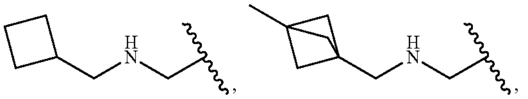
,
,
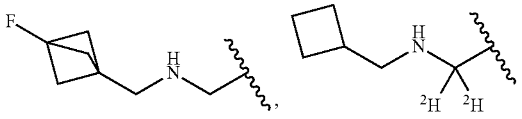
,
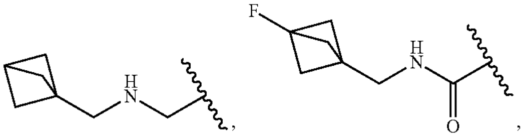
,
,
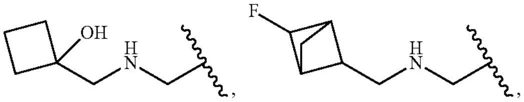
,
,
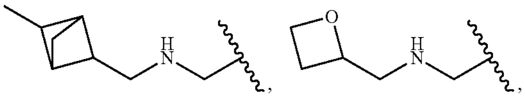
,
,
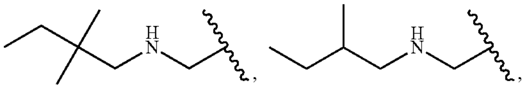
,
,
-continued
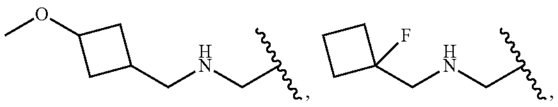
,
,
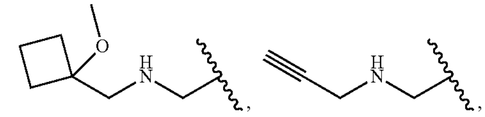
,
,
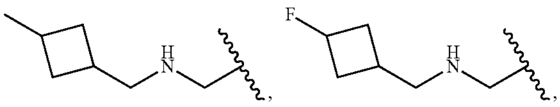
,
,
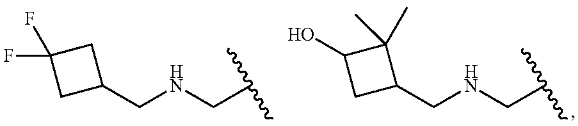
,
,
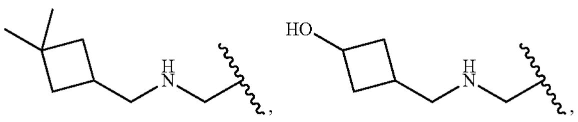
,
,
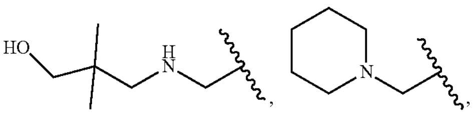
,
,
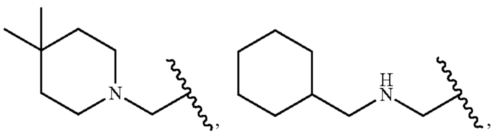
,
,
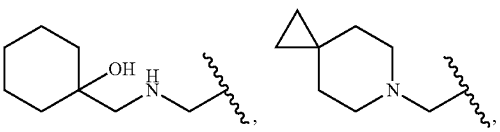
,
,
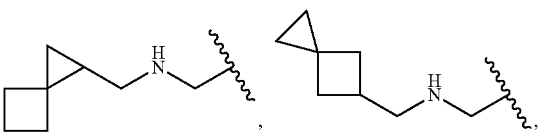
,
,
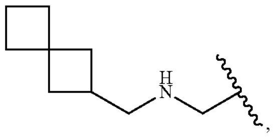
,
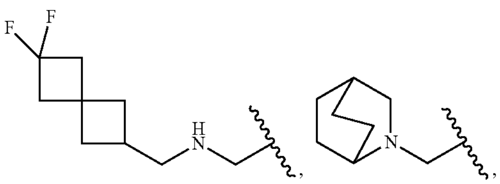
,
,
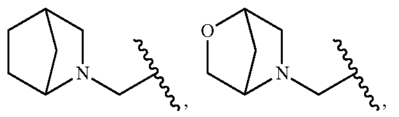
,
,
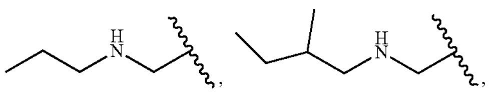
,
,

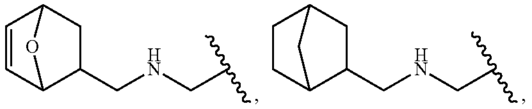
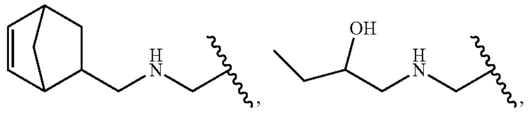
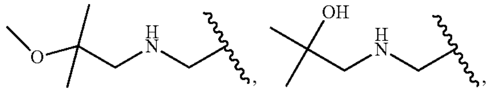
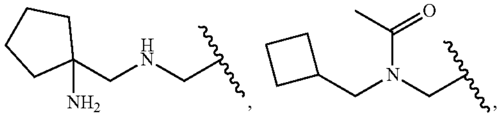
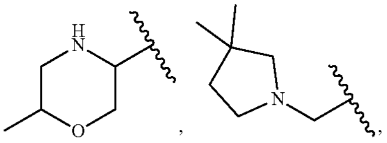
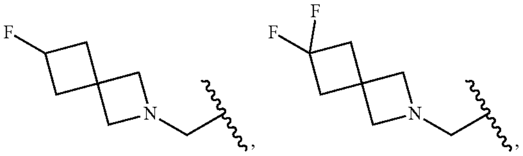
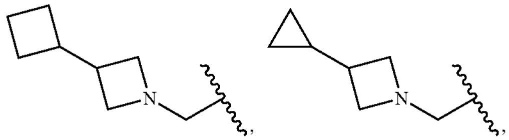
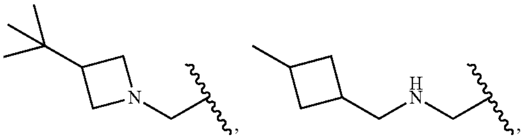
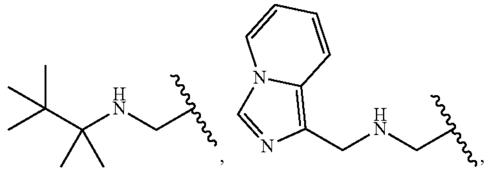
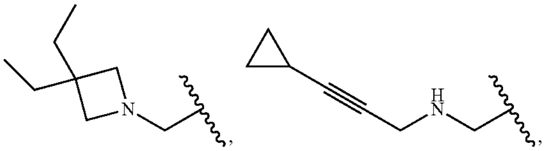
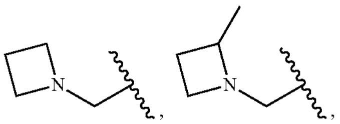
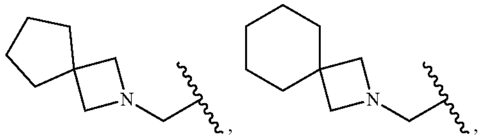
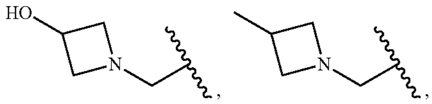
-continued
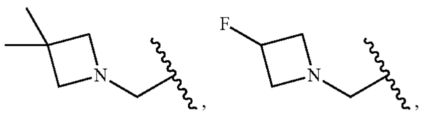
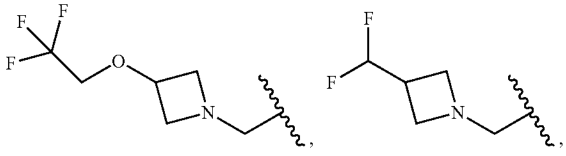
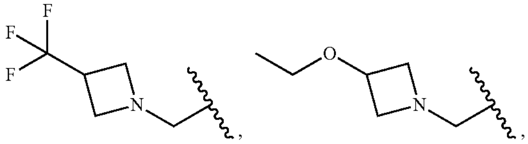
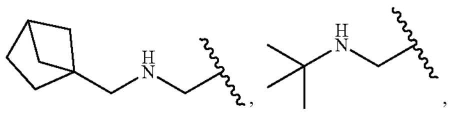
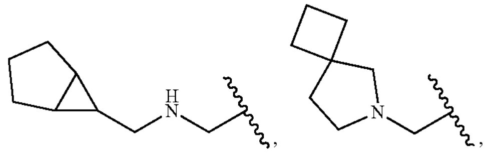
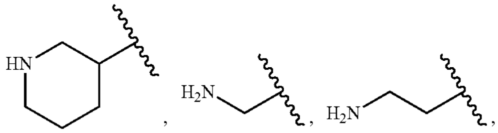
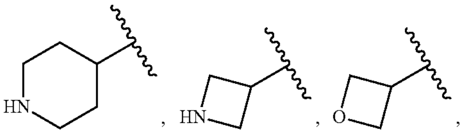
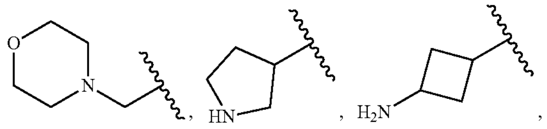
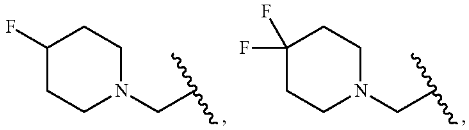
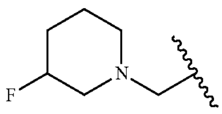
and
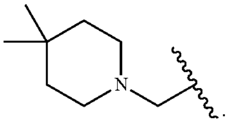
(20) W is selected from:
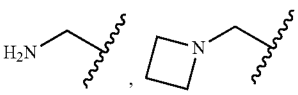
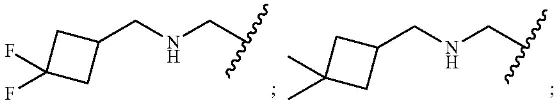
;

-continued
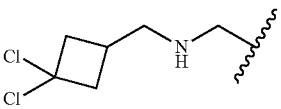 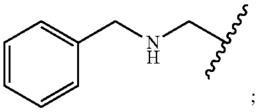 ;
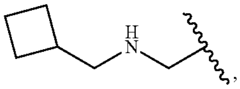 , 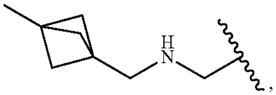 ,
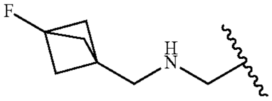 , 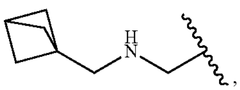 ,
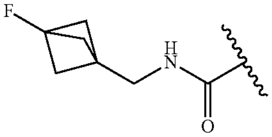 , 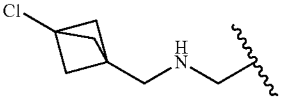 ,
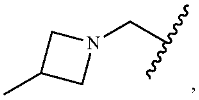 , 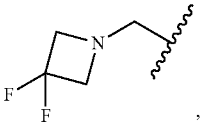 ,
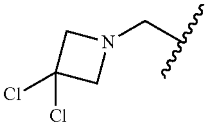 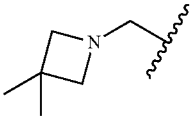
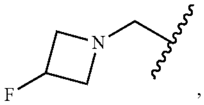 , 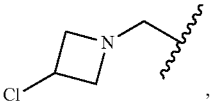 ,
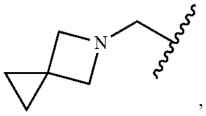 , 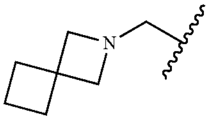 ,
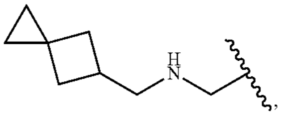 , 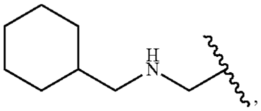 ,
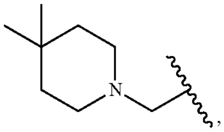 , 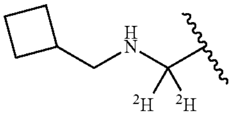
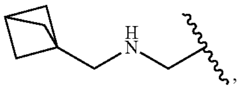 , 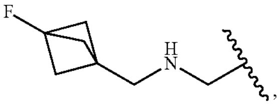 ,
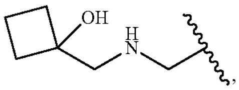 , 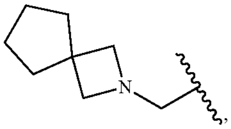 ,
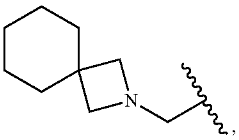 , 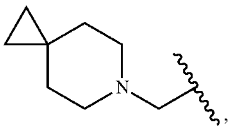 ,
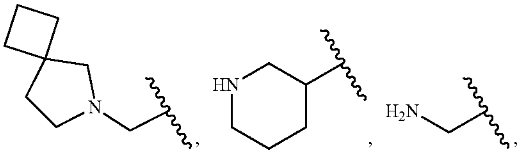 ,
-continued
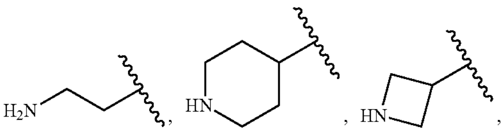 ,
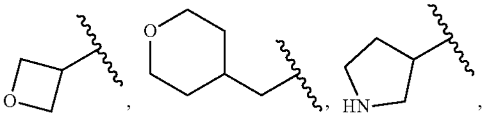 ,
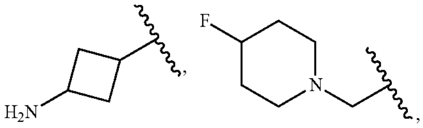 ,
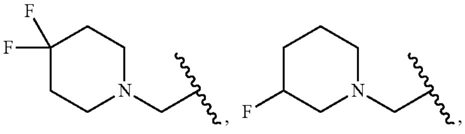 , and
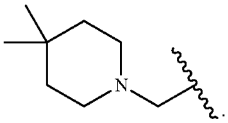 .
(21) W is selected from:
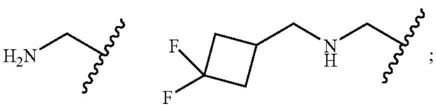 ;
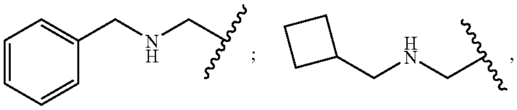 ,
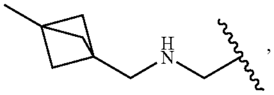 ,
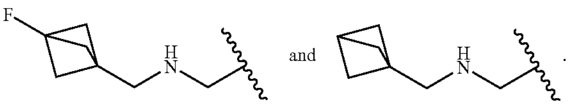 .
(22) W is selected from:
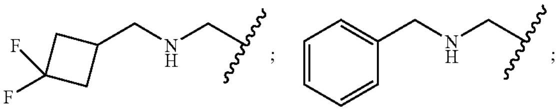 ;
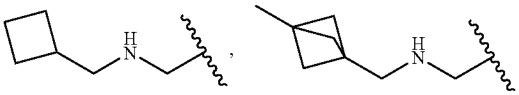 and
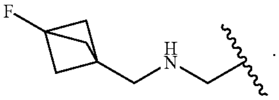 .

(22a) W is selected from:

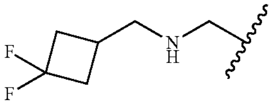 ; 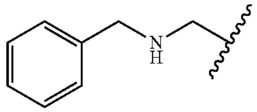 ;

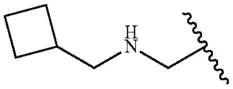 , 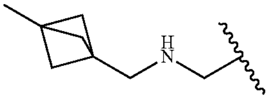 ,

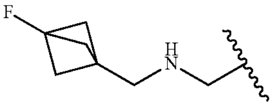 , 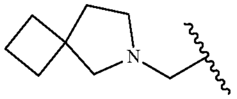 ,

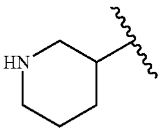 , 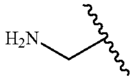 , 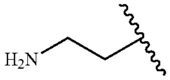 ,

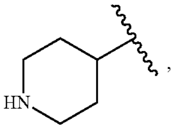 , 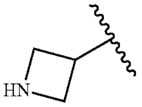 , 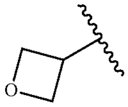 ,

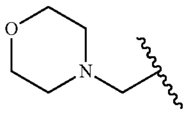 , 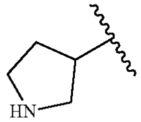 , 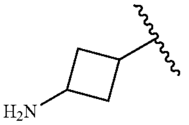 ,

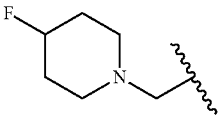 , 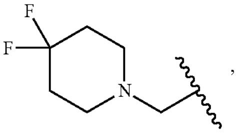 ,

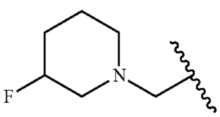 and 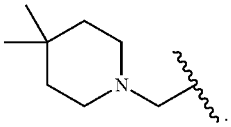 .

(23) W is

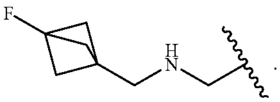 .

(24) X is a group selected from:

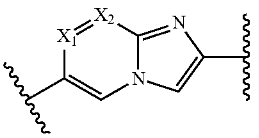 , 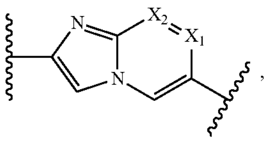 ,

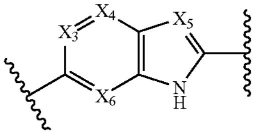 , 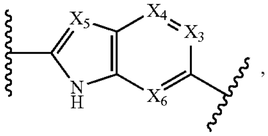 ,

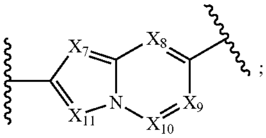 ; 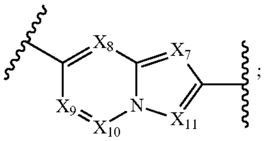 ;

-continued

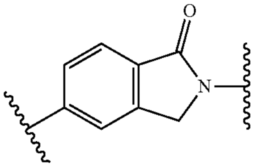 and 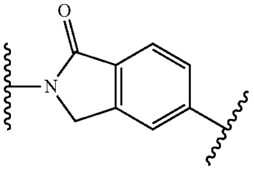 ;

wherein $X_1$, $X_2$, $X_3$, $X_4$, $X_5$, $X_6$, $X_7$, $X_8$, $X_9$, $X_{10}$ and $X_{11}$ are as defined herein;

(25) X is a group selected from:

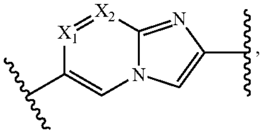 , 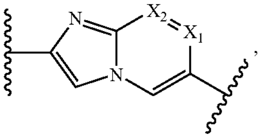 ,

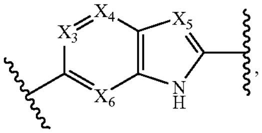 , 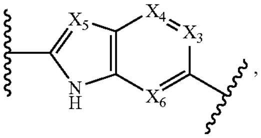 , wherein each of $X_1$, $X_2$, $X_3$, $X_4$, $X_5$ and $X_6$ as defined herein;

(26) X is a group selected from:

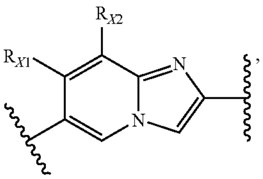 , 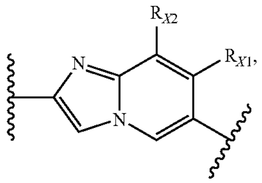

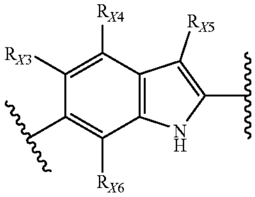 or 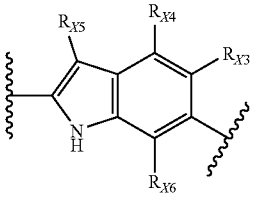

wherein:

$R_{X1}$ is H or halo;

$R_{X2}$ is H or halo;

$R_{X3}$ is H or halo;

$R_{X4}$ is H or halo;

$R_{X5}$ is H or halo; and $R_{X6}$ is H or halo;

(27) X is a group selected from:

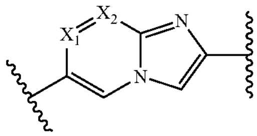 or 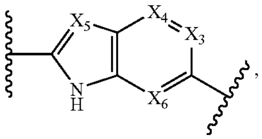 , wherein each of $X_1$, $X_2$, $X_3$, $X_4$, $X_5$ and $X_6$ as defined herein;

(28) X is selected from

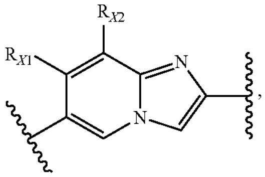, 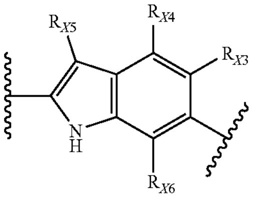

wherein $R_{X1}$ is H or halo;

$R_{X2}$ is H or halo;

$R_{X3}$ is H or halo;

$R_{X4}$ is H or halo;

$R_{X5}$ is H or halo; and $R_{X6}$ is H or halo;

(29) X is selected from:

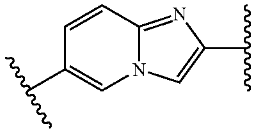 or 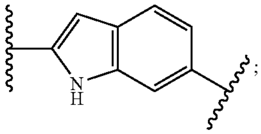;

(30) X is $C_{2-6}$alkenylene, optionally substituted by one or more hydroxy;

(31) X is $C_{3-6}$alkenylene, optionally substituted by one or more hydroxy;

(32) X is a group of the formula:

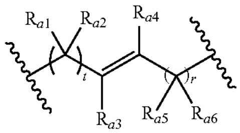

wherein t is an integer selected from 0, 1, 2 or 3 wherein r is an integer selected from 0, 1, 2 or 3; and $R_{a1}$, $R_{a2}$, $R_{a3}$, $R_{a4}$, $R_{a5}$ and $R_{a6}$ are independently selected from hydrogen or hydroxy;

(33) X is a group of the formula:

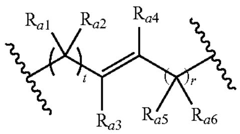

wherein t is an integer selected from 1 or 2 wherein r is an integer selected from 0, 1 or 2; and $R_{a1}$, $R_{a2}$, $R_{a3}$, $R_{a4}$, $R_{a5}$ and $R_{a6}$ are independently selected from hydrogen or hydroxy;

(34) X is a group of the formula:

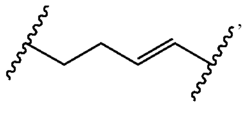, 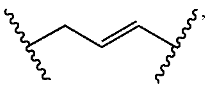,

-continued

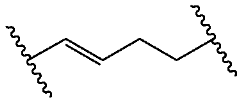 or 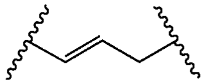

(35) X is a group of the formula:

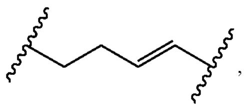, 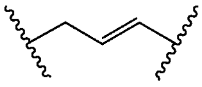 or

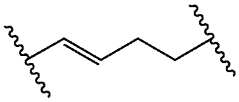

(35a) X is a group of the formula:

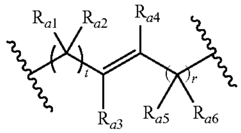

wherein t is an integer selected from 0, 1, 2 or 3 wherein r is an integer selected from 0 or 1; and $R_{a1}$, $R_{a2}$, $R_{a3}$, $R_{a4}$, $R_{a5}$ and $R_{a6}$ are independently selected from hydrogen or hydroxy;

(35b) X is a group of the formula:

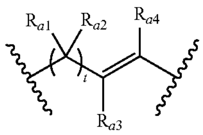

wherein t is an integer selected from 0, 1 or 2; and $R_{a1}$, $R_{a2}$, $R_{a3}$ and $R_{a4}$ are independently selected from hydrogen or hydroxy;

(35c) X is a group of the formula:

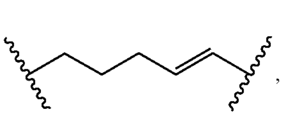, 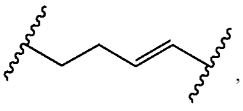,

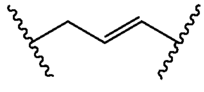 or 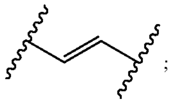;

(35d) X is a group of the formula:

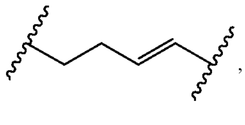, 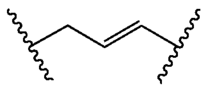 or

-continued

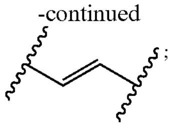

(36) X is a group of the formula:

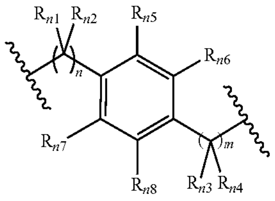

wherein n and m are each independently an integer selected from 0, 1, 2, 3 or 4; and each occurrence of $R_{n1}$, $R_{n2}$, $R_{n3}$ and $R_{n4}$ are independently selected from hydrogen or halo;

$R_{n5}$, $R_{n6}$, $R_{n7}$ and $R_{n8}$ are each independently selected from hydrogen, halo, hydroxy, cyano, $C_{1-3}$alkyl, $C_{1-3}$haloalkyl, $C_{1-3}$alkoxy, $C_{1-3}$haloalkoxy and $NR_{n9}R_{n10}$, wherein each of $R_{n9}$ and $R_{n10}$ are independently selected from hydrogen or $C_{1-2}$alkyl;

wherein each of $C_{1-3}$alkyl and $C_{1-3}$alkoxy are optionally further substituted by halo, cyano or hydroxy;

wherein n and m are each independently an integer selected from 0, 1, 2, 3 or 4; and each occurrence of $R_{n1}$, $R_{n2}$, $R_{n3}$ and $R_{n4}$ are independently selected from hydrogen or halo;

(37) X is a group of the formula;

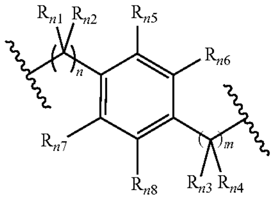

wherein n and m are each independently an integer selected from 0, 1, 2 or 3; and each occurrence of $R_{n1}$, $R_{n2}$, $R_{n3}$ and $R_{n4}$ are independently selected from hydrogen or halo; $R_{n5}$, $R_{n6}$, $R_{n7}$ and $R_{n6}$ are each independently selected from hydrogen, halo, hydroxy, cyano, methyl, methoxy and $NH_2$,

(38) X is a group of the formula:

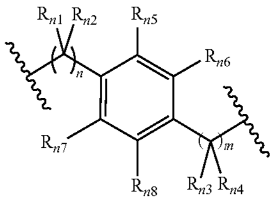

wherein m and n are each independently an integer selected from 0, 1 or 2; and each occurrence of $R_{n1}$, $R_{n2}$, $R_{n3}$ and $R_{n4}$ is independently selected from hydrogen or halo; $R_{n5}$, $R_{n6}$, $R_{n7}$ and $R_{n8}$ are each independently selected from hydrogen or halo.

(39) X is a group of the formula:

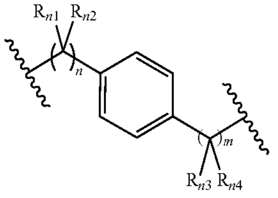

wherein m is 0 or 1 n is an integer selected from 0, 1 or 2; and each occurrence of $R_{n1}$, $R_{n2}$, $R_{n3}$ and $R_{n4}$ is independently selected from hydrogen or halo.

(40) X is a group of the formula:

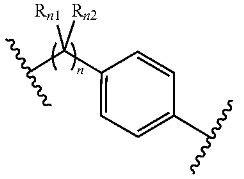

wherein:

n is an integer selected from 0, 1 or 2; and each of $R_{n1}$ and $R_{n2}$ is independently selected from hydrogen or halo.

(41) X is a group of the formula:

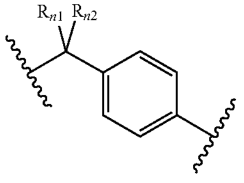

or

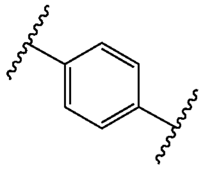

wherein $R_{n1}$ and $R_{n2}$ are independently selected from hydrogen or halo.

(42) X is a group of the formula:

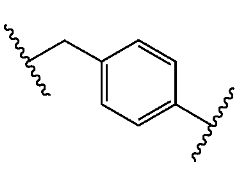

or

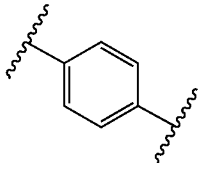

.

(43) X is selected from:

a) a group selected from;

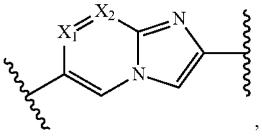,
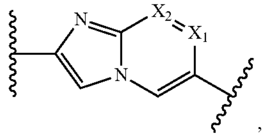,
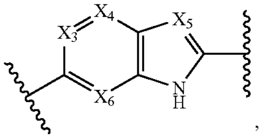,
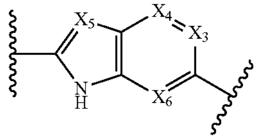, wherein:

$X_1$ is N or $CR_{X1}$, wherein $R_{X1}$ is H or halo;

$X_2$ is N or $CR_{X2}$, wherein $R_{X2}$ is H or halo;

$X_3$ is N or $CR_{X3}$, wherein $R_{X3}$ is H or halo;

$X_4$ is N or $CR_{X4}$, wherein $R_{X4}$ is H or halo;

$X_5$ is N or $CR_{X5}$, wherein $R_{X5}$ is H or halo; and $X_6$ is N or $CR_{X6}$, wherein $R_{Xe}$ is H or halo;

b) $C_{3-6}$alkenylene, optionally substituted by one or more hydroxy;

c) a group of the formula;

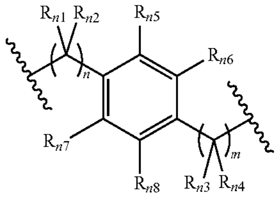

wherein n and m are each independently an integer selected from 0, 1, 2 or 3; and each occurrence of $R_{n1}$, $R_{n2}$, $R_{n3}$ and $R_{n4}$ are independently selected from hydrogen or halo; $R_{n5}$, $R_{n6}$, $R_{n7}$ and $R_{n8}$ are each independently selected from hydrogen, halo, hydroxy, cyano, methyl, methoxy and $NH_2$.

(44) X is selected from:

a) a group selected from;

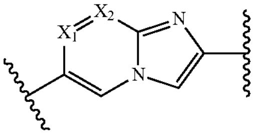

or

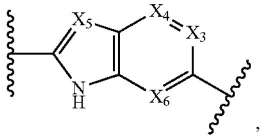, wherein:

$X_1$ is N or $CR_{X1}$, wherein $R_{X1}$ is H or halo;

$X_2$ is N or $CR_{X2}$, wherein $R_{X2}$ is H or halo;

$X_3$ is N or $CR_{X3}$, wherein $R_{X3}$ is H or halo;

$X_4$ is N or $CR_{X4}$, wherein $R_{X4}$ is H or halo;

$X_5$ is N or $CR_{X5}$, wherein $R_{X5}$ is H or halo;

$X_6$ is N or $CR_{X6}$, wherein $R_{X6}$ is H or halo;

b) $C_{3-4}$alkenylene, optionally substituted by one or more hydroxy;

c) a group of the formula;

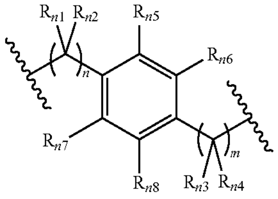

wherein m and n are each independently an integer selected from 0, 1 or 2; and each occurrence of $R_{n1}$, $R_{n2}$, $R_{n3}$ and $R_{n4}$ is independently selected from hydrogen or halo; $R_{n5}$, $R_{n6}$, $R_{n7}$ and $R_{n5}$ are independently selected from hydrogen or halo.

(45) X is selected from:

a) a group selected from;

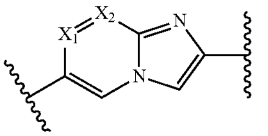

or

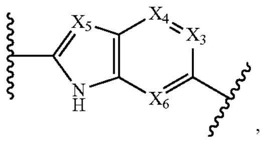, wherein:

$X_1$ is N or $CR_{X1}$, wherein $R_{X1}$ is H or halo;

$X_2$ is N or $CR_{X2}$, wherein $R_{X2}$ is H or halo;

$X_3$ is N or $CR_{X3}$, wherein $R_{X3}$ is H or halo;

$X_4$ is N or $CR_{X4}$, wherein $R_{X4}$ is H or halo;

$X_5$ is N or $CR_{x5}$, wherein $R_{X5}$ is H or halo;

$X_6$ is N or $CR_{X6}$, wherein $R_{X6}$ is H or halo;

b) a group of the formula:

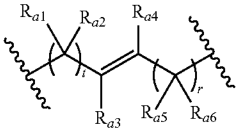

wherein t is an integer selected from 0, 1, 2 or 3 wherein r is an integer selected from 0, 1, or 2 or 3; and $R_{a1}$, $R_{a2}$, $R_{a3}$, $R_{a4}$, $R_{a5}$ and $R_{a6}$ are independently selected from hydrogen or hydroxy;

c) a group of the formula;

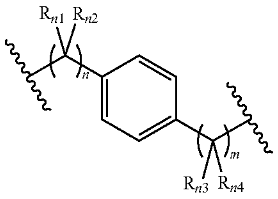

wherein m is 0 or 1 n is an integer selected from 0, 1 or 2; and each occurance of $R_{n1}$, $R_{n2}$, $R_{n3}$ and $R_{n4}$ is independently selected from hydrogen or halo.

(46) X is selected from:

a) a group selected from;

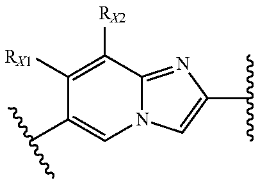

or

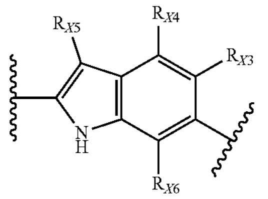

wherein:

$R_{X1}$ is H or halo;

$R_{X2}$ is H or halo;

$R_{X3}$ is H or halo;

$R_{X4}$ is H or halo;

$R_{X5}$ is H or halo; and $R_{X6}$ is H or halo;

b) a group of the formula:

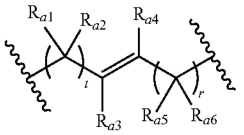

wherein t is an integer selected from 1, 2 or 3 wherein r is an integer selected from 0, 1 or 2; and $R_{a1}$, $R_{a2}$, $R_{a3}$, $R_{a4}$, $R_{a5}$ and $R_{a6}$ are independently selected from hydrogen or hydroxy;

c) a group of the formula;

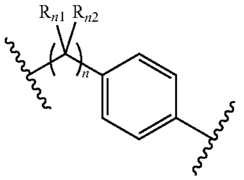

n is an integer selected from 0, 1 or 2; and each occurance of $R_{n1}$ and $R_{n2}$ is independently selected from hydrogen or halo.

(47) X is selected from:

a) a group selected from;

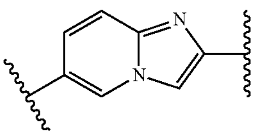

or

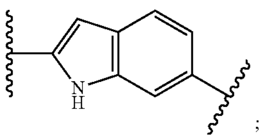

;

b) a group of the formula:

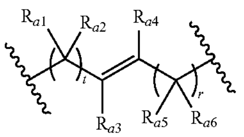

wherein t is an integer selected from 1 or 2 wherein r is an integer selected from 0, 1 or 2; and $R_{a1}$, $R_{a2}$, $R_{a3}$, $R_{a4}$, $R_{a5}$ and $R_{a6}$ are independently selected from hydrogen or hydroxy;

c) a group of the formula;

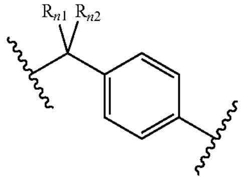

or

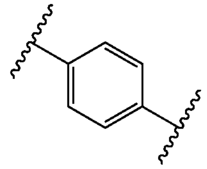

each of $R_{n1}$ and $R_{n2}$ is independently selected from hydrogen or halo.

(48) X is selected from:

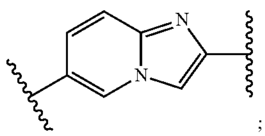

;

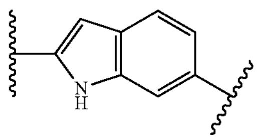

;

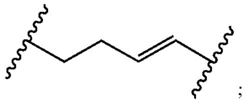

;

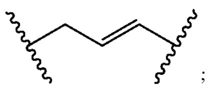

;

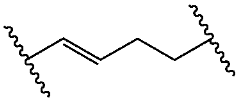

;

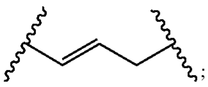

;

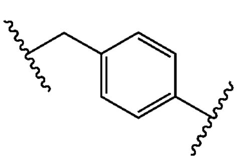

or

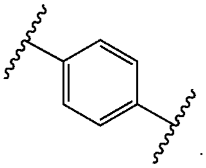

.

(49) X is selected from:

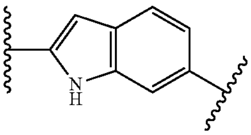

;

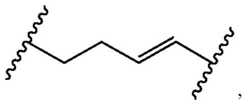

,

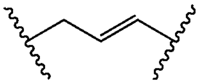

;

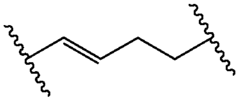

;

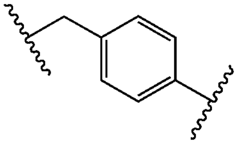

or

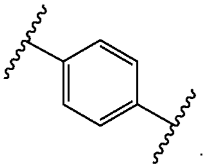

.

(49a) X is selected from:

a) a group selected from;

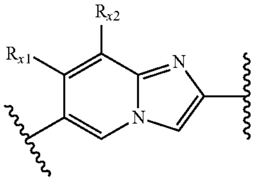 or 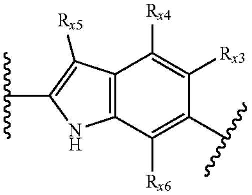

wherein:

$R_{X1}$ is H or halo;

$R_{X2}$ is H or halo;

$R_{X3}$ is H or halo;

$R_{X4}$ is H or halo;

$R_{X5}$ is H or halo; and $R_{X6}$ is H or halo;

b) a group of the formula:

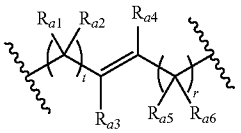

wherein t is an integer selected from 0, 1 or 2;

wherein r is an integer selected from 0 or 1; and $R_{a1}$, $R_{a2}$, $R_{a3}$, $R_{a4}$, $R_{a5}$ and $R_{a6}$ are independently selected from hydrogen or hydroxy;

c) a group of the formula;

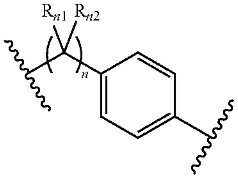

wherein:

n is an integer selected from 0, 1 or 2; and each occurance of $R_{n1}$ and $R_{n2}$ is independently selected from hydrogen or halo.

(49b) X is selected from:

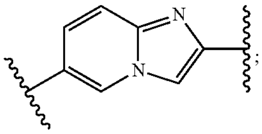; 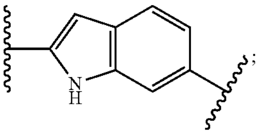;

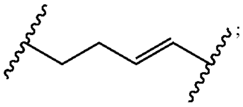; 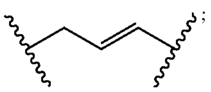;

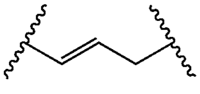; 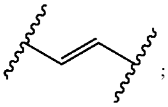;

-continued

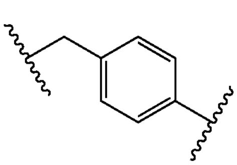 or 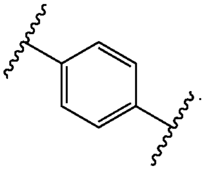.

(49c) X is selected from:

a) a group selected from;

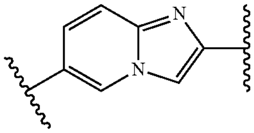 or 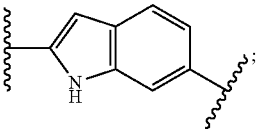;

b) a group of the formula:

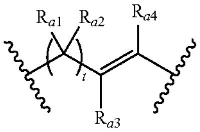

wherein t is an integer selected from 0, 1 or 2; and $R_{a1}$, $R_{a2}$, $R_{a3}$ and $R_{a4}$ are independently selected from hydrogen or hydroxy;

c) a group of the formula;

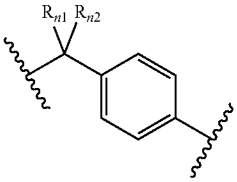 or 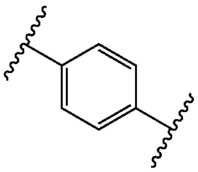

each of $R_{1j}$ and $R_{n2}$ is independently selected from hydrogen or halo.

(49d) X is selected from:

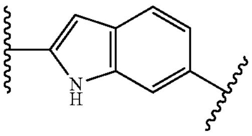; 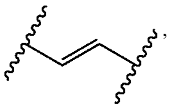,

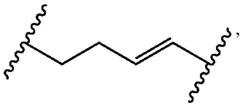, 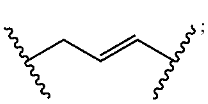;

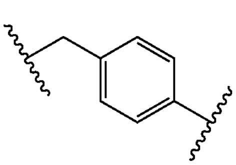 or 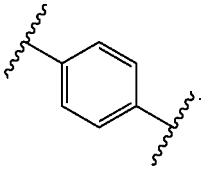.

(49e) X is selected from:

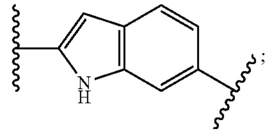;
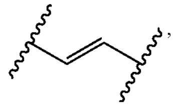,
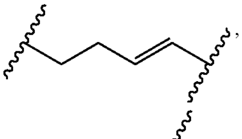,
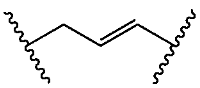 or
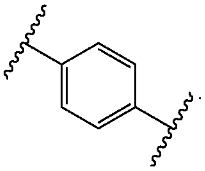.

(50) $X_1$ is $CR_{X1}$, wherein $R_{X1}$ is H or halo;
$X_2$ is $CR_{X2}$, wherein $R_{X2}$ is H or halo;
$X_3$ is $CR_{X3}$, wherein $R_{X3}$ is H or halo;
$X_4$ is $CR_{X4}$, wherein $R_{X4}$ is H or halo;
$X_5$ is N or $CR_{X5}$, wherein $R_{X5}$ is H or halo; and
$X_6$ is $CR_{X5}$, wherein $R_{X6}$ is H or halo;
$X_7$ is N or $CR_{X7}$, wherein $R_{X7}$ is H or halo;
$X_8$ is $CR_{X8}$, wherein $R_{X8}$ is H or halo;
$X_9$ is $CR_{X9}$, wherein $R_{X9}$ is H or halo;
$X_{10}$ is $CR_{X10}$, wherein $R_{X10}$ is H or halo; and
$X_{11}$ is $CR_{X11}$, wherein $R_{X11}$ is H or halo;

(51) $X_1$, $X_2$, $X_3$, $X_4$, $X_5$, $X_6$, $X_8$, $X_9$ and $X_{10}$ and $X_{11}$ are OH.

(52) $Y_1$ is selected from O or $CR_{y1}R_{y2}$ wherein each of $R_{y1}$ and $R_{y2}$ are independently selected from hydrogen, $C_{1-2}$alkyl and halo;

(53) $Y_1$ is selected from O or $CR_{y1}R_{y2}$ wherein each of $R_{y1}$ and $R_{y2}$ are independently selected from hydrogen, methyl or halo.

(54) $Y_1$ is selected from O or $CR_{y1}R_{y2}$ wherein each of $R_{y1}$ and $R_{y2}$ are independently selected from hydrogen or halo;

(55) $Y_1$ is selected from O or $CH_2$

(56) $R_1$ and $R_2$, together with the carbon atoms to which they are attached, are linked together to form a saturated or unsaturated 4 to 6 membered carbocyclic or heterocyclic ring system, wherein the carbocylic or heterocyclic ring is optionally substituted with one or more substituents selected from $C_{1-4}$alkyl, cyano, halo, hydroxy, $C_{1-4}$alkoxy or amino.

(57) $R_1$ and $R_2$, together with the carbon atoms to which they are attached, are linked together to form a saturated or unsaturated 4 to 6 membered carbocyclic or heterocyclic ring system, wherein the carbocylic or heterocyclic ring is optionally substituted with one or more substituents selected from methyl, cyano, fluoro, chloro, bromo, hydroxy or methoxy or amino.

(58) Ri and $R_2$, together with the carbon atoms to which they are attached, are linked together to form a saturated or unsaturated 4 to 6 membered carbocyclic or heterocyclic ring system, wherein the carbocylic or heterocyclic ring is optionally substituted with one or more substituents selected from methyl, hydroxy, methoxy or amino.

(59) $R_1$ and $R_2$, together with the carbon atoms to which they are attached, are linked together to form a saturated or unsaturated 4 to 6 membered carbocyclic or heterocyclic ring system, wherein the carbocylic or heterocyclic ring is optionally substituted with one or more hydroxy or amino.

(60) $R_1$ and $R_2$, together with the carbon atoms to which they are attached, are linked together to form a saturated or unsaturated 4 to 6 membered carbocyclic or heterocyclic ring system, wherein the carbocylic or heterocyclic ring is substituted with one or more hydroxy.

(61) Y is a group selected from:

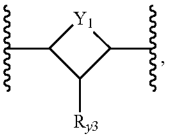,
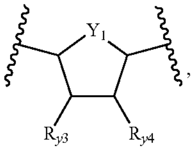,
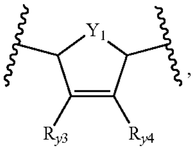,
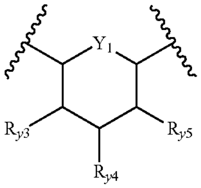

wherein:

$Y_1$ is as defined herein;

each of $R_{y3}$, $R_{y4}$, and $R_{y5}$ are as defined herein;

(62) Y is a group of the formula:

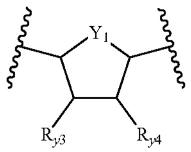

wherein:

$Y_1$ is as defined herein;

$R_{y3}$ and $R_{y4}$ are as defined herein.

(63) Y is a group selected from:

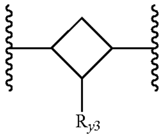,
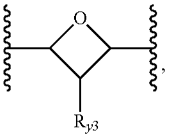,
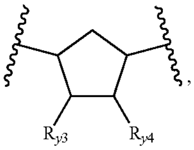,
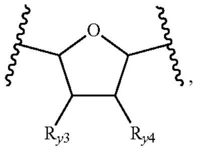,
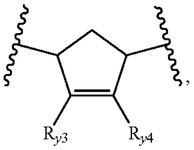,
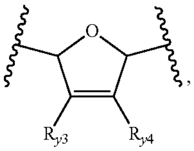,
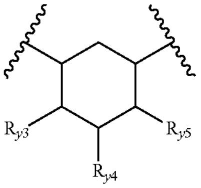 or -continued
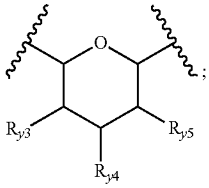;
wherein:
each of $R_{y3}$, $R_{y4}$, and $R_{y5}$ are as defined herein.
(63a) Y is a group selected from:
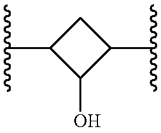, 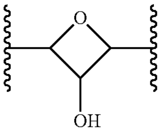, 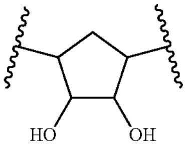, 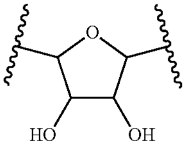, 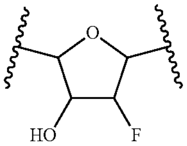, 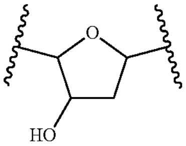, 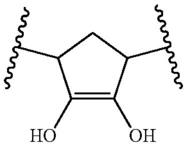, 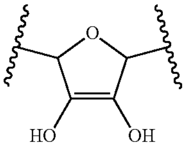, 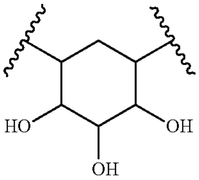 and 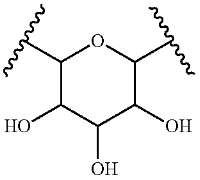.
(64) Y is a group selected from:
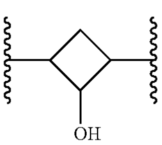, 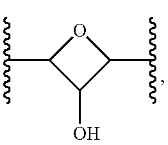, 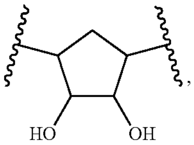, 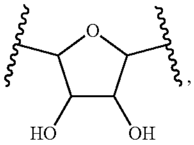, 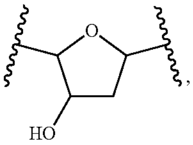, 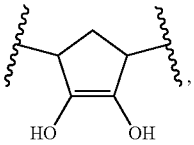, 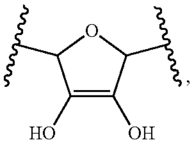,
-continued
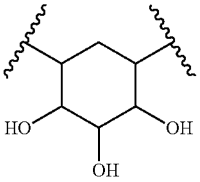 and 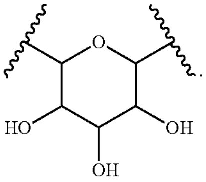.
(64a) Y is a group selected from:
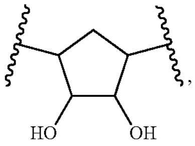, 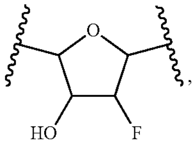, 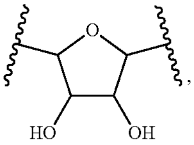, 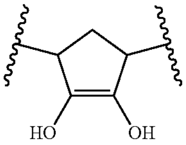 and 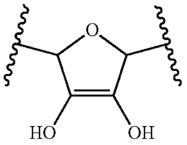.
(65) Y is a group selected from:
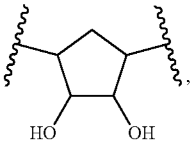, 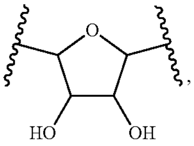, 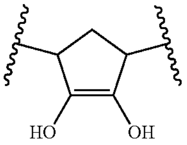 and 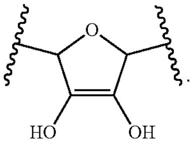.
(65a) Y is a group selected from:
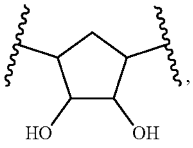, 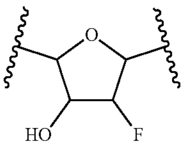 and 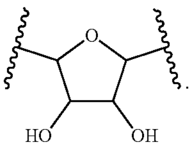.

(66) Y is a group selected from:

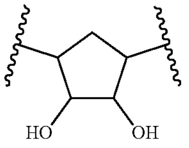

and

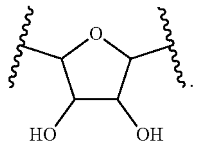

(67) $R_{y3}$, $R_{y4}$, and $R_{y5}$ are independently selected from hydrogen, $C_{1-6}$alkyl, cyano, halo, hydroxy, $C_{1-4}$alkoxy, $C_{1-4}$haloalkoxy or amino.

(68) $R_{y3}$, $R_{y4}$, and $R_{y5}$ are independently selected from hydrogen, $C_{1-4}$alkyl, hydroxy, halo, $C_{1-6}$alkoxy or amino.

(69) $R_{y3}$, $R_{y4}$, and $R_{y5}$ are independently selected from hydrogen, methyl, cyano, fluoro, chloro, hydroxy, methoxy or amino.

(69a) $R_{y3}$, $R_{y4}$, and $R_{y5}$ are independently selected from hydrogen, hydroxy or fluoro.

(70) $R_{y3}$, $R_{y4}$, and $R_{y5}$ are independently selected from hydrogen and hydroxy.

(71) $R_{y3}$, $R_{y4}$, and $R_{y5}$ are hydroxy.

(72) $Z_2$ is selected from $CR_{Z2}$ or N, wherein $R_{Z2}$ is selected from hydrogen, halo, cyano, $C_{1-4}$alkyl, $C_{1-4}$haloalkyl, $C_{3-6}$cycloalkyl, aryl, heterocyclyl or heteroaryl, wherein each of any $C_{1-4}$alkyl, $C_{1-4}$haloalkyl, $C_{3-6}$cycloalkyl, heteroaryl, aryl, heterocyclyl is optionally substituted with one or more substituents selected from, $C_{1-4}$alkyl, $C_{1-4}$haloalkyl, halo, trifluoromethyl, trifluoromethoxy, amino, cyano, hydroxy, or amino.

(73) $Z_2$ is selected from $CR_{Z2}$ or N, wherein $R_{Z2}$ is selected from hydrogen, halo, $C_{1-4}$alkyl, $C_{1-4}$haloalkyl, $C_{3-6}$cycloalkyl, wherein each of any $C_{1-4}$alkyl, $C_{1-4}$haloalkyl, $C_{3-6}$cycloalkyl is optionally substituted with one or more substituents selected from, $C_{1-4}$alkyl, $C_{1-4}$haloalkyl, halo, amino, cyano, hydroxy, or amino.

(74) $Z_2$ is selected from $CR_{Z2}$ or N, wherein $R_{Z2}$ is selected from hydrogen, halo, $C_{1-3}$alkyl, wherein $C_{1-3}$alkyl is optionally substituted with one or more fluoro.

(75) $Z_2$ is N or $CR_{Z2}$ wherein $R_{Z2}$ is hydrogen, halo or methyl.

(76) $Z_2$ is N or $CR_{Z2}$ wherein $R_{Z2}$ is hydrogen, fluoro, chloro, bromo or methyl, wherein methyl is optionally substituted with one or more fluoro.

(77) $Z_2$ is $CR_{Z2}$ wherein $R_{Z2}$ is hydrogen, fluoro, chloro, bromo or methyl, wherein methyl is optionally substituted with one or more fluoro.

(78) $Z_2$ is $CR_{Z2}$ wherein $R_{Z2}$ is halo.

(79) $Z_2$ is $CR_{Z2}$ wherein $R_{Z2}$ is bromo.

(80) Z is a group of the formula:

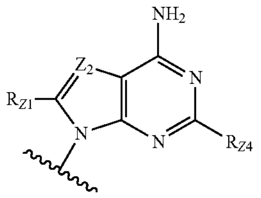

wherein $R_{Z1}$ and $R_{Z4}$ are independently selected from hydrogen, halo or cyano; and $Z_2$ is as defined herein.

(81) Z is a group of the formula:

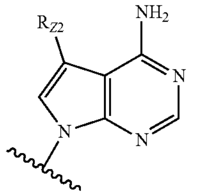

wherein $R_{Z2}$ is as defined herein.

(82) Z is selected from:

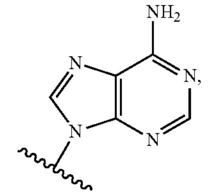

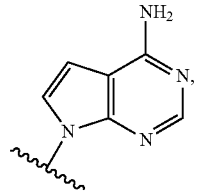

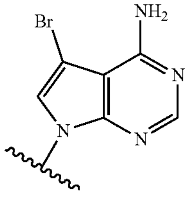

or

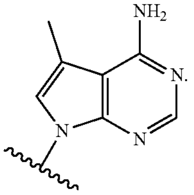

(83) Z is a group of the formula:

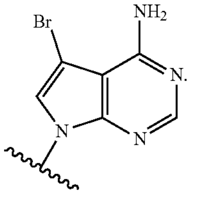 [SMILES: *n1cc(Br)c2c(N)ncnc21]

(84) $R_{Z1}$, $R_{Z3}$, $R_{Z4}$ and $R_{Z5}$ are independently selected from hydrogen, halo or cyano.

(85) $R_{Z1}$, $R_{Z3}$, $R_{Z4}$ and $R_{Z5}$ are independently selected from hydrogen or halo.

(86) $R_{Z1}$, $R_{Z3}$, $R_{Z4}$ and $R_{Z5}$ are hydrogen.

Suitably, a heteroaryl or heterocyclyl group as defined herein is a monocyclic heteroaryl or heterocyclyl group comprising one, two or three heteroatoms selected from N, O or S.

Suitably, a heteroaryl is a 5- or 6-membered heteroaryl ring comprising one, two or three heteroatoms selected from N, O or S.

Suitably, a heterocyclyl group is a 4-, 5- or 6-membered heterocyclyl ring comprising one, two or three heteroatoms selected from N, O or S. Most suitably, a heterocyclyl group is a 5- or 6-membered ring comprising one, two or three heteroatoms selected from N, O or S [e.g. morpholinyl (e.g. 4-morpholinyl), oxetane, methyloxetane (e.g. 3-methyloxetane), pyrrolidinone (e.g. pyrrolidin-2-one)].

Suitably, an aryl group is phenyl.

Suitably, W is as defined in any one of paragraphs (1) to (14) or any one of paragraphs (15) to (23). Suitably, W is as defined in any one of paragraphs (8) to (14) or any one of paragraphs (20) to (23). Most suitably, W is as defined in paragraph (12), (14), (22), (22a) or (23)

Suitably, X is as defined in any one of paragraphs (24) to (49). More suitably, X is as defined in any one of paragraphs (43) to (49). Most suitably, X is as defined in paragraph (46), (47), (48) or (49).

Suitably, X is as defined in any one of paragraphs (24) to (49e). More suitably, X is as defined in any one of paragraphs (43) to (49e). Most suitably, X is as defined in paragraph (46), (47), (48) or (49). X may also be as defined in any of paragraphs (48a), (49a), (49b), (49c), (49d) or (49e).

Suitably, $X_1$, $X_2$, $X_3$, $X_4$, $X_5$, $X_6$, $X_7$, $X_8$, $X_9$, $X_{10}$ and $X_{11}$ are as defined in paragraphs (50) or (51). Most suitably, $X_1$, $X_2$, $X_3$, $X_4$, $X_5$, $X_6$, $X_7$, $X_5$, $X_9$, $X_{10}$ and $X_{11}$ are as defined in paragraph (51).

Suitably, $Y_1$ is as defined in any one of paragraphs (52) to (55). More suitably, $Y_1$ is as defined in any one of paragraphs (53) to (55). Most suitably, $Y_1$ is as defined in paragraph (55)

Suitably, $R_1$ and $R_2$ are as defined in any one of paragraphs (56) to (60). More suitably, $R_1$ and $R_2$ are as defined in any one of paragraphs (58) to (60). Most suitably, $R_1$ and $R_2$ are as defined in paragraph (60).

Suitably, Y is as defined in any one of paragraphs (61) to (66). More suitably, Y is as defined in any one of paragraphs (64) to (66). Most suitably, Y is as defined in paragraph (66).

Suitably, $R_{y3}$, $R_{y4}$, and $R_{y5}$ are as defined in any one of paragraphs (67) to (71). More suitably, $R_{y3}$, $R_{y4}$, and $R_{y5}$ are as defined in any one of paragraphs (69) to (71). Most suitably, $R_{y3}$, $R_{y4}$, and $R_{y5}$ are as defined in paragraph (71), i.e. $R_{y3}$, $R_{y4}$, and $R_{y5}$ are hydroxy.

Suitably, $Z_2$ is as defined in any one of paragraphs (72) to (79). More suitably, $Z_2$ is as defined in any one of paragraphs (75) to (79). Most suitably, $Z_2$ is as defined in paragraph (79).

Suitably, Z is as defined in any one of paragraphs (80) to (83). More suitably Z is as defined in paragraph (82) or (83). Most suitably, Z is as defined in paragraph (83).

Suitably, $R_{Z1}$, $R_{Z3}$, $R_{Z4}$ and $R_{Z5}$ are as defined in any one of paragraphs (84) to (86). More suitably $R_{Z1}$, $R_{Z3}$, $R_{Z4}$ and $R_{Z5}$ are as defined in paragraph (85) or (86). Most suitably, $R_{Z1}$, $R_{Z3}$, $R_{Z4}$ and $R_{Z5}$ are as defined in paragraph (86).

In a particular group of compounds of the invention, Y is as defined in paragraph (62), i.e. the compounds have a structural formula (II) (a sub-definition of formula (II) shown below, or a pharmaceutically acceptable salt thereof:

(II)

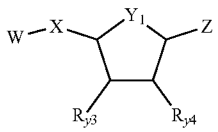

wherein, $Y_1$, $R_{y3}$, $R_{y4}$, W, X and Z each have any one of the meanings defined herein.

In an embodiment of the compounds of formula (II):

$R_{y3}$ and $R_{y4}$ are as defined in any one of paragraphs (67) to (71);

$Y_1$ is as defined in any one of paragraphs (52) to (55);

W is as defined in any one of paragraphs (1) to (14) or any one of paragraphs (15) to (23);

X is as defined in any one of paragraphs (24) to (49) and (49a) to (49e); and

Z is as defined in any one of paragraphs (80) to (83).

In an embodiment of the compounds of formula (II):

$R_{y3}$ and $R_{y4}$ are as defined in any one of paragraphs (69) to (71);

$Y_1$ is as defined in any one of paragraphs (53) to (55);

W is as defined in any one of paragraphs (8) to (14) or any one of paragraphs (20) to (23);

X is as defined in any one of paragraphs (43) to (49) and (49c) to (49e); and

Z is as defined in any one of paragraphs (82) or (83).

In an embodiment of the compounds of formula (II):

$R_{y3}$ and $R_{y4}$ are as defined in paragraph (71);

$Y_1$ is as defined in paragraph (55);

W is as defined in paragraph (12), (14), (22), (22a) or (23);

X is as defined in paragraph (49) or (49e); and

Z is as defined in paragraph (83).

In a particular group of compounds of the invention, Z is as defined in paragraph (80) i.e. the compounds have a structural formula (III) (a sub-definition of formula (I)) shown below, or a pharmaceutically acceptable salt thereof:

(III)

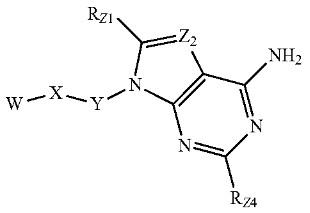

wherein, W, X, Y, $R_{Z1}$, $R_{Z4}$ and $Z_2$ each have any one of the meanings defined herein.

In an embodiment of the compounds of formula (III):

W is as defined in any one of paragraphs (1) to (14) or any one of paragraphs (15) to (23);

X is as defined in any one of paragraphs (24) to (49) and (49a) to (49e); and

Y is as defined in any one of paragraphs (61) to (66);

$R_{Z1}$ and $R_{Z4}$ are as defined in any one of paragraphs (84) to (86); and $Z_2$ is as defined in any one of paragraphs (72) to (79).

In an embodiment of the compounds of formula (III):

W is as defined in any one of paragraphs (8) to (14) or any one of paragraphs (20) to (23);

X is as defined in any one of paragraphs (43) to (49) and (49c) to (49e);

Y is as defined in any one of paragraphs (64) to (66);

$R_{Z1}$ and $R_{Z4}$ are as defined in any one of paragraphs (85) or (86); and $Z_2$ is as defined in any one of paragraphs (75) to (79).

In an embodiment of the compounds of formula (III):

W is as defined in paragraph (12), (14), (22), (22a) or (23);

X is as defined in paragraph (49) or (49e); and

Z is as defined in paragraph (83),

Y is as defined in paragraph (66);

$R_{Z1}$ and $R_{Z4}$ are as defined in in paragraph (86); and $Z_2$ is as defined in in paragraph (79).

In a particular group of compounds of the invention, Y is as defined in paragraph (62) and Z is as deinfed in paragraph (80) i.e. the compounds have a structural formula (IV) (a sub-definition of formula (I)) shown below, or a pharmaceutically acceptable salt thereof:

(IV)

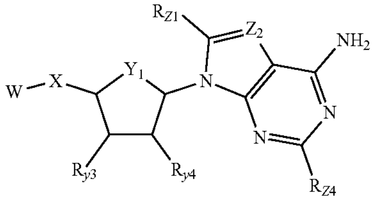

wherein, W, X, $Y_1$, $R_{y3}$, $R_{y4}$, $R_{Z1}$, $R_{Z4}$ and $Z_2$ each have any one of the meanings defined herein.

In an embodiment of the compounds of formula (IV):

$R_{y3}$ and $R_{y4}$ are as defined in any one of paragraphs (67) to (71);

$Y_1$ is as defined in any one of paragraphs (52) to (55);

W is as defined in any one of paragraphs (1) to (14) or any one of paragraphs (15) to (23);

X is as defined in any one of paragraphs (24) to (49) and (49a) to (49e);

$R_{Z1}$ and $R_{Z4}$ are as defined in any one of paragraphs (84) to (86); and $Z_2$ is as defined in any one of paragraphs (72) to (79).

In an embodiment of the compounds of formula (IV):

$R_{y3}$ and $R_{y4}$ are as defined in any one of paragraphs (69) to (71);

$Y_1$ is as defined in any one of paragraphs (53) to (55);

W is as defined in any one of paragraphs (8) to (14) or any one of paragraphs (20) to (23);

X is as defined in any one of paragraphs (43) to (49) and (49c) to (49e);

$R_{Z1}$ and $R_{Z4}$ are as defined in any one of paragraphs (85) or (86); and $Z_2$ is as defined in any one of paragraphs (75) to (79).

In an embodiment of the compounds of formula (IV):

$R_{y3}$ and $R_{y4}$ are as defined in paragraph (71);

$Y_1$ is as defined in paragraph (55);

W is as defined in paragraph (12), (14), (22), (22a) or (23);

X is as defined in paragraph (49) or (49e);

$R_{Z1}$ and $R_{Z4}$ are as defined in in paragraph (86); and $Z_2$ is as defined in in paragraph (79).

In an embodiment of the compounds of formula (IV):

$R_{y3}$ and $R_{y4}$ are as defined in (69) to (71);

$Y_1$ is as defined in any one of paragraphs (53) to (55);

W is as defined in any one of paragraphs (8) to (14) or any one of paragraphs (20) to (23);

X is as defined in any one of paragraphs (43) to (49);

$R_{Z1}$ and $R_{Z4}$ are as defined in any one of paragraphs (85) or (86); and $Z_2$ is as defined in any one of paragraphs (75) to (79).

In a particular group of compounds of the invention, the compounds have a structural formula (V), (VI) or (VIII), (sub-definitions of formula (I)) shown below, or a pharmaceutically acceptable salt thereof:

(V)

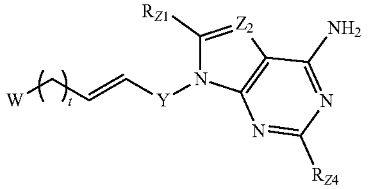

-continued (VI)

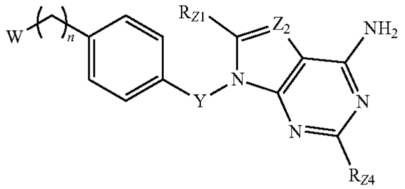

(VII)

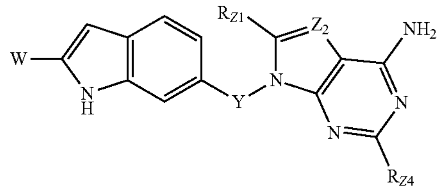

wherein:

t is an integer selected from 0, 1 or 2;

n is an integer selected from 0 or 1; and

W, Y, $R_{Z1}$, $R_{Z4}$ and $Z_2$ each have any one of the meanings defined herein.

In an embodiment of the compounds of formula (V), (VI) or (VIII):

W is as defined in any one of paragraphs (1) to (14) or any one of paragraphs (15) to (23);

Y is as defined in any one of paragraphs (61) to (66);

$R_{Z1}$ and $R_{Z4}$ are as defined in any one of paragraphs (84) to (86); and $Z_2$ is as defined in any one of paragraphs (72) to (79).

In an embodiment of the compounds of formula (V), (VI) or (VIII):

W is as defined in any one of paragraphs (8) to (14) or any one of paragraphs (20) to (23);

Y is as defined in any one of paragraphs (64) to (66);

$R_{Z1}$ and $R_{Z4}$ are as defined in any one of paragraphs (85) or (86); and $Z_2$ is as defined in any one of paragraphs (75) to (79).

In an embodiment of the compounds of formula (V), (VI) or (VIII):

W is as defined in paragraph (12), (14), (22), (22a) or (23);

Y is as defined in paragraph (66);

$R_{Z1}$ and $R_{Z4}$ are as defined in in paragraph (86); and $Z_2$ is as defined in in paragraph (79).

In a particular group of compounds of the invention, the compounds have a structural formula (VIII), (IX) or (X), (sub-definitions of formula (I)) shown below, or a pharmaceutically acceptable salt thereof:

(VIII)

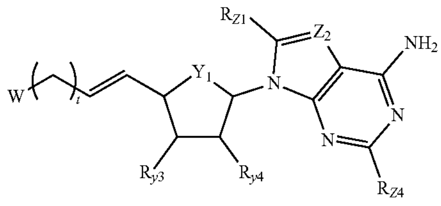

-continued

IX

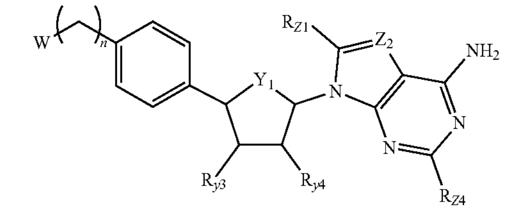

(X)

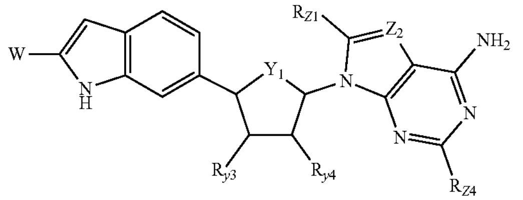

wherein:

t is an integer selected from 0, 1 or 2;

n is an integer selected from 0 or 1; and

W, $Y_1$, $R_{y3}$, $R_{y4}$, $R_{Z1}$, $R_{Z4}$ and $Z_2$ each have any one of the meanings defined herein.

In an embodiment of the compounds of formula (VIII), (IX) or (X), $R_{y3}$ and $R_{y4}$ are as defined in any one of paragraphs (67) to (71);

$Y_1$ is as defined in any one of paragraphs (52) to (55);

W is as defined in any one of paragraphs (1) to (14) or any one of paragraphs (15) to (23);

$R_{Z1}$ and $R_{Z4}$ are as defined in any one of paragraphs (84) to (86); and $Z_2$ is as defined in any one of paragraphs (72) to (79).

In an embodiment of the compounds of formula (VIII), (IX) or (X), $R_{y3}$ and $R_{y4}$ are as defined in any one of paragraphs (69) to (71);

$Y_1$ is as defined in any one of paragraphs (53) to (55);

W is as defined in any one of paragraphs (8) to (14) or any one of paragraphs (20) to (23);

$R_{Z1}$ and $R_{Z4}$ are as defined in any one of paragraphs (85) or (86); and $Z_2$ is as defined in any one of paragraphs (75) to (79).

In an embodiment of the compounds of formula (VIII), (IX) or (X), $R_{y3}$ and $R_{y4}$ are as defined in paragraph (71);

$Y_1$ is as defined in paragraph (55);

W is as defined in paragraph (12), (14), (22), (22a) or (23);

$R_{Z1}$ and $R_{Z4}$ are as defined in in paragraph (86); and $Z_2$ is as defined in in paragraph (79).

In an embodiment of the compounds of formula (VIII), (IX) or (X), $R_{y3}$ and $R_{y4}$ are as defined in (69) to (71);

$Y_1$ is as defined in any one of paragraphs (53) to (55);

W is as defined in any one of paragraphs (8) to (14) or any one of paragraphs (20) to (23);

$R_{Z1}$ and $R_{Z4}$ are as defined in any one of paragraphs (85) or (86); and $Z_2$ is as defined in any one of paragraphs (75) to (79).

Particular compounds of the present invention include any of the compounds exemplified in the present application, or a pharmaceutically acceptable salt thereof, and, in particular, any of the following:

(2R,3R,4S,5R)-2-(4-amino-5-bromo-7H-pyrrolo[2,3-d]pyrimidin-7-yl)-5-((E)-5-(benzylamino)pent-1-en-1-yl)tetrahydrofuran-3,4-diol;

(2R,3R,4S,5R)-2-{4-amino-5-bromo-7H-pyrrolo[2,3-d]pyrimidin-7-yl}-5-[(1E)-5-[(cyclobutylmethyl)amino]pent-1-en-1-yl]oxolane-3,4-diol;

(2R,3R,4S,5R)-2-{4-amino-5-bromo-7H-pyrrolo[2,3-d]pyrimidin-7-yl}-5-[(1E)-4-(benzylamino)but-1-en-1-yl]oxolane-3,4-diol;

(2R,3R,4S,5R)-2-{4-amino-5-bromo-7H-pyrrolo[2,3-d]pyrimidin-7-yl}-5-[(1E)-5-{[(3,3-difluorocyclobutyl)methyl]amino}pent-1-en-1-yl]oxolane-3,4-diol;

(2R,3R,4S,5R)-2-[4-amino-5-bromo-7H-pyrrolo[2,3-d]pyrimidin-7-yl)-5-[(1E)-5-(benzylamino)pent-1-en-1-yl]oxolane-3,4-diol;

(2R,3R,4S,5R)-2-[4-amino-5-bromo-7H-pyrrolo[2,3-d]pyrimidin-7-yl)-5-[(1E)-5-[({3-fluorobicyclo[1.1.1]pentan-1-yl}methyl)amino]pent-1-en-1-yl]oxolane-3,4-diol;

(2R,3R,4S,5R)-2-[4-amino-5-bromo-7H-pyrrolo[2,3-d]pyrimidin-7-yl)-5-[(1E)-4-aminobut-1-en-1-yl]oxolane-3,4-diol;

(2R,3R,4S,5R)-2-{4-amino-5-bromo-7H-pyrrolo[2,3-d]pyrimidin-7-yl}-5-[(1E)-5-aminopent-1-en-1-yl]oxolane-3,4-diol;

(2R,3R,4S,5R)-2-(4-amino-5-bromo-7H-pyrrolo[2,3-d]pyrimidin-7-yl)-5-((E)-5-(benzylamino)pent-3-en-1-yl)tetrahydrofuran-3,4-diol;

(1R,2S,3R,5R)-3-(4-amino-5-bromo-7H-pyrrolo[2,3-d]pyrimidin-7-yl)-5-(4-(((cyclobutylmethyl)amino)methyl)phenyl)cyclopentane-1,2-diol;

(1R,2S,3R,5R)-3-{4-amino-5-bromo-7H-pyrrolo[2,3-d]pyrimidin-7-yl}-5-(2-{[({3-fluorobicyclo[1.1.1]pentan-1-yl}methyl)amino]methyl}-1H-indol-6-yl)cyclopentane-1,2-diol; and (1R,2S,3R,5R)-3-{4-amino-5-bromo-7H-pyrrolo[2,3-d]pyrimidin-7-yl}-5-(4-{2-[({3-fluorobicyclo[1.1.1]pentan-1-yl}methyl)amino]ethyl}phenyl)cyclopentane-1,2-diol.

Particular compounds of the present invention include any of the compounds exemplified in the present application, or a pharmaceutically acceptable salt thereof, and, in particular, any of the following:

(2R,3R,4S,5R)-2-(4-amino-5-bromo-7H-pyrrolo[2,3-d]pyrimidin-7-yl)-5-((E)-5-(benzylamino)pert-1-en-1-yl)tetrahydrofuran-3,4-diol (2R,3R,4S,5R)-2-[4-amino-5-bromo-7H-pyrrolo[2,3-d]pyrimidin-7-yl)-5-[(1E)-5-[(cyclobutylmethyl)amino]pent-1-en-1-yl]oxolane-3,4-diol (2R,3R,4S,5R)-2-{4-amino-5-bromo-7H-pyrrolo[2,3-d]pyrimidin-7-yl}-5-[(1E)-4-(benzylamino)but-1-en-1-yl]oxolane-3,4-diol (2R,3R,4S,5R)-2-[4-amino-5-bromo-7H-pyrrolo[2,3-d]pyrimidin-7-yl)-5-[(1E)-5-{[(3,3-difluorocyclobutyl)methyl]amino}pent-1-en-1-yl]oxolane-3,4-diol (2R,3R,4S,5R)-2-{4-amino-5-bromo-7H-pyrrolo[2,3-d]pyrimidin-7-yl}-5-[(1E)-5-(benzylamino)pent-1-en-1-yl]oxolane-3,4-diol (2R,3R,4S,5R)-2-{4-amino-5-bromo-7H-pyrrolo[2,3-d]pyrimidin-7-yl}-5-[(1E)-5-[({3-fluorobicyclo[1.1.1]pentan-1-yl}methyl)amino]pent-1-en-1-yl]oxolane-3,4-diol (2R,3R,4S,5R)-2-{4-amino-5-bromo-7H-pyrrolo[2,3-d]pyrimidin-7-yl}-5-[(1E)-4-aminobut-1-en-1-yl]oxolane-3,4-diol (2R,3R,4S,5R)-2-{4-amino-5-bromo-7H-pyrrolo[2,3-d]pyrimidin-7-yl}-5-[(1E)-5-aminopent-1-en-1-yl]oxolane-3,4-diol (2R,3R,4S,5R)-2-(4-amino-5-bromo-7H-pyrrolo[2,3-d]pyrimidin-7-yl)-5-((E)-5-(benzylamino)pent-3-en-1-yl)tetrahydrofuran-3,4-diol (1R,2S,3R,5R)-3-(4-amino-5-bromo-7H-pyrrolo[2,3-d]pyrimidin-7-yl)-5-(4-(((cyclobutylmethyl)amino)methyl)phenyl)cyclopentane-1,2-diol (1R,2S,3R,5R)-3-{4-amino-5-bromo-7H-pyrrolo[2,3-d]pyrimidin-7-yl}-5-(2-{[({3-fluorobicyclo[1.1.1]pentan-1-yl}methyl)amino]methyl}-1H-indol-6-yl)cyclopentane-1,2-diol (1R,2S,3R,5R)-3-{4-amino-5-bromo-7H-pyrrolo[2,3-d]pyrimidin-7-yl}-5-(4-{2-[({3-fluorobicyclo[1.1.1]pentan-1-yl}methyl)amino]ethyl}phenyl)cyclopentane-1,2-diol (2R,3R,4S,5R)-2-{4-amino-5-bromo-7H-pyrrolo[2,3-d]pyrimidin-7-yl}-5-[(1E)-2-(azetidin-3-yl)ethenyl]oxolane-3,4-diol (2R,3R,4S,5R)-2-{4-amino-5-bromo-7H-pyrrolo[2,3-d]pyrimidin-7-yl}-5-[(1E)-2-(piperidin-4-yl)ethenyl]oxolane-3,4-diol (2R,3R,4S,5R)-2-{4-amino-5-bromo-7H-pyrrolo[2,3-d]pyrimidin-7-yl}-5-[(1E)-2-(piperidin-3-yl)ethenyl]oxolane-3,4-diol (2R,3R,4S,5R)-2-{4-amino-5-bromo-7H-pyrrolo[2,3-d]pyrimidin-7-yl}-5-[(1E)-2-(pyrrolidin-3-yl)ethenyl]oxolane-3,4-diol (2R,3R,4S,5R)-2-{4-amino-5-bromo-7H-pyrrolo[2,3-d]pyrimidin-7-yl}-5-[(1E)-2-(3-aminocyclobutyl)ethenyl]oxolane-3,4-diol (2R,3R,4S,5R)-2-[4-amino-5-bromo-7H-pyrrolo[2,3-d]pyrimidin-7-yl)-5-[(1E)-2-(oxetan-3-yl)ethenyl]oxolane-3,4-diol (2R,3R,4S,5R)-2-[4-amino-5-bromo-7H-pyrrolo[2,3-d]pyrimidin-7-yl)-5-[(1E)-3-(azetidin-3-yl)prop-1-en-1-yl]oxolane-3,4-diol (2R,3R,4S,5R)-2-[4-amino-5-(1H-pyrazol-3-yl)-7H-pyrrolo[2,3-d]pyrimidin-7-yl]-5-[(1E)-5-[({3-fluorobicyclo[1.1.1]pentan-1-yl}methyl)amino]pent-1-en-1-yl]oxolane-3,4-diol ((2R,3R,4S,5R)-2-{4-amino-5-bromo-7H-pyrrolo[2,3-d]pyrimidin-7-yl}-5-[(1E)-5-{6-azaspiro[3.4]octan-6-yl}pent-1-en-1-yl]oxolane-3,4-diol (2R,3S,5R)-5-(4-amino-5-bromo-pyrrolo[2,3-d]pyrimidin-7-yl)-2-[(E)-5-[(3-fluoro-1-bicyclo[1.1.1]pentanyl)methylamino]pent-1-enyl]tetrahydrofuran-3-ol (2R,3R,4S,5R)-2-{4-amino-5-bromo-7H-pyrrolo[2,3-d]pyrimidin-7-yl}-5-[(1E)-5-(4,4-difluoropiperidin-1-yl)pent-1-en-1-yl]oxolane-3,4-diol (2R,3R,4S,5R)-2-{4-amino-5-bromo-7H-pyrrolo[2,3-d]pyrimidin-7-yl}-5-[(1E)-5-(4-fluoropiperidin-1-yl)pent-1-en-1-yl]oxolane-3,4-diol (2R,3R,4S,5R)-2-{4-amino-5-bromo-7H-pyrrolo[2,3-d]pyrimidin-7-yl}-5-[(1E)-5-(morpholin-4-yl)pent-1-en-1-yl]oxolane-3,4-diol (2R,3R,4S,5R)-2-{4-amino-5-bromo-7H-pyrrolo[2,3-d]pyrimidin-7-yl}-5-[(1E)-5-(3-fluoropiperidin-1-yl)pent-1-en-1-yl]oxolane-3,4-diol (2R,3R,5S)-2-{4-amino-5-bromo-7H-pyrrolo[2,3-d]pyrimidin-7-yl}-5-[(1E)-5-[({3-fluorobicyclo[1.1.1]pentan-1-yl}methyl)amino]pent-1-en-1-yl]oxolan-3-ol (2R,3S,4R,5R)-2-{4-amino-5-bromo-7H-pyrrolo[2,3-d]pyrimidin-7-yl}-4-fluoro-5-[(1E)-5-[({3-fluorobicyclo[1.1.1]pentan-1-yl}methyl)amino]pent-1-en-1-yl]oxolan-3-ol (1R,2S,3R,5R)-3-{4-amino-5-fluoro-7H-pyrrolo[2,3-d]pyrimidin-7-yl}-5-(2-{[({3-fluorobicyclo[1.1.1]pentan-1-yl}methyl)amino]methyl}-1H-indol-6-yl)cyclopentane-1,2-diol (1R,2S,3R,5R)-3-{4-amino-5-chloro-7H-pyrrolo[2,3-d]pyrimidin-7-yl}-5-(2-{[({3-fluorobicyclo[1.1.1]pentan-1-yl}methyl)amino]methyl}-1H-indol-6-yl)cyclopentane-1,2-diol (1R,2S,3R,5R)-3-{4-amino-5-bromo-7H-pyrrolo[2,3-d]pyrimidin-7-yl}-5-(2-{[({3-fluorobicyclo[1.1.1]pentan-1-yl}methyl)amino]methyl}-1H-indol-5-yl)cyclopentane-1,2-diol (1R,2S,3R,5R)-3-{4-amino-5-bromo-7H-pyrrolo[2,3-d]pyrimidin-7-yl}-5-[2-({6-azaspiro[3.4]octan-6-yl}methyl)-1H-indol-6-yl]cyclopentane-1,2-diol (1R,2S,3R,5R)-3-{4-amino-7H-pyrrolo[2,3-d]pyrimidin-7-yl}-5-[2-({6-azaspiro[3.4]octan-6-yl}methyl)-1H-indol-6-yl]cyclopentane-1,2-diol (1R,2S,3R,5R)-3-{4-amino-5-bromo-7H-pyrrolo[2,3-d]pyrimidin-7-yl}-5-(4-{[({3-fluorobicyclo[1.1.1]pentan-1-yl}methyl)amino]methyl}phenyl)cyclopentane-1,2-diol (1R,2S,3R,5R)-3-{4-amino-5-bromo-7H-pyrrolo[2,3-d]pyrimidin-7-yl}-5-[4-({6-azaspiro[3.4]octan-6-yl}methyl)phenyl]cyclopentane-1,2-diol (1R,2S,3R,5R)-3-{4-amino-5-bromo-7H-pyrrolo[2,3-d]pyrimidin-7-yl}-5-{4-[(4,4-dimethylpiperidin-1-yl)methyl]phenyl}cyclopentane-1,2-diol (1R,2S,3R,5R)-3-{4-amino-5-bromo-7H-pyrrolo[2,3-d]pyrimidin-7-yl}-5-(3-{2-[({3-fluorobicyclo[1.1.1]pentan-1-yl}methyl)amino]ethyl}phenyl)cyclopentane-1,2-diol (1R,2S,3R,5R)-3-{4-amino-5-bromo-7H-pyrrolo[2,3-d]pyrimidin-7-yl}-5-[3-({6-azaspiro[3.4]octan-6-yl}methyl)phenyl]cyclopentane-1,2-diol (1R,2S,3R,5R)-3-{4-amino-5-bromo-7H-pyrrolo[2,3-d]pyrimidin-7-yl}-5-(3-{[({3-fluorobicyclo[1.1.1]pentan-1-yl}methyl)amino]methyl}phenyl)cyclopentane-1,2-diol 3-[(1R,2R,3S,4R)-4-[4-amino-5-bromo-7H-pyrrolo[2,3-d]pyrimidin-7-yl)-2,3-dihydroxycyclopentyl]-N-({3-fluorobicyclo[1.1.1]pentan-1-yl}methyl)benzamide.

A further compound of the invention is (2R,3R,4R,5R)-5-{4-amino-5-bromo-7H-pyrrolo[2,3-d]pyrimidin-7-yl}-4-fluoro-2-[(1E)-5-[({3-fluorobicyclo[1.1.1]pentan-1-yl}methyl)amino]pent-1-en-1-yl]oxolan-3-ol, or a pharmaceutically acceptable salt thereof.

The various functional groups and substituents making up the compounds of the formula (I) are typically chosen such that the molecular weight of the compound of the formula (I) does not exceed 1000. More usually, the molecular weight of the compound will be less than 900, for example less than 800, or less than 750, or less than 700, or less than 650. More preferably, the molecular weight is less than 600 and, for example, is 550 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess antiproliferative activity.

The present invention also encompasses compounds of the invention as defined herein which comprise one or more isotopic substitutions. For example, H may be in any isotopic form, including $^{1}H$, $^{2}H(D)$, and $^{3}H$ (T); C may be in any isotopic form, including $^{12}C$, $^{13}C$, and $^{14}C$; and O may be in any isotopic form, including $^{16}O$ and $^{18}O$; and the like.

It is also to be understood that certain compounds of the formula (I) (and compounds of formula (II), (III) and (IV)) may exist in solvated as well as unsolvated forms such as, for example, hydrated forms. It is to be understood that the invention encompasses all such solvated forms that possess antiproliferative activity.

It is also to be understood that certain compounds of the formula (I) (and compounds of formula (II), (III) and (IV)) may exhibit polymorphism, and that the invention encompasses all such forms that possess antiproliferative activity.

Compounds of the formula (I) (and compounds of formula (II), (III) and (IV)) may exist in a number of different tautomeric forms and references to compounds of the formula (I) include all such forms. For the avoidance of doubt, where a compound can exist in one of several tautomeric forms, and only one is specifically described or shown, all others are nevertheless embraced by formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

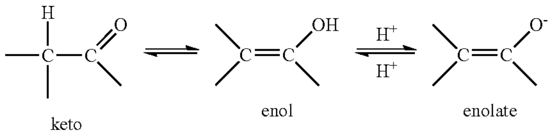

Compounds of the formula (I) containing an amine function may also form N-oxides. A reference herein to a compound of the formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, $4^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

The compounds of formula (I) may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula (I) and in-vivo cleavable amide derivatives that may be formed at a carboxy group or an amino group in a compound of the formula (I).

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula (I) that are produced by organic synthetic means and also such compounds that are produced in the human or animal body by way of metabolism of a precursor compound, that is a compound of the formula (I) may be a synthetically-produced compound or a metabolically-produced compound.

A suitable pharmaceutically acceptable pro-drug of a compound of the formula (I) is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);

d) H. Bundgaard, *Advanced Drug Delivery Reviews,* 8, 1-38 (1992);
e) H. Bundgaard, et al., *Journal of Pharmaceutical Sciences,* 77, 285 (1988);
f) N. Kakeya, et al., *Chem. Pharm. Bull.,* 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula (I) that possesses a carboxy group is, for example, an in vivo cleavable ester thereof. An in vivo cleavable ester of a compound of the formula (I) containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_3$acycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$ alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula (I) that possesses a hydroxy group is, for example, an in vivo cleavable ester or ether thereof. An in vivo cleavable ester or ether of a compound of the formula (I) containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula (I) that possesses a carboxy group is, for example, an in vivo cleavable amide thereof, for example an amide formed with an amine such as ammonia, a $C_{1-4}$alkylamine such as methylamine, a $(C_{1-4}alkyl)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula (I) that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula (I) may be exerted in part by one or more metabolites that are formed within the human or animal body after administration of a compound of the formula (I). As stated hereinbefore, the in vivo effects of a compound of the formula (I) may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of formula I will vary depending on the nature of the variable groups. Suitable processes for their preparation are described further in the accompanying Examples.

Once a compound of formula I has been synthesised by any one of the processes defined herein, the processes may then further comprise the additional steps of:

(i) removing any protecting groups present;

(ii) converting the compound formula I into another compound of formula I;

(iii) forming a pharmaceutically acceptable salt, hydrate or solvate thereof; and/or (iv) forming a prodrug thereof.

The resultant compounds of formula I can be isolated and purified using techniques well known in the art.

Biological Activity

The METTL3 enzyme and cell assays described in accompanying Example section may be used to measure the pharmacological effects of the compounds of the present invention.

Although the pharmacological properties of the compounds of formula I vary with structural change, as expected, the compounds of the invention were found to be active in these METTL3 assays.

In general, the compounds of the invention demonstrate an $IC_{50}$ of 10 μM or less in the METTL3 enzyme assay described herein, with preferred compounds of the invention demonstrating an $IC_{50}$ of 5 μM or less and the most preferred compounds of the invention demonstrating an $IC_{50}$ of 2 μM or less.

In the METTL3 cell assay described in the Example section, the compounds of formula (I) suitably possess an activity of less than 10 μM, with preferred compounds of the invention demonstrating an $IC_{50}$ of 5 μM or less and the most preferred compounds demonstrating an activity of 2 μM or less.

Pharmaceutical Compositions

According to a further aspect of the invention there is provided a pharmaceutical composition which comprises a compound of the invention as defined hereinbefore, or a pharmaceutically acceptable salt thereof, and one or more pharmaceutically acceptable excipients.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition and/or treat or prevent an autoimmune disease referred to herein, slow its progression and/or reduce the symptoms associated with the condition and/or disease.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula (I) will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as inhibitors of METTL3 activity.

The present invention therefore provides a method of inhibiting METTL3 activity in vitro or in vivo, said method comprising contacting a cell with an effective amount of a compound, or a pharmaceutically acceptable salt thereof, or a pharmaceutical composition as defined herein.

The present invention also provides a method of treating a disease or disorder in which METTL3 activity is implicated in a patient in need of such treatment, said method comprising administering to said patient a therapeutically effective amount of a compound, or a pharmaceutically acceptable salt thereof, or a pharmaceutical composition as defined herein. Suitably, the disease or disorder in which METTL3 activity is implicated is cancer, such as lung cancer, renal cancer, solid organ cancer, pancreatic cancer or leukaemia, type 2 diabetes, a neuropsychiatric behavioural disorder, infection (e.g. viral infection) or a depressive disorder.

The present invention provides a method of inhibiting cell proliferation, in vitro or in vivo, said method comprising contacting a cell with an effective amount of a compound, or a pharmaceutically acceptable salt thereof, as defined herein.

The present invention provides a method of treating a proliferative disorder, said method comprising administering to a subject in need thereof a therapeutically effective amount of a compound, or a pharmaceutically acceptable salt thereof, or a pharmaceutical composition as defined herein.

The present invention provides a method of treating cancer, said method comprising administering to a subject in need thereof a therapeutically effective amount of a compound, or a pharmaceutically acceptable salt thereof, or a pharmaceutical composition as defined herein. Suitably the cancer is lung cancer, renal cancer, solid organ cancer, pancreatic cancer or leukaemia suitably AML leukaemia or chronic myeloid leukaemia.

The present invention provides a method of treating leukaemia, said method comprising administering to a subject in need thereof a therapeutically effective amount of a compound, or a pharmaceutically acceptable salt thereof, or a pharmaceutical composition as defined herein.

The present invention provides a method of treating AML leukaemia, said method comprising administering to a subject in need thereof a therapeutically effective amount of a compound, or a pharmaceutically acceptable salt thereof, or a pharmaceutical composition as defined herein.

The present invention provides a method of treating an autoimmune disease, said method comprising administering to a subject in need thereof a therapeutically effective amount of a compound, or a pharmaceutically acceptable salt thereof, or a pharmaceutical composition as defined herein. Suitably the autoimmune disease is colitis, multiple sclerosis, rheumatoid arthritis, lupus, cirrhosis, or dermatitis.

The present invention provides a method of treating a neurological disease, said method comprising administering to a subject in need thereof a therapeutically effective amount of a compound, or a pharmaceutically acceptable salt thereof, or a pharmaceutical composition as defined herein.

The present invention provides a method of treating an infectious disease, said method comprising administering to a subject in need thereof a therapeutically effective amount of a compound, or a pharmaceutically acceptable salt thereof, or a pharmaceutical composition as defined herein.

The present invention provides a method of treating an inflammatory disease, said method comprising administering to a subject in need thereof a therapeutically effective amount of a compound, or a pharmaceutically acceptable salt thereof, or a pharmaceutical composition as defined herein.

The present invention provides a compound, or a pharmaceutically acceptable salt thereof, or a pharmaceutical composition as defined herein for use in therapy.

The present invention provides a compound, or a pharmaceutically acceptable salt thereof, or a pharmaceutical composition as defined herein for use in the treatment of a proliferative condition.

The present invention provides a compound, or a pharmaceutically acceptable salt thereof, or a pharmaceutical composition as defined herein for use in the treatment of cancer. In a particular embodiment, the cancer is human cancer. Suitably the cancer is lung cancer, renal cancer, solid organ cancer, pancreatic cancer or leukaemia suitably AML leukaemia or chronic myeloid leukaemia.

The present invention provides a compound, or a pharmaceutically acceptable salt thereof, or a pharmaceutical composition as defined herein for use in the treatment of leukaemia.

The present invention provides a compound, or a pharmaceutically acceptable salt thereof, or a pharmaceutical composition as defined herein for use in the treatment of AML leukaemia.

The present invention provides a compound, or a pharmaceutically acceptable salt thereof, or a pharmaceutical composition as defined herein for use in the inhibition of METTL3 activity.

The present invention provides a compound, or a pharmaceutically acceptable salt thereof, or a pharmaceutical composition as defined herein for use in the treatment of an autoimmune disease. Suitably the autoimmune disease is colitis, multiple sclerosis, rheumatoid arthritis, lupus, cirrhosis, or dermatitis.

The present invention provides a compound, or a pharmaceutically acceptable salt thereof, or a pharmaceutical composition as defined herein for use in the treatment of an neurological disease.

The present invention provides a compound, or a pharmaceutically acceptable salt thereof, or a pharmaceutical composition as defined herein for use in the treatment of an infectious disease.

The present invention provides a compound, or a pharmaceutically acceptable salt thereof, or a pharmaceutical composition as defined herein for use in the treatment of an inflammatory disease.

The present invention provides a compound, or a pharmaceutically acceptable salt thereof, as defined herein for use in the treatment of a disease or disorder in which METTL3 activity is implicated. Suitably, the disease or disorder in which METTL3 activity is implicated is cancer, such as lung cancer, renal cancer, solid organ cancer, pancreatic cancer or leukaemia, type 2 diabetes, a neuropsychiatric behavioural disorder or a depressive disorder.

The present invention provides a use of a compound, or a pharmaceutically acceptable salt thereof, as defined herein in the manufacture of a medicament for the treatment of a proliferative condition.

The present invention provides a use of a compound, or a pharmaceutically acceptable salt thereof, as defined herein in the manufacture of a medicament for the treatment of cancer. Suitably, the medicament is for use in the treatment of human cancers. Suitably the cancer is lung cancer, renal cancer, solid organ cancer, pancreatic cancer or leukaemia suitably AML leukaemia or chronic myeloid leukaemia.

The present invention provides a use of a compound, or a pharmaceutically acceptable salt thereof, as defined herein in the manufacture of a medicament for the treatment of leukaemia.

The present invention provides a use of a compound, or a pharmaceutically acceptable salt thereof, as defined herein in the manufacture of a medicament for the treatment of AML leukaemia.

The present invention provides a use of a compound, or a pharmaceutically acceptable salt thereof, as defined herein in the manufacture of a medicament for the treatment of an autoimmune disease. Suitably the autoimmune disease is colitis, multiple sclerosis, rheumatoid arthritis, lupus, cirrhosis, or dermatitis.

The present invention provides a use of a compound, or a pharmaceutically acceptable salt thereof, as defined herein in the manufacture of a medicament for the treatment of a neurological disease.

The present invention provides a use of a compound, or a pharmaceutically acceptable salt thereof, as defined herein in the manufacture of a medicament for the treatment of an inflammatory disease.

The present invention provides a use of a compound, or a pharmaceutically acceptable salt thereof, as defined herein in the manufacture of a medicament for the treatment of an infectious disease.

The present invention provides a use of a compound, or a pharmaceutically acceptable salt thereof, as defined herein in the manufacture of a medicament for the inhibition of METTL3 activity.

The present invention provides a use of a compound, or a pharmaceutically acceptable salt thereof, as defined herein in the manufacture of a medicament for the treatment of a disease or disorder in which METTL3 activity is implicated. Suitably, the disease or disorder in which METTL3 activity is implicated is cancer, such as lung cancer, renal cancer, solid organ cancer, pancreatic cancer or leukaemia, type 2 diabetes, a neuropsychiatric behavioural disorder or a depressive disorder.

The term "proliferative disorder" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain and skin.

The anti-proliferative effects of the compounds of the present invention have particular application in the treatment of human cancers (by virtue of their inhibition of METTL3 activity).

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

In a particular embodiment of the invention, the proliferative condition to be treated is cancer.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™] the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors; (v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin av[33 function and angiostatin)]; (vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan; (viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies; and (xi) Agents used to treat AML leukaemia, including for example, cytarabine, FLT3 inhibitors, BCL2 inhibitors or IDH1/2 inhibitors.

In a particular embodiment, the antiproliferative treatment defined hereinbefore may involve, in addition to the compound of the invention, conventional surgery or radiotherapy or chemotherapy.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt thereof, and any one of the anti-tumour agents listed herein above.

In a further aspect of the invention there is provided a compound of the invention or a pharmaceutically acceptable salt thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt thereof, in combination with an anti-tumour agent (optionally selected from one listed herein above), in association with a pharmaceutically acceptable diluent or carrier.

In another embodiment, the invention relates to a therapeutic combination comprising a compound as defined herein and another agent ised to treat AML leukaemia e.g., cytarabine, FLT3 inhibitors, BCL2 inhibitors or IDH1/2 inhibitors.

Examples

Spectroscopic Methods:

Analytical HPLC/LCMS:

Method A refers to low pH analysis using a mobile phase consisting of 0.1% formic acid in a gradient of 5-100%

MeCN in water over 1.2 min at a flow rate of 1.2 mL/min. The stationary phase consisted of a Kinetex Core-Shell C18, 2.1 mm×50 mm, 5 μm. The experiment was run at 40° C.

Method B refers to high pH analysis using a mobile phase consisting of 2 mM ammonium bicarbonate, buffered to pH10 in a gradient of 5-100% MeCN in water over 2.1 min at a flow rate of 1 mL/min. The stationary phase consisted of a Phenomenex Gemini-NX C18, 2.0×50 mm, 3 μm. The experiment was run at 40° C.

Method C refers to high pH analysis using a mobile phase consisting of 2 mM ammonium bicarbonate, buffered to pH10 in a gradient of 5-100% MeCN in water over 5.8 min at a flow rate of 0.6 mL/min. The stationary phase consisted of a Waters UPLC® BEH™ C18, 2.1×100 mm, 1.7 μm. The experiment was run at 40° C.

Method D refers to high pH analysis using a mobile phase consisting of 2 mM ammonium bicarbonate, buffered to pH10 in a gradient of 5-100% MeCN in water over 5.9 min at a flow rate of 0.6 mL/min. The stationary phase consisted of a Phenomenex Gemini-NX C18, 2.0×100 mm, 3 μm. The experiment was run at 40° C.

Method E refers to low pH analysis using a mobile phase consisting of 0.1% formic acid in a gradient of 5-100% MeCN in water over 5.3 min at a flow rate of 0.6 mL/min. The stationary phase consisted of a Phenomenex Kinetix-XB C18, 2.1 mm×100 mm, 1.7 μm. The experiment was run at 40° C.

LCMS Method J refers to high pH analysis using a mobile phase consisting of 2 mM ammonium bicarbonate, buffered to pH10 in a gradient of 1-100% MeCN over 1.35 min at a flow rate of 1 mL/min. The stationary phase consisted of a Waters UPLC® BEH™ 018 2.1×30 mm, 1.7 μm. The experiment was run at 40° C.

LCMS Method M refers to a Low pH analysis using a mobile phase consisting of 0.1% Formic acid in water in a gradient of 5-100% of 0.1% formic acid in water: 0.1% formic acid in acetonitrile over 2.25 min at a flow rate of 1.2 mL/min. The stationary phase consisted of Phenomenex Kinetex Core-Shell C8 50×2.1 mm, 2.6 □m. The experiment was run at 40° C.

Method UC_03_WATER_SLOW_LC refers to neutral pH analysis using a mobile phase consisting of water (100%) in a gradient of 0-100% acetonitrile in water over 9.0 min at a flow rate of 0.8 mL/min. The stationary phase consisted of a sunfire C18, 4.6×150 mm, 3.5 μm. The experiment was run at 30° C.

Method LC04_ABR2 refers to high pH analysis using a mobile phase consisting of 5 mM ammonium bicarbonate, buffered to pH10 in a gradient of 10-100% acetonitrile in water over 9.0 min at a flow rate of 1.0 mL/min. The stationary phase consisted of a Waters UPLC® BEH™ 018 4.6×150 mm, 3.5 μm. The experiment was run at 30° C.

Method LC_04_WATER_ACN refers to neutral pH analysis using a mobile phase consisting of water (100%) in a gradient of 0-100% Acetonitrile in water over 9.0 min at a flow rate of 0.8 mL/min. The stationary phase consisted of a sunfire C18, 4.6×150 mm, 3.5 μm. The experiment was run at 30° C.

Method LC05_FAR1_01 refers to low pH analysis using a mobile phase consisting of 0.1% Formic acid in water (pH=2.70) in a gradient of 8-100% of 0.1% formic acid in water: acetonitrile (10:90) in over 4.20 min at a flow rate of 1.0 mL/min. The stationary phase consisted of xtimate C18, 4.6×50 mm, 5 μm column. The experiment was run at 30° C.

Method LC05_FAR1_17 min refers to low pH analysis using a mobile phase consisting of 0.1% Formic acid in water (pH=2.7) in a gradient of 10-100% of acetonitrile in over 9.00 min at a flow rate of 1.0 mL/min. The stationary phase consisted of xtimate C18, 4.6×150 mm, 5 μm column. The experiment was run at 30° C.

Method LC05_FAR1_01 refers to low pH analysis using a mobile phase consisting of 0.1% Formic acid in water (pH=2.70) in a gradient of 8-100% of 0.1% formic acid in water: acetonitrile (10:90) in water over 3.00 min at a flow rate of 1.0 mL/min. The stationary phase consisted of a xtimate C18 4.6×50 mm, 5.0 μm. The experiment was run at 30° C.

Method UC03_ABR2 refers to high pH analysis using a mobile phase consisting of 5 mM ammonium bicarbonate, buffered to pH10 in a gradient of 3-100% Acetonitrile in water over 3.0 min at a flow rate of 0.5 mL/min. The stationary phase consisted of a Waters UPLC® BEH™ 018 2.1×50 mm, 2.5 μm. The experiment was run at 30° C.

HP05_TFAR01 refers to low pH analysis using a mobile phase consisting of 0.1% trifluoroacetic acid in water, pH ~2.0 in a gradient of 10-100% Acetonitrile in water over 9.0 min at a flow rate of 1 mL/min. The stationary phase consisted of a Xtimate column C18, 4.6×150 mm, 5 μm. The experiment was run at 30° C.

HP05_TFAR1_ELSD_02 refers to low pH analysis using a mobile phase consisting of 0.1% trifluoroacetic acid in water, pH~2.0 in a gradient of 10-100% Acetonitrile in water over 9.0 min at a flow rate of 1.0 mL/min. The stationary phase consisted of a Xtimate column C18, 4.6×150 mm, 5 μm. The experiment was run at 30° C. with ELSD parameter evaporator temperature 60° C., nebulizer temperature is 40° C. and gas flow 1.60 SLM.

HP_07_TFAR1 refers to low pH analysis using a mobile phase consisting of 0.05% trifluoroacetic acid in water, pH ~2.0 in a gradient of 10-100% Acetonitrile in water over 9.0 min at a flow rate of 1 mL/min. The stationary phase consisted of a Xtimate column C18, 4.6×150 mm, 5 μm. The experiment was run at 30° C.

Preparative HPLC:

Method A refers to low pH purification using a mobile phase consisting of 0.1% Formic acid in a gradient of 10-95% MeCN in water over 14.4 min at a flow rate of 40 mL/min. The stationary phase consisted of a Waters Sunfire C18, 30×100 mm, 10 μm.

Method B refers to high pH purification using a mobile phase consisting of 0.2% ammonium hydroxide in a gradient of 30-95% MeCN in water over 10 min at a flow rate of 40 mL/min. The stationary phase consisted of a Waters XBridge™ C18 OBD™, 30×100 mm, 10 μm.

The following abbreviations have been used in the Examples:

HATU—[dimethylamino(triazolo[4,5-b]pyridin-3-yloxy) methylene]-dimethyl-ammonium;hexafluorophosphate DBU—1,8-Diazabicyclo[5.4.0]undec-7-ene DIPEA—N-ethyl-N-isopropyl-propan-2-amine DIAD—Di-isoproylazodicarboxylate DMF—Dimethylformamide DCM—Dichloromethane EtOAC—Ethyl Acetate THF—Tetrahydrofuran RT—Retention Time Phase sep cartridge—Telos phase separator 6 mL Example 1: Synthesis of (2R,3R,4S,5R)-2-(4-amino-5-bromo-7H-pyrrolo[2,3-d]pyrimidin-7-yl)-5-((E)-5-(benzylamino)pent-1-en-1-yl)tetrahydrofuran-3,4-diol

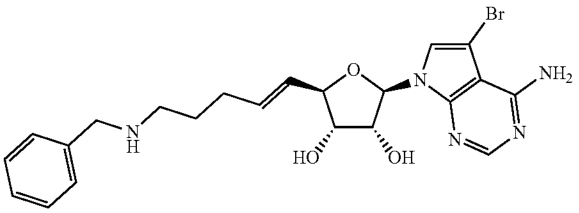 [SMILES: Nc1ncnc2c1c(Br)cn2[C@@H]1O[C@H](/C=C/CCCNCc2ccccc2)[C@@H](O)[C@H]1O]

Step-1: (1R,5R,6S,8R)-8-Methoxy-3,3-dimethyl-2,4,7-trioxabicyclo[3.3.0]octane-6-carbaldehyde

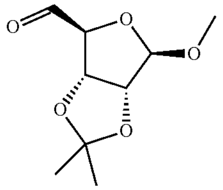

Procedure

A solution of oxalyl chloride (11.7 mL, 134.6 mmol) in DCM (200 mL) was added to a mixture of DMSO (11.0 mL, 208.0 mmol) and DCM (25 mL) at −78° C. The resulting reaction mixture was stirred at −78° C. for 10 min. A solution of {(1R,5R,6R,8R)-8-Methoxy-3,3-dimethyl-2,4,7-trioxabicyclo[3.3.0]oct-6-yl}methanol (25 g, 122.4 mmol) in DCM (25 mL) was added dropwise at −78° C. and stirred for 15 min. Diisopropylethylamine (104.5 mL, 612.02 mmol) was added dropwise to the reaction mixture and the resulting solution was stirred at −78° C. for 30 min. The reaction mixture was allowed to warm to room temperature and stirred for additional 1.5 hours. TLC analysis showed full conversion. A second batch on the same scale was prepared and the batches combined together for work up. The mixture was diluted with saturated $NaHCO_3$ solution and extracted with DCM ($3\times10^{00}$ mL). The combined organic layers were dried over $Na_2SO_4$ and concentrated under reduced pressure to afford (1R,5R,6S,8R)-8-methoxy-3,3-dimethyl-2,4,7-trioxabicyclo[3.3.0]octane-6-carbaldehyde (49.3 g, 99.58%). H NMR: ($CDCl_3$, 400 MHz) δ 9.57 (s, 1H), 5.08 (s, 1H), 5.04 (d, J=6 Hz, 1H), 4.49 (d, J=6 Hz, 1H), 4.47 (s, 1H), 3.44 (s, 3H), 1.48 (s, 3H), 1.32 (s, 3H).

Step-2: (1R,5R,6R,8R)-6-Methoxy-3,3-dimethyl-8-vinyl-2,4,7-trioxabicyclo[3.3.0]octane

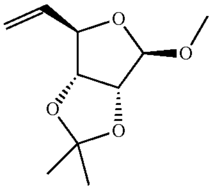

Procedure

To a stirred suspension of tBuOK (83.16 g, 742.5 mmol) in $Et_2O$ (1000 mL) was added Methyltriphenyl phosphonium bromide (265.0 g, 742.5 mmol) at 0° C. The resulting reaction mixture was stirred for 2 hours. A solution of (1R,5R,6S,8R)-8-methoxy-3,3-dimethyl-2,4,7-trioxabicyclo[3.3.0]octane-6-carbaldehyde (50.0 g, 247.5 mmol) in $Et_2O$ (300 mL) was added drop wise at 0° C. The reaction mixture was allowed to stir at room temperature for 24 hours. The resulting reaction mixture was filtered under vacuum and washed with n-pentane (700 mL). The resulting filtrate was concentrated under reduced pressure at 35° C. temperature (500 mbar). The obtained crude was cooled at −78° C. and triturated with n-pentane (500 mL) three times. The combined pentane layer was concentrated under reduced pressure 35° C. temperature (500 mbar) to afford (1R,5R,6R,8R)-6-methoxy-3,3-dimethyl-8-vinyl-2,4,7-trioxabicyclo[3.3.0]octane (47.10 g, 96.46%); $^1$H NMR: (DMSO, 400 MHz) δ 5.86-5.77 (m, 1H), 5.30-5.26 (dt, J=1.6, 1H), 5.15-5.11 (dt, J=1.2, 1H), 4.92 (s, 1H), 4.63 (d, J=5.6, 1H) 4.58 (d, J=6, 1H), 4.52 (d, J=8.4, 1H), 3.23 (s, 3H), 1.38 (s, 3H), 1.25 (s, 3H).

Step-3: (2R,3R,4S,5R)-5-vinyltetrahydrofuran-2,3,4-triol

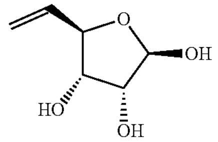

Procedure

To a stirred suspension of (3aR,4R,6R,6aR)-4-methoxy-2,2-dimethyl-6-vinyltetrahydrofuro[3,4-d][1,3]dioxole (23.5 g, 117.3 mmol) in acetone (122.5 mL) was added 10% $H_2SO_4$ (122.50 mL) at room temperature and stirred at 75° C. for 5 hours. A second batch on the same scale was prepared and the batches combined together for work up. The mixture was neutralizing with saturated $NaHCO_3$ solution and extracted with 20% THE in ethyl acetate (1000 mL×3). The combined organic layers were dried over $Na_2SO_4$ and concentrated under reduced pressure to afford (2R,3R,4S,5R)-5-vinyltetrahydrofuran-2,3,4-triol (11.6 g, 33.74%). $^1$H NMR: (D20, 400 MHz) δ 5.78-5.70 (m, 1H), 5.28-5.11 (m, 3H), 4.27-4.16 (m, 1H), 3.99-3.82 (m, 2H).

Step-4: (2R,3R,4S,5R)-2-(5-bromo-4-chloro-7H-pyrrolo[2,3-d]pyrimidin-7-yl)-5-vinyltetrahydrofuran-3,4-diol

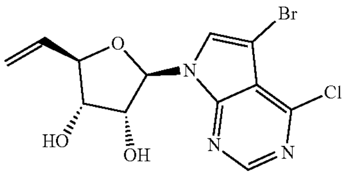 [SMILES: C=C[C@H]1O[C@@H](n2cc(Br)c3c(Cl)ncnc32)[C@H](O)[C@@H]1O]

Procedure

To a stirred solution 5-Bromo-4-chloro-7H-pyrrolo[2,3-d]pyrimidine (CAS No. 22276-95-5) (2.3 g, 9.91 mmol) and (2R,3R,4S,5R)-5-vinyltetrahydrofuran-2,3,4-triol (2.9 g, 19.8 mmol) in THF (30 mL) was added DBU (1.80 g, 11.8 mmol) and stirred for 15 min. $P(n\text{-}Bu)_3$ (4.91 mL, 20.7 mmol) was added followed by addition of DIAD (4.0 mL, 19.8 mmol) at room temperature. The reaction mixture was stirred for 1 hour. Three more batches of same scale using above identical method were combined for work up. The reaction mixture was diluted with water (60 mL) and extracted with ethyl acetate (4×100 mL). The combined organic layer was dried over anhydrous $Na_2SO_4$, concentrated under reduced pressure. The obtained crude material was purified by silica gel (60-120 mesh) column chromatography using 22% ethyl acetate in Hexane to afford (2R,3R,4S,5R)-2-(5-bromo-4-chloro-7H-pyrrolo[2,3-d]pyrimidin-7-yl)-5-vinyltetrahydrofuran-3,4-diol (5.1 g, 17.34%). 1H NMR: (DMSO, 400 MHz) 5 8.73 (s, 1H), 8.22 (s, 1H), 6.23 (d, J=5.2, 1H), 6.14-6.05 (m, 1H), 5.57 (d, J=6, 1H), 5.44 (d, J=5.6, 1H), 5.29 (d, J=16.8, 1H), 5.21 (d, J=10.4, 1H), 4.50 (q, J=10.8, 5.6 Hz, 1H), 4.32 (t, J=6.4 Hz, 1H), 4.03 (q, J=9.2, 4.8 Hz, 1H); LCMS: 4.141 min, MS: ES+ 359.6 [M+1], 361.6 [M+3]. (LCMS method: LC05_FAR1_01).

Step-5: tert-butyl benzyl((E)-5-((2R,3S,4R,5R)-5-(5-bromo-4-chloro-7H-pyrrolo[2,3-d]pyrimidin-7-yl)-3,4-dihydroxytetrahydrofuran-2-yl)pent-4-en-1-yl)carbamate

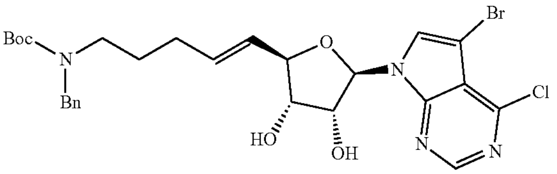 [SMILES: CC(C)(C)OC(=O)N(CCC/C=C/[C@H]1O[C@@H](n2cc(Br)c3c(Cl)ncnc32)[C@H](O)[C@@H]1O)Cc1ccccc1]

Procedure

A stirred solution of (2R,3R,4S,5R)-2-(5-bromo-4-chloro-7H-pyrrolo[2,3-d]pyrimidin-7-yl)-5-vinyltetrahydrofuran-3,4-diol (0.150 g, 0.417 mmol) and tert-butyl benzyl (pent-4-en-1-yl) carbamate (INT-1) (0.172 g, 0.626 mmol) in DCM (15 mL) was degassed with nitrogen gas at room temperature for 30 min. Grubs $2^{nd}$ gen. catalyst (CAS Number 246047-72-3) (0.035 g, 0.0417 mmol) was added and the resulting reaction mixture was stirred at 40° C. for 24 hours. The reaction mixture was diluted with water (60 mL) and extracted with ethyl acetate (3×100 mL). The combined organic layer was dried over anhydrous $Na_2SO_4$, concentrated under reduced pressure. The obtained crude material was purified by reverse phase flash column chromatography by using 42% MeCN in water on C18 silica to afford tert-butyl benzyl((E)-5-((2R,3S,4R,5R)-5-(5-bromo-4-chloro-7H-pyrrolo[2,3-d]pyrimidin-7-yl)-3,4-dihydroxytetrahydrofuran-2-yl)pent-4-en-1-yl)carbamate (0.450 g, 33.89%). LCMS: 2.638 min, MS: ES+507.0 [M−100+1], 509.0 [M−100+3]. (UC01_FAR1)

Step-6: tert-butyl ((E)-5-((2R,3S,4R,5R)-5-(4-amino-5-bromo-7H-pyrrolo[2,3-d]pyrimidin-7-yl)-3,4-dihydroxytetrahydrofuran-2-yl)pent-4-en-1-yl)(benzyl)carbamate

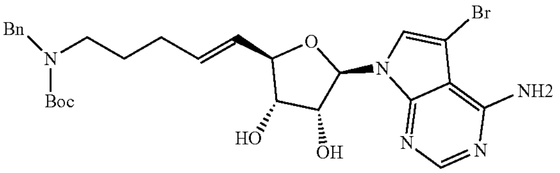 [SMILES: CC(C)(C)OC(=O)N(CCC/C=C/[C@H]1O[C@@H](n2cc(Br)c3c(N)ncnc32)[C@H](O)[C@@H]1O)Cc1ccccc1]

Procedure

To a stirred solution of tert-butyl benzyl((E)-5-((2R,3S,4R,5R)-5-(5-bromo-4-chloro-7H-pyrrolo[2,3-d]pyrimidin-7-yl)-3,4-dihydroxytetrahydrofuran-2-yl)pent-4-en-1-yl) carbamate (0.430 g, 0.709 mmol) in 1,4-dioxane (3.0 mL) was added 28% $NH_3$ in water (4.0 mL) at room temperature. The reaction mixture was further heated at 100° C. for 3 hours. The reaction mixture was cooled to room temperature and diluted with water (100 mL) and extracted with ethyl acetate (3×100 mL). The combined organic layer was dried over anhydrous $Na_2SO_4$, concentrated under reduced pressure. The obtained crude material was further triturated with n-pentane (3×20 mL) to afford tert-butyl ((E)-5-((2R,3S,4R,5R)-5-(4-amino-5-bromo-7H-pyrrolo[2,3-d]pyrimidin-7-yl)-3,4-dihydroxytetrahydrofuran-2-yl)pent-4-en-1-yl)(benzyl)carbamate (0.240 g, 57.39%). LCMS: 2.064 min, MS: ES+588.3 [M+1], 590.2 [M+3]. (UC01_FAR1)

Step-7: (2R,3R,4S,5R)-2-(4-amino-5-bromo-7H-pyrrolo[2,3-d]pyrimidin-7-yl)-5-((E)-5-(benzylamino)pent-1-en-1-yl)tetrahydrofuran-3,4-diol

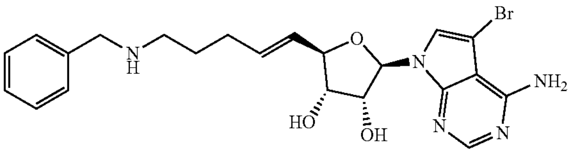 [SMILES: Nc1ncnc2c1c(Br)cn2[C@@H]1O[C@H](/C=C/CCCNCc2ccccc2)[C@@H](O)[C@H]1O]

Procedure

To a stirred solution of tert-butyl ((E)-5-((2R,3S,4R,5R)-5-(4-amino-5-bromo-7H-pyrrolo[2,3-d]pyrimidin-7-yl)-3,4-dihydroxytetrahydrofuran-2-yl)pent-4-en-1-yl)(benzyl)carbamate (0.220 g, 0.374 mmol) in 1,4-dioxane (2.2 mL, 10V) was added 4M HCl in 1,4-dioxane (2.2 mL, 10V) at room temperature. The resulting reaction mixture was stirred at room temperature for 2 hours. The reaction mixture was concentrated under reduced pressure to afford crude material which was further triturated with diethyl ether (6 mL×2). The obtained material was further purified by prep. TLC using 10% MeOH in DCM. Appropriate fractions were concentrated under reduced pressure to afford tert-butyl ((E)-5-((2R,3S,4R,5R)-5-(4-amino-5-bromo-7H-pyrrolo[2,3-d]pyrimidin-7-yl)-3,4-dihydroxytetrahydrofuran-2-yl)

pent-4-en-1-yl)(benzyl)carbamate (0.026 g, 24.10%). $^1$H NMR: (MeOD, 400 MHz) δ 8.12 (s, 1H), 7.37-7.28 (m, 5H), 6.15 (d, J=4.8 Hz, 1H), 5.88-5.79 (m, 1H), 5.72-5.67 (m, 1H), 4.42 (t, J=5.2 Hz, 1H), 4.36 (t, J=5.2 Hz, 1H), 4.07 (t, J=5.2 Hz, 1H), 3.80 (s, 2H), 2.69 (t, J=7.2 Hz, 2H), 2.19-2.14 (q, J=7.2, 14.4 Hz, 2H), 1.73-1.67 (m, 2H). HPLC: 4.967 min, purity: 99.11%; LSMS: 1.200 mu, MS: ES+488.1, 490.1 [(M+1), (M+3)]. (HPLC method: HP05_TAR01, LCMS method: UC01_FAR1).

The following examples were made by the method of Example 1 using (2R,3R,4S,5R)-2-(5-bromo-4-chloro-7H-pyrrolo[2,3-d]pyrimidin-7-yl)-5-vinyltetrahydrofuran-3,4-diol (Example 1 step 4) and the corresponding literature reported alkene or with that prepared in the intermediates section:

The compounds in the following table were prepared using the methods described in Examples 1, 10, 11 and 23

| Example | Structure | Name | LCMS method | Retention time | Mass Ion |
|---|---|---|---|---|---|
| 2 | 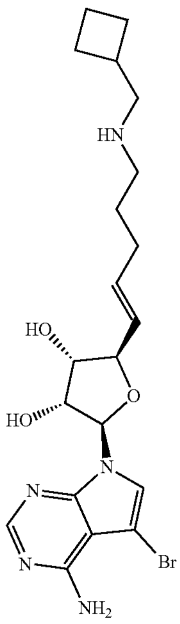 [SMILES: Nc1ncnc2c1c(Br)cn2[C@@H]1O[C@H](/C=C/CCCNCC2CCC2)[C@@H](O)[C@H]1O] | (2R,3R,4S,5R)-2-{4-amino-5-bromo-7H-pyrrolo[2,3-d]pyrimidin-7-yl}-5-[(1E)-5-[(cyclobutylmethyl)amino]pent-1-en-1-yl]oxolane-3,4-diol | UC03_LC_ABR2 | 1.62 min | 466.5, 468.6 |
| 3 | 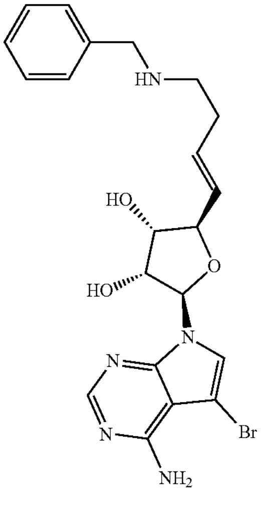 [SMILES: Nc1ncnc2c1c(Br)cn2[C@@H]1O[C@H](/C=C/CCNCc2ccccc2)[C@@H](O)[C@H]1O] | (2R,3R,4S,5R)-2-{4-amino-5-bromo-7H-pyrrolo[2,3-d]pyrimidin-7-yl}-5-[(1E)-4-(benzylamino)but-1-en-1-yl]oxolane-3,4-diol | UC03_WATER_SLOW_LC | 4.62 min | 474.6, 476.6 |

-continued
| Example | Structure | Name | LCMS method | Retention time | Mass Ion |
|---|---|---|---|---|---|
| 4 | 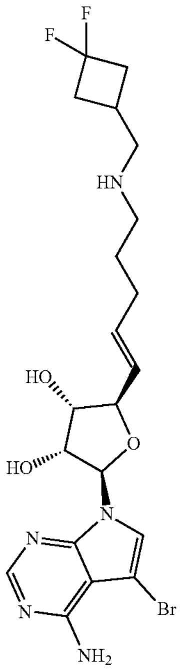 [SMILES: Nc1ncnc2c1c(Br)cn2[C@@H]1O[C@H](/C=C/CCCNCC2CC(F)(F)C2)[C@@H](O)[C@H]1O] | (2R,3R,4S,5R)-2-{4-amino-5-bromo-7H-pyrrolo[2,3-d]pyrimidin-7-yl}-5-[(1E)-5-{[(3,3-difluorocyclobutyl)methyl]amino}pent-1-en-1-yl]oxolane-3,4-diol | LC05_FAR1_01 | 4.64 min | 502.8, 504.7 |
| 5 | 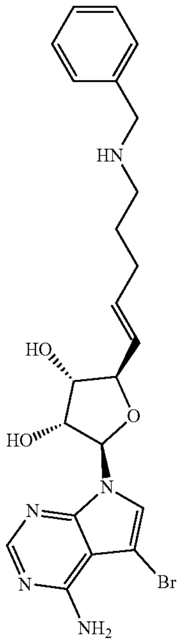 [SMILES: Nc1ncnc2c1c(Br)cn2[C@@H]1O[C@H](/C=C/CCCNCc2ccccc2)[C@@H](O)[C@H]1O] | (2R,3R,4S,5R)-2-{4-amino-5-bromo-7H-pyrrolo[2,3-d]pyrimidin-7-yl}-5-[(1E)-5-(benzylamino)pent-1-en-1-yl]oxolane-3,4-diol | LC05_FAR1 17 min | 1.59 min | 486.7, 488.8 |

-continued
| Example | Structure | Name | LCMS method | Retention time | Mass Ion |
|---|---|---|---|---|---|
| 6 | 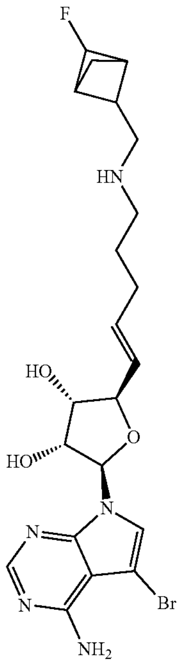 [SMILES: Nc1ncnc2c1c(Br)cn2[C@@H]1O[C@H](/C=C/CCCNCC2C3CC2C3F)[C@@H](O)[C@H]1O] | (2R,3R,4S,5R)-2-{4-amino-5-bromo-7H-pyrrolo[2,3-d]pyrimidin-7-yl}-5-[(1E)-5-[{{3-fluorobicyclo[1.1.1]pentan-1-yl}methyl)amino]pent-1-en-1-yloxolane-3,4-diol | LC05_FAR1_01 | 2.59 min | 495.1, 497.1 |
| 7 | 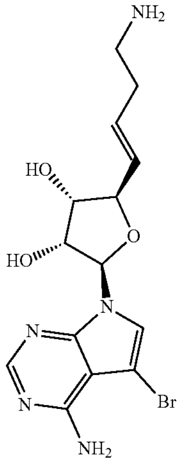 [SMILES: NCC/C=C/[C@H]1O[C@@H](n2cc(Br)c3c(N)ncnc32)[C@H](O)[C@@H]1O] | (2R,3R,4S,5R)-2-{4-amino-5-bromo-7H-pyrrolo[2,3-d]pyrimidin-7-yl}-5-[(1E)-4-aminobut-1-en-1-yl]oxolane-3,4-diol | LCMS-019-0-20-80-7-1-25-UV-Rot-4 | 2.82 min | 384.0, 386.0 |

-continued
| Example | Structure | Name | LCMS method | Retention time | Mass lon |
|---|---|---|---|---|---|
| 8 | 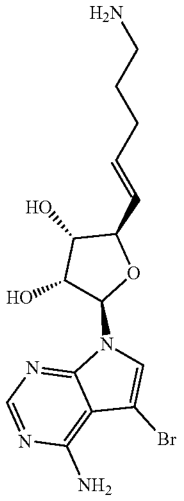 [SMILES: NCCC/C=C/[C@H]1O[C@@H](n2cc(Br)c3c(N)ncnc32)[C@H](O)[C@@H]1O] | (2R,3R,4S,5R)-2-{4-amino-5-bromo-7H-pyrrolo[2,3-d]pyrimidin-7-yl}-5-[(1E)-5-aminopent-1-en-1-yl]oxolane-3,4-diol | LCMS-019-0-20-80-7-1-25-UV-Rot-4 | 2.62 | 398.0, 400.0 |
| 13 | 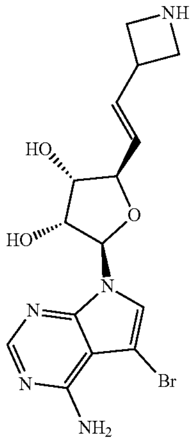 [SMILES: Nc1ncnc2c1c(Br)cn2[C@@H]1O[C@H](/C=C/C2CNC2)[C@@H](O)[C@H]1O] | (2R,3R,4S,5R)-2-{4-amino-5-bromo-7H-pyrrolo[2,3-d]pyrimidin-7-yl}-5-[(1E)-2-(azetidin-3-yl)ethenyl]oxolane-3,4-diol | D | 2.97 | 396.1, 398.1 |
| 14 | 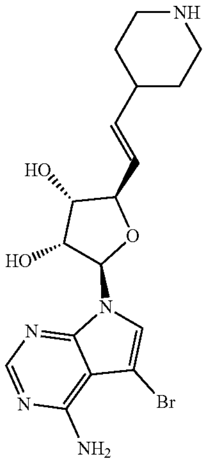 [SMILES: Nc1ncnc2c1c(Br)cn2[C@@H]1O[C@H](/C=C/C2CCNCC2)[C@@H](O)[C@H]1O] | (2R,3R,4S,5R)-2-{4-amino-5-bromo-7H-pyrrolo[2,3-d]pyrimidin-7-yl}-5-[(1E)-2-(piperidin-4-yl)ethenyl]oxolane-3,4-diol | C | 1.59 | 424.2, 426.2 |

-continued
| Example | Structure | Name | LCMS method | Retention time | Mass Ion |
|---|---|---|---|---|---|
| 15 | 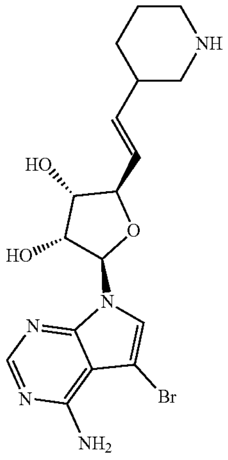 [SMILES: Nc1ncnc2c1c(Br)cn2[C@@H]1O[C@H](/C=C/C2CCCNC2)[C@@H](O)[C@H]1O] | (2R,3R,4S,5R)-2-{4-amino-5-bromo-7H-pyrrolo[2,3-d]pyrimidin-7-yl}-5-[(1E)-2-(piperidin-3-yl)ethenyl]oxolane-3,4-diol | UC_03_WATER_SLOW_LC | 4.01 | 424, 426 |
| 16 | 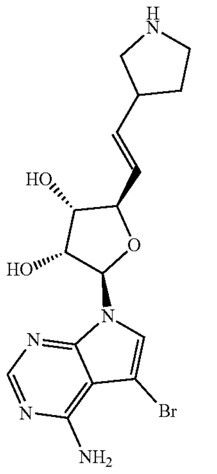 [SMILES: Nc1ncnc2c1c(Br)cn2[C@@H]1O[C@H](/C=C/C2CCNC2)[C@@H](O)[C@H]1O] | (2R,3R,4S,5R)-2-{4-amino-5-bromo-7H-pyrrolo[2,3-d]pyrimidin-7-yl}-5-[(1E)-2-(pyrrolidin-3-yl)ethenyl]oxolane-3,4-diol | C | 1.50 | 410.2, 412.2 |
| 17 | 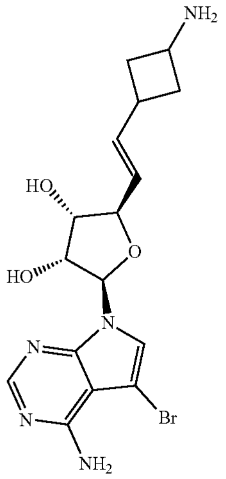 [SMILES: Nc1ncnc2c1c(Br)cn2[C@@H]1O[C@H](/C=C/C2CC(N)C2)[C@@H](O)[C@H]1O] | (2R,3R,4S,5R)-2-{4-amino-5-bromo-7H-pyrrolo[2,3-d]pyrimidin-7-yl}-5-[(1E)-2-(3-aminocyclobutyl) ethenyl]oxolane-3,4-diol | UC_03_WATER_SLOW_LC | 3.91 | 410, 412 |

-continued
| Example | Structure | Name | LCMS method | Retention time | Mass Ion |
|---|---|---|---|---|---|
| 18 | 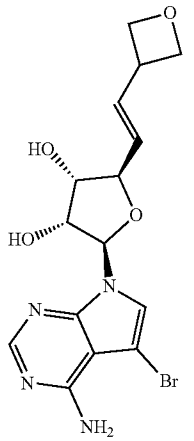 [SMILES: Nc1ncnc2c1c(Br)cn2[C@@H]1O[C@H](/C=C/C2COC2)[C@@H](O)[C@H]1O] | (2R,3R,4S,5R)-2-{4-amino-5-bromo-7H-pyrrolo[2,3-d]pyrimidin-7-yl}-5-[(1E)-2-(oxetan-3-yl)ethenyl]oxolane-3,4-diol | D | 2.51 | 397.1, 399.1 |
| 19 | 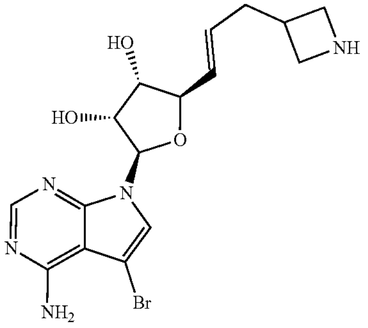 [SMILES: Nc1ncnc2c1c(Br)cn2[C@@H]1O[C@H](/C=C/CC2CNC2)[C@@H](O)[C@H]1O] | (2R,3R,4S,5R)-2-{4-amino-5-bromo-7H-pyrrolo[2,3-d]pyrimidin-7-yl}-5-[(1E)-3-(azetidin-3-yl)prop-1-en-1-yl]oxolane-3,4-diol | C | 1.43 | 410.2, 412.2 |
| 24 | 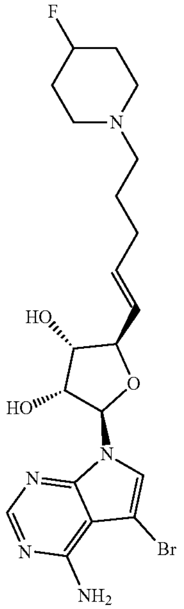 [SMILES: Nc1ncnc2c1c(Br)cn2[C@@H]1O[C@H](/C=C/CCCN2CCC(F)CC2)[C@@H](O)[C@H]1O] | (2R,3R,4S,5R)-2-{4-amino-5-bromo-7H-pyrrolo[2,3-d]pyrimidin-7-yl}-5-[(1E)-5-(4-fluoropiperidin-1-yl)pent-1-en-1-yl]oxolane-3,4-diol | C | 2.42 | 484.3, 486.3 |

-continued
| Example | Structure | Name | LCMS method | Retention time | Mass Ion |
| --- | --- | --- | --- | --- | --- |
| 25 | 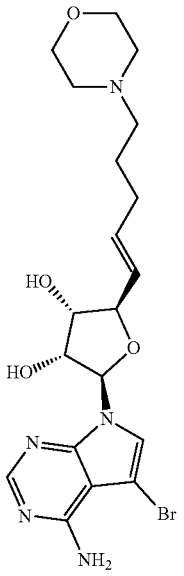 [SMILES: Nc1ncnc2c1c(Br)cn2[C@@H]1O[C@H](/C=C/CCCN2CCOCC2)[C@@H](O)[C@H]1O] | (2R,3R,4S,5R)-2-{4-amino-5-bromo-7H-pyrrolo[2,3-d]pyrimidin-7-yl}-5-[(1E)-5-(morpholin-4-yl)pent-1-en-1-yl]oxolane-3,4-diol | C | 2.06 | 468.2, 470.2 |
| 26 | 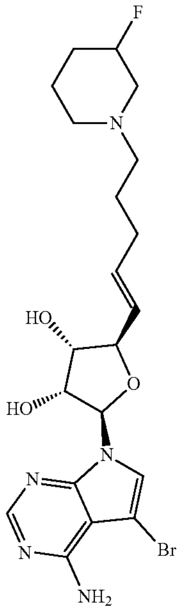 [SMILES: Nc1ncnc2c1c(Br)cn2[C@@H]1O[C@H](/C=C/CCCN2CCCC(F)C2)[C@@H](O)[C@H]1O] | (2R,3R,4S,5R)-2-{4-amino-5-bromo-7H-pyrrolo[2,3-d]pyrimidin-7-yl}-5-[(1E)-5-(3-fluoropiperidin-1-yl)pent-1-en-1-yl]oxolane-3,4-diol | C | 2.53 | 484.3, 486.3 |
| 29 | 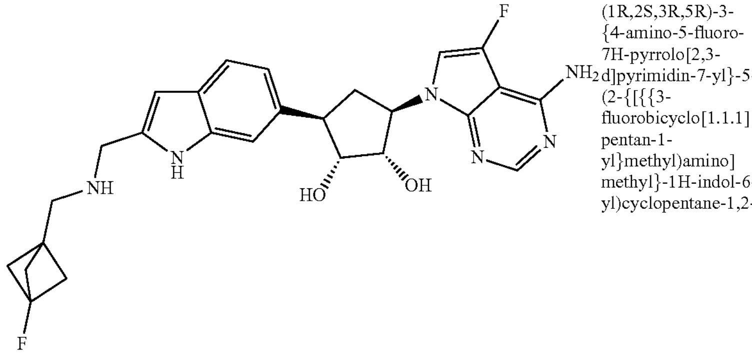 | (1R,2S,3R,5R)-3-{4-amino-5-fluoro-7H-pyrrolo[2,3-d]pyrimidin-7-yl}-5-(2-{[({3-fluorobicyclo[1.1.1]pentan-1-yl}methyl)amino]methyl}-1H-indol-6-yl)cyclopentane-1,2-diol | C | 2.85 | 495.4 |

-continued

| Example | Structure | Name | LCMS method | Retention time | Mass Ion |
|---|---|---|---|---|---|
| 30 | 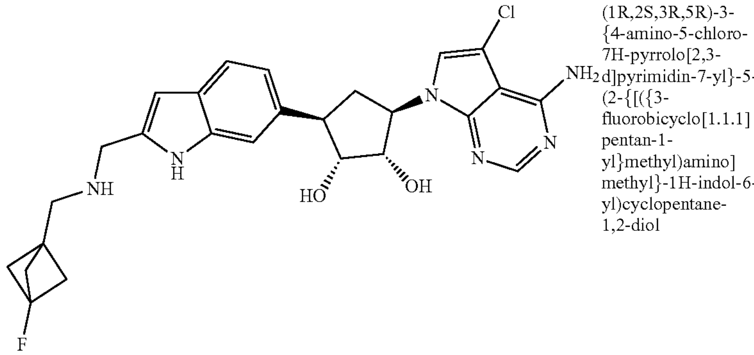 | (1R,2S,3R,5R)-3-{4-amino-5-chloro-7H-pyrrolo[2,3-d]pyrimidin-7-yl}-5-(2-{[({3-fluorobicyclo[1.1.1]pentan-1-yl}methyl)amino]methyl}-1H-indol-6-yl)cyclopentane-1,2-diol | C | 3.00 | 511.4/ 513.4 |
| 31 | 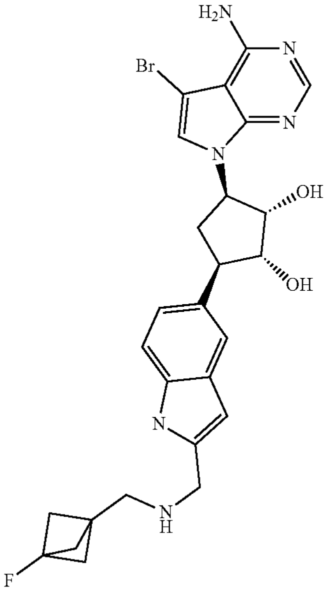 [SMILES: Nc1ncnc2c1c(Br)cn2[C@@H]1C[C@H](c2ccc3[nH]c(CNCC45CC(F)(C4)C5)cc3c2)[C@@H](O)[C@H]1O] | (1R,2S,3R,5R)-3-{4-amino-5-bromo-7H-pyrrolo[2,3-d]pyrimidin-7-yl}-5-(2-{[({3-fluorobicyclo[1.1.1]pentan-1-yl}methyl)amino]methyl}-1H-indol-5-yl)cyclopentane-1,2-diol | C | 2.77 | 555.3/ 557.3 |
| 32 | 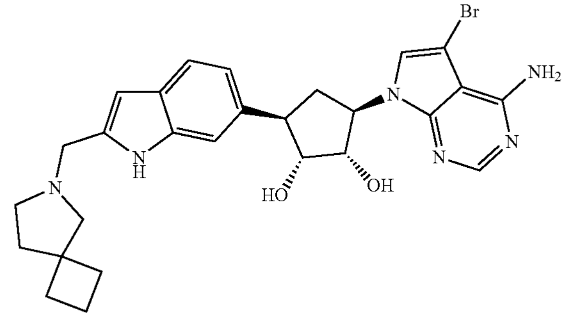 [SMILES: Nc1ncnc2c1c(Br)cn2[C@@H]1C[C@H](c2ccc3cc(CN4CCC5(CCC5)C4)[nH]c3c2)[C@@H](O)[C@H]1O] | (1R,2S,3R,5R)-3-{4-amino-5-bromo-7H-pyrrolo[2,3-d]pyrimidin-7-yl}-5-[2-({6-azaspiro[3.4]octan-6-yl}methyl)-1H-indol-6-yl]cyclopentane-1,2-diol | C | 3.55 | 551.4/ 553.4 |
| 33 | 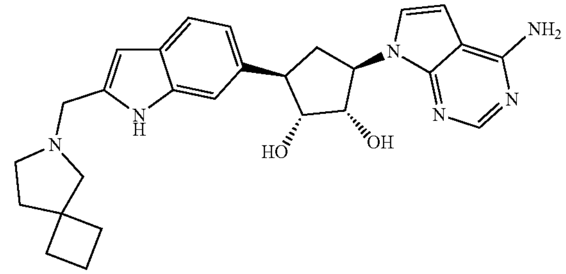 [SMILES: Nc1ncnc2c1ccn2[C@@H]1C[C@H](c2ccc3cc(CN4CCC5(CCC5)C4)[nH]c3c2)[C@@H](O)[C@H]1O] | (1R,2S,3R,5R)-3-{4-amino-7H-pyrrolo[2,3-d]pyrimidin-7-yl}-5-[2-({6-azaspiro[3.4]octan-6-yl}methyl)-1H-indol-6-yl]cyclopentane-1,2-diol | C | 3.17 | 473.6/ 474.6 |

-continued

| Example | Structure | Name | LCMS method | Retention time | Mass Ion |
|---|---|---|---|---|---|
| 34 | 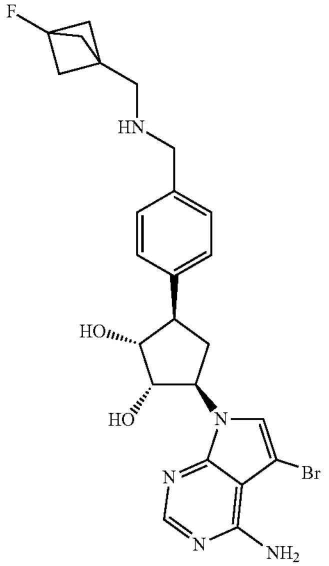 [SMILES: Nc1ncnc2c1c(Br)cn2[C@@H]1C[C@H](c2ccc(CNCC34CC(F)(C3)C4)cc2)[C@@H](O)[C@H]1O] | (1R,2S,3R,5R)-3-{4-amino-5-bromo-7H-pyrrolo[2,3-d]pyrimidin-7-yl}-5-(4-{[({3-fluorobicyclo[1.1.1]pentan-1-yl}methyl)amino]methyl}phenyl)cyclopentane-1,2-diol | C | 2.89 | 516.4/518.4 |
| 35 | 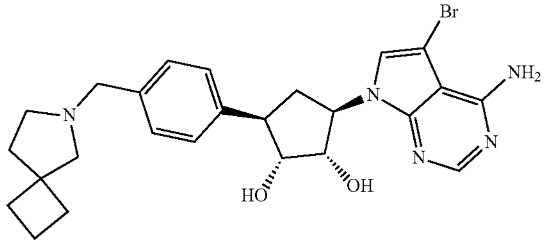 [SMILES: Nc1ncnc2c1c(Br)cn2[C@@H]1C[C@H](c2ccc(CN3CCC4(CCC4)C3)cc2)[C@@H](O)[C@H]1O] | (1R,2S,3R,5R)-3-{4-amino-5-bromo-7H-pyrrolo[2,3-d]pyrimidin-7-yl}-5-[4-({6-azaspiro[3.4]octan-6-yl}methyl)phenyl]cyclopentane-1,2-diol | C | 3.46 | 512.4/514.4 |
| 36 | 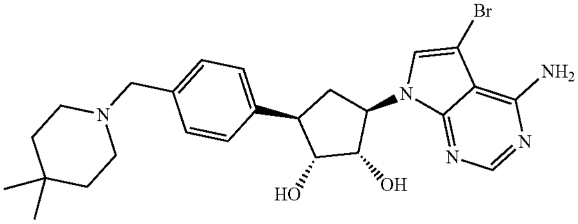 [SMILES: CC1(C)CCN(Cc2ccc([C@H]3C[C@@H](n4cc(Br)c5c(N)ncnc54)[C@H](O)[C@@H]3O)cc2)CC1] | (1R,2S,3R,5R)-3-{4-amino-5-bromo-7H-pyrrolo[2,3-d]pyrimidin-7-yl}-5-{4-[(4,4-dimethylpiperidin-1-yl)methyl]phenyl}cyclopentane-1,2-diol | C | 3.56 | 514.4/516.3 |
| 37 | 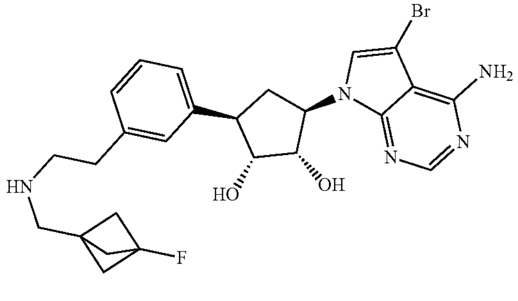 [SMILES: Nc1ncnc2c1c(Br)cn2[C@@H]1C[C@H](c2cccc(CCNCC34CC(F)(C3)C4)c2)[C@@H](O)[C@H]1O] | (1R,2S,3R,5R)-3-{4-amino-5-bromo-7H-pyrrolo[2,3-d]pyrimidin-7-yl}-5-(3-{2-[{{3-fluorobicyclo[1.1.1]pentan-1-yl}methyl)amino]ethyl}phenyl)cyclopentane-1,2-diol(1R,2S,3R,5R)- | C | 2.91 | 530.3/532.3 |

-continued

| Example | Structure | Name | LCMS method | Retention time | Mass Ion |
|---|---|---|---|---|---|
| 38 | 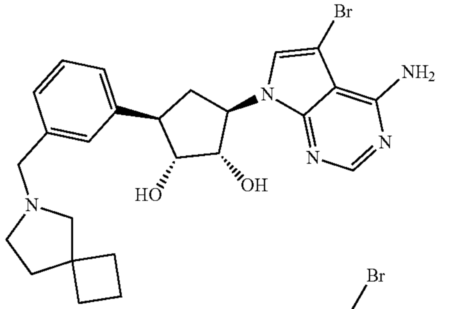 | 3-{4-amino-5-bromo-7H-pyrrolo[2,3-d]pyrimidin-7-yl}-5-[3-({6-azaspiro[3.4]octan-6-yl}methyl)phenyl] cyclopentane-1,2-diol | C | 3.49 | 512.5/ 514.5 |
| 39 | 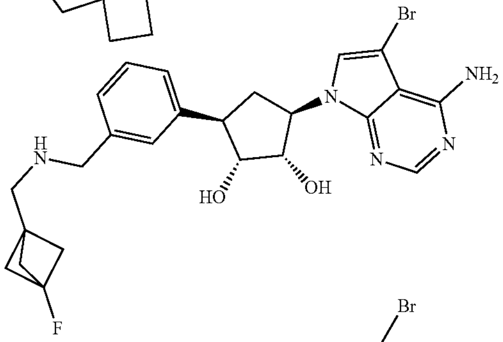 | (1R,2S,3R,5R)-3-{4-amino-5-bromo-7H-pyrrolo[2,3-d]pyrimidin-7-yl}-5-(3-{[({3-fluorobicyclo[1.1.1] pentan-1-yl}methyl)amino] methyl}phenyl) cyclopentane-1,2-diol | C | 2.95 | 516.4/ 518.3 |
| 40 | 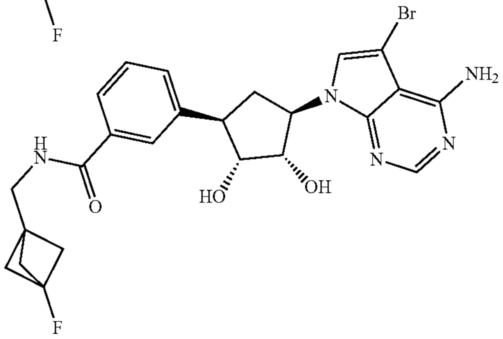 | 3-[(1R,2R,3S,4R)-4-{4-amino-5-bromo-7H-pyrrolo[2,3-d]pyrimidin-7-yl}-2,3-dihydroxycyclopentyl]-N-({3-fluorobicyclo[1.1.1] pentan-1-yl}methyl)benzamide | C | 2.64 | 530.4/ 532.4 |

Example 9: Synthesis of (2R,3R,4S,5R)-2-(4-amino-5-bromo-7H-pyrrolo[2,3-d]pyrimidin-7-yl)-5-((E)-5-(benzylamino)pent-3-en-1-yl)tetrahydrofuran-3,4-diol

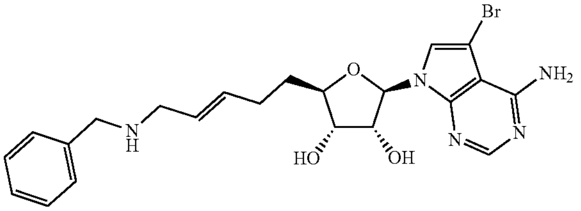 [SMILES: Nc1ncnc2c1c(Br)cn2[C@@H]1O[C@H](CC/C=C/CNCc2ccccc2)[C@@H](O)[C@H]1O]

Step-1: (1R,5R,6R,8R)-8-Methoxy-3,3-dimethyl-6-[(p-tolylsulfonyloxy)methyl]-2,4,7-trioxabicyclo[3.3.0]octane

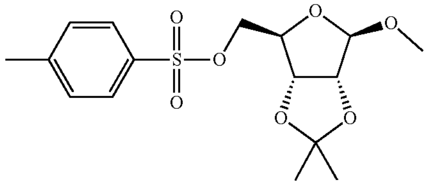

Procedure

To a stirred solution Methyl 2,3-O-(1-methylethylidene)-β-D-ribofuranoside (10.00 g, 49.01 mmol) in DCM (40 mL) were added triethylamine (20.5 mL, 147.05 mmol) and DMAP (0.598 g, 4.901 mmol) at 0° C. The resulting reaction mixture stirred at room temperature for 2 hours. The reaction mixture was diluted with water (50 mL) and extracted with DCM (3×100 mL). The combined organic layer was dried over anhydrous $Na_2SO_4$, filtered and concentrated under reduced pressure. The obtained crude material was purified by manual column chromatography using 60-120 mesh silica gel and eluted with 6% EtOAc in Hexane. Appropriate fractions were concentrated to afford (1R,5R,6R,8R)-8-methoxy-3,3-dimethyl-6-[(p-tolylsulfonyloxy)methyl]-2,4,7-trioxabicyclo[3.3.0]octane (15.00 g, Yield: 91.17%,). $^1H$ NMR: (CDCl3, 400 MHz) δ 7.71 (d, j=8.0 Hz 2H), 7.37 (d, j=8.4 Hz 2H), 4.93 (S, 1H), 4.61-4.53 (dd, J=5.6 Hz, 2H), 4.31 (t, J=7.2 Hz, 1H), 4.05-4.00 (m, 2H), 3.23 (S, 3H), 2.46 (S, 3H), 1.45 (S, 3H), 1.29 (S, 3H); LCMS: 2.29 min, MS: ES+358 (M+1) (UC01_FAR1).

Step-2: (1R,5R,6R,8R)-6-(3-Butenyl)-8-methoxy-3,3-dimethyl-2,4,7-trioxabicyclo[3.3.0]octane

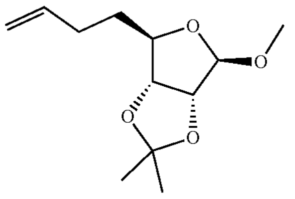 [SMILES: C=CCC[C@H]1O[C@@H](OC)[C@@H]2OC(C)(C)O[C@@H]21]

Procedure

To a stirred solution ((3aR,4R,6R,6aR)-6-methoxy-2,2-dimethyltetrahydrofuro[3,4-d][1,3]dioxol-4-yl)methyl 4-methylbenzenesulfonate (5.00 g, 14.005 mmol) in Diethyl ether (40.0 mL) was added TMEDA (10.5 mL, 70.028 mmol) at room temperature and stirred reaction mixture for 10 min. Allylmagnesium bromide (1M in diethyl ether) (70.0 mL, 70.028 mmol) was added at room temperature and stirred for 16 hours. The resulting reaction mixture was quenched with aqueous ammonium chloride solution (100 mL) and extracted with diethyl ether (3×200 mL). The combined organic layer was dried over anhydrous $Na_2SO_4$, filtered and concentrated under reduced pressure (35° C. at 275 mbar)). The obtained crude material was purified by manual column chromatography using 60-120 mesh silica gel and eluted with 3% diethyl ether in n-hexane. Appropriate fractions concentrated at 35° C. (275 mbar) to afford (3aR,4R,6R,6aR)-4-(but-3-en-1-yl)-6-methoxy-2,2-dimethyltetrahydrofuro[3,4-d][1,3]dioxole (1.40 g, Yield: 54.95%). $^1$H NMR: (CDCl3, 400 MHz) complies with addition peaks.

Step-3:_(2R, 3R, 4S, 5R)-5-(but-3-en-1-yl) tetrahydrofuran-2, 3, 4-triol

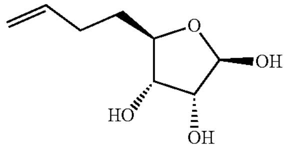

Procedure

To a stirred solution (3aR,4R,6R,6aR)-4-(but-3-en-1-yl)-6-methoxy-2,2-dimethyltetrahydrofuro[3,4-d][1,3]dioxole (2.00 g, 8.77 mmol) in acetone (20.0 mL) was added 2N Sulphuric acid solution (40.0 mL) at room temperature. The resulting reaction mixture was stirred at 60° C. for 16 hours. The reaction mixture was quenched with solid sodium bicarbonate (pH adjusted to 7 to 7.5) followed by diluted with water (100 mL). The aqueous layer was extracted with 20% THE in ethyl acetate (4×300 mL). The combined organic layer was dried over anhydrous $Na_2SO_4$, filtered and concentrated under reduced pressure. The obtained crude material was purified by manual column chromatography by using 60-120 mesh silica gel and eluted with 3% MeOH in DCM to afford (2R, 3R, 4S, 5R)-5-(but-3-en-1-yl) tetrahydrofuran-2, 3, 4-triol (0.400 g, Yield: 31.45%). $^1$H NMR: (CDCl3, 400 MHz) δ 5.90-5.81 (m, 1H), 5.10 (m, 1H), 4.08-4.05 (m, 2H) 3.55 (d, J=4.8 Hz 1H), 3.41 (m, 1H), 2.91 (m, 1H), 2.64-2.56 (m, 2H), 2.24-2.12 (m, 2H), 1.35-1.27 (m, 3H).

Step-4: Synthesis of (2R, 3R, 4S, 5R)-2-(5-bromo-4-chloro-7H-pyrrolo [2, 3-d]pyrimidin-7-yl)-5-(but-3-en-1-yl) tetrahydrofuran-3

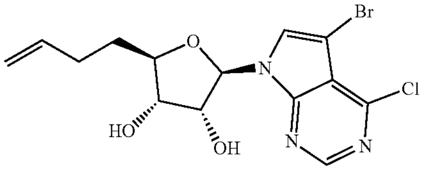 [SMILES: C=CCC[C@H]1O[C@@H](n2cc(Br)c3c(Cl)ncnc32)[C@H](O)[C@@H]1O]

Procedure

To a stirred mixture of 5-bromo-4-chloro-7H-pyrrolo[2, 3-d]pyrimidine (0.533 g, 2.298 mmol) and (2R, 3R, 4S, 5R)-5-(but-3-en-1-yl) tetrahydrofuran-2, 3, 4-triol (0.40 g, 2.298 mmol) in THE (15 mL) was added DBU (0.349 g, 2.298 mmol) and stirred at room temperature for 20 min. Tri-n-butylphoshphine (1.10 mL, 48.25 mmol) was added drop wise followed by addition of DIAD (0.91 mL, 45.977 mmol, available from GLR) at room temperature. The resulting reaction mixture was stirred at room temperature for 2 hours. The reaction mixture was diluted with water (60 mL) and extracted with ethyl acetate (4×100 mL). The combined organic layer was dried over anhydrous $Na_2SO_4$, concentrated under reduced pressure. The obtained crude was purified by manual column chromatography by using 60-120 mesh silica gel and eluted with 17% ethyl acetate in n-hexane. Appropriate fractions concentrated to afford (2R, 3R, 4S, 5R)-2-(5-bromo-4-chloro-7H-pyrrolo [2, 3-d]pyrimidin-7-yl)-5-(but-3-en-1-yl) tetrahydrofuran-3, 4-diol (0.400 g, Yield: 34.06%). $^1$H NMR: (DMSO, 400 MHz) δ 8.71 (s, 1H), 8.22 (s, 1H), 6.16 (d, J=5.6 Hz 1H), 5.87-5.77 (m, 1H), 5.47 (d, J=6.0 Hz, 1H), 5.24 (d, J=5.6 Hz 1H), 5.05-4.95 (m, 2H), 4.49-4.62 (m, 1H), 4.00-3.95 (m, 1H), 3.87-3.83 (m, 1H), 2.15-2.06 (m, 2H), 1.77-1.72 (m, 2H), LCMS: 4.59 min, MS: ES+387 (M+1) (LC05_FAR1._01).

Step-5: tert-butyl benzyl((E)-5-((2R,3S,4R,5R)-5-(5-bromo-4-chloro-7H-pyrrolo[2,3-d]pyrimidin-7-yl)-3,4-dihydroxytetrahydrofuran-2-yl)pent-2-en-1-yl)carbamate

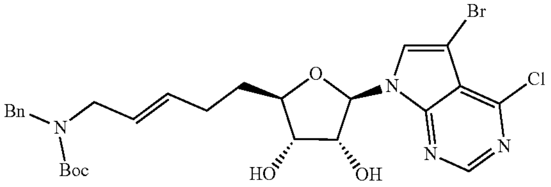 [SMILES: CC(C)(C)OC(=O)N(C/C=C/CC[C@H]1O[C@@H](n2cc(Br)c3c(Cl)ncnc32)[C@H](O)[C@@H]1O)Cc1ccccc1]

Procedure

A stirred solution of (2R,3R,4S,5R)-2-(5-bromo-4-chloro-7H-pyrrolo[2,3-d]pyrimidin-7-yl)-5-(but-3-en-1-yl)

tetrahydrofuran-3,4-diol (0.400 g, 1.034 mmol) and tert-butyl allyl(benzyl)carbamate (Int 3; 0.510 g, 02.0671 mmol) in DCM (40.0 mL) was degassed with $N_2$ gas for 30 min at room temperature. Grubs 2nd gen. catalyst (0.070 g, 0.10335 mmol) was added and reaction mixture was stirred at 40° C. for 16 hours. The reaction mixture was concentrated under reduced pressure. The obtained crude material was purified by flash column chromatography using 60-120 mesh silica gel and eluted with 3% methanol in DCM to afford tert-butyl benzyl((E)-5-((2R,3S,4R,5R)-5-(5-bromo-4-chloro-7H-pyrrolo[2,3-d]pyrimidin-7-yl)-3,4-dihydroxytetrahydrofuran-2-yl)pent-2-en-1-yl)carbamate (0.280 g, Yield: 58.45%). $^1$H NMR: (DMSO, 400 MHz) δ 8.71 (s, 1H), 8.21 (s, 1H), 7.33-7.11 (m, 5H), 6.17 (t, J=5.2 Hz 1H), 5.52-5.22 (m, 4H), 4.46 (d, J=5.2 Hz 1H), 4.25 (m, 2H), 3.98-3.84 (m, 2H), 3.69-3.63 (m, 1H), 2.06 (m, 2H), 1.72-1.70 (m, 3H), 1.40-1.17 (m, 9H), LCMS: 5.44 min, MS: ES+606 (M−100) (LC05_FAR1_01).

Step-6: tert-butyl ((E)-5-((2R,3S,4R,5R)-5-(4-amino-5-bromo-7H-pyrrolo[2,3-d]pyrimidin-7-yl)-3,4-dihydroxytetrahydrofuran-2-yl)pent-2-en-1-yl)(benzyl)carbamate

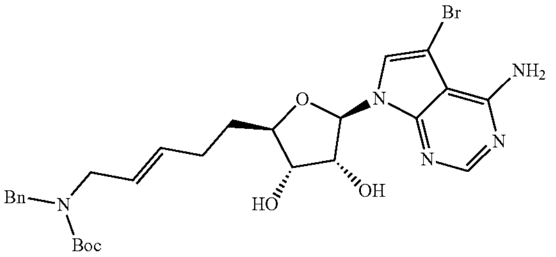 [SMILES: CC(C)(C)OC(=O)N(C/C=C/CC[C@H]1O[C@@H](n2cc(Br)c3c(N)ncnc32)[C@H](O)[C@@H]1O)Cc1ccccc1]

Procedure

To a stirred solution tert-butyl benzyl((E)-5-((2R,3S,4R,5R)-5-(5-bromo-4-chloro-7H-pyrrolo[2,3-d]pyrimidin-7-yl)-3,4-dihydroxytetrahydrofuran-2-yl)pent-2-en-1-yl)carbamate (0.15 g, 0.4125 mmol) in 1,4-dioxane (5.0 mL) was added 25% aqueous $NH_3$ solution (10 mL) at room temperature and heated at 80° C. for 16 hours. The resulting reaction mixture was directly concentrated under reduced pressure. The obtained crude material was purified by flash column chromatography using 200-400 mesh silica gel and eluted with 1.6% methanol in DCM to afford tert-butyl ((E)-5-((2R,3S,4R,5R)-5-(4-amino-5-bromo-7H-pyrrolo[2,3-d]pyrimidin-7-yl)-3,4-dihydroxytetrahydrofuran-2-yl)pent-2-en-1-yl)(benzyl)carbamate (0.067 g, Yield: 52.51%). LCMS: 4.36 min, MS: ES+587 (M+1), (M+3) (LC05_FAR1_01).

Step-7:_(2R,3R,4S,5R)-2-(4-amino-5-bromo-7H-pyrrolo[2,3-d]pyrimidin-7-yl)-5-((E)-5-(benzylamino)pent-3-en-1-yl)tetrahydrofuran-3,4-diol

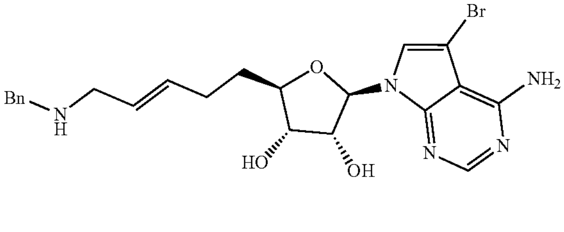 [SMILES: Nc1ncnc2c1c(Br)cn2[C@@H]1O[C@H](CC/C=C/CNCc2ccccc2)[C@@H](O)[C@H]1O]

Procedure

To a stirred solution of tert-butyl ((E)-5-((2R,3S,4R,5R)-5-(4-amino-5-bromo-7H-pyrrolo[2,3-d]pyrimidin-7-yl)-3,4-dihydroxytetrahydrofuran-2-yl)pent-2-en-1-yl)(benzyl)carbamate (0.067 g, 0.1141 mmol) in DCM (3.0 mL) was added TFA (0.01 mL) at room temperature. The resulting reaction mixture was stirred at room temperature for 5 hours. The reaction mixture was neutralize with saturated $NaHCO_3$ solution (10 mL). The aqueous layer was extracted with 10% methanol in DCM (3x50 mL). The combined organic layer was dried over anhydrous $Na_2SO_4$, concentrated under reduced pressure. The obtained crude material was purified by reverse phase flash chromatography using 1.8% acetonitrile in 0.1 M ammonium bicarbonate solution on C18 silica gel. Appropriate fractions were lyophilized to afford (2R,3R,4S,5R)-2-(4-amino-5-bromo-7H-pyrrolo[2,3-d]pyrimidin-7-yl)-5-((E)-5-(benzylamino)pent-3-en-1-yl)tetrahydrofuran-3,4-diol (0.014 g, Yield: 25.18%). $^1$H NMR: (MeOH, 400 MHz) δ 8.11 (s, 1H), 7.37-7.28 (m, 6H), 6.12 (d, J=4.8 Hz 1H), 5.78-5.74 (m, 1H), 5.63-5.57 (m, 1H), 4.45-4.41 (m, 1H), 4.05 (t, J=5.2 Hz 1H), 3.99-3.95 (m, 1H), 3.80 (s, 2H), 3.27 (d, J=6.0 Hz 2H), 2.27-2.20 (m, 2H), 1.86-1.79 (m, 2H), LCMS: 2.93 min, MS: ES+387 (M+1), (M+3) (LC05_FAR1_01). HPLC: 3.80 min, (HP05_TFAR1_ELSD_02).

Example 10: (1R,2S,3R,5R)-3-(4-amino-5-bromo-7H-pyrrolo[2,3-d]pyrimidin-7-yl)-5-(4-(((cyclobutylmethyl)amino)methyl)phenyl)cyclopentane-1,2-diol

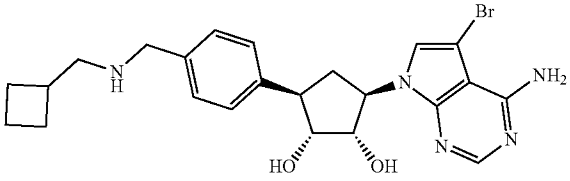 [SMILES: Nc1ncnc2c1c(Br)cn2[C@@H]1C[C@H](c2ccc(CNCC3CCC3)cc2)[C@@H](O)[C@H]1O]

Step-1: tert-Butyl p-{(1R,5R,6R)-3,3-dimethyl-8-oxo-2,4-dioxabicyclo[3.3.0]oct-6-yl}benzoate

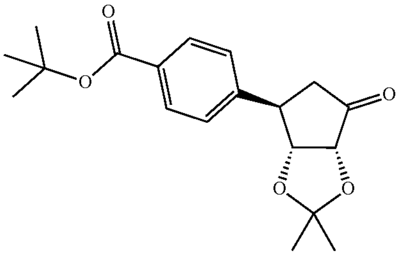 [SMILES: CC(C)(C)OC(=O)c1ccc([C@H]2CC(=O)[C@@H]3OC(C)(C)O[C@H]23)cc1]

Procedure

To a solution of 1,1-Dimethylethyl 4-iodobenzoate (2.25 g, 7.40 mmol) in dry THE (20 mL) was added isopropyl magnesium bromide (14.80 mL, 11.10 mmol, 0.75M solution in THF) at −78° C. The reaction mixture was allowed to stir at −78° C. for 2.5 hours. In another round bottom flask a solution (3aR,6aR)-3a,6a-Dihydro-2,2-dimethyl-4H-cyclopenta-1,3-dioxol-4-one (1.80 g, 11.68 mmol) in dry THF (20 mL) was added trimethylsilyl chloride (3.01 mL, 23.73 mmol) and hexamethylphosphoramide (5.10 mL, 29.20 mmol) at −78° C. The resulting reaction mixture was stirred for 20 min. Copper (I) bromide dimethyl sulfide complex (0.212 g, 0.93 mmol) and above freshly prepared Grignard reagent was added dropwise at −78° C. The resulting reaction mixture was stirred at −78° C. for 3 hours. The reaction mixture was warmed to room temperature and quenched with $NH_4Cl$ solution (40 mL) and extracted with EtOAc (100 mL×4). The combined organic layer was dried over anhydrous $Na_2SO_4$, concentrated under vacuum. The obtained crude material was purified by silica gel column chromatography using 2% EtOAc in hexane to obtain tert-butyl p-[(1R,5R,6R)-3,3-dimethyl-8-oxo-2,4-dioxabicyclo[3.3.0]oct-6-yl)benzoate (1.30 g, 33.50%). $^1H$ NMR: (DMSO-d6, 400 MHz) δ 7.87 (d, J=8.4 Hz, 2H), 7.38 (d, J=8.4 Hz, 2H); 4.72 (dd, J=2.8, 5.6 Hz, 1H), 4.60 (d, J=6.0 Hz, 1H), 3.60-3.66 (m, 1H), 2.97 (dd, J=9.2, 18.4 Hz, 1H), 2.54-2.61 (m, 1H), 1.54 (s, 9H), 1.41 (s, 3H), 1.29 (s, 3H).

Step-2: tert-Butyl p-{(1S,5R,6R,8S)-8-hydroxy-3,3-dimethyl-2,4-dioxabicyclo[3.3.0]oct-6-yl}benzoate

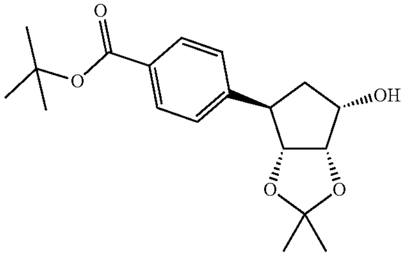 [SMILES: CC(C)(C)OC(=O)c1ccc([C@H]2C[C@H](O)[C@@H]3OC(C)(C)O[C@@H]32)cc1]

Procedure

To a solution of tert-butyl p-{(1R,5R,6R)-3,3-dimethyl-8-oxo-2,4-dioxabicyclo[3.3.0]oct-6-yl}benzoate (1.30 g, 3.92 mmol) in methanol (13 mL) was added sodium borohydride (0.44 g, 11.75 mmol) portion wise at 0° C. The reaction mixture was allowed to warm to room temperature and stirred for a further for 30 min. The reaction mixture was quenched with water (50 mL) and aqueous layer was extracted with EtOAc (100 mL×4). The combined organic layer was dried over anhydrous $Na_2SO_4$, concentrated under vacuum to afford tert-butyl p-{(1S,5R,6R,8S)-8-hydroxy-3,3-dimethyl-2,4-dioxabicyclo[3.3.0]oct-6-yl}benzoate (0.80 g, 61.17%). $^1H$ NMR: (DMSO-d6, 400 MHz) δ 7.83 (d, J=8.0 Hz, 2H), 7.33 (d, J=8.0 Hz, 2H), 4.60-4.68 (m, 1H), 4.50-4.56 (m, 2H), 4.05-3.95 (m, 1H), 3.30-3.23 (m, 1H), 2.10-2.16 (m, 1H), 1.85-1.74 (m, 1H), 1.54 (s, 9H), 1.47 (s, 3H), 1.29 (s, 3H).

Step-3: tert-Butyl p-{(1S,5R,6R,8R)-8-(3-bromo-4-chloro-1,5,7-triaza-1H-inden-1-yl)-3,3-dimethyl-2,4-dioxabicyclo[3.3.0]oct-6-yl}benzoate

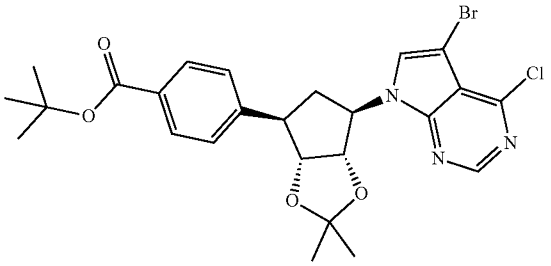 [SMILES: CC(C)(C)OC(=O)c1ccc([C@H]2C[C@@H](n3cc(Br)c4c(Cl)ncnc43)[C@@H]3OC(C)(C)O[C@@H]32)cc1]

Procedure

To a solution of tert-butyl p-{(1S,5R,6R,8S)-8-hydroxy-3,3-dimethyl-2,4-dioxabicyclo[3.3.0]oct-6-yl}benzoate (0.36 g, 1.08 mmol,) and 5-bromo-4-chloro-7H-pyrrolo[2,3-d]pyrimidine (0.37 g, 1.62 mmol) in THF (10 mL) was added triphenylphosphine (1.12 g, 4.32 mmol). The reaction mixture was allowed to stir at room temperature for 5 min. The resulting reaction mixture was heated at 60° C. followed by addition of DIAD (0.87 g, 4.32 mmol) drop-wise at 60° C. The resulting reaction mixture was stirred for 30 minutes at 60° C. Two further batches of same scale using the method above were combined for work up and purification. The reaction mixture was cooled to room temperature and diluted with water (150 mL) and aqueous layer was extracted with EtOAc (100 mL×4). The combined organic layer was dried over anhydrous $Na_2SO_4$, concentrated under vacuum. The obtained crude material was purified by silica gel column chromatography using 6% EtOAc in hexane to afford tert-butyl p-{(1S,5R,6R,8R)-8-(3-bromo-4-chloro-1,5,7-triaza-1H-inden-1-yl)-3,3-dimethyl-2,4-dioxabicyclo[3.3.0]oct-6-yl}benzoate (0.67 g, 37.8%). $^1H$ NMR: (DMSO-d6, 400 MHz) δ 8.72 (s, 1H), 8.44 (s, 1H), 7.89 (d, J=8.0 Hz, 2H), 7.53 (d, J=8.0 Hz, 2H), 5.32-5.38 (m, 1H), 4.94-4.99 (m, 1H), 4.79-4.74 (m, 1H), 3.35-3.42 (m, 1H), 2.56-2.62 (m, 1H), 1.54 (s, 9H), 1.47 (s, 3H), 1.23 (s, 6H). LCMS: 6.139 min, MS: ES+547.8 [M+1]549.8 [M+3]. Method: LC05_FAR1_01.

Step-4: tert-Butyl p-{(1S,5R,6R,8R)-8-(4-amino-3-bromo-1,5,7-triaza-1H-inden-1-yl)-3,3-dimethyl-2,4-dioxabicyclo[3.3.0]oct-6-yl}benzoate

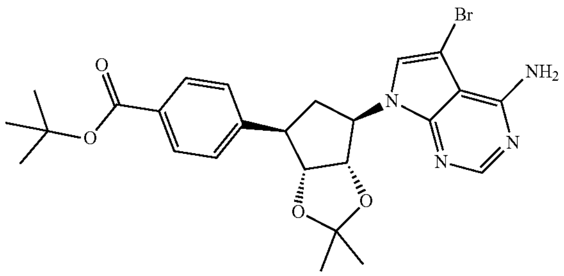 [SMILES: CC(C)(C)OC(=O)c1ccc([C@H]2C[C@@H](n3cc(Br)c4c(N)ncnc43)[C@@H]3OC(C)(C)O[C@@H]32)cc1]

Procedure

To a stirred solution of tert-butyl p-{(1S,5R,6R,8R)-8-(3-bromo-4-chloro-1,5,7-triaza-1H-inden-1-yl)-3,3-dimethyl-2,4-dioxabicyclo[3.3.0]oct-6-yl}benzoate (0.18 g, 0.33 mmol) in 1,4-dioxane (7 mL) was added 25% $NH_3$ in water (10 mL) at room temperature. The reaction mixture was further stirred at 80° C. for 6 hours. Three further batches were prepared using the method above and combined for work up and purification. The reaction mixture was cooled to room temperature and concentrated under vacuum. The obtain crude material was further triturated with n-pentane (20 mL×3) to afford tert-butyl p-{(1S,5R,6R,8R)-8-(4-amino-3-bromo-1,5,7-triaza-1H-inden-1-yl)-3,3-dimethyl-2,4-dioxabicyclo[3.3.0]oct-6-yl}benzoate (0.560 g, 80.63%). LCMS: 2.134 min, MS: ES+529.1 [M+1], 531.1 [M+3]. Method: UC01_FAR1.

Step-5: 4-((1S,2S,3R,4S)-4-(4-amino-5-bromo-7H-pyrrolo[2,3-d]pyrimidin-7-yl)-2,3-dihydroxycyclopentyl)benzoic acid

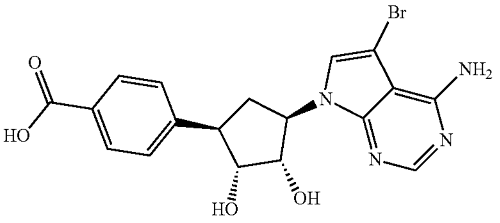 [SMILES: Nc1ncnc2c1c(Br)cn2[C@@H]1C[C@H](c2ccc(C(=O)O)cc2)[C@@H](O)[C@H]1O]

Procedure

To a stirred solution of tert-butyl 4-((3aS,4S,6S,6aR)-6-(4-amino-5-bromo-7H-pyrrolo[2,3-d]pyrimidin-7-yl)-2,2-dimethyltetrahydro-4H-cyclopenta[d][1,3]dioxol-4-yl)benzoate (0.560 g, 1.06 mmol) in DCM (5 mL, 10V) was added TFA (5 mL, 10V) at 0° C. The resulting reaction mixture was stirred for 18 hours at room temperature. The reaction mixture was concentrated under reduced pressure to afford crude material which was further triturated with diethyl ether (20 mL×3) and n-pentane (20 mL×3) to afford 4-((1S,2S,3R,4S)-4-(4-amino-5-bromo-7H-pyrrolo[2,3-d]pyrimidin-7-yl)-2,3-dihydroxycyclopentyl)benzoic acid (0.40 g, 87.27%). $^1H$ NMR: (DMSO-d6, 400 MHz) δ 8.11 (s, 1H), 7.91 (d, J=7.6 Hz, 2H), 7.75 (s, 1H), 7.49 (d, J=7.6 Hz, 2H), 6.74 (br s, 2H), 5.05-5.11 (m, 1H), 4.93-5.01 (m, 1H), 4.26-4.31 (m, 1H), 4.02-4.09 (m, 1H), 3.11-3.17 (m, 1H), 2.33-2.38 (m, 1H), 3.11-3.17 (m, 2H), 2.06-1.97 (m, 1H). LCMS: 3.145 min, MS: ES+432.8 [M+1], 434.8 [M+3]. Method: LC05_AR1_01.

Step-6: 4-((1R,2R,3S,4R)-4-(4-amino-5-bromo-7H-pyrrolo[2,3-d]pyrimidin-7yl)-2,3-dihydroxycyclopentyl)-N-methoxy-N-methylbenzamide

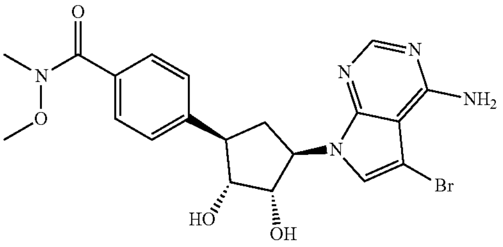 [SMILES: CON(C)C(=O)c1ccc([C@H]2C[C@@H](n3cc(Br)c4c(N)ncnc43)[C@H](O)[C@@H]2O)cc1]

Procedure

To a stirred solution of 4-((1R,2R,3S,4R)-4-(4-amino-5-bromo-7H-pyrrolo[2,3-d]pyrimidin-7-yl)-2,3-dihydroxycyclopentyl)benzoic acid (0.300 g, 0.69 mmol) in DMF (8.0 mL) was added HATU (0.527 g, 1.38 mmol) at 0° C. The resulting reaction mixture was stirred at 0° C. for 15 min. DIPEA (0.593 mL, 3.472 mmol) was added at 0° C. followed by addition of N,O-dimethyl hydroxylamine hydrochloride (0.203 g, 2.08 mmol). The resulting reaction mixture was allowed to stir at room temperature for 4 hours. The resulting reaction mixture was diluted with water (100 mL) and extracted with ethyl acetate (100 mL×3). The combined organic layer was dried over anhydrous $Na_2SO_4$, filtered and concentrated under reduced pressure. The obtain crude material was purified by silica gel column chromatography using 3% MeOH in DCM to afford 4-((1R,2R,3S,4R)-4-(4-amino-5-bromo-7H-pyrrolo[2,3-d]pyrimidin-7yl)-2,3-dihydroxycyclopentyl)-N-methoxy-N-methylbenzamide as light yellow solid (0.176 g, 53.36%); 1H-NMR: (DMSO-d6, 400 MHz) δ 8.12 (s, 1H), 7.57 (s, 1H), 7.57 (d, J=8.0 Hz, 2H), 7.48 (d, J=8.0 Hz, 2H), 6.77 (br s, 2H), 5.048 (d, J=5.6 Hz, 1H), 4.93-4.98 (m, 2H), 4.27 (q, J=6.8, 6.0 Hz, 1H), 4.09-4.18 (m, 1H), 3.56 (s, 3H), 3.25 (s, 3H), 3.09-3.14 (m, 1H), 2.31-2.40 (m, 1H), 1.97-2.06 (m, 1H). LCMS: 3.161 min, MS: ES+476.0 [M+1], 478 [M+3]. Method: LC05_AR1_01.

Step-7: 4-((1R,2R,3S,4R)-4-(4-amino-5-bromo-7H-pyrrolo[2,3-d]pyrimidin-7yl)-2,3-dihydroxycyclopentyl)benzaldehyde

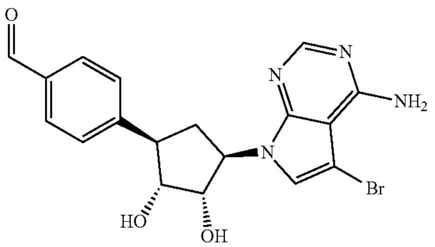 [SMILES: Nc1ncnc2c1c(Br)cn2[C@@H]1C[C@H](c2ccc(C=O)cc2)[C@@H](O)[C@H]1O]

Procedure

To a stirred solution of 4-((1R,2R,3S,4R)-4-(4-amino-5-bromo-7H-pyrrolo[2,3-d]pyrimidin-7yl)-2,3-dihydroxycyclopentyl)-N-methoxy-N-methylbenzamide (0.150 g, 0.3157 mmol) in THE (5 mL) was added DIBAL-H (1.0 M in THF) (1.26 mL, 1.262 mmol) drop wised at 0° C. The resulting reaction mixture was stirred at 0° C. for 4 hours. The resulting reaction mixture was quenched by adding saturated $NH_4Cl$ solution in water (50 mL) and extracted with ethyl acetate (100 mL×3). The combined organic layer was dried over anhydrous $Na_2SO_4$, filtered and concentrated under reduced pressure. The obtained crude material was purified by triturated with n-pentane (50 mL×3) to afford 4-((1R,2R,3S,4R)-4-(4-amino-5-bromo-7H-pyrrolo[2,3-d]pyrimidin-7yl)-2,3-dihydroxycyclopentyl)benzaldehyde (0.110 g, 83.0%); LCMS: 3.228 min, MS: ES+416.8 [M+1], 418.8 [M+3]. Method: LC05_FAR1_01.

Step-8: (1R,2S,3R,5R)-3-(4-amino-5-bromo-7H-pyrrolo[2,3-d]pyrimidin-7-yl)-5-(4-(((cyclobutylmethyl)amino)methyl)phenyl)cyclopentane-1,2-diol

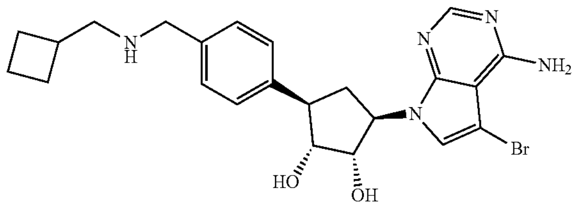 [SMILES: Nc1ncnc2c1c(Br)cn2[C@@H]1C[C@H](c2ccc(CNCC3CCC3)cc2)[C@@H](O)[C@H]1O]

Procedure

To a stirred solution of 4-((1R,2R,3S,4R)-4-(4-amino-5-bromo-7H-pyrrolo[2,3-d]pyrimidin-7yl)-2,3-dihydroxycyclopentyl)benzaldehyde (0.095 g, 0.23 mmol) in ethylene dichloride (5 mL) was added cyclobutylmethanamine (0.029 g, 0.34 mmol,) followed by acetic acid (2 drops) at room temperature. The resulting reaction mixture was stirred at room temperature for 1 hour. The reaction mixture was then cooled to 0° C. whereupon sodium triacetoxyborohydride (0.096 g, 0.46 mmol) was added. The resulting reaction mixture was stirred at 0° C. for 30 min then allowed to warm up to room temperature and stirred for 3 hours. The resulting reaction mixture was quenched by saturated $NaHCO_3$ solution in water (50 mL) and extracted with ethyl acetate (100 mL×3). The combined organic layer was dried over anhydrous $Na_2SO_4$, filtered and concentrated under reduced pressure. The obtained crude material was purified by reverse phase chromatography using 15% ACN in Water on C18 silica gel to afford white solid (0.019 g, 18%); 1H-NMR: (MeOD, 400 MHz) δ 8.13 (s, 1H), 7.48 (s, 1H), 7.43 (d, J=8.0 Hz, 2H), 7.37 (d, J=8.0 Hz, 2H), 4.95-5.02 (m, 1H), 4.48 (t, J=6.8 Hz, 1H), 4.24 (t, J=6.4 Hz, 1H), 3.84 (s, 2H), 3.20-3.26 (m, 1H), 2.72 (d, J=7.2 Hz, 2H), 2.49-2.58 (m, 2H), 2.12-2.17 (m, 3H), 1.88-1.97 (m, 2H), 1.70-1.76 (m, 2H). LCMS: 4.383 min, MS: ES+486.2 [M+1], 488.2 [M+3]. Method: HP07_TFAR1

Example 11: (1R,2S,3R,5R)-3-{4-amino-5-bromo-7H-pyrrolo[2,3-d]pyrimidin-7-yl}-5-(2-{[({3-fluorobicyclo[1.1.1]pentan-1-yl}methyl)amino]methyl}-1H-indol-6-yl)cyclopentane-1,2-diol

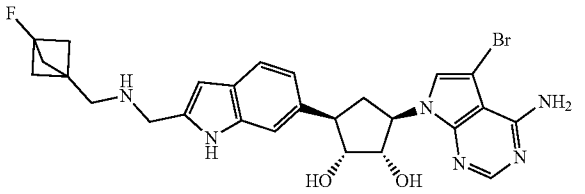 [SMILES: Nc1ncnc2c1c(Br)cn2[C@@H]1C[C@H](c2ccc3cc(CNCC45CC(F)(C4)C5)[nH]c3c2)[C@@H](O)[C@H]1O]

Step 1: [(6-bromo-1H-indol-2-yl)methyl]([3-fluorobicyclo[1.1.1]pentan-1-yl)methyl)amine

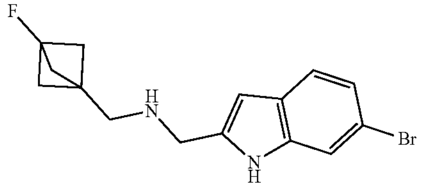 [SMILES: FC12CC(CNCc3cc4ccc(Br)cc4[nH]3)(C1)C2]

To a suspension of 6-bromo-1H-indole-2-carbaldehyde (750 mg, 3.35 mmol) in ethanol (30 mL) was added {3-fluorobicyclo[1.1.1]pentan-1-yl}methanamine hydrochloride (508 mg, 3.35 mmol) and N-ethyl-N-isopropyl-propan-2-amine (1.8 mL, 10.0 mmol) and the mixture was stirred at 70° C. for 2 hours. After cooling to room temperature, sodium borohydride (380 mg, 10.0 mmol) was added and the resulting mixture was stirred at room temperature for 16 hours. The mixture was concentrated to dryness and the residue was partitioned between EtOAc (60 mL), water (30 mL) and $Na_2CO_3$ (sat., 20 mL). The organic layer was separated, washed with brine (20 mL), dried ($Na_2SO_4$), and concentrated at reduced pressure. The residue was purified by chromatography on silica gel [eluting with 0-100% EtOAc in heptane] to afford the title compound (1.07 g, 93%) as an orange oil that solidified upon standing.

Method J: LC-MS (electrospray): m/z=323.2/325.2 $(M+H)^+$, RT=0.87 min.

Step 2: tert-butyl 6-bromo-2-({[(tert-butoxy)carbonyl]({3-fluorobicyclo[1.1.1]pentan-1-yl}methyl)amino}methyl)-1H-indole-1-carboxylate

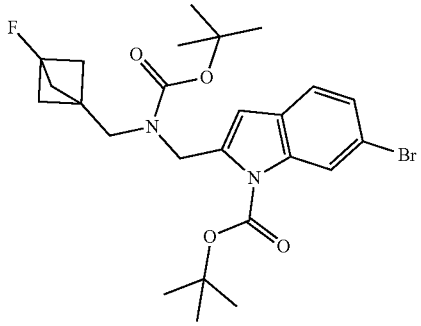 [SMILES: CC(C)(C)OC(=O)N(Cc1cc2ccc(Br)cc2n1C(=O)OC(C)(C)C)CC12CC(F)(C1)C2]

A solution of [(6-bromo-1H-indol-2-yl)methyl]({3-fluorobicyclo[1.1.1]pentan-1-yl}methyl)amine (1.05 g, 3.05 mmol) and di-tert-butyl dicarbonate (2.0 g, 9.16 mmol) in acetonitrile (20 mL) was treated with N,N-dimethylpyridin-4-amine (37 mg, 0.31 mmol) and the mixture was stirred at 40° C. for 1 hour then at room temperature for 17 hours. The mixture was concentrated under vacuum and the residue was partitioned between water (10 mL) and DCM (25 mL) and extracted with DCM (10 mL). The extracts were washed with water (5 mL), brine (5 mL), dried over sodium sulfate and concentrated to give the crude product as a red glass (1.77 g). The material was purified by chromatography on silica gel [eluting with 0-100% of EtOAc/heptane followed by 0-50% MeOH/DCM] to give the title compound (1.54 g, 89%) as a light yellow solid. $^1$H NMR (400 MHz, DMSO) δ 8.30-8.18 (m, 1H), 7.59-7.50 (m, 1H), 7.38 (dd, J=8.3, 1.8 Hz, 1H), 6.44-6.30 (m, 1H), 4.70-4.56 (m, 2H), 3.67-3.53 (m, 2H), 2.00 (s, 6H), 1.65 (s, 9H), 1.44 (s, 7H), 1.34-1.29 (m, 2H).

Step 3: tert-butyl 2-([[(tert-butoxy)carbonyl]({3-fluorobicyclo[1.1.1]pentan-1-yl}methyl)amino)methyl)-6-(4,4,5,5-tetramethyl-1,3,2-dioxaborolan-2-yl)-1H-indole-1-carboxylate

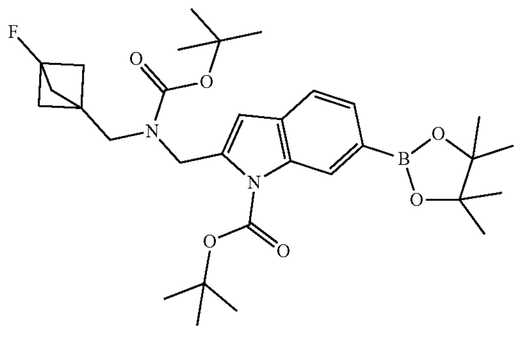 [SMILES: CC(C)(C)OC(=O)N(Cc1cc2ccc(B3OC(C)(C)C(C)(C)O3)cc2n1C(=O)OC(C)(C)C)CC12CC(F)(C1)C2]

An oven-dried three neck flask equipped with a reflux condenser and an oil bubbler was purged thoroughly with nitrogen and charged with tert-butyl 6-bromo-2-({[(tert-butoxy)carbonyl]({3-fluorobicyclo[1.1.1]pentan-1-yl}methyl)amino}methyl)-1H-indole-1-carboxylate (500 mg, 0.96 mmol), 4,4,4',4',5,5,5',5'-octamethyl-2,2'-bi-1,3,2-dioxaborolane (291 mg, 1.15 mmol), potassium acetate (284 mg, 2.87 mmol), [1,1'-Bis(diphenylphosphino)ferrocene]dichloropalladium(II), complex with dichloromethane (78 mg, 0.06 mmol) and anhydrous THE (15 mL). The reaction was de-oxygenated by passing a stream of nitrogen gas through the contents for 15 minutes during which time the reaction turned from orange to dark brown. The reaction was placed in a pre-heated heating block at 60° C., kept under a slow flow of nitrogen and stirred at 60° C. for 15 hours. The mixture was cooled to room temperature and filtered through a bed of Celite, rinsing with ethyl acetate. The filtrate was concentrated to give the crude product as a black oil. The material was purified by chromatography on silica gel [eluting with 0-100% of EtOAc/heptane followed by 0-50% of MeOH/DCM] to give the title compound (467 mg, 81%) as a white foam.

Method J: LC-MS (electrospray): m/z=593.3 (M+H)$^+$, RT=4.7 min.

Step 4: tert-butyl 6-[(3aR,4R,6aR)-2,2-dimethyl-6-oxo-hexahydrocyclopenta[d][1,3]dioxol-4-yl]-2-({[(tert-butoxy)carbonyl]({3-fluorobicyclo[1.1.1]pentan-1-yl}methyl)amino}methyl)-1H-indole-1-carboxylate

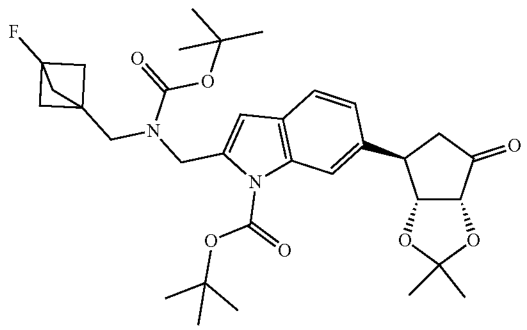 [SMILES: CC(C)(C)OC(=O)N(Cc1cc2ccc([C@H]3CC(=O)[C@@H]4OC(C)(C)O[C@H]34)cc2n1C(=O)OC(C)(C)C)CC12CC(F)(C1)C2]

A three-neck 25 mL flask equipped with a reflux condenser and an oil bubbler was purged with nitrogen and charged with tert-butyl 2-({[(tert-butoxy)carbonyl]({3-fluorobicyclo[1.1.1]pentan-1-yl)methyl)amino}methyl)-6-(4,4,5,5-tetramethyl-1,3,2-dioxaborolan-2-yl)-1H-indole-1-carboxylate (467 mg, 0.78 mmol), (3aR,6aR)-2,2-dimethyl-2H,3aH,4H,6aH-cyclopenta[d][1,3]dioxol-4-one (120 mg, 0.78 mmol), [Rh(COD)Cl]2 (19 mg, 0.039 mmol), 1,4-Dioxane (10 mL), Water (2 mL) and triethylamine (325 mL, 2.33 mmol). The reaction mixture was de-oxygenated by passing a flow of nitrogen through the contents for 15 minutes. The mixture was kept under a positive nitrogen pressure and placed in a pre-heated heating block at 50° C. and stirred for 3 hours. The reaction was cooled to room temperature diluted with DCM (20 mL) and water (5 mL) and extracted with DCM (2×10 mL) and $CHCl_3$/IPA (3:1, 10 mL). The combined organics were washed with water (5 mL), brine (5 mL), dried over sodium sulfate and concentrated to give the crude product as a brown viscous oil (694 mg) which was purified by chromatography on silica gel [eluting with 0-100% EtOAc/heptane followed by 0-50% DCM/MeOH to give the title compound (387 mg, 75%) as a yellow oil.

Method J: LC-MS (electrospray): m/z=621.3 (M+H)$^+$, RT=4.43 min.

Step 5: tert-butyl 6-[(3aR,4R,6S,6aS)-6-hydroxy-2,2-dimethyl-hexahydrocyclopenta[d][1,3]dioxol-4-yl]-2-({[(tert-butoxy)carbonyl]({3-fluorobicyclo[1.1.1]pentan-1-yl}methyl)amino}methyl)-1H-indole-1-carboxylate

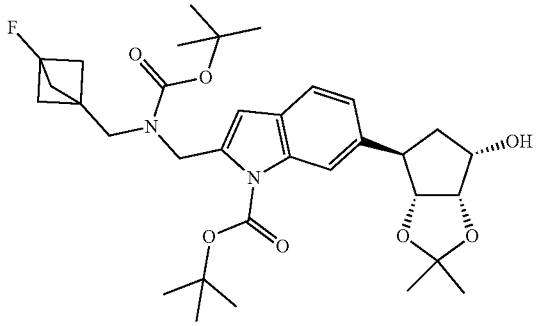 [SMILES: CC(C)(C)OC(=O)N(Cc1cc2ccc([C@H]3C[C@H](O)[C@@H]4OC(C)(C)O[C@@H]43)cc2n1C(=O)OC(C)(C)C)CC12CC(F)(C1)C2]

A solution containing tert-butyl 6-[(3aR,4R,6aR)-2,2-dimethyl-6-oxo-hexahydrocyclopenta[d][1,3]dioxol-4-yl]-2-({[(tert-butoxy)carbonyl]({3-fluorobicyclo[1.1.1]pentan-1-yl}methyl)amino}methyl)-1H-indole-1-carboxylate (387 mg, 0.582 mmol) in methanol (3 mL) was cooled to 0° C. and treated with sodium borohydride (66 mg, 1.75 mmol). The mixture was stirred for 1 hour and then diluted with water (5 mL) and DCM (20 mL). The mixture was warmed to room temperature and the phases were separated. The aqueous phase was extracted with DCM (3×10 mL). The combined organics were washed with water (5 mL), brine (5 mL), dried over sodium sulfate and concentrated to give the crude product as a white solid. The material was purified by chromatography on silica gel [eluting with 0-100% EtOAc/heptane] to give the title compound (260 mg, 71%) as a white foam along with tert-butyl 6-[(3aR,4R,6R,6aS)-6-hydroxy-2,2-dimethyl-hexahydrocyclopenta[d][1,3]dioxol-4-yl]-2-({[(tert-butoxy)carbonyl]({3 fluorobicyclo[1.1.1]pentan-1-yl}methyl)amino}methyl)-1H-indole-1-carboxylate (44 mg, 12%) as a white foam.

Method J: LC-MS (electrospray): m/z=623.3 $(M+H)^+$, RT=4.36 min.

Step 6: tert-butyl 6-[(3aR,4R,6R,6aS)-6-{5-bromo-4-chloro-7H-pyrrolo[2,3-d]pyrimidin-7-yl}-2,2-dimethyl-hexahydrocyclopenta[d][1,3]dioxol-4-yl]-2-({[(tert-butoxy)carbonyl]({3-fluorobicyclo[1.1.1]pentan-1-yl}methyl)amino}methyl)-1H-indole-1-carboxylate

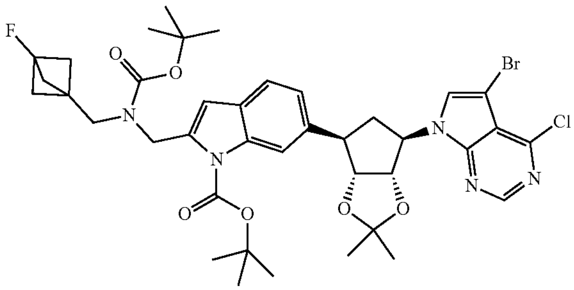 [SMILES: CC(C)(C)OC(=O)N(Cc1cc2ccc([C@H]3C[C@@H](n4cc(Br)c5c(Cl)ncnc54)[C@@H]4OC(C)(C)O[C@@H]43)cc2n1C(=O)OC(C)(C)C)CC12CC(F)(C1)C2]

An oven-dried three-neck 25 mL flask equipped with a reflux condenser and oil bubbler was flushed with nitrogen and charged with tert-butyl 6-[(3aR,4R,6S,6aS)-6-hydroxy-2,2-dimethyl-hexahydrocyclopenta[d][1,3]dioxol-4-yl]-2-({[(tert-butoxy)carbonyl]({3-fluorobicyclo[1.1.1]pentan-1-yl}methyl)amino}methyl)-1H-indole-1-carboxylate (50 mg, 0.08 mmol), triphenylphosphine (62 mg, 0.24 mmol), 5-bromo-4-chloro-7H-pyrrolo[2,3-d]pyrimidine (55 mg, 0.24 mmol) and anhydrous THF (3.5 mL) and the mixture was heated to 50° C. before DBU (1 M in THF, 0.24 mL, 0.24 mmol) was added quickly followed by a solution of diethyl azodicarboxylate (37 mL, 0.23 mmol) in anhydrous THF (1.5 mL) and the reaction was stirred at 50° C. for 2.5 hours. A solution containing triphenylphosphine (21 mg, 0.08 mmol) in anhydrous THF (0.5 mL) was added followed by diethyl azodicarboxylate (12 mL, 0.08 mmol) in anhydrous THF (1 mL) and the mixture was stirred at 50° C. for 1 hour. The mixture was cooled to room temperature diluted with $NaHCO_3$ (sat., 5 mL) and brine (5 mL) and extracted with EtOAc (1×20 mL and 2×10 mL). The combined organics were washed with brine (5 mL), dried over sodium sulfate and concentrated to give a brown oil (277 mg), which crystallised on standing overnight. The material was purified by chromatography on silica gel [eluting with 0-100% EtOAc/heptane followed by 0-50% MeOH/DCM. To give the title compound (41 mg, 60%) as a white foam.

Method C: LC-MS (electrospray): m/z=814.6/816.6 $(M+H)^+$, RT=5.77 min.

Step 7: tert-butyl 6-[(3aR,4R,6R,6aS)-6-{4-amino-5-bromo-7H-pyrrolo[2,3-d]pyrimidin-7-yl)-2,2-dimethyl-hexahydrocyclopenta[d][1,3]dioxol-4-yl]-2-({[(tert-butoxy)carbonyl]({3-fluorobicyclo[1.1.1]pentan-1-yl}methyl)amino}methyl)-1H-indole-1-carboxylate

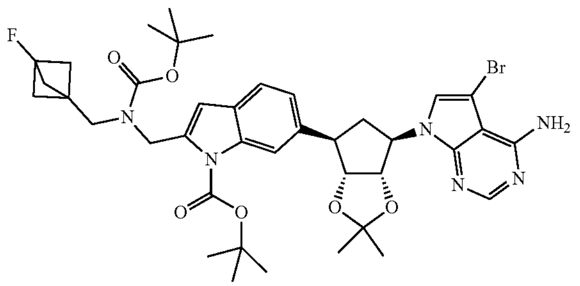 [SMILES: CC(C)(C)OC(=O)N(Cc1cc2ccc([C@H]3C[C@@H](n4cc(Br)c5c(N)ncnc54)[C@@H]4OC(C)(C)O[C@@H]43)cc2n1C(=O)OC(C)(C)C)CC12CC(F)(C1)C2]

A microwave vial was charged with tert-butyl 6-[(3aR,4R,6R,6aS)-6-{5-bromo-4-chloro-7H-pyrrolo[2,3-d]pyrimidin-7-yl}-2,2-dimethyl-hexahydrocyclopenta[d][1,3]dioxol-4-yl]-2-({[(tert-butoxy)carbonyl]({3-fluorobicyclo[1.1.1]pentan-1-yl}methyl)amino}methyl)-1H-indole-1-carboxylate (41 mg, 0.048 mmol), 1,4-Dioxane (1.5 mL) and ammonia (37% in water) (1.5 mL, 0.048 mmol). The vial was sealed and the reaction heated at 60° C. for 7 hours and at 75° C. for 16 hours and then at 85° C. for 5 hours. The mixture was diluted with 1,4-Dioxane (1 mL) and heated at 85° C. for 15 hours. The reaction was concentrated and the residue was partitioned between DCM (10 mL) and water (5 mL). The aqueous phase was extracted with DCM (5 mL) and the combined organics were filtered through a hydrophobic frit and concentrated to give the title compound (42 mg, Quant) as a yellow solid which contained 34% of the partially de-protected product tert-butyl N-({6-[(3aR,4R,6R,6aS)-6-{4-amino-5-bromo-7H-pyrrolo[2,3-d]pyrimidin-7-yl}-2,2-dimethyl-hexahydrocyclopenta[d][1,3]dioxol-4-yl]-1H-indol-2-yl}methyl)-N-({3-fluorobicyclo[1.1.1]pentan-1-yl}methyl)carbamate. This mixture was telescoped into the next reaction.

Method C: LC-MS (electrospray): m/z=795.6/797.6 $(M+H)^+$, RT=5.23 min; 695.6/697.6 $(M+H)^+$, RT=4.67 min.

Step 8: (1R,2S,3R,5R)-3-{4-amino-5-bromo-7H-pyrrolo[2,3-d]pyrimidin-7-yl}-5-(2-{[({3-fluorobicyclo[1.1.1]pentan-1-yl}methyl)amino]methyl}-1H-indol-6-yl)cyclopentane-1,2-diol

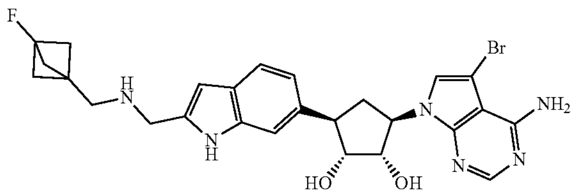 [SMILES: Nc1ncnc2c1c(Br)cn2[C@@H]1C[C@H](c2ccc3cc(CNCC45CC(F)(C4)C5)[nH]c3c2)[C@@H](O)[C@H]1O]

A solution of tert-butyl 6-[(3aR,4R,6R,6aS)-6-{4-amino-5-bromo-7H-pyrrolo[2,3-d]pyrimidin-7-yl}-2,2-dimethyl-hexahydrocyclopenta[d][1,3]dioxol-4-yl]-2-({[(tert-butoxy)carbonyl]({3-fluorobicyclo[1.1.1]pentan-1-yl}methyl)amino}methyl)-1H-indole-1-carboxylate and tert-butyl N-({6-[(3aR,4R,6R,6aS)-6-{4-amino-5-bromo-7H-pyrrolo[2,3-d]pyrimidin-7-yl}-2,2-dimethyl-hexahydrocyclopenta[d][1,3]dioxol-4-yl]-1H-indol-2-yl}methyl)-N-({3-fluorobicyclo[1.1.1]pentan-1-yl}methyl)carbamate (42 mg, 0.05 mmol) in methanol (2 mL) was treated with HCl (4M in dioxane, 1 mL, 4 mmol) and the mixture was stirred at room temperature for 20 hours. Further HCl (4M in dioxane, 1 mL, 4 mmol) was added and the mixture was stirred at room temperature for 3 hours and then at 40° C. for 3 hours. The reaction was quenched with $Na_2CO_3$ (sat., 5 mL, pH 10-11) and concentrated to remove organics and partitioned between water (5 mL) and DCM (20 mL). The aqueous phase was extracted with DCM (2×10 mL). The combined organics were washed with water (5 mL), dried over sodium sulfate and concentrated to give a brown oil (28 mg). The material was purified by preparative HPLC (Method B) and evaporated under vacuum to provide a residue which was dissolved in MeCN and concentrated. The residue was triturated with diethyl ether to give the title compound (4.2 mg, 14%) as a light-brown solid.

Method C: LC-MS (electrospray): m/z=555.4/557.4 $(M+H)^+$, RT=3.07 min.

Example 12: (1R,2S,3R,5R)-3-{4-amino-5-bromo-7H-pyrrolo[2,3-d]pyrimidin-7-yl}-5-(4-{2-[({3-fluorobicyclo[1.1.1]pentan-1-yl}methyl)amino]ethyl}phenyl)cyclopentane-1,2-diol

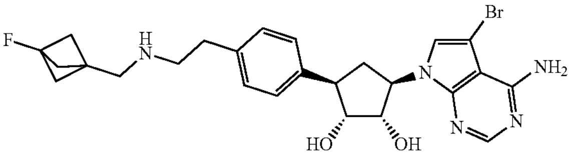 [SMILES: Nc1ncnc2c1c(Br)cn2[C@@H]1C[C@H](c2ccc(CCNCC34CC(F)(C3)C4)cc2)[C@@H](O)[C@H]1O]

The title compound was prepared from 2-(4-bromophenyl)acetaldehyde in an analogous fashion to Example 11 to give (33 mg, 34%) as a white solid.

Method C: LC-MS (electrospray): m/z=530.5/532.4 $(M+H)^+$, RT=2.98 min.

Example 20: (2R,3R,4S,5R)-2-[4-amino-5-(1H-pyrazol-3-yl)-7H-pyrrolo[2,3-d]pyrimidin-7-yl]-5-[(1E)-5-[({3-fluorobicyclo[1.1.1]pentan-1-yl}methyl)amino]pent-1-en-1-yl]oxolane-3,4-diol

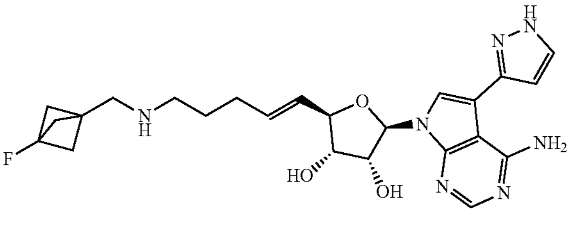 [SMILES: Nc1ncnc2c1c(-c1cc[nH]n1)cn2[C@@H]1O[C@H](/C=C/CCCNCC23CC(F)(C2)C3)[C@@H](O)[C@H]1O]

A pressure vial was charged with (2R,3R,4S,5R)-2-(4-amino-5-bromo-pyrrolo[2,3-d]pyrimidin-7-yl)-5-[(E)-5-[(3-fluoro-1-bicyclo[1.1.1]pentanyl)methylamino]pent-1-enyl]tetrahydrofuran-3,4-diol (Example 6, 24 mg, 0.05 mmol), 1,4-Dioxane (2 mL), 1H-pyrazol-5-ylboronic acid (10 mg, 0.09 mmol) and sodium carbonate (2M, 0.14 mL, 0.28 mmol). The resulting suspension was de-oxygenated by passing a flow of nitrogen through it for 15 minutes before cyclopentyl(diphenyl)phosphane;dichloromethane;dichloropalladium;iron (3.8 mg, 4.6 μmol) was added. The vial was sealed and placed in a pre-heated heating block at 80° C. and stirred for 3 hours.

After cooling to room temperature the mixture was partitioned between $NaHCO_3$ (sat., 10 mL) and chloroform/2-propanol (3:1, 20 mL). The organic layer was separated and the aqueous layer was extracted with chloroform/2-propanol (3:1, 10 mL). The combined organic layers were washed with brine (5 mL), dried ($Na_2SO_4$) and concentrated at reduced pressure.

The residue was purified by Preparative HPLC (Method B). The product containing fraction was lyophilised to afford the title compound (0.70 mg, 3.1%) as a colourless solid.

Method C: LC-MS (electrospray): m/z=484.5 $(M+H)^+$, RT=2.43 min.

Example 21: ((2R,3R,4S,5R)-2-(4-amino-5-bromo-7H-pyrrolo[2,3-d]pyrimidin-7-yl)-5-[(1E)-5-{6-azaspiro[3.4]octan-6-yl}pent-1-en-1-yl]oxolane-3,4-diol

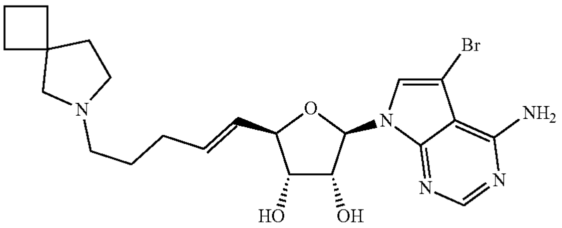 [SMILES: Nc1ncnc2c1c(Br)cn2[C@@H]1O[C@H](/C=C/CCCN2CCC3(CCC3)C2)[C@@H](O)[C@H]1O]

Step 1: 7-[(3aR,4R,6R,6aR)-6-ethenyl-2,2-dimethyl-tetrahydro-2H-furo[3,4-d][1,3]dioxol-4-yl]-5-bromo-4-chloro-7H-pyrrolo[2,3-d]pyrimidine

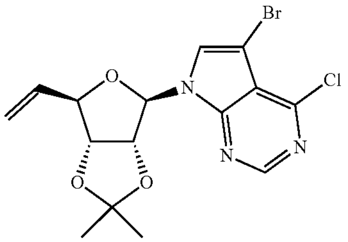 [SMILES: C=C[C@H]1O[C@@H](n2cc(Br)c3c(Cl)ncnc32)[C@@H]2OC(C)(C)O[C@@H]21]

A mixture of (2R,3R,4S,5R)-2-(5-bromo-4-chloro-pyrrolo[2,3-d]pyrimidin-7-yl)-5-vinyl-tetrahydrofuran-3,4-diol (Example 1 Step 4, 400 mg, 0.56 mmol), 2,2-dimethoxypropane (1.2 mL, 9.98 mmol) and camphorsulfonic acid (129 mg, 0.56 mmol) in Acetone (6 mL) was stirred at room temperature for 18 hours.

The reaction mixture was evaporated to dryness and purified by chromatography on silica gel (eluting with 0-80% EtOAc in heptane) and evaporated to dryness under reduced pressure to afford the title compound (414 mg, 93%) as a pale yellow oil.

Method J: LC-MS (electrospray): m/z=400.3/402.3 $(M+H)^+$, RT=0.90 min.

Step 2: 7-[(3aR,4R,6R,6aR)-6-ethenyl-2,2-dimethyl-tetrahydro-2H-furo[3,4-d][1,3]dioxol-4-yl]-5-bromo-7H-pyrrolo[2,3-d]pyrimidin-4-amine

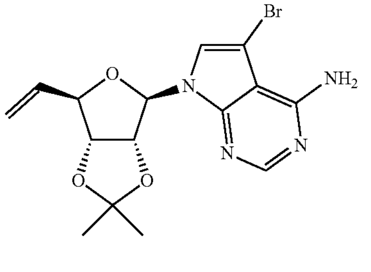 [SMILES: C=C[C@H]1O[C@@H](n2cc(Br)c3c(N)ncnc32)[C@@H]2OC(C)(C)O[C@@H]21]

A sealed tube containing a solution of 7-[(3aR,4R,6R,6aR)-2,2-dimethyl-6-vinyl-3a,4,6,6a-tetrahydrofuro[3,4-d][1,3]dioxol-4-yl]-5-bromo-4-chloro-pyrrolo[2,3-d]pyrimidine (410 mg, 1.02 mmol) in aqueous ammonia (35%, 5.7 mL, 0.1 mol) and 1,4-Dioxane (11 mL) was stirred at 80° C. for 18 hours.

The reaction mixture was evaporated to dryness and purified by chromatography on silica gel (eluting with 0-100% EtOAc in heptane) to afford the title compound (310 mg, 78%) as a colourless gum.

Method A: LC-MS (electrospray): m/z=381.1/383.1 $(M+H)^+$, RT=1.03 min.

Step 3: tert-butyl N-{7-[(3aR,4R,6R,6aR)-6-ethenyl-2,2-dimethyl-tetrahydro-2H-furo[3,4-d][1,3]dioxol-4-yl]-5-bromo-7H-pyrrolo[2,3-d]pyrimidin-4-yl}-N-[(tert-butoxy)carbonyl]carbamate

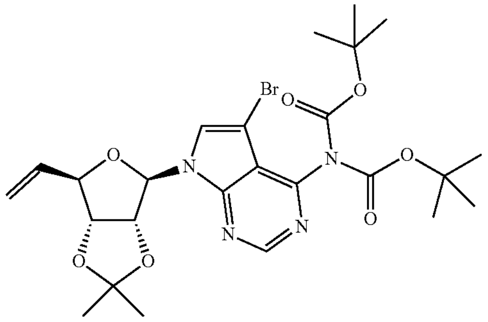 [SMILES: C=C[C@H]1O[C@@H](n2cc(Br)c3c(N(C(=O)OC(C)(C)C)C(=O)OC(C)(C)C)ncnc32)[C@@H]2OC(C)(C)O[C@@H]21]

DMAP (43 mg, 0.35 mmol) was added to a solution of 7-[(3aR,4R,6R,6aR)-2,2-dimethyl-6-vinyl-3a,4,6,6a-tetrahydrofuro[3,4-d][1,3]dioxol-4-yl]-5-bromo-pyrrolo[2,3-d]pyrimidin-4-amine (1350 mg, 3.54 mmol) and Boc anhydride (2319 mg, 10.6 mmol) in THF (43 mL) and the mixture was stirred at 40° C. for 18 hours.

The reaction mixture was evaporated to dryness and purified by Chromatography on silica gel (eluting with 0-50% EtOAc in heptane) to afford the title compound (2060 mg, 90%) as a yellow oil.

Method M: LC-MS (electrospray): m/z=603.1/605.1 $(M+H)^+$, RT=1.75 min.

Step 4: tert-butyl N-{7-[(3aR,4R,6R,6aR)-6-[(1E)-5-hydroxypent-1-en-1-yl]-2,2-dimethyl-tetrahydro-2H-furo[3,4-d][1,3]dioxol-4-yl]-5-bromo-7H-pyrrolo[2,3-d]pyrimidin-4-yl}-N-[(tert-butoxy)carbonyl]carbamate

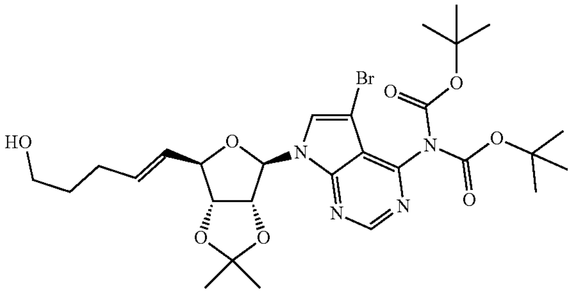 [SMILES: CC(C)(C)OC(=O)N(C(=O)OC(C)(C)C)c1ncnc2c1c(Br)cn2[C@@H]1O[C@H](/C=C/CCCO)[C@H]2OC(C)(C)O[C@H]21]

The title compound was prepared from tert-butyl N-{7-[(3aR,4R,6R,6aR)-6-ethenyl-2,2-dimethyl-tetrahydro-2H-furo[3,4-d][1,3]dioxol-4-yl]-5-bromo-7H-pyrrolo[2,3-d]pyrimidin-4-yl}-N-[(tert-butoxy)carbonyl]carbamate and pent-4-en-1-ol using the procedure described in Example 1 Step 5 to give (320 mg, 77%) as a yellow gum.

Method M: LC-MS (electrospray): m/z=661.1/663.1 $(M+H)^+$, RT=1.61 min.

Step 5: (4E)-5-[(2R,3S,4R,5R)-5-{4-amino-5-bromo-7H-pyrrolo[2,3-d]pyrimidin-7-yl}-3,4-dihydroxyoxolan-2-yl]pent-4-en-1-yl methanesulfonate

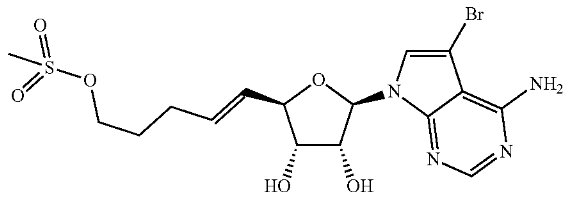 [SMILES: CS(=O)(=O)OCCC/C=C/[C@H]1O[C@@H](n2cc(Br)c3c(N)ncnc32)[C@H](O)[C@@H]1O]

Mesyl chloride (45 uL, 0.58 mmol) was added to a solution of tert-butyl N-[7-[(3aR,4R,6R,6aR)-6-[(E)-5-hydroxypent-1-enyl]-2,2-dimethyl-3a,4,6,6a-tetrahydrofuro[3,4-d][1,3]dioxol-4-yl]-5-bromo-pyrrolo[2,3-d]pyrimidin-4-yl]-N-tert-butoxycarbonyl-carbamate (320 mg, 0.47 mmol) and DIPEA (246 uL, 1.4 mmol) in DCM (9.6 mL) and the mixture was stirred at room temperature for an hour.

The mixture was diluted with water (5 mL) and extracted with DCM (3×5 mL) using a Telos phase separator. The extracts were evaporated to dryness to the crude mesylate 370 mg.

TFA (0.20 mL, 2.6 mmol) was added to a solution of the crude mesylate (100 mg, 0.14 mmol) in DCM (0.4 mL) and the mixture was stirred at room temperature for an hour. MeOH (0.2 mL) was added and the mixture was stirred at room temperature for 2 hours.

TFA (0.2 mL) and MeOH (0.2 mL) were added and the mixture was stirred at room temperature for 67 hours and at 40° C. for 27 hours.

The mixture was evaporated to dryness to afford the title compound (66 mg, 66%) as a yellow oil.

Method A: LC-MS (electrospray): m/z=477.0/479.0 $(M+H)^+$, RT=0.86 min.

Step 6: ((2R,3R,4S,5R)-2-{4-amino-5-bromo-7H-pyrrolo[2,3-d]pyrimidin-7-yl}-5-[(1E)-5-{6-azaspiro[3.4]octan-6-yl}pent-1-en-1-yl]oxolane-3,4-diol

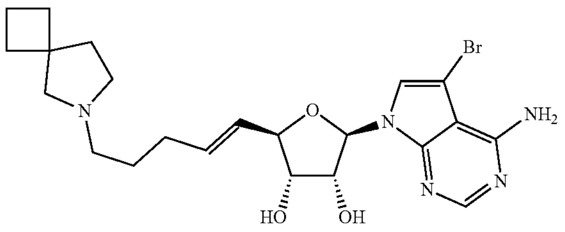 [SMILES: Nc1ncnc2c1c(Br)cn2[C@@H]1O[C@H](/C=C/CCCN2CCC3(CCC3)C2)[C@@H](O)[C@H]1O]

6-azaspiro[3.4]octane (21 mg, 0.19 mmol) was added to a solution of [(E)-5-[(2R,3S,4R,5R)-5-(4-amino-5-bromo-pyrrolo[2,3-d]pyrimidin-7-yl)-3,4-dihydroxy-tetrahydro-furan-2-yl]pent-4-enyl]methanesulfonate (45 mg, 0.0943 mmol), DIPEA (33 uL, 0.189 mmol) and sodium iodide (1.4 mg, 9.43 μmol) in DMF-Anhydrous (1 mL) and the mixture was stirred at 45° C. for 18 hours.

The mixture was evaporated to dryness, purified by Preparative HPLC (Method B) and freeze dried to afford the title compound (7.0 mg, 15%) as a white powder.

Method C: LC-MS (electrospray): m/z=492.3/494.3 $(M+H)^+$, RT=3.30 min.

Example 22: (2R,3S,5R)-5-(4-amino-5-bromo-pyrrolo[2,3-d]pyrimidin-7-yl)-2-[(E)-5-[(3-fluoro-1-bicyclo[1.1.1]pentanyl)methylamino]pent-1-enyl]tetrahydrofuran-3-ol

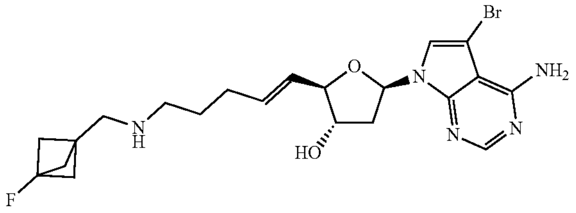 [SMILES: Nc1ncnc2c1c(Br)cn2[C@H]1C[C@H](O)[C@@H](/C=C/CCCNCC23CC(F)(C2)C3)O1]

Step 1: (2S,3S,5R)-5-(4-amino-5-bromo-pyrrolo[2,3-d]pyrimidin-7-yl)-3-[tert-butyl(dimethyl)silyl]oxy-tetrahydrofuran-2-carbaldehyde

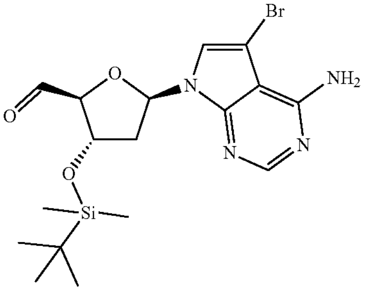 [SMILES: CC(C)(C)[Si](C)(C)O[C@H]1C[C@H](n2cc(Br)c3c(N)ncnc32)O[C@@H]1C=O]

A mixture of [(2R,3S,5R)-5-(4-amino-5-bromo-pyrrolo[2,3-d]pyrimidin-7-yl)-3-[tert-butyl(dimethyl)silyl]oxy-tetrahydrofuran-2-yl]methanol [Prepared according to_Girijavallabhan, Vinay M. et al, WO 2015148746](1 g, 2.26 mmol) and IBX (stabilised, 1.89 g, 6.77 mmol) in Acetonitrile (100 mL) was heated at 80° C. for 2.5 hours. The mixture was cooled in an ice/water bath and filtered. The residue was washed with acetonitrile and the combined filtrates were evaporated under vacuum to afford the title compound (1.46 g, 58%, 40% purity) as an orange foam.

Method J: LC-MS (electrospray): m/z=459.2/461.2 $(M+H)^+$, RT=0.82 min for the aldehyde hydrate.

Step 2: 5-bromo-7-[(2R,4S,5R)-4-[tert-butyl(dimethyl)silyl]oxy-5-vinyl-tetrahydrofuran-2-yl]pyrrolo[2,3-d]pyrimidin-4-amine

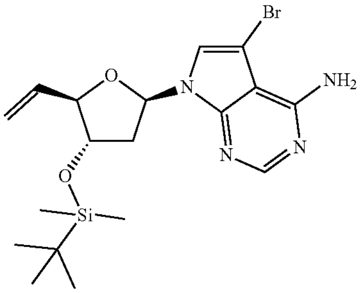 [SMILES: C=C[C@H]1O[C@@H](n2cc(Br)c3c(N)ncnc32)C[C@@H]1O[Si](C)(C)C(C)(C)C]

Methyltriphenylphosphonium iodide (1.64 g, 4.08 mmol) and KOtBu (610 mg, 5.44 mmol) were combined in THF-Anhydrous (40 mL) to give a yellow suspension. The mixture was stirred at room temperature for 1 hour, then (2S,3S,5R)-5-(4-amino-5-bromo-pyrrolo[2,3-d]pyrimidin-7-yl)-3-[tert-butyl(dimethyl)silyl]oxy-tetrahydrofuran-2-carbaldehyde 1.2 g, 2.72 mmol) was added and the mixture stirred at room temperature for 2 hours. The reaction mixture was diluted with diethyl ether (50 ml) and filtered. The residue was washed with diethyl ether and the combined filtrates were evaporated under vacuum. The resultant residue was purified by chromatography on silica gel (eluting with 0-100% EtOAc/heptane) to afford the title compound (549 mg, 33%) as a yellow oil.

Method J: LC-MS (electrospray): m/z=439.2/441.2 $(M+H)^+$, RT=1.02 min

Step 3: tert-butyl N-[5-bromo-7-[(2R,4S,5R)-4-[tert-butyl(dimethyl)silyl]oxy-5-vinyl-tetrahydrofuran-2-yl]pyrrolo[2,3-d]pyrimidin-4-yl]-N-tert-butoxycarbonyl-carbamate

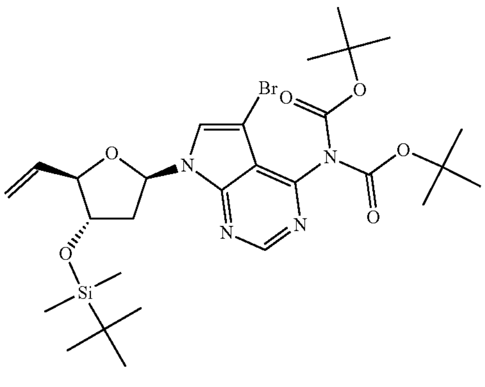 [SMILES: C=C[C@H]1O[C@@H](n2cc(Br)c3c(N(C(=O)OC(C)(C)C)C(=O)OC(C)(C)C)ncnc32)C[C@@H]1O[Si](C)(C)C(C)(C)C]

5-bromo-7-[(2R,4S,5R)-4-[tert-butyl(dimethyl)silyl]oxy-5-vinyl-tetrahydrofuran-2-yl]pyrrolo[2,3-d]pyrimidin-4-amine (549 mg, 1.25 mmol), DMAP (15 mg, 0.12 mmol) and di-tert-butyl dicarbonate (818 mg, 3.75 mmol) were combined in THF (20 mL) and the mixture heated at 60° C. for 2 hours, then at room temperature for 16 hours. The mixture was evaporated under vacuum and the residue was purified by chromatography on silica gel (eluting with 0-100% EtOAc/heptane) to afford the title compound (220 mg, 22%) as a colourless oil.

Method J: LC-MS (electrospray): m/z=639.4/641.4 $(M+H)^+$, RT=1.20 min

Step 4: tert-butyl N-[(E)-5-[(2R,3S,5R)-5-[4-[bis(tert-butoxycarbonyl)amino]-5-bromo-pyrrolo[2,3-d]pyrimidin-7-yl]-3-[tert-butyl(dimethyl)silyl]oxy-tetrahydrofuran-2-yl]pent-4-enyl]-N-[(3-fluoro-1-bicyclo[1.1.1]pentanyl)methyl]carbamate

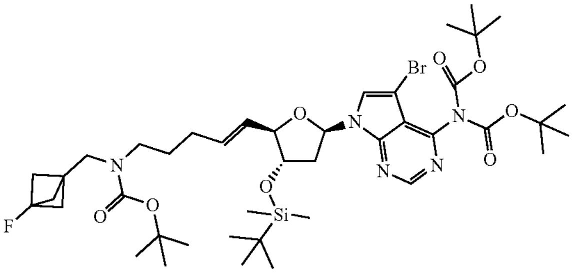 [SMILES: CC(C)(C)OC(=O)N(CCC/C=C/[C@H]1O[C@@H](n2cc(Br)c3c(N(C(=O)OC(C)(C)C)C(=O)OC(C)(C)C)ncnc32)C[C@@H]1O[Si](C)(C)C(C)(C)C)CC12CC(F)(C1)C2]

Tert-butyl N-[5-bromo-7-[(2R,4S,5R)-4-[tert-butyl(dimethyl)silyl]oxy-5-vinyl-tetrahydrofuran-2-yl]pyrrolo[2,3-d]pyrimidin-4-yl]-N-tert-butoxycarbonyl-carbamate (200 mg, 0.31 mmol), tert-butyl N-[(3-fluoro-1-bicyclo[1.1.1]pentanyl)methyl]-N-pent-4-enyl-carbamate [INT-5](266 mg, 0.94 mmol) and Grubbs-Hoyveda 2nd generation (10 mg, 0.02 mmol) were combined in DCM (2 mL) and the mixture heated at 40° C. under a flowing atmosphere of nitrogen for 22 hours. Further tert-butyl N-[(3-fluoro-1-bicyclo[1.1.1]pentanyl)methyl]-N-pent-4-enyl-carbamate [INT-5](266 mg, 0.94 mmol) and Grubbs-Hoyveda 2nd generation (10 mg, 0.02 mmol) were added and heating continued for a further 24 hours. The mixture was cooled to room temperature and evaporated under vacuum and the resultant residue was purified by chromatography on silica gel (eluting with 0-100% EtOAc/heptane) to afford the title compound (383 mg, 88%) as a pale brown oil; material contains partially de-Boc material as a by-product.

Method M: LC-MS (electrospray): m/z=916.35/918.35 $(M+Na)^+$, RT=2.29 min

Step 5: (2R,3S,5R)-5-(4-amino-5-bromo-pyrrolo[2,3-d]pyrimidin-7-yl)-2-[(E)-5-[(3-fluoro-1-bicyclo[1.1.1]pentanyl)methylamino]pent-1-enyl]tetrahydrofuran-3-ol

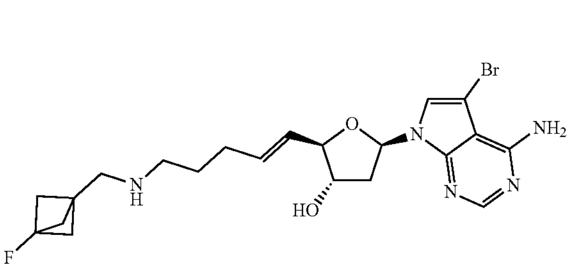 [SMILES: Nc1ncnc2c1c(Br)cn2[C@H]1C[C@H](O)[C@@H](/C=C/CCCNCC23CC(F)(C2)C3)O1]

Tert-butyl N-[(E)-5-[(2R,3S,5R)-5-[4-[bis(tert-butoxycarbonyl)amino]-5-bromo-pyrrolo[2,3-d]pyrimidin-7-yl]-3-[tert-butyl(dimethyl)silyl]oxy-tetrahydrofuran-2-yl]pent-4-enyl]-N-[(3-fluoro-1-bicyclo[1.1.1]pentanyl)methyl]carbamate (380 mg, 0.27 mmol) was dissolved in a mixture of DCM (3 mL), Methanol (3 mL) and TFA (3 mL) and the mixture was stirred at room temperature for 4 days. Further TFA (3 mL) was added after 1 hour and after 20 hours. The reaction mixture was evaporated under vacuum and the residue was purified by ion exchange (SCX-2, 5 g, washing with DCM and MeOH and eluted with ammonia in MeOH (7M). The eluent was evaporated under vacuum and the resultant residue was purified by preparative HPLC (Method B). The clean product-containing fractions combined and evaporated under vacuum to afford the title compound (34 mg, 26%) as a white solid.

Method C: LC-MS (electrospray): m/z=480.3/482.3 $(M+H)^+$, RT=2.79 min

Example 23: (2R,3R,4S,5R)-2-{4-amino-5-bromo-7H-pyrrolo[2,3-d]pyrimidin-7-yl}-5-[(1E)-5-(4,4-difluoropiperidin-1-yl)pent-1-en-1-yl]oxolane-3,4-diol

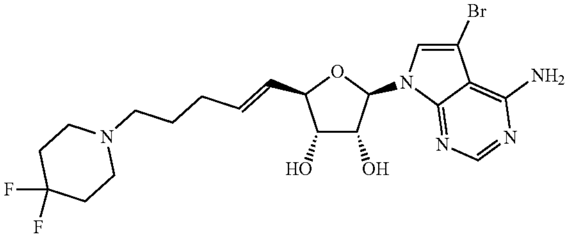 [SMILES: Nc1ncnc2c1c(Br)cn2[C@@H]1O[C@H](/C=C/CCCN2CCC(F)(F)CC2)[C@@H](O)[C@H]1O]

A suspension containing (2R,3R,4S,5R)-2-(4-amino-5-bromo-pyrrolo[2,3-d]pyrimidin-7-yl)-5-vinyl-tetrahydrofuran-3,4-diol (Int-10, 100 mg, 0.293 mmol) and 4,4-difluoro-1-pent-4-enyl-piperidine (INT-6, 118 mg, 0.586 mmol) in DCM (5 mL) was stirred rapidly under air at 50° C. and treated with a mixture of Grubbs-Hoveyda 2nd Gen (9.2 mg, 0.0147 mmol) and 4-methylbenzenesulfonic acid hydrate (335 mg, 1.76 mmol). The reaction was stirred under air for −30 seconds resulting in the green colouration turning light brown. A condenser and nitrogen supply was attached to the reaction, which was then stirred at 50° C. for 2.5 hours. Further Grubbs-Hoveyda 2nd Gen (9.2 mg, 0.0147 mmol) was added and the heating was continued for 45 minutes, further Grubbs-Hoveyda 2nd Gen (4.6 mg, 7.33 μmol) was added and the mixture was stirred at 50° C. for 30 min, cooled to room temperature, diluted with DCM and washed with $Na_2CO_3$ (sat.). The aqueous was extracted with DCM (2×10 mL). The combined organics were washed with water (10 mL), dried over sodium sulfate and concentrated to give a dark-green/black residue which was purified by preparative HPLC (Method B). The clean product-containing fractions were concentrated to give an off-white solid. The material was transferred using ethanol, concentrated, triturated with water (sonication). The supernatant was discarded and the solid was dried under vacuum to afford the title compound (19 mg, 13%) as an off-white solid.

Method C: LC-MS (electrospray): m/z=502.2/504.2 $(M+H)^+$, RT=2.72 min

Example 27: (2R,3R,5S)-2-{4-amino-5-bromo-7H-pyrrolo[2,3-d]pyrimidin-7-yl)-5-[(1E)-5-[({3-fluoro-bicyclo[1.1.1]pentan-1-yl}methyl)amino]pent-1-en-1-yl]oxolan-3-ol

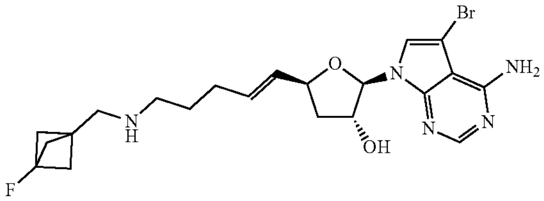 [SMILES: Nc1ncnc2c1c(Br)cn2[C@@H]1O[C@H](/C=C/CCCNCC23CC(F)(C2)C3)C[C@H]1O]

Step 1: (2R,3R,5S)-2-{4-amino-5-bromo-7H-pyrrolo[2,3-d]pyrimidin-7-yl}-5-ethenyloxolan-3-ol

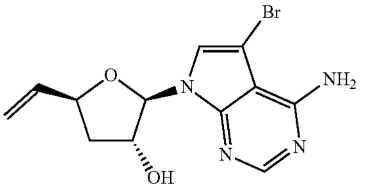 [SMILES: C=C[C@@H]1C[C@@H](O)[C@H](n2cc(Br)c3c(N)ncnc32)O1]

5-bromo-7-[(1R,2R,4R,5R)-4-vinyl-3,6-dioxabicyclo[3.1.0]hexan-2-yl]pyrrolo[2,3-d]pyrimidin-4-amine (INT-11, 187 mg, 0.58 mmol) was dissolved in THF-Anhydrous (5 mL) and $LiBHEt_3$ (1M in THF, 1.16 bmL, 1.16 mmol) was added slowly—gas evolution and the mixture was heated at 60° C. for 2 hours.

The mixture was cooled to room temperature and slowly quenched with AcOH (5% v/v aq, 20 ml)—gas evolution. The mixture was further diluted with water (10 mL) and extracted with chloroform/isopropanol (3:1, 3x20 mL). The combined organic extracts were dried over sodium sulfate and evaporated under vacuum.

The resultant residue was purified by chromatography on silica gel (eluting with 0-20% MeOH/DCM) to afford the title compound (94 mg, 45%) as an off white solid Method J: LC-MS (electrospray): m/z=325.1/327.1 $(M+H)^+$, RT=0.53 min Step 2: tert-butyl N-[(4E)-5-[(2S,4R,5R)-5-{4-amino-5-bromo-7H-pyrrolo[2,3-d]pyrimidin-7-yl}-4-hydroxyoxolan-2-yl]pent-4-en-1-yl]-N-({3-fluoro-bicyclo[1.1.1]pentan-1-yl)methyl)carbamate

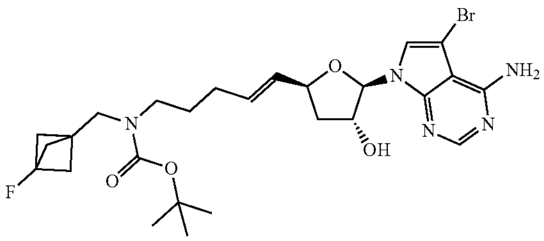 [SMILES: CC(C)(C)OC(=O)N(CCC/C=C/[C@@H]1C[C@@H](O)[C@H](n2cc(Br)c3c(N)ncnc32)O1)CC12CC(F)(C1)C2]

The title compound was prepared using the procedure described in Example 22 Step 4 to give (128 mg, 25%) as a green residue.

Method A: LC-MS (electrospray): m/z=580.7/582.7 $(M+H)^+$, RT=1.11 min

Step 3: (2R,3R,5S)-2-{4-amino-5-bromo-7H-pyrrolo[2,3-d]pyrimidin-7-yl}-5-[(1E)-5-[({3-fluorobicyclo[1.1.1]pentan-1-yl}methyl)amino]pent-1-en-1-yl]oxolan-3-ol

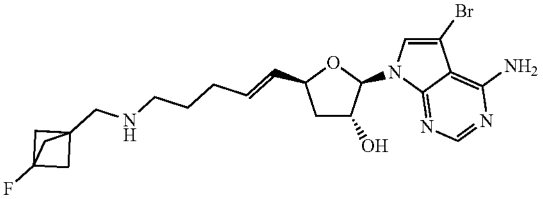 [SMILES: Nc1ncnc2c1c(Br)cn2[C@@H]1O[C@H](/C=C/CCCNCC23CC(F)(C2)C3)C[C@H]1O]

tert-butyl N-[(E)-5-[(2S,4R,5R)-5-(4-amino-5-bromo-pyrrolo[2,3-d]pyrimidin-7-yl)-4-hydroxy-tetrahydrofuran-2-yl]pent-4-enyl]-N-[(3-fluoro-1-bicyclo[1.1.1]pentanyl)methyl]carbamate (128 mg, 0.22 mmol) was dissolved in DCM (2 mL) and TFA (3 mL) and the mixture incubated at room temperature for an hour—pink colour forms within 5 minutes.

The mixture was evaporated under vacuum and the residue was purified by Preparative HPLC (Method B) to afford the title compound (20 mg, 19%) as a white solid Method C: LC-MS (electrospray): m/z=480.3/482.3 $(M+H)^+$, RT=2.87 min Example 28: (2R,3S,4R,5R)-2-{4-amino-5-bromo-7H-pyrrolo[2,3-d]pyrimidin-7-yl)-4-fluoro-5-[(1E)-5-[({3-fluorobicyclo[1.1.1]pentan-1-yl}methyl)amino]pent-1-en-1-yl]oxolan-3-ol

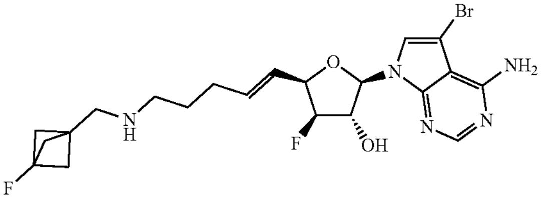 [SMILES: Nc1ncnc2c1c(Br)cn2[C@@H]1O[C@H](/C=C/CCCNCC23CC(F)(C2)C3)[C@H](F)[C@H]1O]

Step 1: (2R,3S,4R,5R)-2-{4-amino-5-bromo-7H-pyrrolo[2,3-d]pyrimidin-7-yl)-5-ethenyl-4-fluorooxolan-3-ol

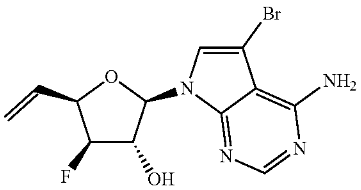 [SMILES: C=C[C@H]1O[C@@H](n2cc(Br)c3c(N)ncnc32)[C@H](O)[C@H]1F]

A flask containing 5-bromo-7-[(1R,2R,4R,5R)-4-vinyl-3,6-dioxabicyclo[3.1.0]hexan-2-yl]pyrrolo[2,3-d]pyrimidin-4-amine (INT-11, 100 mg, 0.309 mmol) was treated with TBAF.3$H_2O$ (195 mg, 0.619 mmol) followed by potassium hydrogen fluoride (24 mg, 0.31 mmol) and the mixture was placed under a nitrogen atmosphere and heated ay 70° C. for 24 hours.

The mixture was cooled to room and left standing overnight.

The mixture was cautiously basified (sat., $NaHCO_3$) and extracted with DCM followed by IPA/$CHCl_3$ (1:3) (phase separator cartridge) and the extracts were evaporated under vacuum to a dark gum which was purified by chromatography on silica gel (eluting with 0-100% EtOAc in heptane) to give the title compound (38 mg, 36%) as a pale gum.

Method C: LC-MS (electrospray): m/z=343.1/345.1 $(M+H)^+$, RT=2.51 min

Step 2: (2R,3S,4R,5R)-2-{4-amino-5-bromo-7H-pyrrolo[2,3-d]pyrimidin-7-yl}-4-fluoro-5-[(1E)-5-[({3-fluorobicyclo[1.1.1]pentan-1-yl}methyl)amino]pent-1-en-1-yl]oxolan-3-ol

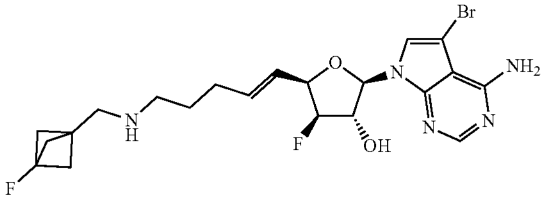 [SMILES: Nc1ncnc2c1c(Br)cn2[C@@H]1O[C@H](/C=C/CCCNCC23CC(F)(C2)C3)[C@H](F)[C@H]1O]

The title compound was prepared using the procedures described in Example 27 Steps 2 and 3 to give (1.5 mg, 30%) as a white powder.

Method C: LC-MS (electrospray): m/z=498.2/500.2 $(M+H)^+$, RT=3.14 min

Example 41: (2R,3R,4R,5R)-5-{4-amino-5-bromo-7H-pyrrolo[2,3-d]pyrimidin-7-yl}-4-fluoro-2-[(1E)-5-[({3-fluorobicyclo[1.1.1]pentan-1-yl}methyl)amino]pent-1-en-1-yl]oxolan-3-ol

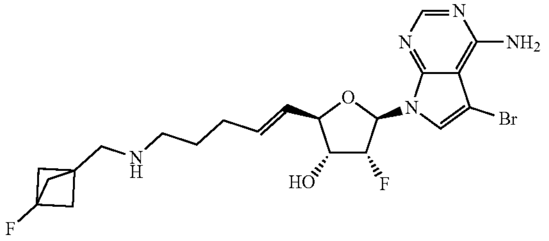 [SMILES: Nc1ncnc2c1c(Br)cn2[C@@H]1O[C@H](/C=C/CCCNCC23CC(F)(C2)C3)[C@@H](O)[C@H]1F]

Step 1: (2R,3R,4R,5R)-5-{4-amino-5-bromo-7H-pyrrolo[2,3-d]pyrimidin-7-yl}-4-fluoro-2-(hydroxymethyl)oxolan-3-ol

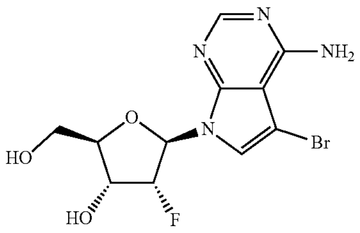 [SMILES: Nc1ncnc2c1c(Br)cn2[C@@H]1O[C@H](CO)[C@@H](O)[C@H]1F]

The title compound was prepared in an analogous fashion to that described for compound 86 (page 167) in WO2014/124430.

Method C: LC-MS (electrospray): m/z=347.1/349.1 $(M+H)^+$, RT=1.41 min

Step 2: 5-bromo-7-[(2R,3R,4R,5R)-4-[tert-butyl(dimethyl)silyl]oxy-5-[[tert-butyl(dimethyl)silyl]oxymethyl]-3-fluoro-tetrahydrofuran-2-yl]pyrrolo[2,3-d]pyrimidin-4-amine

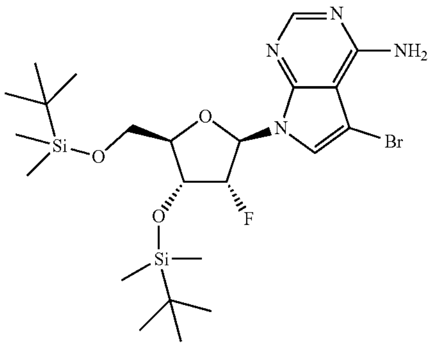 [SMILES: CC(C)(C)[Si](C)(C)OC[C@H]1O[C@@H](n2cc(Br)c3c(N)ncnc32)[C@H](F)[C@@H]1O[Si](C)(C)C(C)(C)C]

A mixture of (2R,3R,4R,5R)-5-(4-amino-5-bromo-pyrrolo[2,3-d]pyrimidin-7-yl)-4-fluoro-2-(hydroxymethyl)tetrahydrofuran-3-ol (300 mg, 0.86 mmol), 1H-imidazole (412 mg, 6.05 mmol) and tert-butyl-chloro-dimethyl-silane (456 mg, 3.02 mmol) in DMF-Anhydrous was stirred at room temperature for three days. The mixture was diluted with EtOAc (40 mL) washed with $NaHCO_3$ (sat., 30 mL) and brine (5×20 mL), dried ($Na_2SO_4$) and evaporated under vacuum. The resultant residue was purified by chromatography on $SiO_2$ [eluting with 0-100% EtOAc/heptane] to afford the title compound (370 mg, 74%) as a pale yellow oil which solidified on standing Method K: LC-MS (electrospray): m/z=575.1/577.1 $(M+H)^+$, RT=1.28 min Step 3: [(2R,3R,4R,5R)-5-(4-amino-5-bromo-pyrrolo[2,3-d]pyrimidin-7-yl)-3-[tert-butyl(dimethyl)silyl]oxy-4-fluoro-tetrahydrofuran-2-yl]methanol

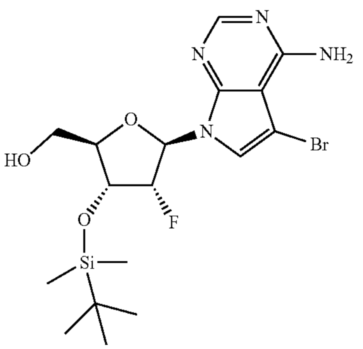 [SMILES: CC(C)(C)[Si](C)(C)O[C@H]1[C@@H](F)[C@H](n2cc(Br)c3c(N)ncnc32)O[C@@H]1CO]

TFA (35% aq, 0.2 mL, 2.61 mmol) was added to an ice-cold solution of 5-bromo-7-[(2R,3R,4R,5R)-4-[tert-butyl(dimethyl)silyl]oxy-5-[[tert-butyl(dimethyl)silyl]oxymethyl]-3-fluoro-tetrahydrofuran-2-yl]pyrrolo[2,3-d]pyrimidin-4-amine (200 mg, 0.35 mmol) in THE (1 mL) and Water (0.2 mL) and the mixture stirred under cooling for 7.5 hours, with addition of further TFA (35% aq, 0.2 mL, 2.6 mmol) after 3 hours and further TFA (50 μl) after 7 hours. The mixture was quenched with $NaHCO_3$ (sat., 30 mL) extracted with DCM (3×30 mL), dried (hydrophobic frit) and evaporated under vacuum. The residue was purified by chromatography on $SiO_2$ [eluting with 0-100% EtOAc/heptane] to afford the title compound (104 mg, 64%) as a white solid.

Method K: LC-MS (electrospray): m/z=460.9/462.9 $(M+H)^+$, RT=0.87 min

Step 4: 5-bromo-7-[(2R,3R,4R,5R)-4-[tert-butyl(dimethyl)silyl]oxy-3-fluoro-5-vinyl-tetrahydrofuran-2-yl]pyrrolo[2,3-d]pyrimidin-4-amine

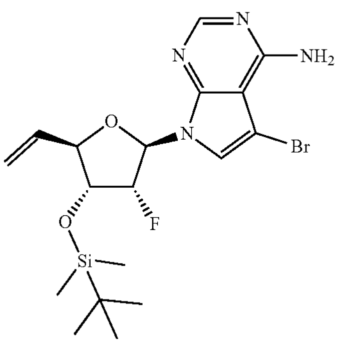 [SMILES: C=C[C@H]1O[C@@H](n2cc(Br)c3c(N)ncnc32)[C@H](F)[C@@H]1O[Si](C)(C)C(C)(C)C]

A solution of [(2R,3R,4R,5R)-5-(4-amino-5-bromo-pyrrolo[2,3-d]pyrimidin-7-yl)-3-[tert-butyl(dimethyl)silyl]oxy-4-fluoro-tetrahydrofuran-2-yl]methanol (90 mg, 0.20 mmol) and Dess-Martin periodinane (91 mg, 0.20 mmol) were combined in DCE (6 mL) and the mixture heated at 80° C. for 1 hour. The mixture was cooled to room temperature quenched with $NaHCO_3$ (sat., 20 mL) and extracted with chloroform/isopropanol (3:1, 3×20 mL). The combined extracts were dried ($Na_2SO_4$) and evaporated under vacuum. The residue was purified by chromatography on $SiO_2$ [eluting with 0-100% EtOAc/heptane followed by 0-20% MeOH/EtOAc] to afford (2S,3R,4R,5R)-5-(4-amino-5-bromo-pyrrolo[2,3-d]pyrimidin-7-yl)-3-[tert-butyl(dimethyl)silyl]oxy-4-fluoro-tetrahydrofuran-2-carbaldehyde (70 mg) as a pale yellow residue.

Methyl(triphenyl)phosphonium iodide (185 mg, 0.46 mmol) was dissolved in THF-Anhydrous (4 mL) and KOtBu (51 mg, 0.46 mmol) was added to give a yellow turbid solution. The mixture was stirred at room temperature for 10 minutes, before (2S,3R,4R,5R)-5-(4-amino-5-bromo-pyrrolo[2,3-d]pyrimidin-7-yl)-3-[tert-butyl(dimethyl)silyl]oxy-4-fluoro-tetrahydrofuran-2-carbaldehyde (70 mg, 0.15 mmol) in THF-Anhydrous (2 mL) was added, and the mixture was stirred at room temperature for 1 hour. The mixture was filtered and the residue washed with THF. The combined filtrates were evaporated under vacuum and the resultant residue was purified by chromatography on SiO2 [eluting with 0-100% EtOAc/heptane] to afford the title compound (20 mg, 29%) as a colourless residue.

Method K: LC-MS (electrospray): m/z=457.0/459.0 $(M+H)^+$, RT=1.11 min

Step 5: (2R,3R,4R,5R)-5-(4-amino-5-bromo-pyrrolo[2,3-d]pyrimidin-7-yl)-4-fluoro-2-vinyl-tetrahydrofuran-3-ol

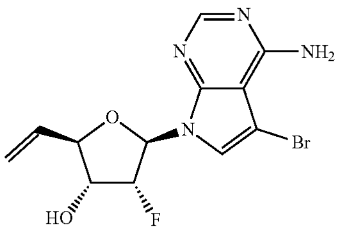 [SMILES: C=C[C@H]1O[C@@H](n2cc(Br)c3c(N)ncnc32)[C@H](F)[C@@H]1O]

A solution of 5-bromo-7-[(2R,3R,4R,5R)-4-[tert-butyl(dimethyl)silyl]oxy-3-fluoro-5-vinyl-tetrahydrofuran-2-yl]pyrrolo[2,3-d]pyrimidin-4-amine (20 mg, 0.04 mmol) in Methanol (1 mL) and TFA (1 mL) was stirred at room temperature for 3 hours. The mixture was evaporated under vacuum and the residue purified by basic preparative HPLC (method B) to afford the title compound (1.6 mg, 11%) as a white solid.

Method C: LC-MS (electrospray): m/z=343.0/345.0 $(M+H)^+$, RT=2.07 min.

Step 6: (2R,3R,4R,5R)-5-{4-amino-5-bromo-7H-pyrrolo[2,3-d]pyrimidin-7-yl)-4-fluoro-2-[(1E)-5-[({3-fluorobicyclo[1.1.1]pentan-1-yl}methyl)amino]pent-1-en-1-yl]oxolan-3-ol

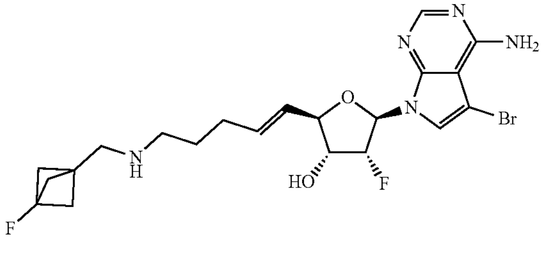 [SMILES: Nc1ncnc2c1c(Br)cn2[C@@H]1O[C@H](/C=C/CCCNCC23CC(F)(C2)C3)[C@@H](O)[C@H]1F]

The title compound was prepared from (2R,3R,4R,5R)-5-(4-amino-5-bromo-pyrrolo[2,3-d]pyrimidin-7-yl)-4-fluoro-2-vinyl-tetrahydrofuran-3-ol and INT-5 using the procedures described in Example 22 Steps 4 & 5 to give the title compound (8 mg, 9%) as a white solid.

Method E: LC-MS (electrospray): m/z=498.0/500.0 $(M+H)^+$, RT=1.24 min.

Intermediates

Int 1: (Benzyl)-N-4-pentenylamino 2,2-dimethyipropionate

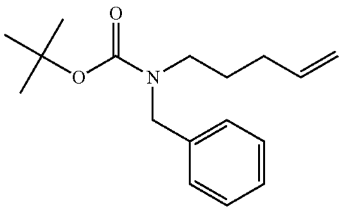 [SMILES: C=CCCCN(Cc1ccccc1)C(=O)OC(C)(C)C]

Step-A: N-benzylpent-4-en-1-amine

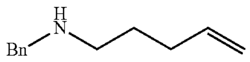

Procedure

To a stirred suspension of 5-bromopent-1-ene (2.0 g, 13.42 mmol) and benzyl amine (1.43 g, 13.42 mmol) in EtOH (25 mL) was added sodium iodide (6.0 g, 40.26 mmol). The reaction mixture was stirred at 85° C. for 12 hours. The resulting reaction mixture was diluted with water (100 mL) and extracted with ethyl acetate (3×200 mL). The combined organic layer was dried over anhydrous $Na_2SO_4$, filtered and concentrated under reduced pressure. The obtained crude was purified by silica gel (60-120 mesh) column chromatography using 5% MeOH in DCM to afford N-benzylpent-4-en-1-amine (2.0 g, 85.03%). LCMS: 1.164 min, MS: ES+176.2 [M+1]. (UC01_FAR1)

Step-B: tert-butyl benzyl (pent-4-en-1-yl) carbamate

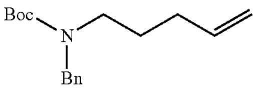 [SMILES: C=CCCCN(Cc1ccccc1)C(=O)OC(C)(C)C]

Procedure

To a stirred suspension of N-benzylpent-4-en-1-amine (2.0 g, 11.42 mmol) in DCM (20 mL) was added TEA (4.77 mL, 34.28 mmol) and Boc anhydride (4.98 g, 22.85 mmol) at room temperature. DMAP (0.697 g, 5.71 mmol) was added at room temperature and then the reaction mixture was stirred at 80° C. for 1 hour. The resulting reaction mixture was diluted with water (100 mL) extracted with ethyl acetate (3×200 mL). The combined organic layer was dried over anhydrous $Na_2SO_4$, filtered and concentrated under reduced pressure. The obtained crude was purified by silica gel column chromatography using 5% ethyl acetate in hexane to afford tert-butyl benzyl (pent-4-en-1-yl) carbamate (1.2 g, 38.19%). LCMS: 2.664 min, MS: ES+220 (M-t-Bu). (UC01_FAR1)

Int 2: tert-butyl (cyclobutylmethyl)(pent-4-en-1-yl)carbamate

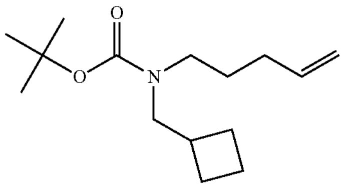 [SMILES: C=CCCCN(CC1CCC1)C(=O)OC(C)(C)C]

Step-A: N-(cyclobutylmethyl)pent-4-en-1-amine

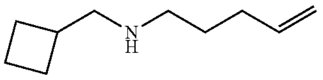

Procedure

To a stirred suspension of 5-bromo-1-pentene (1.14 g, 13.42 mmol) and sodium iodide (2.77 g, 20.13 mmol) in EtOH (20.0 mL) was stirred at room temperature for 5-10 min. $K_2CO_3$ (1.0 g, 6.71 mmol) and cyclobutylmethylamine (2.0 g, 13.42 mmol) was added at room temperature. The reaction mixture was stirred at 80° C. for 6 hours. The resulting reaction mixture was filtered and washed with DCM (3×50 mL). The resulting filtrate was dried over anhydrous $Na_2SO_4$, filtered and concentrated under reduced pressure. The obtained crude was purified by silica gel (60-120 mesh) column chromatography using 10% methanol in DCM to afford N-(cyclobutylmethyl)pent-4-en-1-amine (0.8 g, 22.22%). $^1H$ NMR: (DMSO, 400 MHz) δ 7.59 (brs, 1H), 5.82-5.76 (m, 1H), 5.07-4.98 (m, 2H), 2.83 (d, J=7.2 Hz, 2H), 2.73 (t, J=7.6 Hz, 2H), 2.57-2.53 (m, 1H), 2.08-1.98 (m, 4H), 1.89-1.59 (m, 6H); LCMS: 0.269 min, MS: ES+154 (M+1), (Method—UC01_FAR01).

Step-B: tert-butyl (cyclobutylmethyl)(pent-4-en-1-yl)carbamate

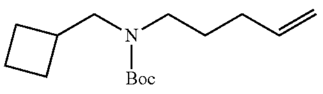 [SMILES: C=CCCCN(CC1CCC1)C(=O)OC(C)(C)C]

Procedure

A solution of N-(cyclobutylmethyl)pent-4-en-1-amine (0.8 g, 5.2287 mmol), EtsN (2.76 mL, 20.49 mmol), and DMAP (0.064 g, 0.5228 mmol) in DCM (520 mL) was stirred at 0° C. for 15 min. $(BOC)_2O$ (2.28 g, 10.457 mmol) was added drop wise and the reaction mixture was stirred at room temperature for 16 hours. The reaction mixture was diluted with water (25 mL) and extracted with DCM (3×50 mL). The combined organic layer was dried over anhydrous $Na_2SO_4$, filtered and concentrated under reduced pressure. The obtained crude was purified by silica gel (60-120 mesh) column chromatography using 30% ethyl acetate in hexane to afford tert-butyl (cyclobutylmethyl)(pent-4-en-1-yl)carbamate (0.8 g, 48.48%). H NMR: (DMSO, 400 MHz) δ 5.83-5.76 (m, 1H), 5.04-4.94 (m 2H), 3.17 (d, J=7.2 Hz, 2H), 3.07 (t, J=7.2 Hz, 2H), 2.47-2.44 (m, 1H), 1.98-1.89 (m, 4H), 1.82-1.76 (m, 2H), 1.69-1.62 (m, 2H), 1.52 (m, 2H), 1.37 (s, 9H); LCMS: 2.875 min, MS: ES+198 (M−56), (Method—UC01_FAR01).

Int 3: tert-butyl allyl(benzyl)carbamate

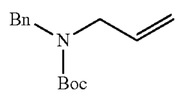 [SMILES: C=CCN(Cc1ccccc1)C(=O)OC(C)(C)C]

Step-A: N-benzylprop-2-en-1-amine

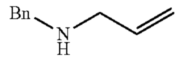

Procedure

To a stirred solution allyl bromide (1.00 g, 8.33 mmol) in ethanol (8.0 mL) were added benzyl amine (1.78 g, 16.66 mmol) and KI (1.38 g, 8.33 mmol) at room temperature. The resulting reaction mixture was stirred at 80° C. for 1 hour. Four further batches were prepared using the method above and combined for work up and purification. The reaction mixture was diluted with water (30 mL) and extracted with ethyl acetate (3×30 mL). The combined organic layer was dried over anhydrous $Na_2SO_4$, filtered and concentrated under reduced pressure. The obtained crude material was purified by manual column chromatography using 60-120 mesh silica gel and eluted with 1.5% MeOH in DCM. Appropriate fractions were concentrated to afford N-benzylprop-2-en-1-amine (2.2 g, Yield: 45.61%,). $^1$H NMR: (MeOD, 400 MHz) δ 7.46-7.40 (m, 5H), 6.00-5.94 (m, 1H), 5.48-5.40 (m, 2H), 4.06 (s, 2H), 3.57 (d, J=0.8 Hz, 2H).

Step-B: tert-Butyl allyl(benzyl)carbamate

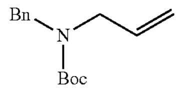 [SMILES: C=CCN(Cc1ccccc1)C(=O)OC(C)(C)C]

Procedure

To a stirred solution N-benzylprop-2-en-1-amine (2.22 g, 8.98 mmol) in THE (20 mL) was added triethylamine (3.75 mL, 26.96 mmol) and followed by addition of Boc anhydride (3.88 g, 17.81 mmol) at room temperature. The resulting reaction mixture stirred at room temperature for 3 hours. The reaction mixture was diluted with water (50 mL) and extracted with ethyl acetate (3×50 mL). The combined organic layer was dried over anhydrous $Na_2SO_4$, filtered and concentrated under reduced pressure. The obtained crude material was purified by manual column chromatography using 60-120 mesh silica gel and eluted with 2.0% ethyl acetate in hexane. Appropriate fractions were concentrated to afford tert-butyl allyl(benzyl)carbamate (2.5 g, Yield: 67.03%,). $^1$H NMR: (MeOD, 400 MHz) δ 7.36-7.22 (m, 5H), 5.77-5.71 (m, 1H), 5.13-5.10 (d, J=10 Hz 2H), 4.39 (s, 2H), 3.78-3.71 (m, 2H), 1.41-1.37 (m, 9H).

Int 4: tert-butyl ((3, 3-difluorocyclobutyl) methyl) (pent-4-en-1-yl) carbamate

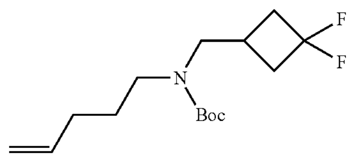 [SMILES: C=CCCCN(CC1CC(F)(F)C1)C(=O)OC(C)(C)C]

Step-1: N-((3, 3-difluorocyclobutyl) methyl) pent-4-en-1-amine

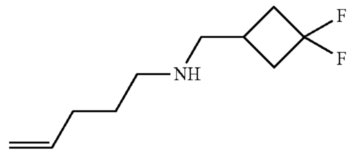

Procedure

To a stirred suspension of (3,3-difluorocyclobutyl)methanamine hydrochloride (0.50 g, 3.184 mmol) and 5-bromopent-1-ene (0.616 g, 4.140 mmol) in EtOH (10 mL) was added sodium iodide (0.474 g, 4.140 mmol). The reaction mixture was stirred at 85° C. for 5 hours. The resulting reaction mixture was extracted with EtOAc (3×50 mL). The combined organic layer was dried over anhydrous $Na_2SO_4$, filtered and concentrated under reduced vacuum. The obtained crude was purified by silica gel column chromatography using 5% MeOH in DCM to afford N-((3, 3-difluorocyclobutyl) methyl) pent-4-en-1-amine (0.350 g, 58.15%). $^1$H NMR: (MeOD, 400 MHz) δ 5.90-5.80 (m, 1H), 5.10-4.99 (m, 1H), 2.82 (d, J=6.8 Hz, 1H), 2.75-2.64 (m, 4H), 2.35-2.24 (m, 3H), 2.13 (q, J=14.0, 6.8 Hz, 2H) 1.70-1.63 (m, 2H).

Step-2: tert-butyl ((3, 3-difluorocyclobutyl) methyl) (pent-4-en-1-yl) carbamate

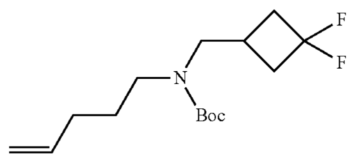 [SMILES: C=CCCCN(CC1CC(F)(F)C1)C(=O)OC(C)(C)C]

Procedure

To a stirred suspension of N-((3, 3-difluorocyclobutyl) methyl) pent-4-en-1-amine (0.350 g, 1.587 mmol) in THF (10 mL) was added TEA. (0.480 g, 1.480 mmol) and Boc anhydride (0.692 g, 3.174 mmol). The reaction mixture was stirred at room temperature for 2 hours. The reaction mixture was diluted with water (75 mL) and extracted with EtOAc (3×50 mL). The combined organic layer was dried over anhydrous $Na_2SO_4$, filtered and concentrated under reduced pressure. The obtained crude was purified by silica gel column chromatography using 2% ethyl acetate in hexane to tert-butyl ((3, 3-difluorocyclobutyl) methyl) (pent-4-en-1-yl) carbamate (0.350 g, 65.40%). $^1H$ NMR: (DMSO, 400 MHz) δ 5.86-5.76 (m, 1H), 4.95-5.05 (m, 2H), 3.29 (d, J=6.4 Hz, 2H), 3.11 (t, J=7.6, 1H), 2.65-2.55 (br s, 1H), 2.35-2.29 (m, 3H), 2.10-1.90 (m, 2H), 1.60-1.50 (m, 2H), 1.39 (s, 9H).

Int 5: tert-butyl ((3-fluorobicyclo[1.1.1]pentan-1-yl) methyl)(pent-4-en-1-yl)carbamate

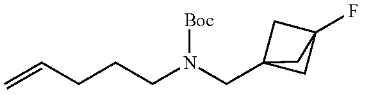

Step-1: bicyclo[1.1.1]pentane-1,3-dicarboxylic acid

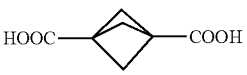

Procedure

To a stirred suspension of 3-(methoxycarbonyl)bicyclo [1.1.1]pentane-1-carboxylic acid (50.0 g, 294.01 mmol) in THE (350 mL) was added the aqueous solution of (150 mL) $LiOH{\cdot}H_2O$ (24.67 g, 588.02 mmol) drop wise at 0° C. The reaction mixture was stirred at room temperature for 2 hours. The reaction mixture was evaporated under reduce pressure to obtain crude material. The crude material was acidifying with 1 N HCl solution (~200 mL) and extracted with 20% IPA in DCM (6×100 mL). The combined organic layer was dried over anhydrous $Na_2SO_4$, filtered and concentrated under reduced pressure to afford bicyclo[1.1.1]pentane-1,3-dicarboxylic acid (44.5 g, 97%). $^1H$ NMR: (DMSO, 400 MHz) δ 12.56 (s, 2H), 2.14 (s, 6H).

Step-2: 3-fluorobicyclo[1.1.1]pentane-1-carboxylic acid

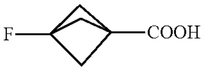

Procedure

To a solution of bicyclo[1.1.1]pentane-1,3-dicarboxylic acid (27.5 g, 156.04 mmol) in water (880 mL) was added selectflour (112.38 g, 317.22 mmol) followed by $AgNO_3$ (5.98 g, 35.24 mmol). The reaction was stirred at 55° C. for 30 min. Additional $AgNO_3$ (8.98 g, 52.87 mmol) was added and the reaction mixture was stirred for an additional 2 hours. The reaction mixture was filtered and the filtrate extracted with ethyl acetate (3×200 mL). The combined organic layer was dried over anhydrous $Na_2SO_4$, concentrated under reduced pressure to afford 3-fluorobicyclo [1.1.1]pentane-1-carboxylic acid (17 g, 37.09%). $^1H$ NMR: (DMSO, 400 MHz) δ 12.72 (s, 1H), 2.30 (s, 6H).

Step-3: 3-fluorobicyclo[1.1.1]pentane-1-carboxamide

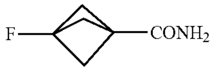

Procedure

To a solution of 3-fluorobicyclo[1.1.1]pentane-1-carboxylic acid (8.5 g, 65.38 mmol) in EDC (187 mL) was added cat. amount of DMF (0.2 mL) and followed by addition of oxalyl chloride drop wise (13.07 mL, 150.38 mmol) at 0° C. The reaction mixture was stirred at room temperature for 3 hours. 28% aqueous $NH_3$ solution (161 mL) was added drop wise at 0° C. The reaction mixture was stirred at room temperature for 2 hours. The reaction mixture was evaporated under reduced pressure to obtain crude material. The crude material was dissolved in water (100 mL) and filtered. The filtrate was extracted with 10% IPA in chloroform (4×200 mL). Residue (recovered during filtration) was dissolved in methanol and heated at 65° C. for 3 hours then filtered. The combined organic layer was dried over anhydrous $Na_2SO_4$ concentrated under reduced pressure to afford 3-fluorobicyclo[1.1.1]pentane-1-carboxamide. (13.5 g, 80.03%). $^1H$ NMR: (DMSO, 400 MHz) δ 7.41 (s, 1H), 7.13 (s, 1H), 2.22 (s, 6H).

Step-4: (3-fluorobicyclo[1.1.1]pentan-1-yl)methanamine hydrochloride

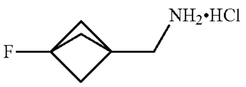

Procedure

A solution of 3-fluorobicyclo [1.1.1]pentane-1-carboxamide (10 g, 77.51 mmol) in THF (200 mL) was purged with nitrogen gas for 15 min. Borane-THF complex (1 M solution in THF) (390 mL, 387.59 mmol) was added dropwise at room temperature. The reaction mixture was stirred at 70° C. for 16 hours. The reaction mixture was cooled to 0° C. and 3M HCl (200 mL) was added drop wise. The reaction mixture was stirred at room temperature for 1.5 hours. The reaction was cooled to 0° C. and aqueous 8M KOH solution (400 mL) was added drop wise. The aqueous layer was extracted with THE (3×200 mL). The combined organic layer was cooled at 0° C. and 4N HCl in 1,4-dioxane (250 mL) was added drop wise. The reaction mixture was stirred at room temperature for 45 mins. The reaction mixture was concentrated under reduced pressure. One further batch was prepared using the method above and combined for work up and purification. The obtained oily product was dissolved in minimum methanol (50 mL) and aziotropically distilled three times. The obtained residue was dissolved in ethanol (120 mL) and solid was precipitated by adding diethyl ether (2000 mL). The solid was filtered and dried under vacuum to afford (3-fluorobicyclo [1.1.1]pentan-1-yl) methanamine hydrochloride (20.0 g, 85.43%). $^1$H NMR: (DMSO, 400 MHz) δ 8.14 (s, 3H), 3.14 (s, 2H), 2.06 (d, J=2.4 Hz, 6H).

Step-5: tert-butyl ((3-fluorobicyclo[1.1.1]pentan-1-yl)methyl)carbamate

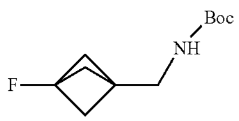 [SMILES: CC(C)(C)OC(=O)NCC12CC(F)(C1)C2]

Procedure

To a solution of (3-fluorobicyclo [1.1.1]pentan-1-yl) methanamine hydrochloride (0.46 g, 3.04 mmol) in ethanol (4.6 mL) at 0° C. was added triethylamine (1.27 mL, 9.13 mmol) followed by portion wise addition of Boc anhydride (0.995 g, 4.56 mmol). The reaction mixture was warmed to room temperature and stirred for 1 hour. The reaction mixture was evaporated under reduce pressure to obtain crude material. The crude material was diluted with water (20 mL) and extracted with ethyl acetate (3×50 mL). The combined organic layer was dried over anhydrous $Na_2SO_4$ and concentrated under reduced pressure. The obtained crude material was purified by silica gel (60-120 mesh) column chromatography using 10% ethyl acetate in hexane to afford tert-butyl ((3-fluorobicyclo[1.1.1]pentan-1-yl) methyl)carbamate (0.595 g, 91.10%). $^1$H NMR: (DMSO, 400 MHz) δ 6.95 (s, 1H), 3.21 (d, J=5.6 Hz, 2H), 1.89 (d, J=2.4 Hz, 6H), 1.38 (s, 9H).

Step-6: tert-butyl ((3-fluorobicyclo[1.1.1]pentan-1-yl)methyl)(pent-4-en-1-yl)carbamate

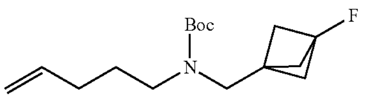 [SMILES: C=CCCCN(CC12CC(F)(C1)C2)C(=O)OC(C)(C)C]

Procedure

To a mixture of 60% NaH (0.404 g, 10.11 mmol) in DMF (6 mL) at 0° C. was added a solution of tert-butyl ((3-fluorobicyclo[1.1.1]pentan-1-yl)methyl)carbamate (0.725 g, 3.37 mmol) in DMF (1.25 mL). 5-bromopent-1-ene (1.5 g, 10.11 mmol) was then added drop wise. The reaction mixture was then allowed to warm to room temperature and stirred at room temperature for 1 hour. The crude material was diluted with water (20 mL) and extracted with ethyl acetate (3×20 mL). The combined organic layer was washed with brine (30 mL) and dried over anhydrous $Na_2SO_4$, then concentrated under reduced pressure. The obtained crude material was purified by silica gel (60-120 mesh) column chromatography using 10% ethyl acetate in hexane to afford tert-butyl ((3-fluorobicyclo[1.1.1]pentan-1-yl)methyl)carbamate (0.65 g, 68.10%). $^1$H NMR: (DMSO, 400 MHz) δ 5.78-5.83 (m, 1H), 4.97-5.06 (m, 2H), 3.45-3.49 (m, 2H), 3.16-3.18 (m, 2H), 2.04-2.05 (m, 2H), 1.99 (s, 6H), 1.46 (s, 9H).

Int 6: 4,4-difluoro-1-(pent-4-en-1-yl)piperidine

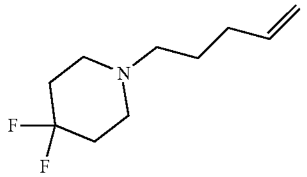

A suspension containing 4,4-difluoropiperidine hydrochloride (500 mg, 3.17 mmol) and 5-bromopent-1-ene (520 mg, 3.49 mmol) in Acetonitrile (3 mL) was treated with triethylamine (1.8 mL, 12.7 mmol) and the resultant thick emulsion was stirred rapidly at room temperature for 72 hours. The mixture was diluted with EtOAc and $Na_2CO_3$ (sat., pH-8) and the mixture was extracted with EtOAc. The combined organics were dried over sodium sulfate and filtered. The colourless filtrate was treated with silica gel and concentrated before Purification by chromatography on silica gel (eluting with 0-100% EtOAc/heptane followed by 0-100% (~0.5M $NH_3$ in MeOH)/EtOAc) to give the title compound (411 mg, 64%) as a pale-yellow oil.

Method J: LC-MS (electrospray): m/z=190.1 $(M+H)^+$, RT=0.78 min

The Intermediates in the following table were prepared in a similar fashion to INT-6.

| INT | Structure | Name | LCMS method | Retention time | Mass Ion |
|---|---|---|---|---|---|
| 7 | 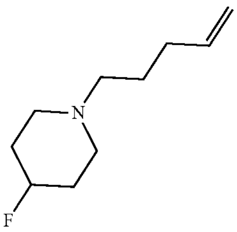 | 4-fluoro-1-(pent-4-en-1-yl)piperidine | M | 0.71 | 172.2 |

-continued

| INT | Structure | Name | LCMS method | Retention time | Mass Ion |
|---|---|---|---|---|---|
| 8 | 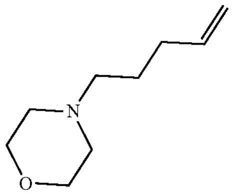 | 4-(pent-4-en-1-yl)morpholine | M | 0.57 | 156.2 |
| 9 | 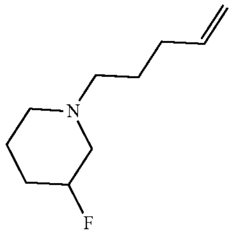 | 3-fluoro-1-(pent-4-en-1-yl)piperidine | M | 0.77 | 172.2 |

Int 10: (2R,3R,4S,5R)-2-{4-amino-5-bromo-7H-pyrrolo[2,3-d]pyrimidin-7-yl)-5-ethenyloxolane-3,4-diol

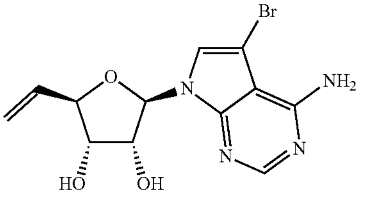 [SMILES: C=C[C@H]1O[C@@H](n2cc(Br)c3c(N)ncnc32)[C@H](O)[C@@H]1O]

A pressure tube containing a solution of (2R,3R,4S,5R)-2-(5-bromo-4-chloro-pyrrolo[2,3-d]pyrimidin-7-yl)-5-vinyl-tetrahydrofuran-3,4-diol (Example 1 Step 4, 2.00 g, 5.55 mmol) in aqueous ammonia (35%, 6.1 mL, 0.111 mol) and 1,4-Dioxane (28 mL) was-stirred at 80° C. for 18 hours The reaction mixture was evaporated to dryness to afford the title compound (1.8 g, 95) as a fluffy white solid.

Method C: LC-MS (electrospray): m/z=341.1/343.1 $(M+H)^+$, RT=1.38 min

INT 11: 5-bromo-7-[(1R,2R,4R,5R)-4-ethenyl-3,6-dioxabicyclo[3.1.0]hexan-2-yl]-7H-pyrrolo[2,3-d]pyrimidin-4-amine

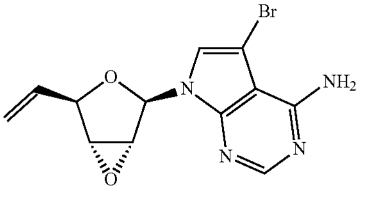 [SMILES: C=C[C@H]1O[C@@H](n2cc(Br)c3c(N)ncnc32)[C@@H]2O[C@@H]21]

A suspension of (2R,3R,4S,5R)-2-(4-amino-5-bromo-pyrrolo[2,3-d]pyrimidin-7-yl)-5-vinyl-tetrahydrofuran-3,4-diol (INT-10, 1.70 g, 4.98 mmol) in Acetonitrile (25 mL) was treated with 1-bromo-2-methyl-1-oxopropan-2-yl acetate (3.7 mL, 24.9 mmol) and the mixture was stirred at room temperature for an hour.

The mixture was quenched by the addition of $NaHCO_3$ (sat, 40 mL) extracted with DCM, dried (MgSO4) and evaporated under vacuum to a pale gum which was diluted with Methanol (25 mL), cooled to 0° C. and treated with potassium carbonate (689 mg, 4.98 mmol). The resultant suspension was stirred and allowed to warm to room temperature overnight, during which time a solid precipitated.

The mixture was diluted with water (~10 mL) and stirred for an hour. The solids were collected by filtration, washed with water and dried on the funnel.

The filtrate was concentrated the materials were combined, diluted with water, extracted with DCM, dried ($MgSO_4$) and evaporated under vacuum to a white solid which was purified by chromatography on silica gel (eluting with 0-100% (10% MeOH in DCM)/DCM) to give the title compound (1.08 g, 67%) as a white solid.

Method J: LC-MS (electrospray): m/z=323.1/325.1 $(M+H)^+$, RT=0.51 min

INT-12 6-[(3aR,4R,6R,6aS)-6-{5-bromo-4-chloro-7H-pyrrolo[2,3-d]pyrimidin-7-yl}-2,2-dimethyl-hexahydrocyclopenta[d][1,3]dioxol-4-yl]-1H-indole-2-carbaldehyde

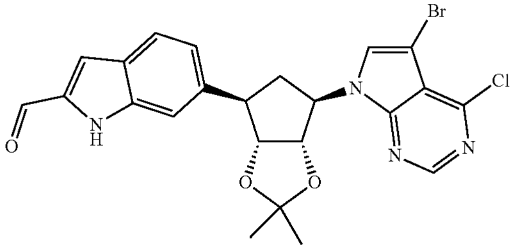 [SMILES: CC1(C)O[C@@H]2[C@H](O1)[C@@H](c1ccc3cc(C=O)[nH]c3c1)C[C@H]2n1cc(Br)c2c(Cl)ncnc21]

Step 1: 6-bromo-2-(dimethoxymethyl)-1H-indole

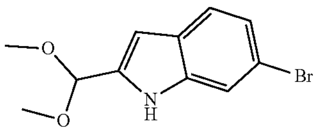

A suspension containing 6-bromo-1H-indole-2-carbaldehyde (1000 mg, 4.46 mmol) in trimethoxymethane (8.0 mL, 73.1 mmol) and Methanol (3 mL) was treated with 4-methylbenzenesulfonic acid hydrate (8.5 mg, 0.0446 mmol) and the mixture was stirred at room temperature for 3 hours resulting in the formation of a black solution. The mixture was diluted with $NaHCO_3$ (sat., 5 mL) and extracted with DCM (3×10 mL). The combined organics were washed with brine (10 mL), dried over sodium sulfate and concentrated to give a brown oil. The material was purified by chromatography on silica gel (eluting with 0-100% DCM/heptane). The product containing fractions were collected to give the title compound (1072 mg, 87%) as a brown oil, which crystallised on standing.

Method C: LC-MS (electrospray): m/z=268.0/270.0 $(M+H)^+$, RT=3.51 min

Step 2: tert-butyl 6-bromo-2-(dimethoxymethyl)-1H-indole-1-carboxylate

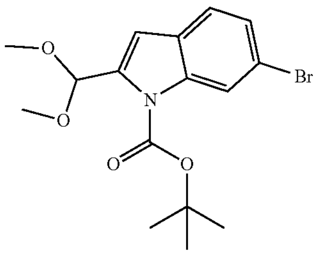 [SMILES: COC(OC)c1cc2ccc(Br)cc2n1C(=O)OC(C)(C)C]

A solution containing 6-bromo-2-(dimethoxymethyl)-1H-indole (1072 mg, 3.89 mmol), di-tert-butyl dicarbonate (1273 mg, 5.83 mmol) and N,N-dimethylpyridin-4-amine (24 mg, 0.19 mmol) in Acetonitrile (15 mL) was stirred at room temperature for 2 hours. The mixture was treated with silica gel and concentrated to give a material which was purified by chromatography on silica gel (eluting 0-100% EtOAc/heptane) to give the title compound (1365 mg, 92%) as a pale yellow oil.

Method J: LC-MS (electrospray): m/z=268.0/270.0 $(M-Boc)^+$, RT=1.05 min

Step 3: tert-butyl 6-[(3aR,4R,6R,6aS)-6-{5-bromo-4-chloro-7H-pyrrolo[2,3-d]pyrimidin-7-yl}-2,2-dimethyl-hexahydrocyclopenta[d][1,3]dioxol-4-yl]-2-(dimethoxymethyl)-1H-indole-1-carboxylate

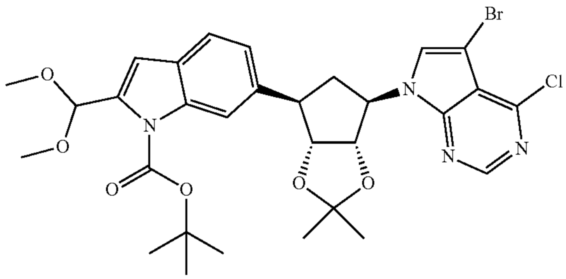 [SMILES: COC(OC)c1cc2ccc([C@H]3C[C@@H](n4cc(Br)c5c(Cl)ncnc54)[C@@H]4OC(C)(C)O[C@@H]43)cc2n1C(=O)OC(C)(C)C]

The title compound was prepared from tert-butyl 6-bromo-2-(dimethoxymethyl)-1H-indole-1-carboxylate using the procedure described in Example 11 to give (810 mg, 59%) as a white foam.

Method M: LC-MS (electrospray): m/z=683.1/685.1 $(M+H)^+$, RT=1.99 min

Step 4: 6-[(3aR,4R,6R,6aS)-6-{5-bromo-4-chloro-7H-pyrrolo[2,3-d]pyrimidin-7-yl}-2,2-dimethyl-hexahydrocyclopenta[d][1,3]dioxol-4-yl]-1H-indole-2-carbaldehyde

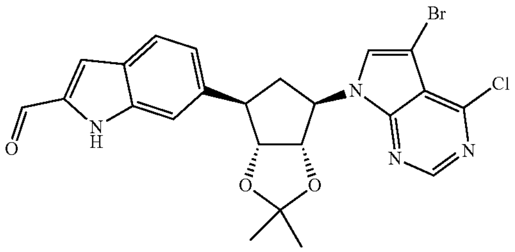 [SMILES: CC1(C)O[C@@H]2[C@H](O1)[C@@H](c1ccc3cc(C=O)[nH]c3c1)C[C@H]2n1cc(Br)c2c(Cl)ncnc21]

To a solution containing tert-butyl 6-[(3aS,4R,6R,6aR)-4-(5-bromo-4-chloro-pyrrolo[2,3-d]pyrimidin-7-yl)-2,2-dimethyl-4,5,6,6a-tetrahydro-3aH-cyclopenta[d][1,3]dioxol-6-yl]-2-(dimethoxymethyl)indole-1-carboxylate (810 mg, 0.95 mmol) in THE (8 mL) was added Water (2.7 mL) resulting in precipitate formation. Additional THE (0.5 mL) was added to clarify the solution and then Acetic acid (2.7 mL) was added. The mixture was stirred at room temperature for 16 hours. The mixture was heated at 30° C. for 1 hour and at 40° C. for 2 hours. The mixture was cooled to room temperature and diluted with water (40 mL) resulting in additional precipitate formation. The mixture was filtered, the solids collected and oven-dried at 40° C. to give the title compound (634 mg, Quant) as a light yellow solid.

Method M: LC-MS (electrospray): m/z=637.0/639.0 $(M+Na)^+$, RT=1.99 min

METTL3/14 Methyltransferase Assay

Biochemical Assay

The enzymatic assay was established to determine $IC_{50}$ values for inhibition of RNA methyltransferase activity. The enzyme used was full-length his-tagged METTL3 co-expressed with full length FLAG-tagged METTL14 in a baculovirus expression system. Enzymatic reactions were performed at room temperature in 384-well plates using a final reaction volume of 20 μL containing 20 mM TrisCl pH 7.6, 1 mM DTT, 0.01% Tween-20. 5 nM final concentration of METTL3/14 was pre-incubated with various compound concentrations for 10 minutes, followed by addition of 0.2 μM final concentration synthetic RNA substrate (5'P-uacacucgaucuggacuaaagcugcuc-3') and 0.5 μM final concentration S-adenosyl-methionine (SAM). The reaction was incubated for a further 60 minutes at room temperature, and then quenched by the addition of 40 μL 7.5% TCA with two internal product standards (D4-SAH and 13C10-SAH). After termination, plates were sealed, centrifuged and stored at 4° C. until analysis.

Mass Spectrometry Analysis

RNA methyltransferase activity was measured label free using the RapidFire™ mass spectrometry (RF/MS) platform. Stopped and stable assay plates were analyzed on the Agilent RF300 integrated autosampler/solid-phase extraction (SPE) system coupled to an ABSciex 4000 mass spectrometer for the generation of the product S-adenosyl homocysteine (SAH) and normalized to the ratio of signal of the two internal product standards, respectively. Solvent A was water containing 0.1% (v/v) TCA. Solvent B was acetonitrile/0.1% ammonium acetate (8:2, v/v). More specifically, plates were centrifuged at 4350 rpm for 10 min, samples were aspirated under vacuum for 600 ms, then loaded onto a C18 solid-phase extraction cartridge and washed for 3 s with solvent A at a flow rate of 1.5 mL/min. Retained product and internal standards were eluted with solvent B at a flow rate of 1 mL/min for 3 s and finally the cartridge was re-equilibrated with solvent A for 500 ms. The mass transition for the product (SAH) was 384.9/135.9 Da. Transitions of the two internal product standards (IS1: D4-SAH and IS2: 13C10-SAH) were 389.1/135.8 Da and 395.0/134.2 Da, respectively. Ratios of SAH/IS1 and SAH/IS2 were used for normalization of matrix effects. $IC_{50}$ values were calculated based on dilution series of individual compounds. Potency of a compound was measured at varied inhibitor concentrations and normalized to control wells without RNA substrate and without inhibition (DMSO only).

| Ex | METTL3 RFMS $IC_{50}$ nM |
|---|---|
| 1 | 44.8 |
| 2 | 42.6 |
| 3 | 317 |
| 4 | 22.7 |
| 5 | 196 |
| 6 | <6 |
| 7 | 568 |
| 8 | 505 |
| 9 | 123 |
| 10 | 150 |
| 11 | <6 |
| 12 | 46.6 |
| 13 | 460 |
| 14 | 413 |
| 15 | 351 |
| 16 | 453 |
| 17 | 1310 |
| 18 | 2930 |
| 19 | 522 |
| 20 | 6.1 |
| 21 | 23.94 |
| 22 | 12.75 |
| 25 | 1090 |
| 24 | 231 |
| 23 | 63.5 |
| 26 | 351 |
| 27 | 9.6 |

-continued

| Ex | METTL3 RFMS $IC_{50}$ nM |
|---|---|
| 28 | 19.7 |
| 29 | 6.1 |
| 30 | 6.1 |
| 32 | 6.1 |
| 33 | 6.22 |
| 31 | 8.24 |
| 34 | 9.11 |
| 35 | 63.7 |
| 36 | 103 |
| 37 | 117 |
| 38 | 2640 |
| 39 | 3010 |
| 40 | 7930 |
| 41 | 60 |

Kasumi Cell Proliferation CTG

Cell culture: KASUMI-1 cells (ACC20, Leibniz-Institut DSMZ Deutsche Sammlung von Mikroorganismen und Zellkulturen GmbH) were grown in RPMI 1640 (31870-025, Gibco) supplemented with 20% fetal bovine serum (F1524, Gibco), 1 mM sodium pyruvate (11360-039, Gibco) and 2 mM Glutamax (35050-038, Gibco) in a 5% CO2 humidified incubator at 37° C.

Cell treatment and cell growth assessment: KASUMI-1 cells were seeded in ultra-low attachment 384-well culture plate (MS-9384WZ, SBio) at a final concentration of 250 000 cells/ml (35 μL/well) and treated for 120 hours with compounds inhibiting the METTL3/14 activity (10 serial semi-log dilutions, 30 μM as top concentration). Upon treatment, Kasumi1 cells were incubated for 10 min at RT with the CellTiter-Glo reagent (G7571, Promega). Measurement of the luminescence signal was performed on a microplate reader (Ensight, PerkinElmer).

| Ex | Kasumi cell proliferation CTG $IC_{50}$ μM |
|---|---|
| 1 | 4.9 |
| 2 | 7.3 |
| 4 | 4.8 |
| 5 | 0.36 |
| 6 | 1.6 |
| 9 | 4.6 |
| 10 | 4.4 |
| 11 | 0.95 |
| 12 | 4.9 |
| 17 | 12.37 |
| 21 | 4.854 |
| 22 | 4.281 |
| 29 | 2.852 |
| 30 | 1.288 |
| 31 | 1.933 |
| 32 | 1.225 |
| 33 | 1.392 |
| 34 | 2.393 |
| 35 | 4.159 |
| 36 | 5.267 |
| 37 | 2.142 |
| 38 | 2.953 |
| 39 | 2.387 |

Caov3 Cell Proliferation CTG

Cell culture: Caov-3 cells (HTB-75, Lot number: 70016791, ATCC) were grown in DMEM (11960-04431053-028, Gibco) supplemented with 10% fetal bovine serum (1600-44, Gibco), 1 mM sodium pyruvate (11360-039, Gibco) and 2 mM Glutamax (35050-038, Gibco) at 37° C. with 5% CO2.

Cell treatment and cell growth assessment: 18 hours post-seeding in white 384-Viewplate (6007480, PerkinElmer) at 1500 cells/well, Caov3 cells were treated for 120 hours with compounds inhibiting the METTL3/14 activity (10 serial semi-log dilutions, 30 μM as top concentration). Upon treatment, Coav-3 cells were incubated for 10 min at RT with the CellTiter-Glo reagent (G7571, Promega). Measurement of the luminescence signal was performed on a microplate reader (Ensight, PerkinElmer).

| Ex | Caov3 cell proliferation CTG $IC_{50}$ μM |
|---|---|
| 2 | 3.8 |
| 5 | 0.33 |
| 6 | 0.40 |
| 9 | 5.7 |
| 10 | 6.5 |
| 11 | 0.25 |
| 12 | 8.3 |
| 20 | 1.69 |
| 21 | 4.569 |
| 22 | 2.876 |
| 29 | 1.543 |
| 30 | 0.556 |
| 31 | 2.649 |
| 32 | 0.5513 |
| 33 | 0.2759 |
| 34 | 1.885 |
| 35 | 4.562 |
| 36 | 7.752 |
| 37 | 3.259 |
| 38 | 6.76 |
| 39 | 4.645 |

Numbered Paragraphs

The following paragraphs serve to define particular aspects and embodiments of the invention.

1. A compound of the formula (I), or a pharmaceutically acceptable salt thereof,

W—X—Y—Z (I)

wherein

W is selected from:

(i) $C_{1-4}$alkyl or $C_{1-4}$alkoxy, each of which being optionally subsetted by halo, cyano, hydroxy, $C_{3-6}$cycloalkyl, $C_{1-4}$alkoxy, $C_{1-4}$haloalkoxy, aryl or heteroaryl; or (ii) a group of the formula:

$—(CR_{w1}R_{w2})_p—NR_{w3}R_{w4}$;

wherein p is an integer selected from 0, 1, 2, 3, 4 or 5 each occurance of $R_{w1}$ and $R_{w2}$ are independently selected from:

(i) hydrogen (including deuterium), (ii) $C_{1-6}$alkyl which is optionally substituted by one more substituents selected from cyano, oxo, hydroxy, $C_{1-4}$alkoxy, halo, $C_{1-4}$-haloalkoxy, $C_{3-6}$cycloalkyl, —O—$C_{3-6}$cycloalkyl, $NR_{1ca}R_{1da}$ or $—S(O)_{0-2}R_{1ca}R_{1da}$, wherein $R_{1ca}$ and $R_{1da}$ are H or $C_{1-2}$alkyl; and wherein $C_{3-6}$cycloalkyl and —O—$C_{3-6}$cycloalkyl are optionally further substituted with halo, cyano or hydroxy;

(iii) $C_{3-4}$cycloalkyl or 3 to 5 membered heterocyclyl, each of which is optionally substituted by $C_{1-4}$alkyl, $C_{1-4}$haloalkyl, cyano, hydroxy, $C_{1-2}$alkoxy, halo, $C_{1-2}$haloalkoxy, $NR_{1ca}R_{1da}$ or $—S(O)_{0-2}R_{1ca}R_{1da}$, wherein $R_{1ca}$ and $R_{1d}$a are H or $C_{1-2}$alkyl; or (iv) $R_{w1}$ and $R_{w2}$ are linked together such that, together with the carbon atom to which they are attached, they form a 3- to 6-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or $—S(O)_{0-2}R_{1ca}R_{1da}$, wherein $R_{1ca}$ and $R_{1da}$ are H or $C_{1-2}$alkyl;

$R_{w3}$ and $R_{w4}$ are each independently selected from:

(i) hydrogen (including deuterium);

(ii) $C_{1-6}$alkyl which is optionally substituted by one more substituents selected from cyano, oxo, hydroxy, $C_{1-2}$alkoxy, halo, $C_{1-2}$haloalkoxy, $NR_{1ea}R_{1fa}$ or $—S(O)_{0-2}R_{1ea}R_{1fa}$, wherein $R_{1ea}$ and $R_{1fa}$ are H or $C_{1-2}$alkyl;

(iii) a group with the formula:

$—(CR_{w5}R_{w6})_q-T_1$ wherein:

q is 0, 1, 2, 3, 4, 5 or 6;

$R_{w5}$ and $R_{w6}$ are independently selected from:

a) hydrogen (including deuterium);

b) $C_{1-6}$alkyl which is optionally substituted by one more substituents selected from cyano, oxo, hydroxy, $C_{1-4}$alkoxy, halo, $C_{1-4}$haloalkoxy, —O—$C_{3-6}$cycloalkyl, $NR_{1ga}R_{1ha}$ or $—S(O)_{0-2}R_{1ga}R_{1ha}$, wherein $R_{1ga}$ and $R_{1ha}$ are H or $C_{1-2}$alkyl; and wherein —O—$C_{3-6}$cycloalkyl is optionally substituted with halo, cyano or hydroxy;

c) an aryl-$C_{1-6}$alkyl, heteroaryl$C_{1-6}$alkyl, $C_{3-6}$cycloalkyl or $C_{3-6}$-cycloalkyl$C_{1-6}$alkyl group, each of which is optionally substituted by one or more substituents selected from $C_{1-2}$-alkyl, cyano, $C_{1-2}$haloalkyl, hydroxy, $C_{1-2}$alkoxy, halo, $C_{1-2}$-haloalkoxy, $NR_{1ga}R_{1ha}$ or $—S(O)_{0-2}R_{1ga}R_{1ha}$, wherein $R_{1ga}$ and $R_{1ha}$ are H or $C_{1-2}$alkyl; or d) or $R_{w5}$ and $R_{w6}$ are optionally linked together such that, together with the carbon atom to which they are attached, they form a 3- to 6-membered cycloalkyl or heterocyclic ring which is optionally substituted by one or more substituents selected from $C_{1-2}$alkyl, cyano, $C_{1-2}$haloalkyl, hydroxy, $C_{1-2}$alkoxy, halo, $C_{1-2}$haloalkoxy, $NR_{1ga}R_{1ha}$ or $—S(O)_{0-2}R_{1ga}R_{1ha}$, wherein $R_{1ga}$ and $R_{1ha}$ are H or $C_{1-2}$alkyl;

and $T_1$ is selected from hydrogen, cyano, hydroxy, $NR_{1t}R_{2t}$ or $—S(O)_{0-2}R_{1t}R_{2t}$ (wherein $R_{1t}$ and $R_{2t}$ are H or $C_{1-4}$alkyl), $C_{3-8}$cycloalkyl, $C_{2-3}$alkenyl, $C_{2-3}$alkynyl, aryl, heterocyclyl, heteroaryl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$-haloalkoxy, $NR_{3t}R_{4t}$ or $—S(O)_{0-2}R_{3t}R_{4t}$, wherein $R_{3t}$ and $R_{4t}$ are H or $C_{1-2}$alkyl;

or $R_{w3}$ and $R_{w4}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl, and/or the mono- or bicyclic hetereocyclic ring formed by $R_{w3}$ and $R_{w4}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl;

X is selected from:

a) a group selected from;

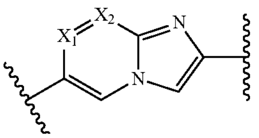 , 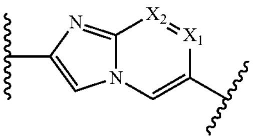 ,

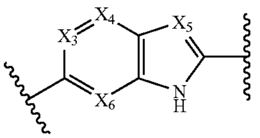 , 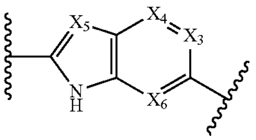 ,

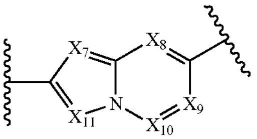 ; 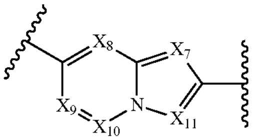 ;

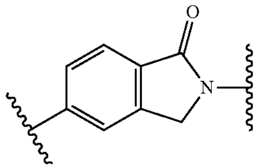 and 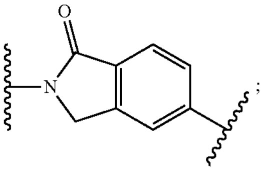 ;

$X_1$ is N or $CR_{X1}$, wherein $R_{X1}$ is H or halo;
$X_2$ is N or $CR_{X2}$, wherein $R_{X2}$ is H or halo;
$X_3$ is N or $CR_{X3}$, wherein $R_{X3}$ is H or halo;
$X_4$ is N or $CR_{X4}$, wherein $R_{X4}$ is H or halo;
$X_5$ is N or $CR_{X5}$, wherein $R_{X5}$ is H or halo;
$X_6$ is N or $CR_{X6}$, wherein $R_{X6}$ is H or halo;
$X_7$ is N or $CR_{X7}$, wherein $R_{X7}$ is H or halo;
$X_8$ is N or $CR_{X8}$, wherein $R_{X8}$ is H or halo;
$X_9$ is N or $CR_{X9}$, wherein $R_{X9}$ is H or halo;
$X_{10}$ is N or $CR_{X10}$, wherein $R_{X10}$ is H or halo;
$X_{11}$ is N or $CR_{X11}$, wherein $R_{X11}$ is H or halo;

b) $C_{2-6}$alkenylene, optionally substituted by one or more hydroxy;

c) a group of the formula;

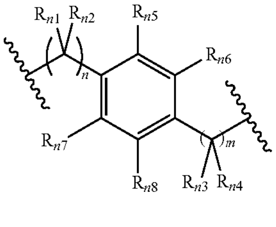

wherein n and m are each independently an integer selected from 0, 1, 2, 3 or 4; and each occurrence of $R_{n1}$, $R_{n2}$, $R_{n3}$ and $R_{n4}$ are independently selected from hydrogen or halo;

$R_{n5}$, $R_{n6}$, $R_{n7}$ and $R_{n8}$ are independently selected from hydrogen, halo, hydroxy, cyano, $C_{1-3}$alkyl, $C_{1-3}$haloalkyl, $C_{1-3}$alkoxy, $C_{1-3}$haloalkoxy and $NR_{n9}R_{n10}$, wherein each of $R_{n9}$ and $R_{n10}$ are independently selected from hydrogen or $C_{1-2}$alkyl;

wherein each of $C_{1-3}$alkyl and $C_{1-3}$alkoxy are optionally further substituted by halo, cyano or hydroxy;

Y is a group of the formula:

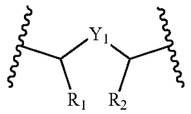

wherein:

$Y_1$ is selected from O, $CR_{y1}R_{y2}$ or $C{=}CR_{y1'}R_{y2'}$, wherein each of $R_{y1}$ and $R_{y2}$ are independently selected from hydrogen, $C_{1-4}$alkyl, halo and cyano;

$R_1$ and $R_2$, together with the carbon atoms to which they are attached, are linked together to form a saturated or unsaturated 4 to 7 membered carbocyclic or heterocyclic ring system, wherein the carbocylic or heterocyclic ring is optionally substituted with one or more substituents selected from $C_{1-4}$alkyl, cyano, halo, hydroxy, $C_{1-4}$alkoxy, $C_{1-4}$haloalkoxy or amino;

Z is a group of the formula:

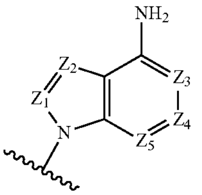

wherein
$Z_1$ is $CR_{Z1}$ or N,
$Z_3$ is $CR_{Z3}$ or N,
$Z_4$ is $CR_{Z4}$ or N,
$Z_5$ is $CR_{Z5}$ or N, wherein each of $R_{Z1}$, $R_{Z3}$, $R_{Z4}$ and $R_{Z5}$ are independently selected from hydrogen, halo or cyano;

$Z_2$ is selected from $CR_{Z2}$ or N, wherein $R_{Z2}$ is selected from hydrogen, halo, cyano, $C_{1-4}$alkyl, $C_{1-4}$haloalkyl, $C_{1-4}$alkoxy, $C_{1-4}$haloalkoxy, $C_{3-6}$cycloalkyl, aryl, heterocyclyl or heteroaryl, wherein each of any $C_{1-4}$alkyl, $C_{1-4}$haloalkyl, $C_{1-4}$alkoxy, $C_{1-4}$haloalkoxy, $C_{3-6}$cycloalkyl, heteroaryl, aryl, heterocyclyl is optionally substituted with one or more substituents selected from, $C_{1-4}$alkyl, $C_{1-4}$haloalkyl, halo, trifluoromethyl, trifluoromethoxy, amino, cyano, hydroxy, or amino;

with the proviso that no more than three of $Z_1$, $Z_2$, $Z_3$, $Z_4$ and $Z_5$ are nitrogen.

2. A compound according to paragraph 1, wherein W is a group of the formula:

$$-(CR_{w1}R_{w2})_p-NR_{w3}R_{w4};$$

wherein p is an integer selected from 0, 1, 2, 3 or 4;

each occurance of $R_{w1}$ and $R_{w2}$ are independently selected from:

(i) hydrogen (including deuterium), (ii) $C_{1-6}$alkyl which is optionally substituted by one more substituents selected from cyano, oxo, hydroxy, $C_{1-4}$alkoxy, halo, $C_{1-4}$haloalkoxy, $C_{3-6}$cycloalkyl, —O—$C_{3-6}$cycloalkyl, $NR_{1ca}R_{1da}$ or —$S(O)_{0-2}R_{1ca}R_{1da}$, wherein $R_{1ca}$ and $R_{1da}$ are H or $C_{1-2}$alkyl; and wherein $C_{3-6}$cycloalkyl and —O—$C_{3-6}$cycloalkyl are optionally further substituted with halo, cyano or hydroxy;

(ii) or $R_{w1}$ and $R_{w2}$ are linked together such that, together with the carbon atom to which they are attached, they form a 3- to 6-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $NR_{1ca}R_{1da}$ or —$S(O)_{0-2}R_{1ca}R_{1da}$, wherein $R_{1ca}$ and $R_{1da}$ are H or $C_{1-2}$alkyl;

$R_{w3}$ and $R_{W4}$ are each independently selected from:

(i) hydrogen (including deuterium); or (ii) $C_{1-3}$alkyl which is optionally substituted by one more substituents selected from cyano, hydroxy, $C_{1-2}$alkoxy, halo, $C_{1-2}$haloalkoxy and $NH_2$;

(iii) a group with the formula:

$—(CR_{w5}R_{w6})_q\text{-}T_1$ wherein:

q is an integer selected from 0, 1, 2, 3, 4, each occurance of $R_{w5}$ and $R_{w6}$ are independently selected from:

a) hydrogen (including deuterium); or b) $C_{1-3}$alkyl, which is optionally substituted by one more substituents selected from cyano, hydroxy, $C_{1-2}$alkoxy, halo, $C_{1-2}$haloalkoxy, —O-$C_3$cycloalkyl, wherein —O—$C_3$cycloalkyl is optionally substituted with halo, cyano or hydroxy;

and $T_1$ is selected from hydrogen, cyano, hydroxy, $NR_{1t}R_{2t}$ or —$S(O)_{0-2}R_{1t}R_{2t}$ (wherein $R_{1t}$ and $R_{2t}$ are H or $C_{1-4}$alkyl), $C_{3-5}$cycloalkyl, $C_{2-3}$alkenyl, $C_{2-3}$alkynyl, aryl, heterocyclyl, heteroaryl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$-haloalkoxy, $NR_{3t}R_{4t}$ or —$S(O)_{0-2}R_{3t}R_{4t}$, wherein $R_{3t}$ and $R_{4t}$ are H or $C_{1-2}$alkyl; or $R_{w3}$ and $R_{w4}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, cyano, hydroxy; $C_{1-4}$alkoxy, halo, $C_{1-4}$haloalkoxy, $NR_{1i}R_{1j}$ or —$S(O)_{0-2}R_{1i}R_{1j}$, wherein $R_1$; and $R_{1i}$ are H or $C_{1-4}$alkyl, and/or the mono- or bicyclic hetereocyclic ring formed by $R_{w3}$ and $R_{w4}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, cyano, hydroxy, $C_{1-4}$alkoxy, halo, $C_{1-4}$haloalkoxy, $NR_{1i}R_{1j}$) or —$S(O)_{0-2}R_{1i}R_{1j}$, wherein $R_{1i}$ and $R_{1j}$ are H or $C_{1-4}$alkyl;

3. A compound according to paragraph 1 or paragraph 2, or a pharmaceutically acceptable salt thereof, wherein W is a group of the formula:

$—(CR_{w1}R_{w2})_p—NR_{w3}R_{w4};$ wherein p is an integer selected from 1 or 2;

$R_{w1}$ and $R_{w2}$ are independently selected from:

(i) hydrogen (including deuterium) or (ii) $C_{1-3}$alkyl which is optionally substituted by one more substituents selected from cyano, oxo, hydroxy, $C_{1-2}$alkoxy, halo, $C_{1-2}$haloalkoxy, —O—$C_3$cycloalkyl;

$R_{w3}$ is selected from hydrogen (including deuterium) or $C_{1-2}$alkyl; and $R_{w4}$ is a group with the formula:

$—(CR_{w5}R_{w6})_q\text{-}T_1$ wherein:

q is 1 or 2;

$R_{w5}$ and $R_{16}$ are independently selected from:

a) hydrogen (including deuterium); or b) $C_{1-2}$alkyl, which is optionally substituted by one more substituents selected from cyano, oxo, hydroxy, $C_{1-2}$alkoxy, halo or $C_{1-2}$haloalkoxy;

and $T_1$ is selected from $C_{1-4}$alkyl, $C_{3-8}$cycloalkyl, aryl, heterocyclyl, a mono- or bicyclic heteroaryl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy or $C_{3-6}$cycloalkyl;

or $R_{w3}$ and $R_{w4}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy, and/or the mono- or bicyclic hetereocyclic ring formed by $R_{w5}$ and $R_{w4}$ is optionally spiro-fused to a $C_{3-6}$cycloalkyl or a heterocyclic ring, which in turn is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy; wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and $R_{1l}$ are H or $C_{1-4}$alkyl.

4. A compound according to any one of the preceding paragraphs, wherein W is a group of the formula:

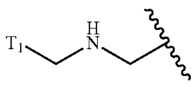, wherein $T_1$ is selected from $C_{3-4}$cycloalkyl, aryl, heteroaryl, heterocyclyl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

5. A compound according to any one of the preceding paragraphs, wherein W is selected from:

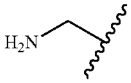 , 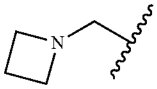

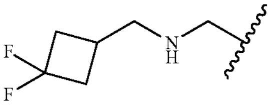 ; 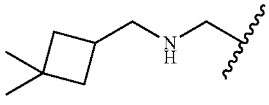 ;

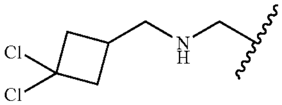 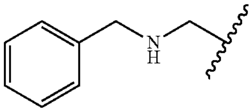 ,

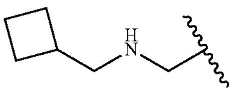 , 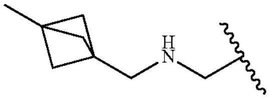 ,

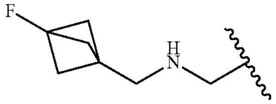 , 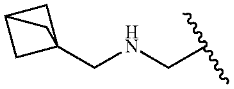 ,

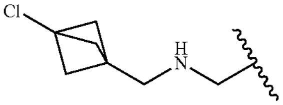 , 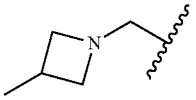 ,

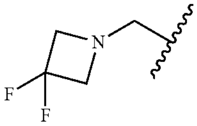 , 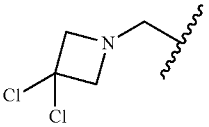

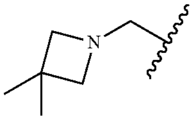 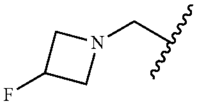 ,

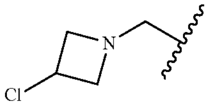 , 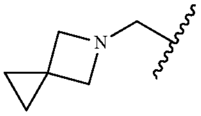 ,

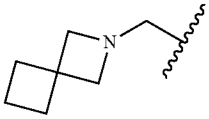 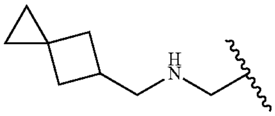 ,

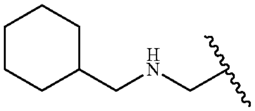 , 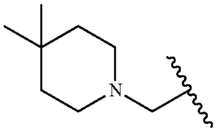 ,

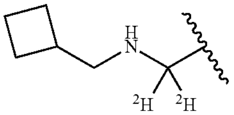 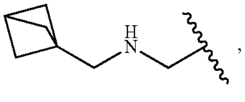 ,

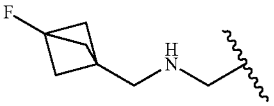 , 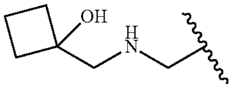 ,

-continued

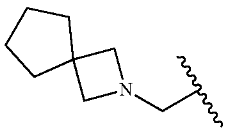 , 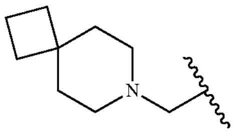

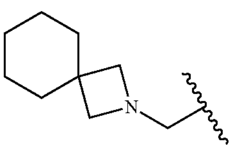 , 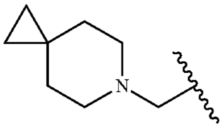 and

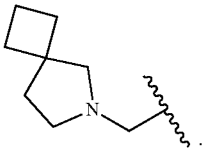 .

6. A compound according to any one of the preceding paragraphs, wherein W is selected from:

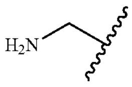 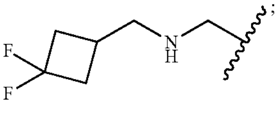 ;

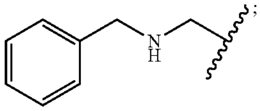 ; 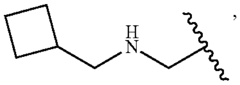 ,

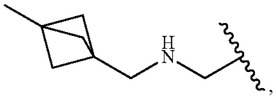 ,

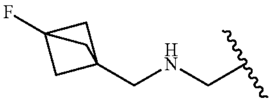 and

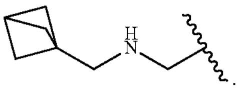 .

7. A compound according to any one of the preceding paragraphs, wherein X is selected from:

a) a group selected from;

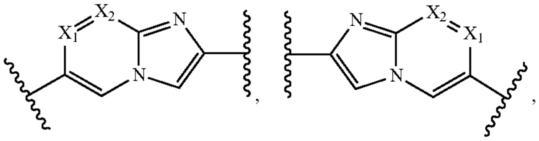

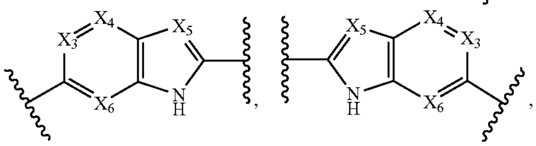

wherein each of $X_1$, $X_2$, $X_3$, $X_4$, $X_5$ and $X_6$ as defined in any one of the preceding paragraphs;

b) $C_{3-6}$alkenylene, optionally substituted by one or more hydroxy;

c) a group of the formula;

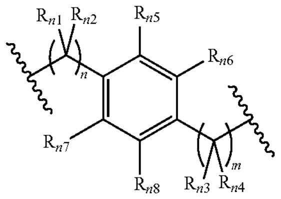

wherein n and m are each independently an integer selected from 0, 1, 2 or 3;

each occurrence of $R_{n1}$, $R_{n2}$, $R_{n3}$ and $R_{n4}$ are independently selected from hydrogen or halo; and each of $R_{n5}$, $R_{n6}$, $R_{n7}$ and $R_{n8}$ are independently selected from hydrogen or halo.

8. A compound according to any one of the preceding paragraphs, or a pharmaceutically acceptable salt thereof, wherein X is selected from:

a) a group selected from;

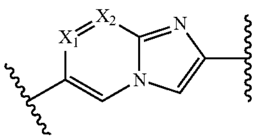

or

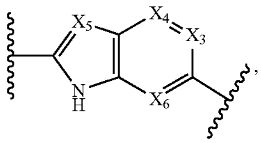

, wherein each of $X_1$, $X_2$, $X_3$, $X_4$, $X_5$ and $X_6$ as defined in any one of the preceding paragraphs;

b) $C_{3-6}$alkenylene, optionally substituted by one or more hydroxy;

c) a group of the formula;

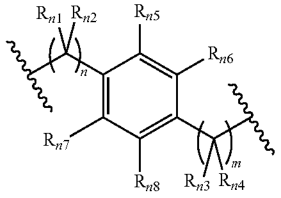

wherein:

m and n are each independently an integer selected from 0, 1 or 2; and each of $R_{n1}$, $R_{n2}$, $R_{n3}$ and $R_{n4}$ is independently selected from hydrogen or halo;

$R_{n5}$, $R_{n6}$, $R_{n7}$ and $R_{n8}$ are independently selected from hydrogen or halo.

9. A compound according to any one of the preceding paragraphs, or a pharmaceutically acceptable salt thereof, wherein X is selected from:

a) a group selected from;

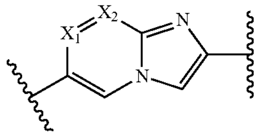

or

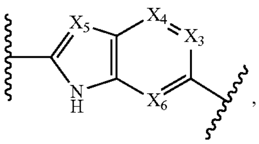

, wherein each of $X_1$, $X_2$, $X_3$, $X_4$, $X_5$ and $X_6$ are $CR_x$, wherein each $R_x$ is independently H or halo;

b) a group of the formula:

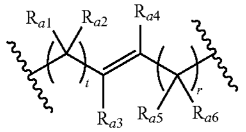

wherein t is an integer selected from 0, 1, 2 or 3 wherein r is an integer selected from 0, 1, or 2 or 3; and $R_{a1}$, $R_{a2}$, $R_{a3}$, $R_{a4}$, $R_{a5}$ and $R_{a6}$ are independently selected from hydrogen or hydroxy;

c) a group of the formula;

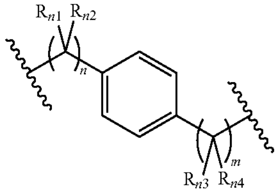

wherein m is 0 or 1 n is an integer selected from 0, 1 or 2; and each occurrence of $R_{n1}$, $R_{n2}$, $R_{n3}$ and $R_{n4}$ is independently selected from hydrogen or halo.

10. A compound according to any one of the preceding paragraphs, or a pharmaceutically acceptable salt thereof, wherein X is selected from:

a) a group selected from;

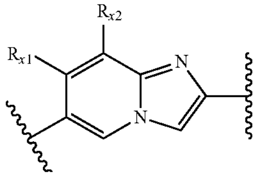

or

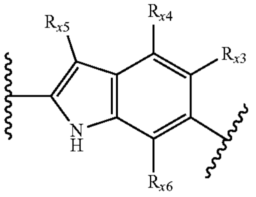

wherein:

$R_{X1}$ is H or halo;

$R_{X2}$ is H or halo;

$R_{X3}$ is H or halo;

$R_{X4}$ is H or halo;

$R_{X5}$ is H or halo; and $R_{X6}$ is H or halo;

b) a group of the formula:

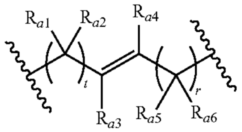

wherein t is an integer selected from 1, 2 or 3
wherein r is an integer selected from 0, 1 or 2; and
$R_{a1}$, $R_{a2}$, $R_{a3}$, $R_{a4}$, $R_{a5}$ and $R_{a6}$ are independently selected from hydrogen or hydroxy;
c) a group of the formula;

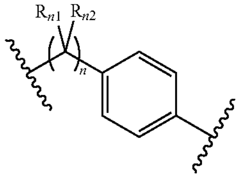

n is an integer selected from 0, 1 or 2; and
each of $R_{n1}$ and $R_{n2}$ is independently selected from hydrogen or halo.

11. A compound according to any one of the preceding paragraphs, or a pharmaceutically acceptable salt thereof, wherein X is selected from:
a) a group selected from;

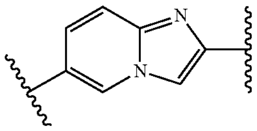
or
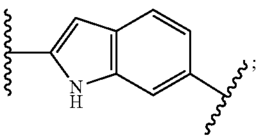
;

b) a group of the formula:

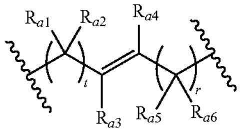

wherein t is an integer selected from 1 or 2
wherein r is an integer selected from 0, 1 or 2; and
$R_{a1}$, $R_{a2}$, $R_{a3}$, $R_{a4}$, $R_{a5}$ and $R_{a6}$ are independently selected from hydrogen or hydroxy;
c) a group of the formula;

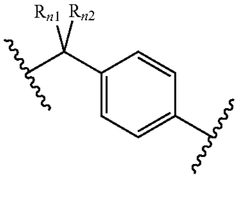
or
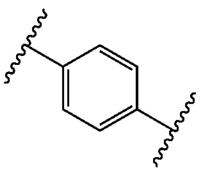

wherein $R_{n1}$ and $R_{n2}$ are independently selected from hydrogen or halo.

12. A compound according to any one of the preceding paragraphs, or a pharmaceutically acceptable salt thereof, wherein X is selected from:
a) a group selected from;

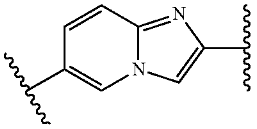
or
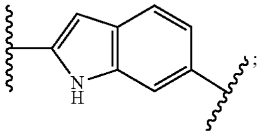
;

b) a group of the formula:

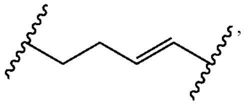
,
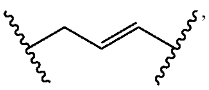
,
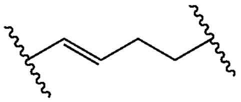
or
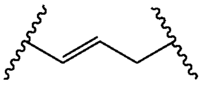

c) a group of the formula;

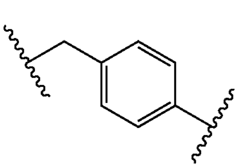
or
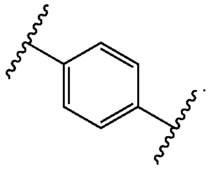
.

13. A compound according to any one of the preceding paragraphs, or a pharmaceutically acceptable salt thereof, wherein X is selected from:
a) a group selected from;

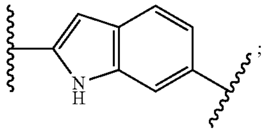 [SMILES: *c1ccc2cc(*)[nH]c2c1]
;

b) a group of the formula:

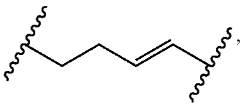
,
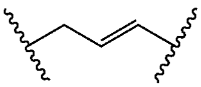
or
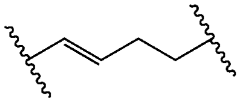

c) a group of the formula;

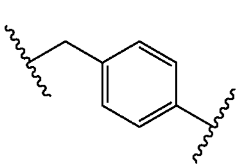 or 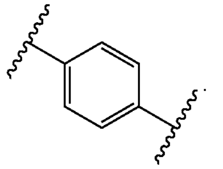.

14. A compound according to any one of the preceding paragraphs, wherein:
   $X_1$ is $CR_{X1}$, wherein $R_{X1}$ is H or halo;
   $X_2$ is $CR_{X2}$, wherein $R_{X2}$ is H or halo;
   $X_3$ is $CR_{X3}$, wherein $R_{X3}$ is H or halo;
   $X_4$ is $CR_{X4}$, wherein $R_{X4}$ is H or halo;
   $X_5$ is $CR_{X5}$, wherein $R_{X5}$ is H or halo; and
   $X_6$ is $CR_{X5}$, wherein $R_{X6}$ is H or halo.
15. A compound according to any one of the preceding paragraphs, or a pharmaceutically acceptable salt thereof, wherein $Y_1$ is selected from O or $CR_{y1}R_{y2}$ wherein each of $R_{y1}$ and $R_{y2}$ are independently selected from hydrogen, $C_{1-2}$alkyl and halo;
16. A compound according to any one of the preceding paragraphs, or a pharmaceutically acceptable salt thereof, wherein $Y_1$ is selected from O or $CR_{y1}R_{y2}$ wherein each of $R_{y1}$ and $R_{y2}$ are independently selected from hydrogen, methyl or halo.
17. A compound according to any one of the preceding paragraphs, or a pharmaceutically acceptable salt thereof, wherein $Y_1$ is selected from O or $CR_{y1}R_{y2}$ wherein each of $R_{y1}$ and $R_{y2}$ are independently selected from hydrogen or halo.
18. A compound according to any one of the preceding paragraphs, or a pharmaceutically acceptable salt thereof, wherein $R_1$ and $R_2$, together with the carbon atoms to which they are attached, are linked together to form a saturated or unsaturated 4 to 6 membered carbocyclic or heterocyclic ring system, wherein the carbocylic or heterocyclic ring is optionally substituted with one or more substituents selected from $C_{1-4}$alkyl, cyano, halo, hydroxy, $C_{1-4}$alkoxy or amino.
19. A compound according to any one of the preceding paragraphs, or a pharmaceutically acceptable salt thereof, $R_1$ and $R_2$, together with the carbon atoms to which they are attached, are linked together to form a saturated or unsaturated 4 to 6 membered carbocyclic or heterocyclic ring system, wherein the carbocylic or heterocyclic ring is optionally substituted with one or more substituents selected from methyl, cyano, fluoro, chloro, bromo, hydroxy or methoxy or amino.
20. A compound according to any one of the preceding paragraphs, or a pharmaceutically acceptable salt thereof, wherein
   $R_1$ and $R_2$, together with the carbon atoms to which they are attached, are linked together to form a saturated or unsaturated 4 to 6 membered carbocyclic or heterocyclic ring system, wherein the carbocylic or heterocyclic ring is optionally substituted with one or more substituents selected from methyl, hydroxy, methoxy or amino.
21. A compound according to any one of the preceding paragraphs, or a pharmaceutically acceptable salt thereof, wherein Y is selected from a group of the formula:

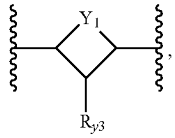, 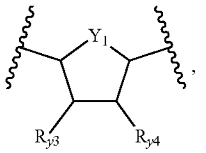,

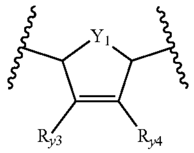 or 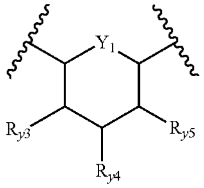

wherein:
   $Y_1$ is selected from O or $CR_{y1}R_{y2}$ wherein each of $R_{y1}$ and $R_{y2}$ are independently selected from hydrogen or halo;
   each of $R_{y3}$, $R_{y4}$, and $R_{y5}$ are independently selected from hydrogen, $C_{1-4}$alkyl, cyano, halo, hydroxy, $C_{1-4}$alkoxy, $C_{1-4}$haloalkoxy or amino.
22. A compound according to any one of the preceding paragraphs, or a pharmaceutically acceptable salt thereof, wherein Y is selected from a group of the formula:

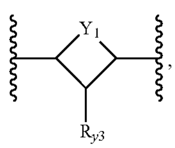, 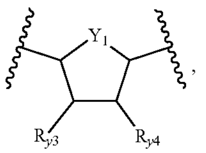,

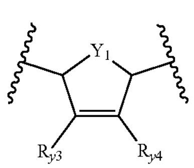 or 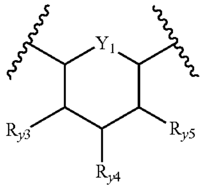

wherein:
$Y_1$ is selected from O or $CH_2$
each of $R_{y3}$, $R_{y4}$, and $R_{y5}$ are independently selected from hydrogen, methyl, cyano, fluoro, chloro, hydroxy or methoxy or amino.
23. A compound according to any one of the preceding paragraphs, or a pharmaceutically acceptable salt thereof, wherein Y is selected from a group of the formula:

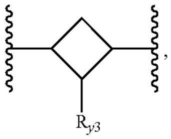, 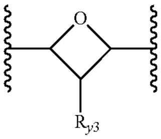,

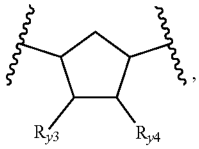, 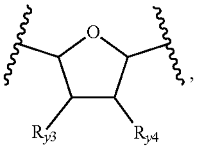,

-continued

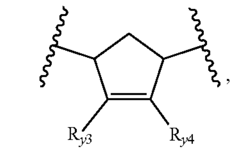, 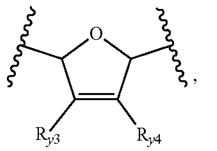,

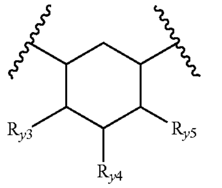 or 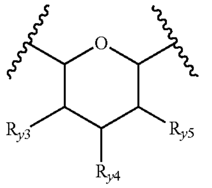

wherein:

each of $R_{y3}$, $R_{y4}$, and $R_{y5}$ are independently selected from hydrogen, methyl, cyano, fluoro, chloro, hydroxy or methoxy or amino.

24. A compound according to any one of the preceding paragraphs, or a pharmaceutically acceptable salt thereof, wherein Y is selected from a group of the formula:

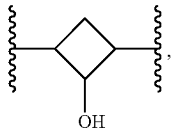, 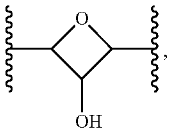,

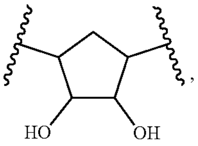, 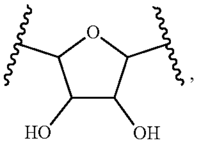,

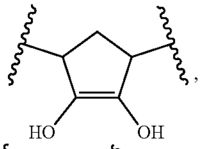, 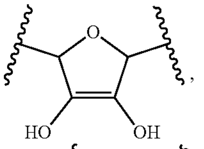,

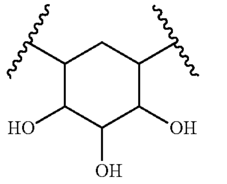 or 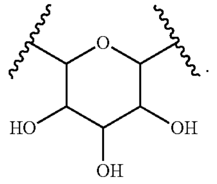.

25. A compound according to any one of the preceding paragraphs, or a pharmaceutically acceptable salt thereof, wherein Y is selected from a group of the formula:

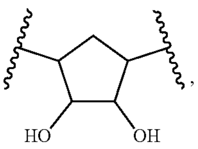, 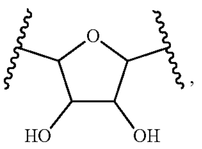,

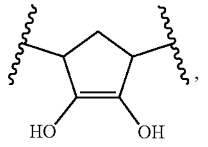, and 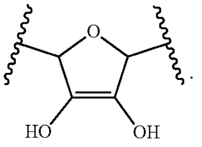.

26. A compound according to any one of the preceding paragraphs, or a pharmaceutically acceptable salt thereof, wherein Y is selected from a group of the formula:

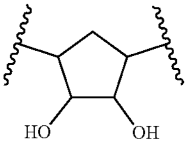 or 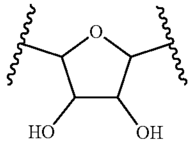

27. A compound according to any one of the preceding paragraphs, or a pharmaceutically acceptable salt thereof, wherein $Z_2$ is selected from $CR_{Z2}$ or N, wherein $R_{Z2}$ is selected from hydrogen, halo, cyano, $C_{1-4}$alkyl, $C_{1-4}$haloalkyl, $C_{3-6}$cycloalkyl, aryl, heterocyclyl or heteroaryl, wherein each of any $C_{1-4}$alkyl, $C_{1-4}$haloalkyl, $C_{3-6}$cycloalkyl, heteroaryl, aryl, heterocyclyl is optionally substituted with one or more substituents selected from, $C_{1-4}$alkyl, $C_{1-4}$haloalkyl, halo, trifluoromethyl, trifluoromethoxy, amino, cyano, hydroxy, or amino.

28. A compound according to any one of the preceding paragraphs, or a pharmaceutically acceptable salt thereof, wherein $Z_2$ is selected from $CR_{Z2}$ or N, wherein $R_{Z2}$ is selected from hydrogen, halo, $C_{1-4}$alkyl, $C_{1-4}$haloalkyl, $C_{3-6}$cycloalkyl, wherein each of any $C_{1-4}$alkyl, $C_{1-4}$haloalkyl, $C_{1-6}$cycloalkyl is optionally substituted with one or more substituents selected from, $C_{1-4}$alkyl, $C_{1-4}$haloalkyl, halo, amino, cyano, hydroxy, or amino.

29. A compound according to any one of the preceding paragraphs, or a pharmaceutically acceptable salt thereof, wherein $Z_2$ is selected from $CR_{Z2}$ or N, wherein $R_{Z2}$ is selected from hydrogen, halo, $C_{1-3}$alkyl, wherein $C_{1-3}$alkyl is optionally substituted with one or more fluoro.

30. A compound according to any one of the preceding paragraphs, or a pharmaceutically acceptable salt thereof, $Z_2$ is N or $CR_{Z2}$ wherein $R_{Z2}$ is hydrogen, halo or methyl.

31. A compound according to any one of the preceding paragraphs, or a pharmaceutically acceptable salt thereof, $Z_2$ is N or $CR_{Z2}$ wherein $R_{Z2}$ is hydrogen, fluoro, chloro, bromo or methyl, wherein methyl is optionally substituted with one or more fluoro.

32. A compound according to any one of the preceding paragraphs, or a pharmaceutically acceptable salt thereof, wherein $R_{Z2}$ is halo.

33. A compound according to any one of the preceding paragraphs, or a pharmaceutically acceptable salt thereof, wherein $R_{Z2}$ is bromo.

34. A compound according to any one of the preceding paragraphs, or a pharmaceutically acceptable salt thereof, wherein Z is a group of the formula:

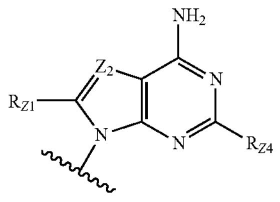

wherein $R_{Z1}$ and $R_{Z4}$ are independently selected from hydrogen, halo or cyano; wherein $Z_2$ is as defined in any one of the preceding paragraphs.

35. A compound according to any one of the preceding paragraphs, or a pharmaceutically acceptable salt thereof, wherein Z is a group of the formula:

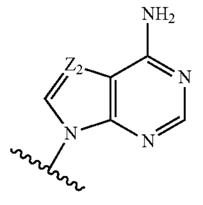

wherein $Z_2$ is as defined in any one of the preceding paragraphs.

36. A compound according to any one of the preceding paragraphs, or a pharmaceutically acceptable salt thereof, wherein Z is selected from:

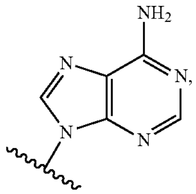

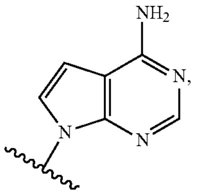

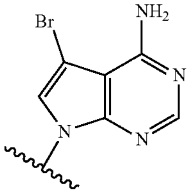

or

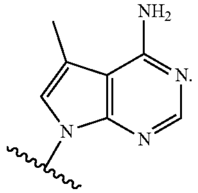

wherein $R_{Z2}$ is as defined in any one of the preceding paragraphs.

37. A compound according to any one of the preceding paragraphs, or a pharmaceutically acceptable salt thereof, wherein Z is a group of the formula:

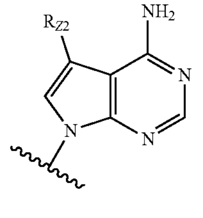

wherein $R_{Z2}$ is as defined in any one of the preceding paragraphs.

38. A compound, or a pharmaceutically acceptable salt thereof, selected from:

(2R,3R,4S,5R)-2-(4-amino-5-bromo-7H-pyrrolo[2,3-d]pyrimidin-7-yl)-5-((E)-5-(benzylamino)pent-1-en-1-yl)tetrahydrofuran-3,4-diol;

(2R,3R,4S,5R)-2-{4-amino-5-bromo-7H-pyrrolo[2,3-d]pyrimidin-7-yl}-5-[(1E)-5-[(cyclobutylmethyl)amino]pent-1-en-1-yl]oxolane-3,4-diol;

(2R,3R,4S,5R)-2-{4-amino-5-bromo-7H-pyrrolo[2,3-d]pyrimidin-7-yl}-5-[(1E)-4-(benzylamino)but-1-en-1-yl]oxolane-3,4-diol;

(2R,3R,4S,5R)-2-{4-amino-5-bromo-7H-pyrrolo[2,3-d]pyrimidin-7-yl}-5-[(1E)-5-{[(3,3-difluorocyclobutyl)methyl]amino}pent-1-en-1-yl]oxolane-3,4-diol;

(2R,3R,4S,5R)-2-{4-amino-5-bromo-7H-pyrrolo[2,3-d]pyrimidin-7-yl}-5-[(1E)-5-(benzylamino)pent-1-en-1-yl]oxolane-3,4-diol;

(2R,3R,4S,5R)-2-{4-amino-5-bromo-7H-pyrrolo[2,3-d]pyrimidin-7-yl}-5-[(1E)-5-[({3-fluorobicyclo[1.1.1]pentan-1-yl}methyl)amino]pent-1-en-1-yl]oxolane-3,4-diol;

(2R,3R,4S,5R)-2-{4-amino-5-bromo-7H-pyrrolo[2,3-d]pyrimidin-7-yl}-5-[(1E)-4-aminobut-1-en-1-yl]oxolane-3,4-diol;

(2R,3R,4S,5R)-2-{4-amino-5-bromo-7H-pyrrolo[2,3-d]pyrimidin-7-yl}-5-[(1E)-5-aminopent-1-en-1-yl]oxolane-3,4-diol;

(2R,3R,4S,5R)-2-(4-amino-5-bromo-7H-pyrrolo[2,3-d]pyrimidin-7-yl)-5-((E)-5-(benzylamino)pent-3-en-1-yl)tetrahydrofuran-3,4-diol;

(1R,2S,3R,5R)-3-(4-amino-5-bromo-7H-pyrrolo[2,3-d]pyrimidin-7-yl)-5-(4-(((cyclobutylmethyl)amino)methyl)phenyl)cyclopentane-1,2-diol;

(1R,2S,3R,5R)-3-{4-amino-5-bromo-7H-pyrrolo[2,3-d]pyrimidin-7-yl}-5-(2-{[({3-fluorobicyclo[1.1.1]pentan-1-yl}methyl)amino]methyl}-1H-indol-6-yl)cyclopentane-1,2-diol; and (1R,2S,3R,5R)-3-{4-amino-5-bromo-7H-pyrrolo[2,3-d]pyrimidin-7-yl}-5-(4-{2-[({3-fluorobicyclo[1.1.1]pentan-1-yl}methyl)amino]ethyl}phenyl)cyclopentane-1,2-diol.

39. A pharmaceutical composition comprising a compound according to any one of paragraphs 1 to 38, or a pharmaceutically acceptable salt thereof, and one or more pharmaceutically acceptable excipients.

40. A compound according to any one of paragraphs 1 to 38, or a pharmaceutically acceptable salt thereof, or a pharmaceutical composition according to paragraph 39, for use in therapy.

41. A compound according to any one of paragraphs 1 to 38, or a pharmaceutically acceptable salt thereof, or a pharmaceutical composition according to paragraph 39, for use in the treatment of a proliferative condition.

42. A compound according to any one of paragraphs 1 to 38, or a pharmaceutically acceptable salt thereof, or a pharmaceutical composition according to paragraph 39, for use in the treatment of cancer.

43. A compound according to any one of paragraphs 1 to 38, or a pharmaceutically acceptable salt thereof, or a pharmaceutical composition according to paragraph 39, for use in the treatment of leukaemia.

44. A compound according to any one of paragraphs 1 to 38, or a pharmaceutically acceptable salt thereof, or a pharmaceutical composition according to paragraph 39, for use in the treatment of AML leukaemia or chronic myeloid leukaemia.

45. A compound according to any one of paragraphs 1 to 38, or a pharmaceutically acceptable salt thereof, or a pharmaceutical composition according to paragraph 39, for use in the inhibition of METTL3 activity.

46. A compound according to any one of paragraphs 1 to 38, or a pharmaceutically acceptable salt thereof, or a pharmaceutical composition according to paragraph 39, for use in the treatment of an autoimmune disease, a neurological disease, an inflammatory disease or an infectious disease.

47. Use of a compound according to any one of paragraphs 1 to 38 or a pharmaceutically acceptable salt thereof, in the manufacture of a medicament for the treatment of a proliferative condition.

48. Use of a compound according to any one of paragraphs 1 to 38 or a pharmaceutically acceptable salt thereof, in the manufacture of a medicament for the treatment of cancer.

49. Use of a compound according to any one of paragraphs 1 to 38 or a pharmaceutically acceptable salt thereof, in the manufacture of a medicament for the treatment of leukaemia.

50. Use of a compound according to any one of paragraphs 1 to 38 or a pharmaceutically acceptable salt thereof, in the manufacture of a medicament for the treatment of AML leukaemia or chronic myeloid leukaemia.

51. Use of a compound according to any one of paragraphs 1 to 38 or a pharmaceutically acceptable salt thereof, in the manufacture of a medicament for the treatment of an autoimmune disease, a neurological disease, an inflammatory disease or an infectious disease.

52. Use of a compound according to any one of paragraphs 1 to 38, or a pharmaceutically acceptable salt thereof, in the manufacture of a medicament for the inhibition of METTL3 activity.

53. A method of treating a proliferative disorder, said method comprising administering to a subject in need thereof a therapeutically effective amount of a compound according to any one of paragraphs 1 to 38, or a pharmaceutically acceptable salt thereof, or a pharmaceutical composition according to paragraph 39.

54. A method of treating cancer, said method comprising administering to a subject in need thereof a therapeutically effective amount of a compound according to any one of paragraphs 1 to 38, or a pharmaceutically acceptable salt thereof, or a pharmaceutical composition according to paragraph 39.

55. A method of treating leukaemia, said method comprising administering to a subject in need thereof a therapeutically effective amount of a compound according to any one of paragraphs 1 to 38, or a pharmaceutically acceptable salt thereof, or a pharmaceutical composition according to paragraph 39.

56. A method of treating AML leukaemia or chronic myeloid leukaemia, said method comprising administering to a subject in need thereof a therapeutically effective amount of a compound according to any one of paragraphs 1 to 38, or a pharmaceutically acceptable salt thereof, or a pharmaceutical composition according to paragraph 39.

57. A method of treating an autoimmune disease, a neurological disease, an inflammatory disease or an infectious disease, said method comprising administering to a subject in need thereof a therapeutically effective amount of a compound according to any one of paragraphs 1 to 38, or a pharmaceutically acceptable salt thereof, or a pharmaceutical composition according to paragraph 39.

58. A method of inhibiting METTL3 activity in vitro or in vivo, said method comprising contacting a cell with an effective amount of a compound according to any one of paragraphs 1 to 38, or a pharmaceutically acceptable salt thereof, or a pharmaceutical composition according to paragraph 39.

59. A method of inhibiting metastasis in vitro or in vivo, said method comprising contacting a cell with an effective amount of a compound according to any one paragraphs 1 to 38, or a pharmaceutically acceptable salt thereof, or a pharmaceutical composition according to paragraph 39.

60. A combination comprising a compound according to any one of paragraphs 1 to 38, or a pharmaceutically acceptable salt there, with one or more additional therapeutic agents.

The invention claimed is:

1. A compound of the formula (I), or a pharmaceutically acceptable salt thereof, $$W—X—Y—Z \quad (I)$$

wherein:

W is a group of the formula:

$$—(CR_{w1}R_{w2})_p—NR_{w3}R_{w4};$$

wherein:

p is an integer selected from 1 or 2:

$R_{w1}$ and $R_{w2}$ are independently selected from:

(i) hydrogen or deuterium, (ii) $C_{1-3}$alkyl which is optionally substituted by one or more substituents selected from cyano, oxo, hydroxy, $C_{1-3}$alkoxy, halo, $C_{1-3}$haloalkoxy, —O—$C_{3-4}$cycloalkyl, or $NH_2$; wherein —O—$C_{3-4}$cycloalkyl is optionally substituted with halo, cyano or hydroxy, (iii) or $R_{w1}$ and $R_{w2}$ are linked together such that, together with the carbon atom to which they are attached, they form a 3- to 5-membered cycloalkyl or heterocyclic ring, or a spirocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy;

$R_{w3}$ is selected from:

(i) hydrogen or deuterium;

(ii) $C_{1-3}$alkyl which is optionally substituted by one or more substituents selected from cyano, oxo, hydroxy, $C_{1-2}$alkoxy, halo, $C_{1-2}$haloalkoxy and $NH_2$;

$R_{w4}$ is a group with the formula:

$$—(CR_{w5}R_{w6})_q\text{-}T_1$$

wherein:

q is 1, 2 or 3;

$R_{w5}$ and $R_{w6}$ are independently selected from:

a) hydrogen or deuterium; or b) $C_{1-3}$alkyl which is optionally substituted by one or more substituents selected from cyano, oxo, hydroxy, $C_{1-4}$alkoxy, halo, $C_{1-4}$haloalkoxy, —O—$C_{3-6}$cycloalkyl, wherein —O—$C_{3-6}$cycloalkyl is optionally substituted with halo, cyano or hydroxy;

c) or $R_{w5}$ and $R_{w6}$ are optionally linked together such that, together with the carbon atom to which they are attached, they form a 3- to 4-membered cycloalkyl or heterocyclic ring which is optionally substituted by one or more substituents selected from $C_{1-2}$alkyl, $C_1$-2haloalkyl, cyano, hydroxy, $C_{1-2}$alkoxy, halo or $C_{1-2}$haloalkoxy;

and $T_1$ is selected from halo, $C_{1-4}$alkyl, $C_{1-4}$haloalkyl, cyano, hydroxy, $NR_{1t}R_{2t}$ or —$S(O)_{0-2}R_{1t}R_{2t}$ (wherein $R_1$ and $R_{2t}$ are H or $C_{1-4}$alkyl), $C_{3-8}$cycloalkyl, $C_{2-3}$alkenyl, $C_{2-3}$alkynyl, aryl, heterocyclyl, a mono- or bicyclic heteroaryl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy, $C_{3-6}$cycloalkyl, $NR_{3t}R_{4t}$ or —$S(O)_{0-2}R_{3t}R_{4t}$, wherein $R_{3t}$ and $R_{4t}$ are H or $C_{1-2}$alkyl;

or $R_{w3}$ and $R_{w4}$ are linked such that, together with the nitrogen atom to which they are attached, they form a mono- or bicyclic-heterocyclic ring, which is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl, and/or the mono- or bicyclic heterocyclic ring formed by $R_{w3}$ and $R_{w4}$ is optionally spiro-fused to a $C_{3-6}$cycloalkyl or a heterocyclic ring, which in turn is optionally substituted by one or more substituents selected from $C_{1-4}$alkyl, $C_{1-4}$haloalkyl, $C_{3-6}$cycloalkyl, cyano, hydroxy, $C_{1-4}$alkoxy, halo, $C_{1-4}$haloalkoxy, $NR_{1i}R_{1j}$ or —$S(O)_{0-2}R_{1i}R_{1j}$, wherein $R_{1i}$ and $R_{1j}$ are H or $C_{1-4}$alkyl;

wherein any alkyl, alkoxy or $C_{3-6}$cycloalkyl is further optionally substituted by one or more substituents selected from cyano, hydroxy, halo, $NR_{1i}R_{1j}$ or —$S(O)_{0-2}R_{1k}R_{1l}$, wherein $R_{1k}$ and $R_{1l}$ are H or $C_{1-4}$alkyl X is selected from:

a) a group selected from;

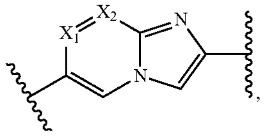,
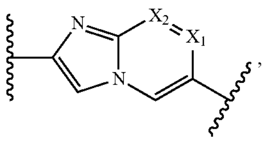,

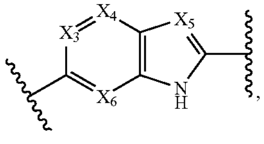,
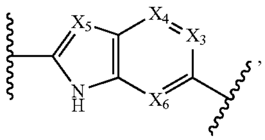,

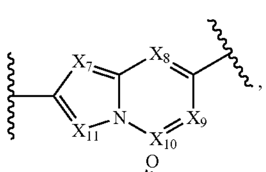,
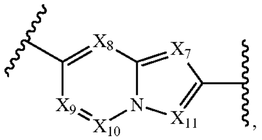,

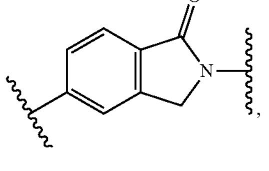, and
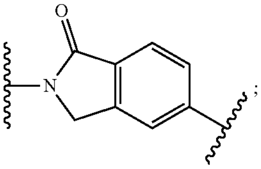;

$X_1$ is N or $CR_{X1}$, wherein $R_{X1}$ is H or halo;

$X_2$ is N or $CR_{X2}$, wherein $R_{X2}$ is H or halo;

$X_3$ is N or $CR_{X3}$, wherein $R_{X3}$ is H or halo;

$X_4$ is N or $CR_{X4}$, wherein $R_{X4}$ is H or halo;

$X_5$ is N or $CR_{X5}$, wherein $R_{X5}$ is H or halo;

$X_6$ is N or $CR_{X6}$, wherein $R_{X6}$ is H or halo;

$X_7$ is N or $CR_{X7}$, wherein $R_{X7}$ is H or halo;

$X_8$ is N or $CR_{X8}$, wherein $R_{X8}$ is H or halo;

$X_9$ is N or $CR_{X9}$, wherein $R_{X9}$ is H or halo;

$X_{10}$ is N or $CR_{X10}$, wherein $R_{X10}$ is H or halo;

$X_{11}$ is N or $CR_{X11}$, wherein $R_{X11}$ is H or halo;

b) $C_{2-6}$alkenylene, optionally substituted by one or more hydroxy; or c) a group of the formula;

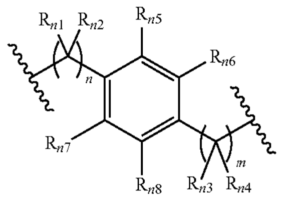

wherein n and m are each independently an integer selected from 0, 1, 2, 3 or 4; and each occurrence of $R_{n1}$, $R_{n2}$, $R_{n3}$ and $R_{n4}$ are independently selected from hydrogen or halo;

$R_{n5}$, $R_{n6}$, $R_{n7}$ and $R_{n8}$ are independently selected from hydrogen, halo, hydroxy, cyano, $C_{1-3}$alkyl, $C_{1-3}$haloalkyl, $C_{1-3}$alkoxy, $C_{1-3}$haloalkoxy and $NR_{n9}R_{n0}$, wherein each of $R_{n9}$ and $R_{n10}$ are independently selected from hydrogen or $C_{1-2}$alkyl;

wherein each of $C_{1-3}$alkyl and $C_{1-3}$alkoxy are optionally further substituted by halo, cyano or hydroxy;

Y is a group of the formula:

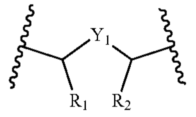

wherein:

$Y_1$ is selected from O, $CR_{y1}R_{y2}$ or $C{=}CR_{y1'}R_{y2'}$, wherein each of $R_{y1}$, $R_{y2}$, $R_{y1'}$, and $R_{y2}'$ are independently selected from hydrogen, $C_{1-4}$alkyl, halo and cyano;

$R_1$ and $R_2$, together with the carbon atoms to which they are attached, are linked together to form a saturated or unsaturated 4 to 7 membered carbocyclic or heterocyclic ring system, wherein the carbocyclic or heterocyclic ring is optionally substituted with one or more substituents selected from $C_{1-4}$alkyl, cyano, halo, hydroxy, $C_{1-4}$alkoxy, $C_{1-4}$haloalkoxy or amino;

Z is a group of the formula:

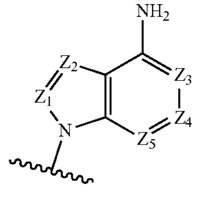

wherein $Z_1$ is $CR_{Z1}$ or N, $Z_3$ is $CR_{Z3}$ or N, $Z_4$ is $CR_{Z4}$ or N, $Z_5$ is $CR_{Z5}$ or N, wherein each of $R_{Z1}$, $R_{Z3}$, $R_{Z4}$ and $R_{Z5}$ are independently selected from hydrogen, halo or cyano;

$Z_2$ is selected from $CR_{Z2}$ or N, wherein $R_{Z2}$ is selected from hydrogen, halo, cyano, $C_{1-4}$alkyl, $C_{1-4}$haloalkyl, $C_{1-4}$alkoxy, $C_{1-4}$haloalkoxy, $C_{3-6}$cycloalkyl, aryl, heterocyclyl or heteroaryl, wherein each of any $C_{1-4}$alkyl, $C_{1-4}$haloalkyl, $C_{1-4}$alkoxy, $C_{1-4}$haloalkoxy, $C_{3-6}$cycloalkyl, heteroaryl, aryl, heterocyclyl is optionally substituted with one or more substituents selected from $C_{1-4}$alkyl, $C_{1-4}$haloalkyl, halo, trifluoromethyl, trifluoromethoxy, cyano, hydroxy, or amino;

with the proviso that no more than three of $Z_1$, $Z_2$, $Z_3$, $Z_4$ and $Z_5$ are nitrogen.

2. A compound according to claim 1, wherein W is a group of the formula:

$$—(CR_{w1}R_{w2})_p—NR_{w3}R_{w4};$$

wherein:

p is an integer selected from 1 or 2;

$R_{w1}$ and $R_{w2}$ are independently selected from:

(i) hydrogen or deuterium; or (ii) $C_{1-3}$alkyl which is optionally substituted by one or more substituents selected from cyano, oxo, hydroxy, $C_{1-2}$alkoxy, halo, $C_{1-2}$haloalkoxy, —O—$C_3$cycloalkyl:

$R_{w3}$ is selected from hydrogen or deuterium or $C_{1-2}$alkyl; and $R_{w4}$ is a group with the formula:

$$—(CR_{w5}R_{w6})_q\text{-}T_1$$

wherein:

q is 1 or 2;

$R_{w5}$ and $R_{w6}$ are independently selected from:

a) hydrogen or deuterium; or b) $C_{1-2}$alkyl, which is optionally substituted by one or more substituents selected from cyano, oxo, hydroxy, $C_{1-2}$alkoxy, halo or $C_{1-2}$haloalkoxy;

and $T_1$ is selected from $C_{1-4}$alkyl, $C_{3-8}$cycloalkyl, aryl, heterocyclyl, a mono- or bicyclic heteroaryl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo, $C_{1-2}$haloalkoxy or $C_{3-6}$cycloalkyl;

or $R_{w3}$ and $R_{w4}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy, and/or the mono- or bicyclic heterocyclic ring formed by $R_{w3}$ and $R_{w4}$ is optionally spiro-fused to a $C_{3-6}$cycloalkyl or a heterocyclic ring, which in turn is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy; wherein any alkyl, alkoxy or $C_{3-6}$cycloalkyl is further optionally substituted by one or more substituents selected from cyano, hydroxy, halo, $NR_{1k}R_{1l}$ or —$S(O)_{0-2}R_{1k}R_{1l}$, wherein $R_{1k}$ and Ri are H or $C_{1-4}$alkyl.

3. A compound according to claim 1, or a pharmaceutically acceptable salt thereof, wherein W is a group of the formula:

$$—(CR_{w1}R_{w2})_p—NR_{w3}R_{w4};$$

wherein p is 1:

$R_{w1}$ and $R_{w2}$ are independently selected from hydrogen or deuterium or $C_{1-2}$alkyl; and $R_{w3}$ and $R_{w4}$ are linked such that, together with the nitrogen atom to which they are attached, they form a mono- or bicyclic-heterocyclic ring, which is optionally substituted by one or more substituents selected from $C_{1-2}$alkyl, $C_{1-2}$haloalkyl, $C_{3-6}$cycloalkyl, cyano, hydroxy, $C_{1-2}$alkoxy, halo or $C_{1-2}$haloalkoxy, and/or the mono- or bicyclic heterocyclic ring formed by $R_{w3}$ and $R_{w4}$ is optionally spiro-fused to a $C_{3-6}$cycloalkyl or a heterocyclic ring, which in turn is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy.

4. A compound according to claim 1, wherein W is a group of the formula:

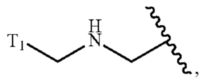, wherein $T_1$ is selected from $C_{3-4}$cycloalkyl, aryl, heteroaryl, heterocyclyl, a spirocyclic carbocyclic or heterocyclic ring system, a bridged $C_{4-8}$cycloalkyl, a bridged bicyclic $C_{5-12}$cycloalkyl, or a bridged heterocyclic ring system, each of which is optionally substituted by one or more substituents selected from $C_{1-2}$alkyl, $C_{1-2}$haloalkyl, cyano, hydroxy, $C_{1-2}$alkoxy, halo or $C_{1-2}$haloalkoxy.

5. A compound according to claim 1, wherein W is selected from:

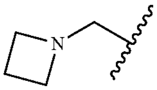 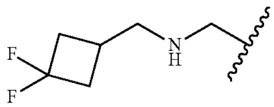,

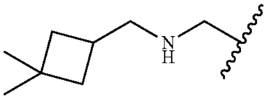, 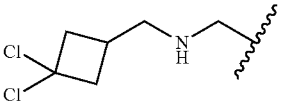

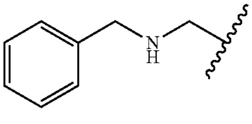 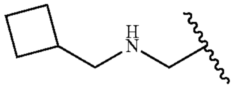,

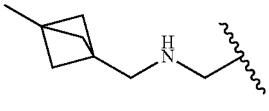, 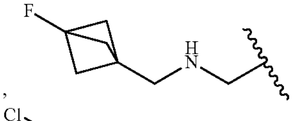,

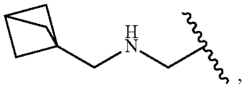, 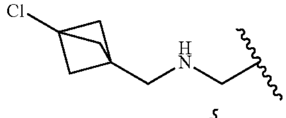,

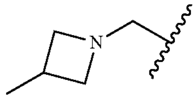, 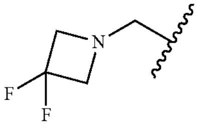,

-continued

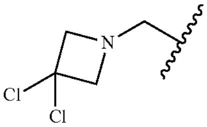, 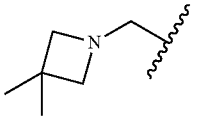,

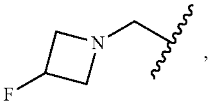, 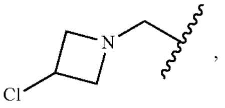,

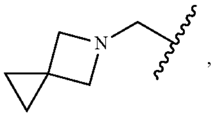, 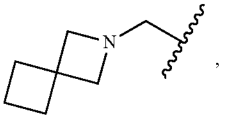,

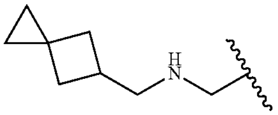, 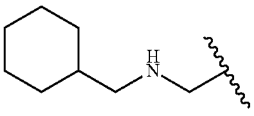,

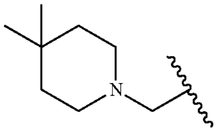, 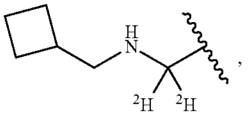,

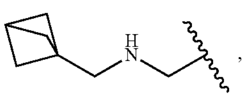, 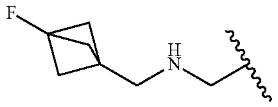,

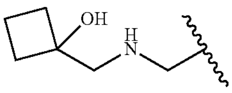, 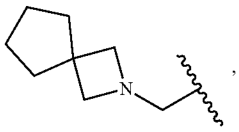,

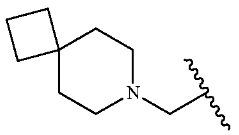, 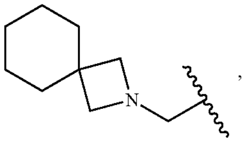,

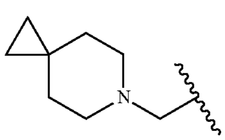, 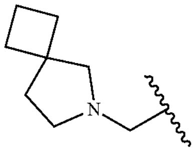,

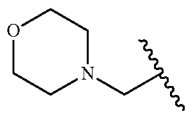, 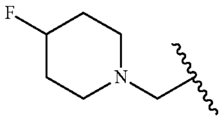,

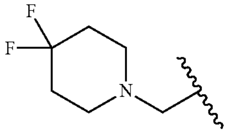, 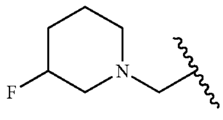, and

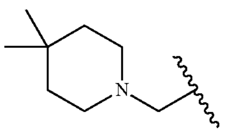.

6. A compound according to claim 1, wherein X is selected from:

a) a group selected from;

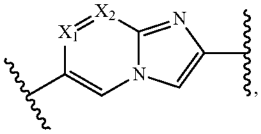,

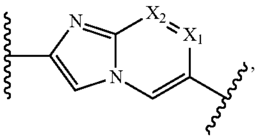,

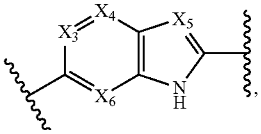, or

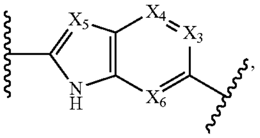, wherein each of $X_1$, $X_2$, $X_3$, $X_4$, $X_5$ and $X_6$ is as defined in claim 1;

b) $C_{3-6}$alkenylene, optionally substituted by one or more hydroxy; or c) a group of the formula;

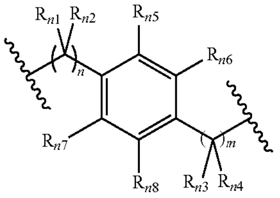

wherein n and m are each independently an integer selected from 0, 1, 2 or 3;

each occurrence of $R_{n1}$, $R_{n2}$, $R_{n3}$ and $R_{n4}$ are independently selected from hydrogen or halo; and each of $R_{n5}$, $R_{n6}$, $R_{n7}$ and $R_{n8}$ are independently selected from hydrogen or halo.

7. A compound according to claim 1, or a pharmaceutically acceptable salt thereof, wherein X is selected from:

a) a group selected from;

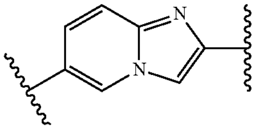 or

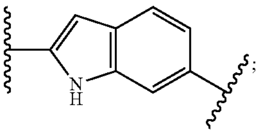;

b) a group of the formula:

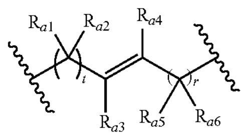

wherein t is an integer selected from 1 or 2;

wherein r is an integer selected from 0, 1 or 2; and $R_{a1}$, $R_{a2}$, $R_{a3}$, $R_{a4}$, $R_{a5}$ and $R_{a6}$ are independently selected from hydrogen or hydroxy;

c) a group of the formula;

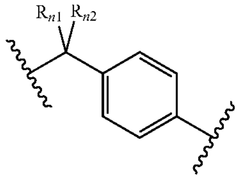

or

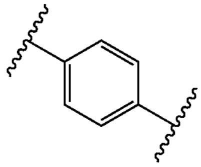

wherein $R_{n1}$ and $R_{n2}$ are independently selected from hydrogen or halo.

8. A compound according to claim 1, or a pharmaceutically acceptable salt thereof, wherein X is selected from:

a) a group of the formula;

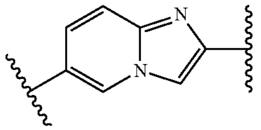

or

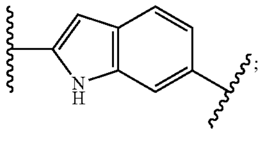

;

b) a group of the formula:

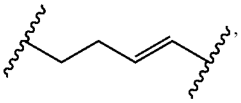

,

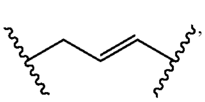

,

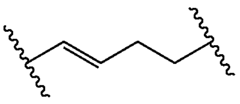

or

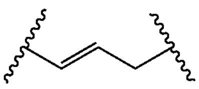

c) a group of the formula;

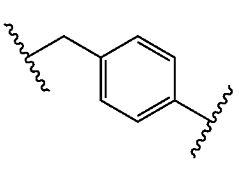

or

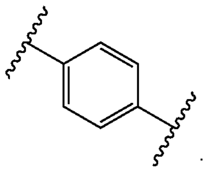

.

9. A compound according to claim 1, or a pharmaceutically acceptable salt thereof, wherein X is selected from:

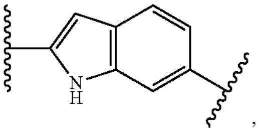

,

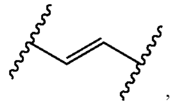

,

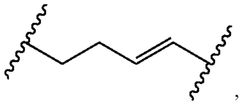

,

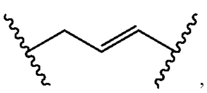

, or

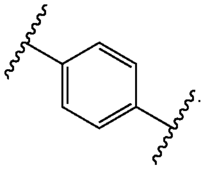

.

10. A compound according to claim 1, wherein:

$X_1$ is $CR_{X1}$, wherein $R_{X1}$ is H or halo;

$X_2$ is $CR_{X2}$, wherein $R_{X2}$ is H or halo;

$X_3$ is $CR_{X3}$, wherein $R_{X3}$ is H or halo;

$X_4$ is $CR_{X4}$, wherein $R_{X4}$ is H or halo;

$X_5$ is $CR_{X5}$, wherein $R_{X5}$ is H or halo; and $X_6$ is $CR_{X6}$, wherein $R_{X6}$ is H or halo.

11. A compound according to claim 1, or a pharmaceutically acceptable salt thereof, wherein $Y_1$ is selected from O or $CR_{y1}R_{y2}$ wherein each of $R_{y1}$ and $R_{y2}$ are independently selected from hydrogen or halo.

12. A compound according to claim 1, or a pharmaceutically acceptable salt thereof, wherein $R_1$ and $R_2$, together with the carbon atoms to which they are attached, are linked together to form a saturated or unsaturated 4 to 6 membered carbocyclic or heterocyclic ring system, wherein the carbocyclic or heterocyclic ring is optionally substituted with one or more substituents selected from methyl, hydroxy, methoxy or amino.

13. A compound according to claim 1, or a pharmaceutically acceptable salt thereof, wherein Y is selected from a group of the formula:

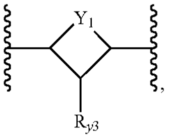

,

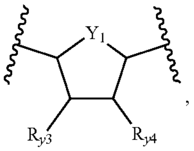

,

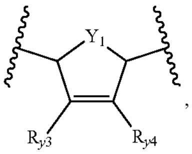

, or

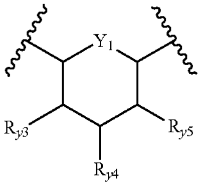

wherein:

$Y_1$ is selected from O or $CR_{y1}R_{y2}$ wherein each of $R_{y1}$ and $R_{y2}$ are independently selected from hydrogen or halo; and each of $R_{y3}$, $R_{y4}$, and $R_{y5}$ are selected from hydrogen, $C_{1-4}$alkyl, cyano, halo, hydroxy, $C_{1-4}$alkoxy, $C_{1-4}$haloalkoxy or amino.

14. A compound according to claim 1, or a pharmaceutically acceptable salt thereof, wherein Y is selected from a group of the formula:

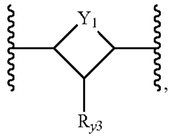,
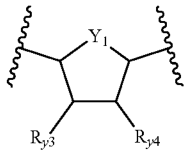,
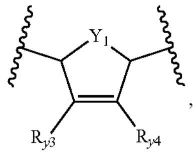, or
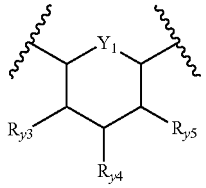

wherein:

$Y_1$ is selected from O or $CH_2$; and each of $R_{y3}$, $R_{y4}$, and $R_{y5}$ are independently selected from hydrogen, methyl, cyano, fluoro, chloro, hydroxy or methoxy or amino.

15. A compound according to claim 1, or a pharmaceutically acceptable salt thereof, wherein Y is selected from a group of the formula:

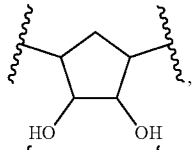,
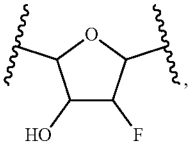, or
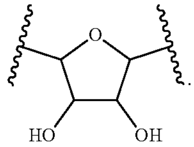.

16. A compound according to claim 1, or a pharmaceutically acceptable salt thereof, wherein $Z_2$ is selected from $CR_{Z2}$ or N, wherein $R_{Z2}$ is selected from hydrogen, halo, cyano, $C_{1-4}$alkyl, $C_{1-4}$haloalkyl, $C_{3-6}$cycloalkyl, aryl, heterocyclyl or heteroaryl, wherein each of any $C_{1-4}$alkyl, $C_{1-4}$haloalkyl, $C_{3-6}$cycloalkyl, heteroaryl, aryl, heterocyclyl is optionally substituted with one or more substituents selected from $C_{1-4}$alkyl, $C_{1-4}$haloalkyl, halo, trifluoromethyl, trifluoromethoxy, cyano, hydroxy, or amino.

17. A compound according to claim 1, or a pharmaceutically acceptable salt thereof, wherein $Z_2$ is N or $CR_{Z2}$ wherein $R_{Z2}$ is hydrogen, fluoro, chloro, bromo or methyl, wherein methyl is optionally substituted with one or more fluoro.

18. A compound according to claim 1, or a pharmaceutically acceptable salt thereof, wherein $Z_2$ is $CR_{Z2}$and $R_{Z2}$ is halo.

19. A compound according to claim 1, or a pharmaceutically acceptable salt thereof, wherein Z is selected from:

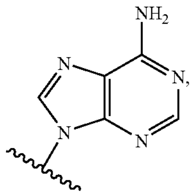
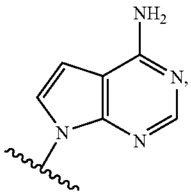

-continued

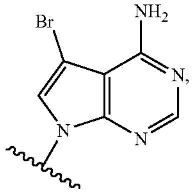 or
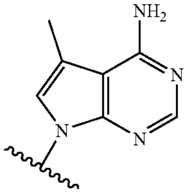

wherein $R_{Z2}$ is as defined in claim 1.

20. A compound according to claim 1, or a pharmaceutically acceptable salt thereof, wherein Z is a group of the formula:

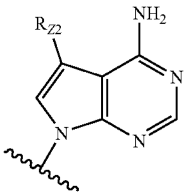

wherein $R_{Z2}$ is as defined in claim 1.

21. A compound, or a pharmaceutically acceptable salt thereof, selected from:

(2R,3R,4S,5R)-2-(4-amino-5-bromo-7H-pyrrolo[2,3-d]pyrimidin-7-yl)-5-((E)-5-(benzylamino)pent-1-en-1-yl)tetrahydrofuran-3,4-diol;

(2R,3R,4S,5R)-2-{4-amino-5-bromo-7H-pyrrolo [2,3-d]pyrimidin-7-yl}-5-[(1E)-5-[(cyclobutylmethyl)amino]pent-1-en-1-yl]oxolane-3,4-diol;

(2R,3R,4S,5R)-2-{4-amino-5-bromo-7H-pyrrolo [2,3-d]pyrimidin-7-yl}-5-[(1E)-4-(benzylamino)but-1-en-1-yl]oxolane-3,4-diol;

(2R,3R,4S,5R)-2-{4-amino-5-bromo-7H-pyrrolo[2,3-d]pyrimidin-7-yl}-5-[(1E)-5-{[(3,3-difluorocyclobutyl)methyl]amino}pent-1-en-1-yl]oxolane-3,4-diol;

(2R,3R,4S,5R)-2-{4-amino-5-bromo-7H-pyrrolo[2,3-d]pyrimidin-7-yl}-5-[(1E)-5-(benzylamino)pent-1-en-1-yl]oxolane-3,4-diol;

(2R,3R,4S,5R)-2-{4-amino-5-bromo-7H-pyrrolo[2,3-d]pyrimidin-7-yl}-5-[(1E)-5-[({3-fluorobicyclo[1.1.1]pentan-1-yl}methyl)amino]pent-1-en-1-yl]oxolane-3,4-diol;

(2R,3R,4S,5R)-2-{4-amino-5-bromo-7H-pyrrolo[2,3-d]pyrimidin-7-yl}-5-[(1E)-4-aminobut-1-en-1-yl]oxolane-3,4-diol;

(2R,3R,4S,5R)-2-{4-amino-5-bromo-7H-pyrrolo[2,3-d]pyrimidin-7-yl}-5-[(1E)-5-aminopent-1-en-1-yl]oxolane-3,4-diol;

(2R,3R,4S,5R)-2-(4-amino-5-bromo-7H-pyrrolo[2,3-d]pyrimidin-7-yl)-5-((E)-5-(benzylamino)pent-3-en-1-yl)tetrahydrofuran-3,4-diol;

(1R,2S,3R,5R)-3-(4-amino-5-bromo-7H-pyrrolo[2,3-d]pyrimidin-7-yl)-5-(4-(((cyclobutylmethyl)amino)methyl)phenyl)cyclopentane-1,2-diol;

(1R,2S,3R,5R)-3-{4-amino-5-bromo-7H-pyrrolo[2,3-d]pyrimidin-7-yl}-5-(2-{[({3-fluorobicyclo[1.1.1]pentan-1-yl}methyl)amino]methyl}-1H-indol-6-yl)cyclopentane-1,2-diol;

(1R,2S,3R,5R)-3-{4-amino-5-bromo-7H-pyrrolo [2,3-d]pyrimidin-7-yl}-5-(4-{2-[({3-fluorobicyclo[1.1.1]pentan-1-yl}methyl)amino]ethyl}phenyl)cyclopentane-1,2-diol;

(2R,3R,4S,5R)-2-{4-amino-5-bromo-7H-pyrrolo [2,3-d]pyrimidin-7-yl}-5-[(1E)-2-(azetidin-3-yl)ethenyl]oxolane-3,4-diol;

(2R,3R,4S,5R)-2-{4-amino-5-bromo-7H-pyrrolo [2,3-d]pyrimidin-7-yl}-5-[(1E)-2-(piperidin-4-yl)ethenyl]oxolane-3,4-diol;

(2R,3R,4S,5R)-2-{4-amino-5-bromo-7H-pyrrolo [2,3-d]pyrimidin-7-yl}-5-[(1E)-2-(piperidin-3-yl)ethenyl]oxolane-3,4-diol;

(2R,3R,4S,5R)-2-{4-amino-5-bromo-7H-pyrrolo [2,3-d]pyrimidin-7-yl}-5-[(1E)-2-(pyrrolidin-3-yl)ethenyl]oxolane-3,4-diol;

(2R,3R,4S,5R)-2-{4-amino-5-bromo-7H-pyrrolo[2,3-d]pyrimidin-7-yl}-5-[(1E)-2-(3-aminocyclobutyl)ethenyl]oxolane-3,4-diol;

(2R,3R,4S,5R)-2-{4-amino-5-bromo-7H-pyrrolo[2,3-d]pyrimidin-7-yl}-5-[(1E)-2-(oxetan-3-yl)ethenyl]oxolane-3,4-diol;

(2R,3R,4S,5R)-2-{4-amino-5-bromo-7H-pyrrolo[2,3-d]pyrimidin-7-yl}-5-[(1E)-3-(azetidin-3-yl)prop-1-en-1-yl]oxolane-3,4-diol;

(2R,3R,4S,5R)-2-[4-amino-5-(1H-pyrazol-3-yl)-7H-pyrrolo[2,3-d]pyrimidin-7-yl]-5-[(1E)-5-[({3-fluorobicyclo[1.1.1]pentan-1-yl}methyl)amino]pent-1-en-1-yl]oxolane-3,4-diol;

(2R,3R,4S,5R)-2-[4-amino-5-bromo-7H-pyrrolo[2,3-d]pyrimidin-7-yl]-5-[(1E)-5-{6-azaspiro[3.4]octan-6-yl}pent-1-en-1-yl]oxolane-3,4-diol;

(2R,3S,5R)-5-(4-amino-5-bromo-pyrrolo[2,3-d]pyrimidin-7-yl)-2-[(E)-5-[(3-fluoro-1-bicyclo[1.1.1]pentanyl)methylamino]pent-1-enyl]tetrahydrofuran-3-ol;

(2R,3R,4S,5R)-2-{4-amino-5-bromo-7H-pyrrolo[2,3-d]pyrimidin-7-yl}-5-[(1E)-5-(4,4-difluoropiperidin-1-yl)pent-1-en-1-yl]oxolane-3,4-diol;

(2R,3R,4S,5R)-2-{4-amino-5-bromo-7H-pyrrolo[2,3-d]pyrimidin-7-yl}-5-[(1E)-5-(4-fluoropiperidin-1-yl)pent-1-en-1-yl]oxolane-3,4-diol;

(2R,3R,4S,5R)-2-{4-amino-5-bromo-7H-pyrrolo[2,3-d]pyrimidin-7-yl}-5-[(1E)-5-(morpholin-4-yl)pent-1-en-1-yl]oxolane-3,4-diol;

(2R,3R,4S,5R)-2-{4-amino-5-bromo-7H-pyrrolo[2,3-d]pyrimidin-7-yl}-5-[(1E)-5-(3-fluoropiperidin-1-yl)pent-1-en-1-yl]oxolane-3,4-diol;

(2R,3R,5S)-2-{4-amino-5-bromo-7H-pyrrolo[2,3-d]pyrimidin-7-yl}-5-[(1E)-5-[({3-fluorobicyclo[1.1.1]pentan-1-yl}methyl)amino]pent-1-en-1-yl]oxolan-3-ol;

(2R,3S,4R,5R)-2-{4-amino-5-bromo-7H-pyrrolo[2,3-d]pyrimidin-7-yl}-4-fluoro-5-[(1E)-5-[({3-fluorobicyclo[1.1.1]pentan-1-yl}methyl)amino]pent-1-en-1-yl]oxolan-3-ol;

(1R,2S,3R,5R)-3-{4-amino-5-fluoro-7H-pyrrolo[2,3-d]pyrimidin-7-yl}-5-(2-{[({3-fluorobicyclo[1.1.1]pentan-1-yl}methyl)amino]methyl}-1H-indol-6-yl)cyclopentane-1,2-diol;

(1R,2S,3R,5R)-3-{4-amino-5-chloro-7H-pyrrolo[2,3-d]pyrimidin-7-yl}-5-(2-{[({3-fluorobicyclo[1.1.1]pentan-1-yl}methyl)amino]methyl}-1H-indol-6-yl)cyclopentane-1,2-diol;

(1R,2S,3R,5R)-3-{4-amino-5-bromo-7H-pyrrolo[2,3-d]pyrimidin-7-yl}-5-(2-{[({3-fluorobicyclo[1.1.1]pentan-1-yl}methyl)amino]methyl}-1H-indol-5-yl)cyclopentane-1,2-diol;

(1R,2S,3R,5R)-3-{4-amino-5-bromo-7H-pyrrolo[2,3-d]pyrimidin-7-yl}-5-[2-({6-azaspiro[3.4]octan-6-yl}methyl)-1H-indol-6-yl]cyclopentane-1,2-diol;

(1R,2S,3R,5R)-3-{4-amino-7H-pyrrolo[2,3-d]pyrimidin-7-yl}-5-[2-({6-azaspiro[3.4]octan-6-yl}methyl)-1H-indol-6-yl]cyclopentane-1,2-diol;

(1R,2S,3R,5R)-3-{4-amino-5-bromo-7H-pyrrolo[2,3-d]pyrimidin-7-yl}-5-(4-{[({3-fluorobicyclo[1.1.1]pentan-1-yl}methyl)amino]methyl}phenyl)cyclopentane-1,2-diol;

(1R,2S,3R,5R)-3-{4-amino-5-bromo-7H-pyrrolo[2,3-d]pyrimidin-7-yl}-5-[4-({6-azaspiro[3.4]octan-6-yl}methyl)phenyl]cyclopentane-1,2-diol;

(1R,2S,3R,5R)-3-{4-amino-5-bromo-7H-pyrrolo[2,3-d]pyrimidin-7-yl}-5-{4-[(4,4-dimethylpiperidin-1-yl)methyl]phenyl}cyclopentane-1,2-diol;

(1R,2S,3R,5R)-3-{4-amino-5-bromo-7H-pyrrolo[2,3-d]pyrimidin-7-yl}-5-(3-{2-[({3-fluorobicyclo[1.1.1]pentan-1-yl}methyl)amino]ethyl}phenyl)cyclopentane-1,2-diol;

(1R,2S,3R,5R)-3-{4-amino-5-bromo-7H-pyrrolo[2,3-d]pyrimidin-7-yl}-5-[3-({6-azaspiro[3.4]octan-6-yl}methyl)phenyl]cyclopentane-1,2-diol;

(1R,2S,3R,5R)-3-{4-amino-5-bromo-7H-pyrrolo[2,3-d]pyrimidin-7-yl}-5-(3-{[({3-fluorobicyclo[1.1.1]pentan-1-yl}methyl)amino]methyl}phenyl)cyclopentane-1,2-diol;

3-[(1R,2R,3S,4R)-4-{4-amino-5-bromo-7H-pyrrolo[2,3-d]pyrimidin-7-yl}-2,3-dihydroxycyclopentyl]-N-({3-fluorobicyclo[1.1.1]pentan-1-yl}methyl)benzamide; and (2R,3R,4R,5R)-5-{4-amino-5-bromo-7H-pyrrolo[2,3-d]pyrimidin-7-yl}-4-fluoro-2-[(1E)-5-[({3-fluorobicyclo[1.1.1]pentan-1-yl}methyl)amino]pent-1-en-1-yl]oxolan-3-ol.

22. A pharmaceutical composition comprising a compound according to claim 1, or a pharmaceutically acceptable salt thereof, and one or more pharmaceutically acceptable excipients.

23. A method of treating cancer, said method comprising administering to a subject in need thereof a therapeutically effective amount of a compound as defined in claim 1, or a pharmaceutically acceptable salt thereof.

24. A method of treating cancer, said method comprising administering to a subject in need thereof a therapeutically effective amount of a pharmaceutical composition as defined in claim 22.

* * * * *